(12) United States Patent
Merla et al.

(10) Patent No.: US 8,158,628 B2
(45) Date of Patent: Apr. 17, 2012

(54) SULFONYLATED 1,2,3,4-TETRAHYDROPYRROLO[1,2-A]PYRAZINE COMPOUNDS AND THEIR USE AS PHARMACEUTICALS

(75) Inventors: Beatrix Merla, Aachen (DE); Stefan Oberboersch, Aachen (DE); Melanie Reich, Aachen (DE); Stefan Schunk, Aachen (DE); Ruth Jostock, Stolberg (DE); Sabine Hees, Aachen (DE); Michael Engels, Turnhout (DE); Tieno Germann, Aachen (DE); Edward Bijsterveld, Nijmegen (NL)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/717,625

(22) Filed: Mar. 4, 2010

(65) Prior Publication Data

US 2010/0234387 A1   Sep. 16, 2010

Related U.S. Application Data

(60) Provisional application No. 61/157,393, filed on Mar. 4, 2009.

(30) Foreign Application Priority Data

Mar. 4, 2009  (EP) .................................... 09003075

(51) Int. Cl.
*A61K 31/495* (2006.01)

(52) U.S. Cl. ........ 514/249; 540/553; 544/116; 544/333; 544/350; 544/359; 546/148; 546/268.1; 548/304.4; 548/335.1; 548/518; 548/560; 549/398; 585/26

(58) Field of Classification Search ............... 514/249; 540/553; 544/116, 333, 350, 359; 546/148; 546/268.1; 548/304.4, 335.1, 518, 560; 549/398; 585/26

See application file for complete search history.

(56) References Cited

FOREIGN PATENT DOCUMENTS

| WO | WO 2006/068928 A1 | 6/2006 |
| WO | WO 2007/124423 A2 | 11/2007 |
| WO | WO 2008/157751 A2 | 12/2008 |

OTHER PUBLICATIONS

European Search Report dated Jul. 6, 2009 with partial English translation (Nine (9) pages).

*Primary Examiner* — James O Wilson
*Assistant Examiner* — Douglas M Willis
(74) *Attorney, Agent, or Firm* — Crowell & Moring LLP

(57) ABSTRACT

Sulfonylated tetrahydroazolopyrazine compounds corresponding to the formula I

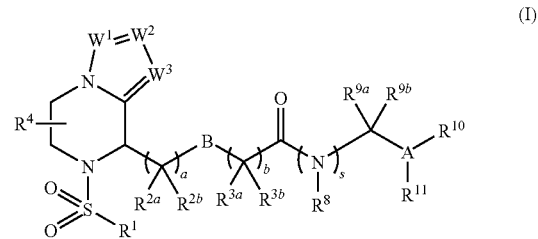

wherein $R^1$, $R^{2a}$, $R^{2b}$, $R^{3a}$, $R^{3b}$, $R^4$, $R^8$, $R^{9a}$, $R^{9b}$, $R^{10}$, $R^{11}$, A, B, $W^1$, $W^2$ and $W^3$ have the meanings defined herein, pharmaceutical compositions containing such compounds, a method for the preparation of such compounds, and the use of such compounds for treating or inhibiting various types of pain and/or other conditions mediated at least in part by the bradykinin 1 receptor (B1R).

20 Claims, No Drawings

SULFONYLATED 1,2,3,4-TETRAHYDROPYRROLO[1,2-A]PYRAZINE COMPOUNDS AND THEIR USE AS PHARMACEUTICALS

CROSS REFERENCE TO RELATED APPLICATIONS

This application claims priority from U.S. provisional patent application No. 61/157,393, filed Mar. 4, 2009, the entire disclosure of which is incorporated herein by reference. Priority is also claimed based on European patent application no. EP 09003075.0, filed Mar. 4, 2009.

BACKGROUND OF THE INVENTION

The present invention relates to sulfonylated tetrahydroazolopyrazines, methods for the preparation thereof, pharmaceutical compositions containing these compounds and the use thereof for the preparation of pharmaceutical compositions.

In contrast to the constitutive expression of the bradykinin 2 receptor (B2R), the bradykinin 1 receptor (B1R) is not expressed or is only weakly expressed in most tissues. Nevertheless, expression of the B1R can be induced on various cells. By way of example, in the course of inflammation reactions a rapid and pronounced induction of the B1R takes place on neuronal cells, but also on various peripheral cells, such as fibroblasts, endothelial cells, granulocytes, macrophages and lymphocytes. Thus, in the course of inflammation reactions a switch from a B2R to a B1R dominance occurs on the cells involved. The cytokines interleukin-1 (IL-1) and tumour necrosis factor alpha (TNFα) are substantially involved in this B1R up-regulation (Passos et al. J. Immunol. 2004, 172, 1839-1847). After activation with specific ligands, B1R-expressing cells can subsequently themselves secrete inflammation-promoting cytokines, such as IL-6 and IL-8 (Hayashi et al., Eur. Respir. J. 2000, 16, 452-458). This leads to inwards migration of further inflammation cells, for example neutrophilic granulocytes (Pesquero et al., PNAS 2000, 97, 8140-8145). The bradykinin B1R system can contribute to the chronification of diseases via these mechanisms. This is demonstrated by a large number of animal studies (overviews in Leeb-Lundberg et al., Pharmacol Rev. 2005, 57, 27-77 and Pesquero et al., Biol. Chem. 2006, 387, 119-126). In humans too, an increased expression of the B1R is seen, for example on enterocytes and macrophages in the affected tissue of patients with inflammatory bowel diseases (Stadnicki et al., Am. J. Physiol. Gastrointest. Liver Physiol. 2005, 289, G361-366) and on T lymphocytes of patients with multiple sclerosis (Prat et al., Neurology. 1999; 53, 2087-2092), or an activation of the bradykinin B2R-B1R system is seen in the course of infections with *Staphylococcus aureus* (Bengtson et al., Blood 2006, 108, 2055-2063). Infections with *Staphylococcus aureus* are responsible for disease profiles such as superficial infections of the skin through to septic shock.

Based on the pathophysiological relationships described, there is great therapeutic potential for the use of B1R antagonists against acute and in particular chronic inflammatory diseases. They include diseases of the respiratory tract (bronchial asthma, allergies, COPD/chronic obstructive pulmonary disease, cystic fibrosis, etc.), inflammatory bowel diseases (ulcerative colitis, CD/Crohn's disease, etc.), neurological diseases (multiple sclerosis, neurodegeneration, etc.), inflammations of the skin (atopic dermatitis, psoriasis, bacterial infections, etc.) and mucous membranes (Behcet's disease, chronic pelvic pain, prostatitis, etc.), rheumatic diseases (rheumatoid arthritis, osteoarthritis, etc.), septic shock and reperfusion syndrome (following heart attack or stroke).

The bradykinin (receptor) system is moreover also involved in the regulation of angiogenesis (potential as an angiogenesis inhibitor in cases of cancer and macula degeneration in the eye), and B1R-knockout mice are protected from the induction of obesity by a particularly high-fat diet (Pesquero et al., Biol. Chem. 2006, 387, 119-126). B1R antagonists are therefore also suitable for the treatment of obesity.

B1R antagonists are particularly suitable for the treatment of pain, in particular inflammatory pain and neuropathic pain (Calixto et al., Br. J. Pharmacol 2004, 1-16), and here in particular diabetic neuropathy (Gabra et al., Biol. Chem. 2006, 387, 127-143). They are also suitable for the treatment of migraine.

In the development of B1R modulators there is the problem, however, that the human and the rat B1R receptor differ so widely that many compounds which are good B1R modulators on the human receptor have only a poor or no affinity for the rat receptor. This makes animal pharmacology studies considerably more difficult, since many studies are usually conducted on the rat. However, if there is no activity on the rat receptor, neither action nor side-effect can be investigated on the rat. This has already meant that transgenic animals with human B1 receptors have been produced for animal pharmacology studies (Hess et al., Biol. Chem. 2006; 387(2):195-201). Working with transgenic animals is, however, more expensive than working with the unmodified animals.

The patent applications WO 2008/040492 and WO 2008/046573 describe compounds which in in-vitro assays exhibit an antagonistic action both on the human B1 receptor and on the B1 receptor of the rat.

The patent applications WO 2007/140383 and WO 2007/101007 describe compounds which in in-vitro assays exhibit an antagonistic action on the macaque B1 receptor. Experimental data on the activity on the human B1 receptor or the B1 receptor of the rat is not disclosed.

Despite the efforts of the prior art, there remains a need for new B1R modulators, wherein B1R modulators which bind both to the rat receptor and to the human receptor offer particular advantages.

SUMMARY OF THE INVENTION

An object of the present invention was therefore to provide novel compounds which are suitable in particular as pharmacological active ingredients in pharmaceutical compositions, preferably in pharmaceutical compositions for the treatment of disorders or diseases which are at least partly mediated by B1R receptors.

This object is achieved by the sulfonylated tetrahydroazolopyrazines according to the invention.

The invention therefore provides compounds having the general formula I

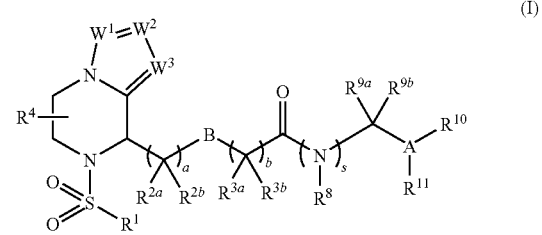

wherein
a stands for 1 or 2;
b stands for 0, 1 or 2;

B stands for $C(R^{6a})(R^{6b})$, $NR^7$, O or a single bond, with the proviso that if b stands for 0 then B does not stand for $NR^7$;

$W^1$, $W^2$ and $W^3$ each independently stand for $CR^5$ or N, with the proviso that at least one of $W^1$, $W^2$ and $W^3$ stands for $CR^5$;

$R^1$ stands for aryl, heteroaryl, $CH(aryl)_2$ or an aryl or heteroaryl bound by a $C_{1-3}$ alkylene group;

$R^{2a}$, $R^{2b}$, $R^{3a}$, $R^{3b}$, $R^{6a}$ and $R^{6b}$ each independently stand for H, F, Cl, Br, I, —$CF_3$, OH, SH, O—$C_{1-6}$ alkyl, $C_{1-6}$ alkyl, $C_{3-8}$ cycloalkyl, aryl or heteroaryl; or for a $C_{3-8}$ cycloalkyl, aryl or heteroaryl bound by a $C_{1-6}$ alkylene group or $C_{2-6}$ alkenylene group; and/or $R^{2a}$ and $R^{2b}$ and/or $R^{3a}$ and $R^{3b}$ can together denote =O;

$R^4$ stands for 0 to 4 substituents independently selected from F; Cl; OH; =O; $C_{1-6}$ alkyl; O—$C_{1-6}$ alkyl; $C_{3-8}$ cycloalkyl; aryl or heteroaryl; $C_{3-8}$ cycloalkyl, aryl or heteroaryl bound by a $C_{1-6}$ alkylene group; and/or two adjacent substituents out of the 0 to 4 substituents $R^4$ form an anellated aryl or heteroaryl ring structure;

$R^5$ stands for H, $C_{1-6}$ alkyl, halogen, —CN or $CF_3$;

$R^7$ stands for H, $C_{1-6}$ alkyl, $C_{3-8}$ cycloalkyl, aryl, heteroaryl or for a $C_{3-8}$ cycloalkyl, aryl or heteroaryl bound by a $C_{1-6}$ alkylene group, $C_{2-6}$ alkenylene group or $C_{2-6}$ alkynylene group;

s=0 or 1, t=0, 1, 2 or 3, $R^8$ stands for H; $C_{1-6}$ alkyl; $C_{3-8}$ cycloalkyl; aryl or heteroaryl; cycloalkyl, aryl or heteroaryl bound by a $C_{1-6}$ alkylene group;

$R^{9a}$ and $R^{9b}$ each independently denote H; F; Cl; OH; $C_{1-6}$ alkyl; O—$C_{1-6}$ alkyl; $C_{3-8}$ cycloalkyl; aryl or heteroaryl; $C_{3-8}$ cycloalkyl, aryl or heteroaryl bound by a $C_{1-6}$ alkylene group;

A stands for N or CH,
with the proviso that if s=1 and t=0 then A stands for CH; and
with the proviso that if s=0 then t=0 and A stands for N;

$R^{10}$ and $R^{11}$ together with A represent a spirocyclic or cyclic group corresponding to formula II or III:

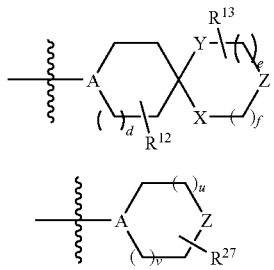

(II)

(III)

wherein c, d, e, f, u and v each independently denote 0, 1 or 2;

$R^{12}$, $R^{13}$ and $R^{27}$ each independently stand for 0 to 4 substituents, which are each independently selected from F; Cl; OH; =O; $C_{1-6}$ alkyl; O—$C_{1-6}$ alkyl; $C_{3-8}$ cycloalkyl; aryl or heteroaryl; $C_{3-8}$ cycloalkyl, aryl or heteroaryl bound by a $C_{1-6}$ alkylene group; and/or two of the 0 to 4 substituents $R^{27}$ together represent a $C_{1-3}$ alkylene bridge such that the cyclic compound represented in the general formula III assumes a bicyclically bridged form; and/or two adjacent substituents out of the 0 to 4 substituents $R^{13}$ form an anellated aryl or heteroaryl; and/or two adjacent substituents out of the 0 to 4 substituents $R^{27}$ form an anellated aryl or heteroaryl;

X stands for $CR^{14a}R^{14b}$, $NR^{15}$ of O;

Y stands for $CR^{16a}R^{16b}$, $NR^{17}$ or O;
with the proviso that X does not denote $NR^{15}$ if Y denotes $NR^{17}$; and
with the proviso that X and Y do not simultaneously denote O;

wherein $R^{14a}$, $R^{14b}$, $R^{16a}$ and $R^{16b}$ each independently denote H; F; Cl; OH; $C_{1-6}$ alkyl; O—$C_{1-6}$ alkyl; $C_{3-8}$ cycloalkyl; aryl or heteroaryl; $C_{3-8}$ cycloalkyl, aryl and heteroaryl bound by a $C_{1-6}$ alkylene group; and/or $R^{14a}$ and $R^{14b}$ can together stand for =O and/or $R^{16a}$ and $R^{16b}$ can together stand for =O;

$R^{15}$ and $R^{17}$ each independently stand for H; $C_{1-6}$ alkyl; $C_{3-8}$ cycloalkyl, aryl or heteroaryl; $C_{3-8}$ cycloalkyl, aryl or heteroaryl bound by a $C_{1-6}$ alkylene group;

Z in formula II stands for $CR^{18a}R^{18b}$, $NR^{19}$ or O; or

Z in formula II, if X stands for O and f stands for 0, denotes —$(C(R^{124})—C(R^{125}))$—, wherein $R^{124}$ and $R^{125}$ together with the carbon atoms linking them form a fused aryl or heteroaryl ring structure; or Z in the general formula II, if X stands for O and f stands for 0, denotes =$(N(CR^{126}))$—, wherein the N atom is singly bound to the O atom, and $R^{126}$ stands for H; $C_{1-6}$ alkyl; $C_{3-8}$ cycloalkyl; aryl or heteroaryl; $C_{3-8}$ cycloalkyl, aryl or heteroaryl bound by a $C_{1-6}$ alkylene group;

Z in the general formula III stands for $CR^{18a}R^{18b}$, $NR^{19}$, O, S, S(=O) or $S(=O)_2$;

wherein $R^{18a}$ stands for H; $C_{1-6}$ alkyl; $C_{3-8}$ cycloalkyl; aryl or heteroaryl; $C_{3-8}$ cycloalkyl, aryl or heteroaryl bound by a $C_{1-6}$ alkylene group; or $R^{18a}$ stands for a group corresponding to formula IV:

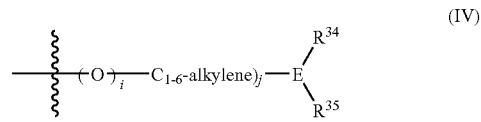

(IV)

wherein i and j each independently stand for 0 or 1;

E stands for N or CH, with the proviso that if i stands for 1 and j stands for 0, then E stands for CH, $R^{34}$ and $R^{35}$ each independently denote H; $C_{1-6}$ alkyl; $C_{3-8}$ cycloalkyl; aryl or heteroaryl; aryl, heteroaryl or $C_{3-8}$ cycloalkyl bound by a $C_{1-3}$ alkylene group; or $R^{34}$ and $R^{35}$ together with E form a 5- or 6-membered aryl or heteroaryl; or $R^{34}$ and $R^{35}$ together with E form a saturated heterocyclic structure corresponding to formula V:

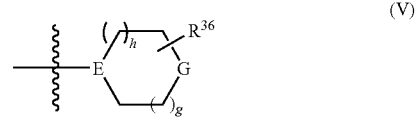

(V)

wherein h and g each independently denote 0, 1 or 2;

G stands for $CR^{37a}R^{37b}$, $NR^{38}$, O, S, S=O or $S(=O)_2$, with the proviso that if E stands for CH then G does not stand for $CR^{37a}R^{37b}$;

$R^{36}$ stands for 0 to 4 substituents which are each independently selected from H; F; Cl; Br; I; OH; SH; =O; O—$C_{1-6}$ alkyl; $C_{1-6}$ alkyl; $C_{3-8}$ cycloalkyl; aryl or heteroaryl; $C_{3-8}$ cycloalkyl, aryl or heteroaryl bound by a $C_{1-6}$ alkylene group; and/or two adjacent substituents $R^{36}$ together represent an anellated aryl or heteroaryl ring structure;

$R^{37a}$ and $R^{37b}$ each independently stand for H; F; Cl; Br; I; OH; SH; =O; O—$C_{1-6}$ alkyl; $C_{1-6}$ alkyl; $C_{3-8}$ cycloalkyl; aryl or heteroaryl; $C_{3-8}$ cycloalkyl, aryl and heteroaryl bound by a $C_{1-6}$ alkylene group;

$R^{38}$ stands for H; $C_{1-6}$ alkyl; $C_{3-8}$ cycloalkyl; aryl or heteroaryl; aryl, heteroaryl or $C_{3-8}$ cycloalkyl bound by a $C_{1-3}$ alkylene group;

wherein $R^{18b}$ stands for H; OH; $C_{1-6}$ alkyl; $C_{3-8}$ cycloalkyl; O—$C_{1-6}$ alkyl; O—($C_{3-8}$ cycloalkyl); ($C_{1-6}$ alkylene)-O—$C_{1-6}$ alkyl; ($C_{1-6}$ alkylene)-O—($C_{3-8}$ cycloalkyl); aryl or heteroaryl; O-aryl or O-heteroaryl; aryl, O-aryl, heteroaryl or O-heteroaryl bound by $C_{1-6}$ alkylene; or $R^{18b}$ stands for a group corresponding to formula VI:

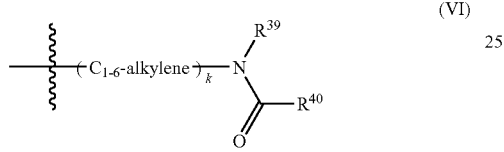

(VI)

wherein k stands for 0 or 1;

$R^{39}$ stands for H; $C_{1-6}$ alkyl; $C_{3-8}$ cycloalkyl; aryl or heteroaryl; $C_{3-8}$ cycloalkyl, aryl or heteroaryl bound by a $C_{1-3}$ alkylene group;

$R^{40}$ stands for $C_{1-6}$ alkyl; $C_{3-8}$ cycloalkyl; aryl or heteroaryl; $C_{3-8}$ cycloalkyl, aryl or heteroaryl bound by a $C_{1-6}$ alkylene group; or $R^{39}$ and $R^{40}$ together with the N—C(=O) group linking them form a ring corresponding to formula VII:

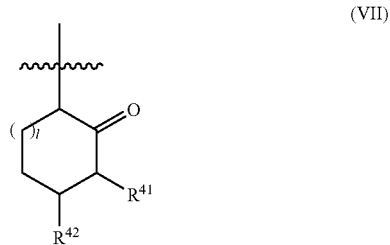

(VII)

wherein l stands for 0, 1 or 2; and $R^{41}$ and $R^{42}$ together with the carbon atoms linking them form an anellated aryl or heteroaryl;

wherein $R^{19}$ stands for H; or $(P)_z$—$R^{22}$, and z stands for 0 or 1;

P stands for C(=O), S(=O)$_2$ or C(=O)—N($R^{24}$); wherein the N atom in the C(=O)—N($R^{24}$) group is linked to $R^{22}$;

$R^{24}$ stands for H; $C_{1-6}$ alkyl; $C_{3-8}$ cycloalkyl; aryl, heteroaryl or $C_{3-8}$ cycloalkyl bound by a $C_{1-3}$ alkylene group;

$R^{22}$ stands for $C_{1-6}$ alkyl; $C_{3-8}$ cycloalkyl; aryl or heteroaryl; aryl, heteroaryl or $C_{3-8}$ cycloalkyl bound by a $C_{1-6}$ alkylene group; or $R^{22}$ stands for a group according to the general formula VIII,

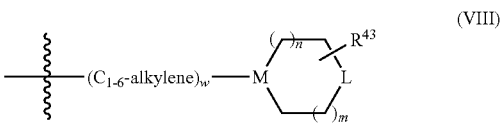

(VIII)

wherein n stands for 0, 1 or 2;

m stands for 0, 1 or 2;

w stands for 0 or 1,

M stands for CH or N;

with the proviso that if P stands for C(=O)—$NR^{24}$ and w stands for 0, then M stands for CH; and with the proviso that if z and w simultaneously stand for 0, then M stands for CH;

L stands for $CR^{44a}R^{44b}$, $NR^{45}$, O, S, S=O or S(=O)$_2$;

$R^{43}$ stands for 0 to 4 substituents which are each independently selected from the group consisting of F; Cl; OH; =O; $C_{1-6}$ alkyl; O—$C_{1-6}$ alkyl; $C_{3-8}$ cycloalkyl; aryl or heteroaryl; $C_{3-8}$ cycloalkyl, aryl or heteroaryl bound by a $C_{1-6}$ alkylene group; and/or two adjacent substituents out of the 0 to 4 substituents $R^{43}$ together represent an anellated aryl or heteroaryl ring structure;

$R^{44a}$ and $R^{44b}$ each independently stand for H; F; Cl; Br; I; OH; $C_{1-6}$ alkyl; O—$C_{1-6}$ alkyl; $C_{3-8}$ cycloalkyl; aryl or heteroaryl; $C_{3-8}$ cycloalkyl, aryl or heteroaryl bound by a $C_{1-6}$ alkylene group; or $R^{44a}$ and $R^{44b}$ can together stand for =O;

$R^{45}$ stands for H; $C_{1-6}$ alkyl; $C_{3-8}$ cycloalkyl; aryl or heteroaryl; aryl, heteroaryl or $C_{3-8}$ cycloalkyl bound by a $C_{1-3}$ alkylene group;

or wherein, if s and t in formula I simultaneously stand for O and A stands for N, $R^{10}$ stands for H, $C_{1-6}$ alkyl, $C_{3-8}$ cycloalkyl or a $C_{3-8}$ cycloalkyl bound by a $C_{1-3}$ alkylene group;

$R^{11}$ stands for a phenyl group or a phenyl group bound by a $C_{1-3}$ alkylene group, wherein the $C_{1-3}$ alkylene group can be substituted with a —C(=O)$R^{280}$ group and $R^{280}$ stands for —N($C_{1-6}$ alkyl)$_2$ or a 4- to 7-membered heterocyclyl, and wherein the phenyl group is substituted with an —($NR^{300}R^{301}$) group or a 4- to 8, preferably 4 to 7-membered heterocyclyl, and the —($NR^{300}R^{301}$) group and the 4- to 8, preferably 4 to 7, -membered heterocyclyl can be bound to the phenyl group by a $C_{1-3}$ alkylene group and $R^{300}$ and $R^{301}$, each independently, stand for H or $C_{1-6}$ alkyl;

wherein the aforementioned $C_{1-6}$ alkyl, $C_{1-3}$ alkylene, $C_{1-6}$ alkylene, $C_{2-6}$ alkenylene, $C_{2-6}$ alkynylene, $C_{3-6}$ cycloalkyl, $C_{3-8}$ cycloalkyl, aryl, heteroaryl and heterocyclyl groups may each be unsubstituted or mono- or polysubstituted with identical or different substituents; and the aforementioned $C_{1-6}$ alkyl, $C_{1-3}$ alkylene, $C_{1-6}$ alkylene, $C_{2-6}$ alkenylene and $C_{2-6}$ alkynylene groups may each be branched or unbranched;

in the form of an isolated enantiomer or an isolated diastereomer, the racemate, the enantiomers, the diastereomers, mixtures of the enantiomers and/or diastereomers, and each in the form of their bases and/or physiologically compatible salts.

In addition to the above described embodiments, the invention further comprises compounds in which in formula (V) two of the 0 to 4 substituents $R^{36}$ together represent a $C_{1-3}$-alkylene bridge, such that the cyclic compound represented by the formula (V) assumes a bicyclically bridged form;

In the foregoing formula (IV) the bonds shown between E and $R^{34}$ and $R^{35}$ should not be understood exclusively as single bonds; they can also be part of an aromatic system.

Within the meaning of the present invention the term "halogen" preferably stands for F, Cl, Br and I, in particular for F and Cl.

Within the meaning of this invention, the expression "$C_{1-6}$ alkyl" includes acyclic saturated hydrocarbon groups having 1, 2, 3, 4, 5 or 6 C atoms, which can be branched or straight-chain (unbranched) and unsubstituted or mono- or polysubstituted, for example di-, tri-, tetra- or pentasubstituted, with identical or different substituents. The alkyl groups can preferably be selected from the group consisting of methyl, ethyl, n-propyl, isopropyl, n-butyl, isobutyl, sec-butyl, tert-butyl, n-pentyl, isopentyl, neopentyl and hexyl. Particularly preferred alkyl groups can be selected from the group consisting of methyl, ethyl, n-propyl, isopropyl, n-butyl, sec-butyl, isobutyl and tert-butyl.

Within the meaning of this invention, the expression "$C_{3-8}$ cycloalkyl" denotes cyclic saturated hydrocarbons having 3, 4, 5, 6, 7 or 8 carbon atoms, which can be unsubstituted or mono- or polysubstituted, for example di-, tri-, tetra- or pentasubstituted, at one or more ring members with identical or different substituents. $C_{3-8}$ cycloalkyl can preferably be selected from the group consisting of cyclopropyl, cyclobutyl, cyclopentyl, cyclohexyl, cycloheptyl and cyclooctyl.

Within the meaning of this invention, the expression "aryl" denotes aromatic hydrocarbons, in particular phenyls and naphthyls. The aryl groups can also be fused to other saturated, (partially) unsaturated or aromatic ring systems. Each aryl group can be present in unsubstituted or mono- or polysubstituted form, for example di-, tri-, tetra- or pentasubstituted, wherein the aryl substituents can be identical or different and can be at any desired and possible position of the aryl. Aryl can advantageously be selected from the group consisting of phenyl, 1-naphthyl and 2-naphthyl, which can be unsubstituted or mono- or polysubstituted, for example with 2, 3, 4 or 5 substituents.

Within the meaning of the present invention, the expression "heteroaryl" stands for a 5-, 6- or 7-membered cyclic aromatic group containing at least 1, optionally also 2, 3, 4 or 5 heteroatoms, wherein the heteroatoms can be identical or different and the heteroaryl can be unsubstituted or mono- or polysubstituted, for example di-, tri-, tetra- or pentasubstituted, with identical or different substituents. The substituents can be bound to any desired and possible position of the heteroaryl. The heterocyclic compound can also be part of a bicyclic or polycyclic system, in particular a mono-, bi- or tricyclic system, which can then in total be more than 7-membered, preferably up to 14-membered. Preferred heteroatoms are selected from the group consisting of N, O and S. The heteroaryl group is preferably selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, phthalazinyl, pyrazolyl, imidazolyl, thiazolyl, oxazolyl, oxadiazolyl, triazole, tetrazole, isoxazoyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl (thiophenyl), pyridinyl (pyridyl), pyrimidinyl, thiazolyl, triazolyl, imidazolyl, oxazolyl, oxadiazolyl, quinazolinyl, quinolinyl and isoquinolinyl, wherein the binding to the general structure (I) can be made via any desired and possible ring member of the heteroaryl group. The heteroaryl group can particularly preferably be selected from the group consisting of thienyl, imidazolyl, thiazolyl, triazolyl, pyridinyl and pyrimidinyl.

In the context of the present invention the expression "3- to 6-membered, 4 to 8 or 4- to 7-membered heterocyclyl", unless specified further, includes both aromatic and saturated or partially unsaturated, 3-, 4-, 5- or 6-, 7 or 8-membered, mono or bicyclic hydrocarbon compounds in which one or more carbon ring members is each independently replaced by a heteroatom or a heteroatom group, in particular by N, O or S. For example, 1, 2 or 3 ring atoms in the heterocyclyl ring can be heteroatoms. Non-aromatic heterocyclyls can be unsubstituted, mono- or polysubstituted with identical or different substituents, wherein the substituents correspond to those described below in connection with the substitution of $C_{3-8}$ cycloalkyls.

Aromatic heterocyclyls are synonymous with heteroaryls. The meaning of the term "heteroaryl" has already been described above and the possible substitution is likewise explained below.

Examples of 3-6-membered heterocyclyls are firstly the 5-6-membered heteroaryls already mentioned in connection with heteroaryls and secondly also pyrrolidinyl, piperidinyl, 2,6-dimethylpiperidine, 4,5-dihydro-1H-imidazo-2-yl or 1-methyl-4,5-dihydroimidazo-2-yl. In connection with the 4- to 7-membered heterocyclyl group in $R^{11}$ this can be selected in particular from pyrrolidinyl, piperidinyl, 2,6-dimethylpiperidine, 1H-pyrrol-1-yl, 1H-pyrrol-2-yl, 4,5-dihydro-1H-imidazo-2-yl, 1-methyl-4,5-dihydroimidazo-2-yl or 4H-1,2,4-triazol-4-yl, each unsubstituted or optionally mono- or polysubstituted.

The expression "3- to 8-membered heterocycloalkyl" denotes saturated heterocyclic compounds which can exhibit 1, 2, 3, 4 or 5 each independently selected identical or different heteroatoms as ring members, preferably from the group N, O or S. If the heterocycloalkyl is bound to a heteroatom, for example N, the binding to the heterocycloalkyl is preferably made via one of the carbon ring members of the heterocycloalkyl. 3- to 8-membered heterocycloalkyls can in particular be 4-, 5- or 6-membered. Examples of 3- to 8-membered heterocycloalkyls include azetidinyl, pyrrolidinyl, piperidinyl, piperazinyl, morpholinyl, tetrahydropyranyl, dioxanyl and dioxolanyl, which optionally may be substituted as described below.

Within the meaning of the present invention, the expression "$C_{1-3}$ alkylene group" or "$C_{1-6}$ alkylene group" includes acyclic saturated hydrocarbon groups having respectively 1, 2 or 3 or 1, 2, 3, 4, 5 or 6 C atoms, which can be branched or straight-chain (unbranched) and unsubstituted or mono- or polysubstituted, for example di-, tri-, tetra- or pentasubstituted, with identical or different substituents and which link a corresponding radical to the higher-order general structure. The alkylene groups are preferably selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$—CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$— and —CH$_2$—(CH$_2$)$_4$—CH$_2$—. The alkylene groups are particularly preferably selected from the group consisting of —CH$_2$—, —CH$_2$—CH$_2$— and —CH$_2$—CH$_2$—CH$_2$—.

Within the meaning of the present invention the expression "—(O)$_{0/1}$—C$_{1-6}$ alkylene group" also includes in addition to the C$_{1-6}$ alkylene groups described above such groups in which these groups are linked by an oxygen atom to the higher-order structure.

Within the meaning of the present invention, the expression "C$_{2-6}$ alkenylene group" includes acyclic mono- or polyunsaturated, for example di-, tri- or tetraunsaturated, hydrocarbon groups having 2, 3, 4, 5 or 6 C atoms, which can be branched or straight-chain (unbranched) and unsubstituted or mono- or polysubstituted, for example di-, tri-, tetra- or pentasubstituted, with identical or different substituents and which link a corresponding radical to the higher-order general structure. The alkenylene groups include at least one C=C double bond. The alkenylene groups are preferably selected from the group consisting of —CH=CH—, —CH=CH—CH$_2$—, —C(CH$_3$)=CH$_2$—, —CH=CH—CH$_2$—CH$_2$—, —CH$_2$—CH=CH—CH$_2$—, —CH=CH—CH=CH—, —C(CH$_3$)=CH—CH$_2$—, —CH=C(CH$_3$)—CH$_2$—, —C(CH$_3$)=C(CH$_3$)—, —C(CH$_2$CH$_3$)=CH—, —CH=CH—CH$_2$—CH$_2$—CH$_2$—, —CH$_2$—CH=CH—CH$_2$—CH$_2$—, —CH=CH—CH=CH—CH$_2$—CH$_2$— and —CH=CH$_2$—CH=CH=CH$_2$—.

Within the meaning of the invention, the expression "C$_{2-6}$ alkynylene group" includes acyclic mono- or polyunsaturated, for example di-, tri- or tetraunsaturated, hydrocarbon groups having 2, 3, 4, 5 or 6 carbon atoms, which can be branched or straight-chain (unbranched) and unsubstituted or mono- or polysubstituted, for example di-, tri-, tetra- or pentasubstituted, with identical or different substituents and which link a corresponding radical to the higher-order general structure. The alkynylene groups include at least one C≡C triple bond. The alkynylene groups are preferably selected from the group consisting of —C≡C—, —C≡C—CH$_2$—, —C≡C—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

Within the meaning of the present invention the expression "aryl or heteroaryl bound by a C$_{1-3}$ alkylene group, a C$_{1-6}$ alkylene group, C$_{2-6}$ alkenylene group or C$_{2-6}$ alkynylene group" means that the C$_{1-3}$ alkylene groups, C$_{1-6}$ alkylene groups, C$_{2-6}$ alkenylene groups, C$_{2-6}$ alkynylene groups and aryl or heteroaryl have the meanings defined above and the aryl or heteroaryl is bound to the higher-order general structure by a C$_{1-3}$ alkylene group, C$_{1-6}$ alkylene group, C$_{2-6}$ alkenylene group or C$_{2-6}$ alkynylene group. Benzyl, phenethyl and phenylpropyl are cited by way of example.

Within the meaning of the present invention, the expression "C$_{3-8}$ cycloalkyl, 3- to 6-membered or 4- to 7-membered heterocyclyl or 3- to 8-membered heterocycloalkyl bound by a C$_{1-3}$ alkylene group, C$_{1-6}$ alkylene group, C$_{2-6}$ alkenylene group or C$_{2-6}$ alkynylene group" means that the C$_{1-3}$ alkylene group, C$_{1-6}$ alkylene group, C$_{2-6}$ alkenylene group, C$_{2-6}$ alkynylene group, C$_{3-8}$ cycloalkyl and heterocycloalkyl have the meanings defined above and C$_{3-8}$ cycloalkyl and heterocycloalkyl are bound to the higher-order general structure by a C$_{1-3}$ alkylene group, C$_{1-6}$ alkylene group, C$_{2-6}$ alkenylene group or C$_{2-6}$ alkynylene group.

In connection with "alkyl", "alkylene", "alkenylene", "alkynylene" and "cycloalkyl", the term "substituted" within the meaning of this invention is understood to mean the replacement of a hydrogen with F, Cl, Br, I, CF$_3$, OCF$_3$, CN, NH$_2$, NH—C$_{1-6}$ alkyl, NH—C$_{1-6}$ alkylene-OH, C$_{1-6}$ alkyl, N(C$_{1-6}$ alkyl)$_2$, N(C$_{1-6}$ alkylene-OH)$_2$, NO$_2$, SH, S—C$_{1-6}$ alkyl, C$_{1-6}$ alkyl, S-benzyl, O—C$_{1-6}$ alkyl, OH, O—C$_{1-6}$ alkylene-OH, =O, O-benzyl, C(=O)C$_{1-6}$ alkyl, CO$_2$H, CO$_2$—C$_{1-6}$ alkyl, phenyl, phenoxy, benzyl, naphthyl, furyl, thienyl and pyridinyl, wherein polysubstituted groups are understood to mean groups which are substituted multiple times, for example twice or three times, at different or the same atoms, for example substituted three times at the same C atom, as in the case of CF$_3$ or CH$_2$CF$_3$, or at different sites, as in the case of CH(Cl)—CH=CH—CHCl$_2$. The polysubstitution can take place with identical or different substituents, as for example in the case of CH(OH)—CH=CH—CHCl$_2$. It should be understood in particular to be the replacement of one or more hydrogens with F, Cl, NH$_2$, OH, phenyl, O—CF$_3$ or O—C$_{1-6}$ alkyl, in particular methoxy.

In connection with "aryl" and "heteroaryl", the term "substituted" within the meaning of this invention is understood to mean the mono- or polysubstitution, for example the di-, tri-, tetra- or pentasubstitution, of one or more hydrogen atoms of the corresponding ring system with F, Cl, Br, I, CN, NH$_2$, NH—C$_{1-6}$ alkyl, NH—C$_{1-6}$ alkylene-OH, N(C$_{1-6}$ alkyl)$_2$, N(C$_{1-6}$ alkylene-OH)$_2$, NH-aryl$^1$, N(aryl$^1$)$_2$, N(C$_{1-6}$ alkyl) aryl$^1$, pyrrolinyl, piperazinyl, morpholinyl, azetidinyl, piperidinyl, thiazolinyl, azepanyl, diazepanyl, (C$_{1-3}$ alkylene)-azetidinyl, (C$_{1-3}$ alkylene)-pyrrolinyl, (C$_{1-3}$ alkylene)-piperidinyl, (C$_{1-3}$ alkylene)-morpholinyl, (C$_{1-3}$ alkylene)-piperazinyl, (C$_{1-3}$ alkylene)-thiazolinyl, (C$_{1-3}$ alkylene)-azepanyl, (C$_{1-3}$ alkylene)-diazepanyl, NO$_2$, SH, S—C$_{1-6}$ alkyl, OH, O—C$_{1-6}$ alkyl, O—C$_{1-6}$ alkyl-OH, C(=O)C$_{1-6}$ alkyl, NHSO$_2$C$_{1-6}$ alkyl, NHCOC$_{1-6}$ alkyl, CO$_2$H, CH$_2$SO$_2$ phenyl, CO$_2$—C$_{1-6}$ alkyl, OCF$_3$, CF$_3$, —O—CH$_2$—O—, —O—CH$_2$—CH$_2$—O—, —O—C(CH$_3$)$_2$—CH$_2$—, unsubstituted C$_{1-6}$ alkyl, pyrrolidinyl, imidazolyl, benzyloxy, phenoxy, phenyl, naphthyl, pyridinyl, —C$_{1-3}$ alkylene-aryl$^1$, benzyl, thienyl, furyl, wherein aryl$^1$ stands for phenyl, thiazolyl, thienyl or pyridinyl, at one or different atoms, wherein the aforementioned substituents—unless otherwise specified—can themselves be substituted with the cited substituents. The polysubstitution of aryl and heteroaryl can be performed with identical or different substituents. Preferred substituents for aryl and heteroaryl can be selected from the group consisting of —O—C$_{1-3}$ alkyl, unsubstituted C$_{1-6}$ alkyl, F, Cl, Br, I, CN, CF$_3$, OCF$_3$, OH, SH, —CH$_2$ azetidinyl, —CH$_2$-pyrrolidinyl, —CH$_2$-piperidinyl, —CH$_2$-piperazinyl, —CH$_2$-morpholinyl, phenyl, naphthyl, thiazolyl, thienyl and pyridinyl, in particular from the group consisting of F, Cl, CN, CF$_3$, CH$_3$; OCH$_3$, OCF$_3$ and —CH$_2$-azetidinyl.

In connection with "anellated aryl" or "anellated heteroaryl", "substituted" within the meaning of this invention is understood to mean, in addition to the possible substituents and substitution models defined above in connection with "aryl" and "heteroaryl", 4- to 7-membered heterocyclyls as further possible substituents, which have the meaning defined above and can optionally be connected to the anellated aryl or heteroaryl by a C$_{1-3}$ alkylene group. In particular the 4- to 7-membered heterocyclyls appearing as substituents can be selected from the group consisting of morpholinyl, azetidinyl, piperidinyl, thiazolinyl, azepanyl, diazepanyl, (C$_{1-3}$ alkylene)-azetidinyl, (C$_{1-3}$ alkylene)-pyrrolinyl, (C$_{1-3}$ alkylene)-piperidinyl, (C$_{1-3}$ alkylene)-morpholinyl, (C$_{1-3}$ alkylene)-piperazinyl, (C$_{1-3}$ alkylene)-thiazolinyl, (C$_{1-3}$ alkylene)-azepanyl, (C$_{1-3}$ alkylene)-diazepanyl, pyrrolidinyl, 2,6-dimethylpiperidine, (C$_{1-3}$ alkylene)-2,6-dimethylpiperidine, 1H-pyrrol-1-yl, (C$_{1-3}$ alkylene)-1H-pyrrol-1-yl, 1H-pyrrol- 2-yl, ($C_{1-3}$ alkylene)-1H-pyrrol-2-yl, 4,5-dihydro-1H-imidazo-2-yl, ($C_{1-3}$ alkylene)-4,5-dihydro-1H-imidazo-2-yl, 1-methyl-4,5-dihydroimidazo-2-yl, ($C_{1-3}$ alkylene)-1-methyl-4,5-dihydroimidazo-2-yl or 4H-1,2,4-triazol-4-yl-($C_{1-3}$ alkylene)-4H-1,2,4-triazol-4-yl, each unsubstituted or optionally mono- or polysubstituted, as defined above. In particular, the 4- to 7-membered heterocyclyls may be substituted with two adjacent substituents which together form an anellated aryl or heteroaryl, especially an anellated phenyl. Especially, piperidinyl may be substituted in such a manner that an 1,2,3,4-tetrahydroquinolinyl or 1,2,3,4-tetrahydroisoquinolinyl is formed.

In connection with "3- to 8-membered heterocycloalkyl" the term "substituted" is understood to mean the replacement of a hydrogen at one or more ring members by F, Cl, Br, I, —CN, $NH_2$, NH—$C_{1-6}$ alkyl, NH—$C_{1-6}$ alkylene-OH, $C_{1-6}$ alkyl, N($C_{1-6}$ alkyl)$_2$, N($C_{1-6}$ alkylene-OH)$_2$, pyrrolinyl, piperazinyl, morpholinyl, $NO_2$, SH, S—$C_{1-6}$ alkyl, S-benzyl, O—$C_{1-6}$ alkyl, OH, O—$C_{1-6}$ alkylene-OH, =O, O-benzyl, C(=O)$C_{1-6}$ alkyl, $CO_2H$, $CO_2$—$C_{1-6}$ alkyl or benzyl. The polysubstitution can be performed with identical or different substituents. A hydrogen bound to an N ring member can be replaced with a $C_{1-6}$ alkyl, $C_{3-8}$ cycloalkyl, aryl, heteroaryl or a $C_{3-8}$ cycloalkyl, aryl or heteroaryl bound by a $C_{1-3}$ alkylene group, wherein these alkyl, cycloalkyl, alkylene and aryl and heteroaryl groups can be unsubstituted or substituted as defined above. Examples of substituted 3- to 8-membered heterocycloalkyl groups include 1-methylpiperidin-4-yl, 1-phenylpiperidin-4-yl, 1-benzylpiperidin-4-yl, 1-methylpyrrolidin-3-yl, 1-phenylpyrrolidin-3-yl, 1-benzylpyrrolidin-3-yl, 1-methylazetidin-3-yl, 1-phenyl-azetidin-3-yl or 1-benzylazetidin-3-yl.

In the chemical structural formulas which are used here to describe the compounds according to the invention, the symbol

is also used to describe one or more substitution models, wherein unlike the representation of a binding to a specific atom, this group is not bound to a specific atom within the chemical structural formula ($R^a$ stands by way of example here for a substituent R having a number represented by the variable "a"). This can be explained by way of example by reference to the group

from the general formula (III) shown above: The definition for $R^{27}$ indicates that $R^{27}$ can stand for 0 to 4 substituents. Thus $R^{27}$ can be absent, or 1, 2, 3 or 4 of the C- or N-bound hydrogen atoms within the substructure represented by the general formula (III) can be replaced by one of the substituents provided in the definition of $R^{27}$, wherein each of the substituents can be selected each independently, in other words they can have different meanings, and C- and/or N-bound hydrogen atoms can be replaced at one or more C or N atoms. $R^{27}$ can thus also replace a hydrogen atom bound to the ring and included in the group Z. As explained in the definition of $R^{27}$, two of the substituents $R^{27}$ can also together represent a $C_{1-3}$ alkylene bridge or an anellated aryl or heteroaryl (also referred to as a fused aryl or heteroaryl or anellated/fused aryl or heteroaryl group), such that $R^{27}$ in the general formula (III) also has the meanings shown below in schemes i) to iii) by way of example, in which $R^{27}$ stands for two substituents at different C atoms or at one C and one N atom. Scheme ii) illustrates the scenario in which the variable u stands for 1. In the scenario illustrated in scheme iii) u and v stand for 1, an $R^{27}$ replaces a hydrogen atom bound to the nitrogen and a further $R^{27}$ a hydrogen atom bound to a carbon atom. Moreover, in the scenarios illustrated in schemes ii) and iii) the anellated aryl is substituted with a substituent selected the group defined above for these terms:

Scheme i)

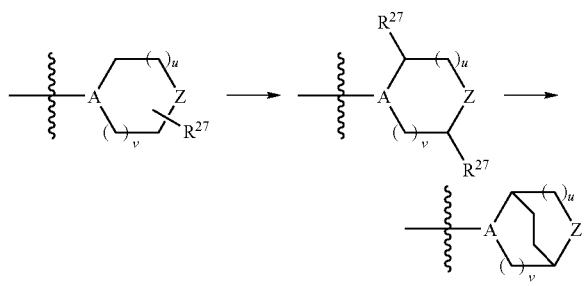

Scheme ii)

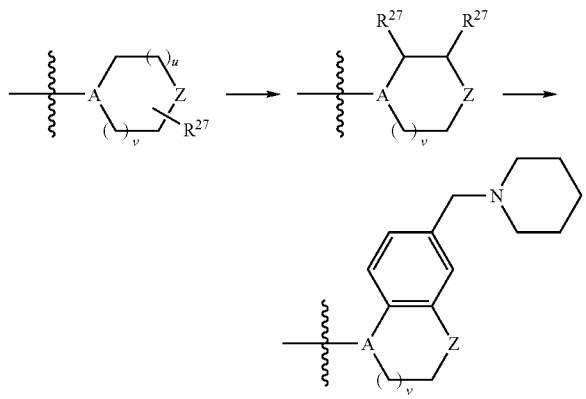

and

Scheme iii)

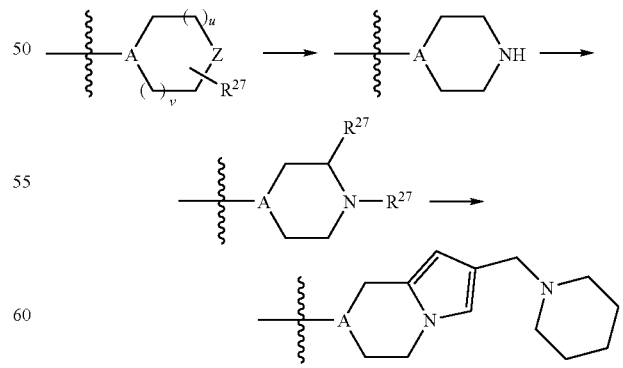

Persons skilled in the art understand from this representation that if two vicinal (adjacent) groups $R^{27}$ form an anellated aryl or heteroaryl ring structure then the carbons borne by the anellated ring can no longer have a hydrogen.

The same applies to the substituents $R^4$, $R^{13}$, $R^{36}$, $R^{43}$ if they form an anellated aryl or heteroaryl ring structure and to $R^{41}$, $R^{42}$, $R^{124}$ and $R^{125}$. For example, in the scenario in which two adjacent substituents $R^4$ form an unsubstituted, anellated aryl, the following scheme arises:

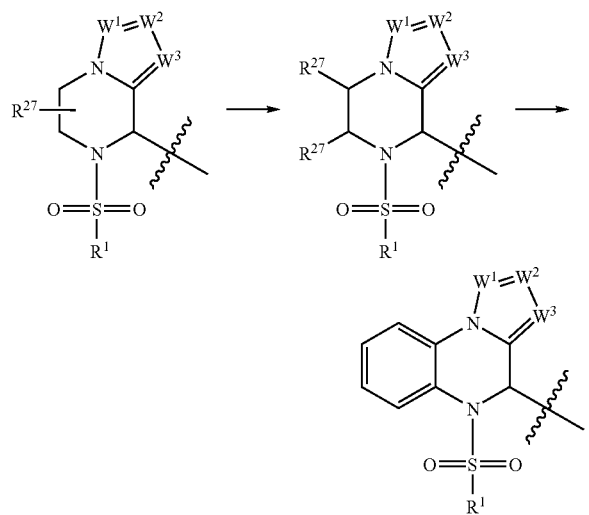

In the context of the present invention, the symbol

used in formulas represents a linking of a corresponding group to a higher-order general structure.

Persons skilled in the art understand that identical radicals used for the definition of different substituents are mutually independent.

Within the meaning of this invention the term "physiologically compatible salt" is understood to mean preferably salts of the compounds according to the invention with inorganic or organic acids, which are physiologically—particularly when used in humans and/or mammals—compatible. Examples of suitable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. The salts of hydrochloric acid (hydrochlorides) and of citric acid (citrates) are particularly preferred.

Within the scope of the invention, the term "isolated" when used with reference to a stereoisomer (e.g., an enantiomer or diastereomer) means substantially separated from the opposite stereoisomer but not necessarily from other substances.

In preferred embodiments of the compounds according to the invention $W^1$, $W^2$ and $W^3$ stand for $CR^5$; or $W^1$ and $W^2$ stand for $CR^5$ and $W^3$ stands for N; or $W^1$ stands for $CR^5$ and $W^2$ and $W^3$ stand for N; or $W^3$ stands for $CR^5$ and $W^1$ and $W^2$ stand for N.

Other preferred embodiments of the compounds according to the invention are those in which B stands for O and $R^{2a}$, $R^{2b}$, $R^{3a}$ and $R^{3b}$ preferably stand for H; or B stands for $C(R^{6a})(R^{6b})$ or a single bond and $R^{2a}$, $R^{2b}$, $R^{3a}$, $R^{3b}$, $R^{6a}$ and $R^{6b}$ each independently stand for H, F, $CF_3$, OH, $C_{1-6}$ alkyl or $C_{1-6}$ alkoxy.

In the compounds according to the invention $R^1$ preferably stands for phenyl, naphthyl, indolyl, benzofuranyl, benzothiophenyl (benzothienyl); benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl (dibenzothienyl), quinolinyl, isoquinolinyl, for a phenyl or naphthyl bound by a $C_{1-3}$ alkylene group, or $CH(phenyl)_2$, preferably for phenyl, naphthyl, benzothiophenyl, quinolinyl, isoquinolinyl or thienyl, particularly preferably for phenyl, naphthyl or benzothiophenyl (benzothienyl), each unsubstituted or mono- or polysubstituted, identically or differently, wherein the substituents are selected in particular from —O—$C_{1-3}$ alkyl, $C_{1-6}$ alkyl, F, Cl, Br, $CF_3$, $OCF_3$, OH, phenyl, naphthyl, thienyl, thiazolyl and pyridinyl, and wherein the alkylene groups cited above are each unsubstituted or mono- or polysubstituted, identically or differently, wherein the substituents are each independently selected from the group consisting of —O—$C_{1-3}$ alkyl, F, Cl, Br, $CF_3$, —$OCF_3$, OH, phenyl, phenoxy, naphthyl, furyl, thienyl and pyridinyl.

$R^1$ can stand in particular for phenyl or naphthyl, wherein the phenyl or naphthyl is unsubstituted or mono- or polysubstituted, for example di-, tri-, tetra- or pentasubstituted, with identical or different substituents selected from the group consisting of methyl, methoxy, $CF_3$, $OCF_3$, F and Cl.

In likewise preferred embodiments of the compounds according to the invention $R^1$ is selected from 4-methylphenyl, 4-methoxy-2,3,6-trimethylphenyl, 4-methoxy-2,6-dimethylphenyl, 4-methoxy-2,3,5-trimethylphenyl, 2,4,6-trimethylphenyl, 1,3-dichloro-5-(trifluoromethyl)phenyl, 2-chloro-6-methylphenyl, 2,4,6-trichlorophenyl, 2-chloro-6-(trifluoromethyl)phenyl, 2,6-dichloro-4-methoxyphenyl, 2,6-dichloro-4-(trifluoromethyl)phenyl, 2-methyl-1-naphthyl, 2-chloro-1-naphthyl, 2-fluoro-1-naphthyl, 6-methoxy-2-naphthyl, 2-chloro-4-(trifluoromethoxy)phenyl, 4-chloro-2,5-dimethylphenyl, 2,6-dichloro-3-methylphenyl, 2,6-dichlorophenyl, 2,3-dichlorophenyl, 3,4-dichlorophenyl, 2,4-dichlorophenyl, 2-(trifluoromethyl)phenyl, 3-(trifluoromethyl)phenyl, 4-(trifluoromethyl)phenyl, 3-(trifluoromethyl)-4-methylphenyl; 1-naphthyl and 2-naphthyl; in particular 4-methoxy-2,6-dimethylphenyl, 2-chloro-6-methylphenyl and 2-(trifluoromethyl)phenyl.

Likewise preferred embodiments of the compounds according to the invention are those in which in the general formula I the group Ac I (Ac I)

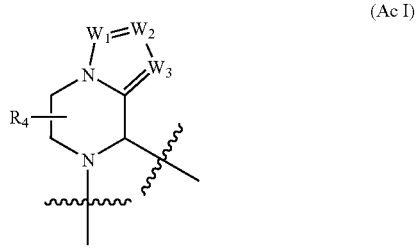

is selected from one of the following groups

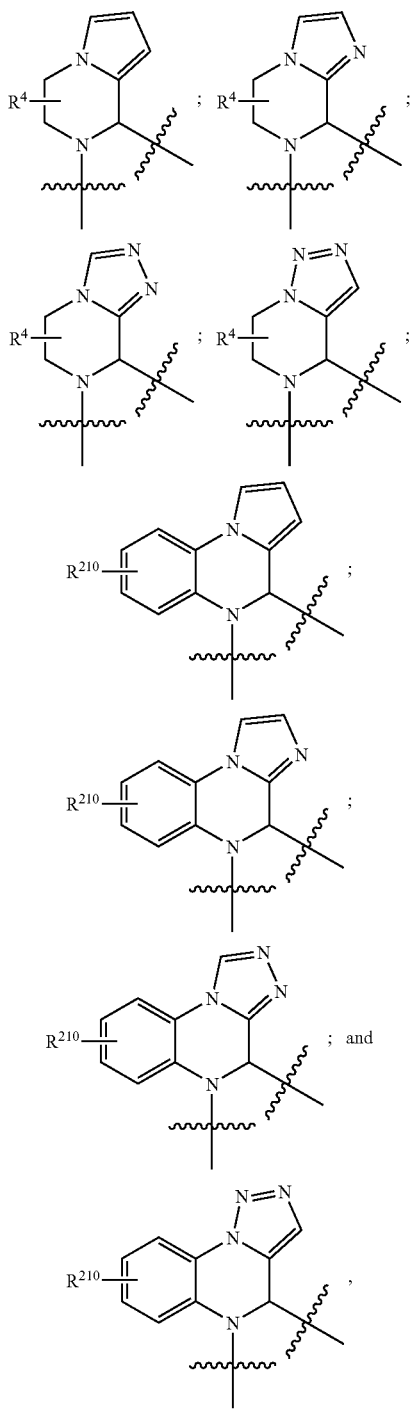

preferably from

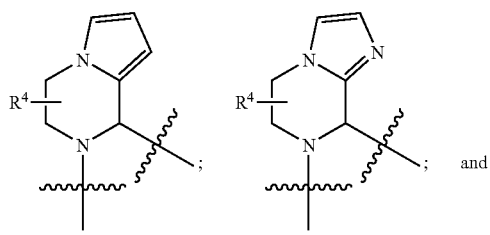

-continued

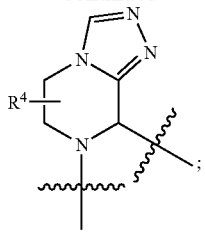

wherein $R^4$ stands for 0 to 4 atoms or groups selected from H, F or $C_{1-6}$ alkyl and/or two of the 0 to 4 substituents $R^4$ together represent an anellated aryl or heteroaryl ring structure;

$R^{210}$ stands for 0 to 4 substituents independently selected from the group consisting of —O—$C_{1-3}$ alkyl, $C_{1-6}$ alkyl, F, Cl, Br, I, $CF_3$, $OCF_3$, OH, SH, phenyl, naphthyl, furyl, thienyl and pyridinyl, preferably from methyl, methoxy, O—$CF_3$, $CF_3$, F, Cl and Br.

In likewise preferred embodiments of the compounds according to the invention in formula (I) a stands for 1, b for 1, B for O and $R^{2a}$, $R^{2b}$, $R^{3a}$ and $R^{3b}$ for H; or a stands for 1 or 2, b for 0, B for a single bond and $R^{2a}$ and $R^{2b}$ for H.

Likewise preferred embodiments of the compounds according to the invention are those in which formula (II) assumes the following substructure (IIa):

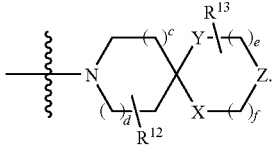

(IIa)

Likewise preferred embodiments of the compounds according to the invention are those according to formula (I) in which a stands for 1, b for 1, B for O, $R^{2a}$, $R^{2b}$, $R^{3a}$ and $R^{3b}$ preferably stand for H and the substructure (B)

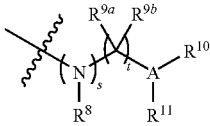

(B)

in formula (I) assumes the above described substructure (IIa) wherein all other residues, variables and indices can have the above described meanings.

Likewise preferred embodiments of the compounds according to the invention are those in which the foregoing formula (III) assumes one of the following substructures (IIIa) or (IIIb):

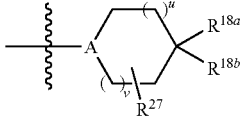

(IIIa)

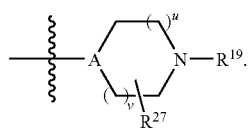

(IIIb)

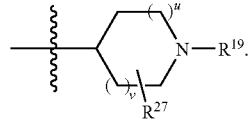

(IIIe)

Likewise preferred embodiments of the compounds according to the invention are those according to the above described general formula (I) in which a stands for 1 or 2, b for 0, B for a single bond and $R^{2a}$ and $R^{2b}$ preferably stand for H, and the substructure (B)

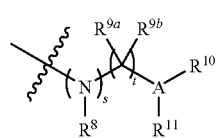

(B)

in formula (I) assumes one of the above shown substructures (IIIa) or (IIIb), wherein all other residues, variables and indices can have the above described meanings.

Likewise preferred embodiments of the compounds according to the invention are those in which the substructure according to the formula (IIa) shown above assumes the following substructure (IIb):

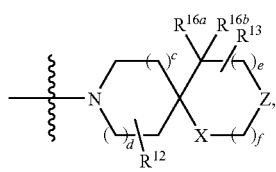

(IIb)

wherein in certain embodiments of these compounds according to the invention $R^8$ stands for H or $C_{1-6}$ alkyl, in each case unsubstituted or mono- or polysubstituted with identical or different substituents, and $R^{9a}$ and $R^{9b}$ each stand for H.

Likewise preferred embodiments of the compounds according to the invention are those compounds in which the substructures according to the formulas (IIIa) and (IIIb) shown above assume one of the following substructures (IIIc), (IIId) or (IIIe):

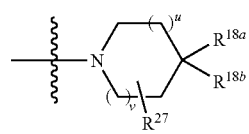

(IIIc)

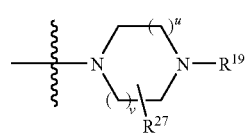

(IIId)

In certain embodiments of these compounds according to the invention s and t each stand for 0.

Likewise preferred embodiments of the compounds according to the invention are those in which the substructures according to the formulas (IIIa) and (IIIb) illustrated above can assume one of the substructures (IIIc) or (IIId) illustrated above and two of the substituents $R^{27}$ together represent a $C_{1-3}$ alkylene bridge, such that the cyclic compound represented in the substructure (IIIc) or (IIId) assumes a bicyclically bridged form. In certain embodiments of these compounds s and t are each 0.

Likewise preferred embodiments of the compounds according to the invention are those in which the substructures according to formulas (IIIa) and (IIIb) illustrated above assume one of the substructures (IIIc) or (IIIe) likewise illustrated above, s stands for 1 and t stands for 1, 2 or 3. In certain embodiments of these compounds according to the invention $R^8$ stands for H, $C_{1-6}$ alkyl or $C_{3-6}$ cycloalkyl, each unsubstituted or mono- or polysubstituted.

Other preferred embodiments of the compounds according to the invention are those in which the substructure according to the formula (IIb) shown above assumes the following substructure (IIc):

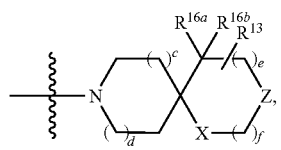

(IIc)

wherein in certain embodiments of these compounds s and t each denote 0.

In other preferred embodiments of the compounds according to the invention the substructures illustrated above according to the formulas (IIIc) or (IIId) assume one of the following substructures (IIIf) or (IIIg),

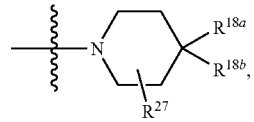

(IIIf)

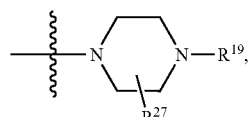

(IIIg)

wherein in certain embodiments of these compounds $R^{27}$ stands for H and/or two of the substituents $R^{27}$ form an anellated aryl or heteroaryl ring structure, in particular a benzo group.

Preferred embodiments of the compounds according to the invention are furthermore such compounds in which the substructures (IIIc) or (IIId) illustrated above represent one of the following groups A to H:

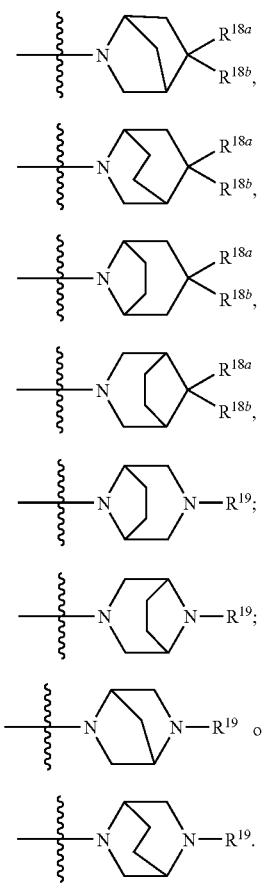

(A)

(B)

(C)

(D)

(E)

(F)

(G)

(H)

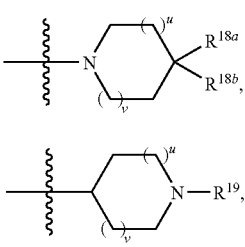

Persons skilled in the art will understand that the representation chosen for groups A to H includes all possible stereoisomers of these groups.

Other preferred embodiments of the compounds according to the invention are compounds in which the substructures (IIIc) or (IIIe) illustrated above represent a group corresponding to formula (IIIh) or formula (IIIi):

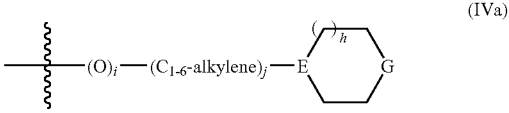

and $R^{9a}$ and $R^{9b}$ each stand for H. In certain embodiments of these compounds u and v each independently stand for 0 or 1. In particular u and v both stand for 1.

Other preferred embodiments of the compounds according to the invention are compounds in which in the substructure (IIc) illustrated above $R^{16a}$ and $R^{16b}$ each stand for H or together form =O; $R^{13}$ stands for H, aryl or heteroaryl and/or two of the substituents $R^{13}$ together form =O and/or two adjacent substituents $R^{13}$ together form an anellated aryl or heteroaryl ring structure, in particular a benzo group, each unsubstituted or mono- or polysubstituted with identical or different substituents.

Other preferred embodiments of the compounds according to the invention are those compounds in which in the substructures illustrated above according to the formulas (IIIf) or (IIIg):

$R^{18a}$ stands for H; $C_{1-6}$ alkyl; $C_{3-8}$ cycloalkyl, —NH($C_{1-6}$ alkyl), —N($C_{1-6}$ alkyl)$_2$, phenyl, pyridyl, thienyl, pyrimidyl, thiazolyl, imidazolyl or triazolyl, each unsubstituted or mono- or polysubstituted; phenyl, pyridyl, thienyl, pyrimidyl, thiazolyl, imidazolyl or triazolyl bound by an —(O)$_{0-1}$—$C_{1-6}$ alkylene group, each unsubstituted or mono- or polysubstituted; or $R^{18a}$ stands for a structure corresponding to formula Iva:

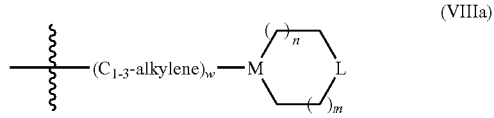

wherein
i stands for 0 or 1;
j stands for 0 or 1;
h stands for 0 or 1;
E stands for N or CH; with the proviso that if i stands for 1 and j stands for 0, then E stands for CH;
G stands for $CR^{37a}R^{37b}$ or $NR^{38}$; wherein
$R^{37a}$ and $R^{37b}$ each independently stand for H, F or $C_{1-6}$ alkyl; and
$R^{38}$ stands for H; $C_{1-6}$ alkyl, $C_{3-6}$ cycloalkyl or pyridyl, in particular pyridin-4-yl;
$R^{18b}$ stands for H; OH; $C_{1-6}$ alkyl; phenyl, pyridyl, thienyl, thiazolyl, pyrimidyl, imidazolyl or triazolyl, each unsubstituted or mono- or polysubstituted; phenyl, pyridyl, thienyl, thiazolyl, pyrimidyl, imidazolyl or triazolyl, O-phenyl or O-pyridyl bound by a $C_{1-6}$ alkylene group, each unsubstituted or mono- or polysubstituted with identical or different substituents; or phenyl, pyridyl or thienyl bridged by $C_{1-6}$ alkylene-NH(C=O), each unsubstituted or mono- or polysubstituted with identical or different substituents;
$R^{19}$ stands for H; $C_{1-6}$ alkyl; $C_{3-8}$ cycloalkyl, or for $C_{1-6}$ alkyl; phenyl, pyridyl, thienyl, thiazolyl, triazolyl, pyrimidinyl or imidazolyl bound by (C=O)$_{0-1}$; each unsubstituted or mono- or polysubstituted with identical or different substituents; or phenyl, pyridyl, thienyl, thiazolyl, pyrimidinyl, triazolyl or imidazolyl bound by a $C_{1-6}$ alkylene group; each unsubstituted or mono- or polysubstituted with identical or different substituents; or
$R^{19}$ stands for a structure corresponding to formula (VIIIa):

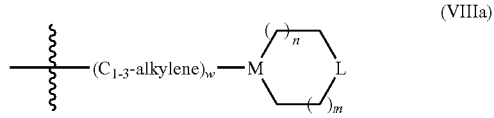

wherein
w stands for 0 or 1;
n stands for 0 or 1;
m stands for 0 or 1;
M stands for CH or N, with the proviso that if w stands for 0, then M stands for CH;
L stands for $CR^{44a}R^{44b}$ or $NR^{45}$; wherein $R^{44a}$ and $R^{44b}$ each independently stand for H, F or $C_{1-6}$ alkyl, each unsubstituted or mono- or polysubstituted with identical or different substituents; and $R^{45}$ stands for H; $C_{1-6}$ alkyl, $C_{3-6}$ alkyl or pyridyl, each unsubstituted or mono- or polysubstituted with identical or different substituents.

Further preferred embodiments of the compounds according to the invention are those compounds in which the substructures according to the formulas (IIIc) or (IIId) illustrated above represent one of the following groups A to H:

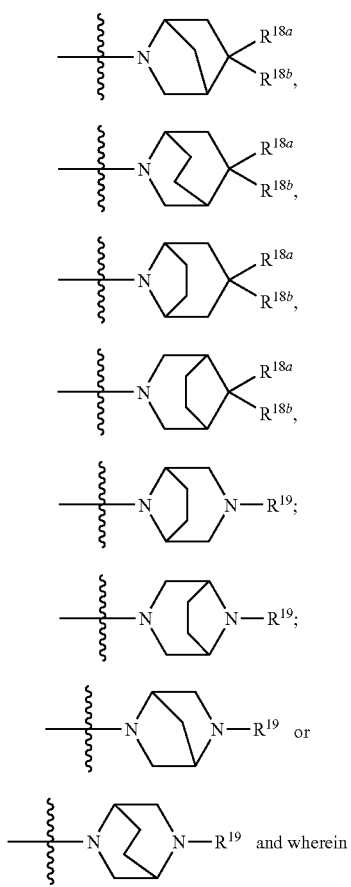

and wherein $R^{18a}$ stands for H; $C_{1-6}$ alkyl; $C_{3-8}$ cycloalkyl, $N(C_{1-6}$ alkyl$)_2$; $NH(C_{1-6}$ alkyl); azetidinyl; pyrrolidinyl, piperidinyl, 4-$(C_{1-6}$ alkyl)-piperazinyl; phenyl or pyridyl, each unsubstituted or mono- or polysubstituted with identical or different substituents; or for $N(C_{1-6}$ alkyl$)_2$, $NH(C_{1-6}$ alkyl), azetidinyl; pyrrolidinyl, piperidinyl, 4-$(C_{1-6}$ alkyl)-piperazinyl, phenyl, imidazolyl, triazolyl or pyridyl bound by an $-(O)_{0-1}-C_{1-6}$ alkylene group, each unsubstituted or mono- or polysubstituted with identical or different substituents;

$R^{18b}$ stands for H; OH; $C_{1-6}$ alkyl; phenyl or pyridyl, each unsubstituted or mono- or polysubstituted with identical or different substituents; or for phenyl or pyridyl bound by a $C_{1-6}$ alkylene group, each unsubstituted or mono- or polysubstituted with identical or different substituents;

$R^{19}$ stands for H; $C_{1-6}$ alkyl; $C_{3-8}$ cycloalkyl, phenyl, pyridyl, thienyl, imidazolyl, thiazolyl or triazolyl, each unsubstituted or mono- or polysubstituted with identical or different substituents; or for phenyl, pyridyl, thienyl, imidazolyl, thiazolyl or triazolyl bound by a $C_{1-6}$ alkylene group or a (C=O) group, each unsubstituted or mono- or polysubstituted with identical or different substituents.

Other preferred embodiments of the compounds according to the invention are those compounds in which in the substructures illustrated above according to the formulas (IIIh) or (IIIi):

$R^{18a}$ stands for H; $C_{1-6}$ alkyl; $C_{3-8}$ cycloalkyl, $N(C_{1-6}$ alkyl$)_2$; $NH(C_{1-6}$ alkyl), azetidinyl; pyrrolidinyl, piperidinyl, 4-$(C_{1-6}$ alkyl)-piperazinyl; phenyl or pyridyl, each unsubstituted or mono- or polysubstituted with identical or different substituents; or for $N(C_{1-6}$ alkyl$)_2$, $NH(C_{1-6}$ alkyl), azetidinyl; pyrrolidinyl, piperidinyl, 4-$(C_{1-6}$ alkyl)-piperazinyl, phenyl, imidazolyl, triazolyl or pyridyl bound by an $-(O)_{0/1}-C_{1-6}$ alkylene group, each unsubstituted or mono- or polysubstituted with identical or different substituents;

$R^{18b}$ stands for H; OH; $C_{1-6}$ alkyl; phenyl or pyridyl, each unsubstituted or mono- or polysubstituted with identical or different substituents; or for phenyl or pyridyl bound by a $C_{1-6}$ alkylene group, each unsubstituted or mono- or polysubstituted with identical or different substituents;

$R^{19}$ stands for H; $C_{1-6}$ alkyl; $C_{3-8}$ cycloalkyl, phenyl, pyridyl, thienyl, imidazolyl, thiazolyl or triazolyl, each unsubstituted or mono- or polysubstituted with identical or different substituents; phenyl or pyridyl bound by a $C_{1-6}$ alkylene group or (C=O) group, each unsubstituted or mono- or polysubstituted with identical or different substituents.

Other preferred embodiments of the compounds according to the invention are compounds in which the substructure corresponding to formula IIc assumes one of the following substructures SP:

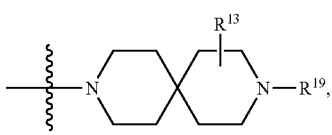

SP 1

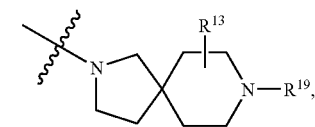

SP 2

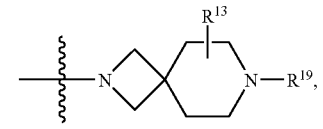

SP 3

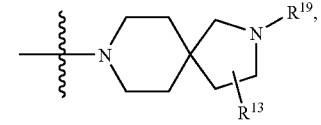

SP 4

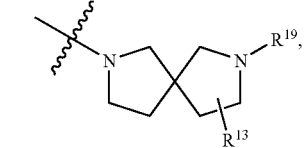

SP 5

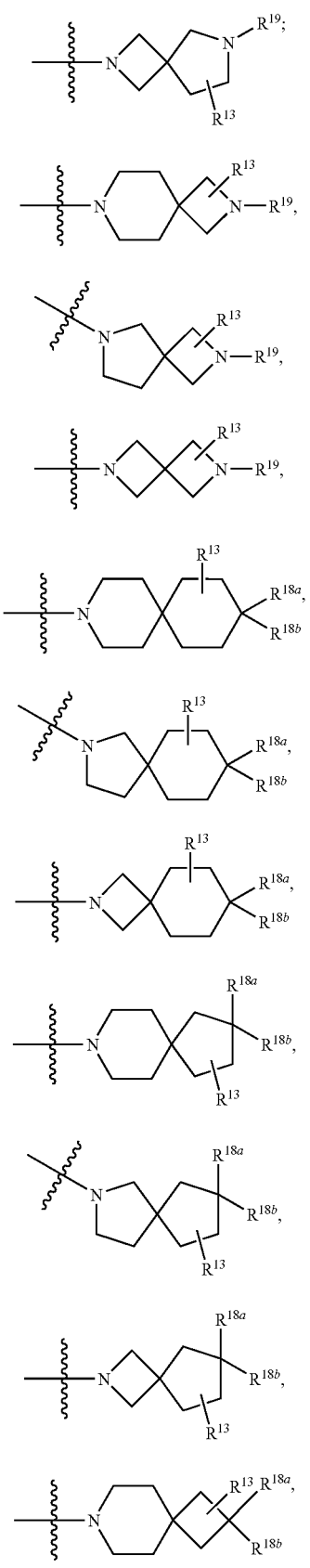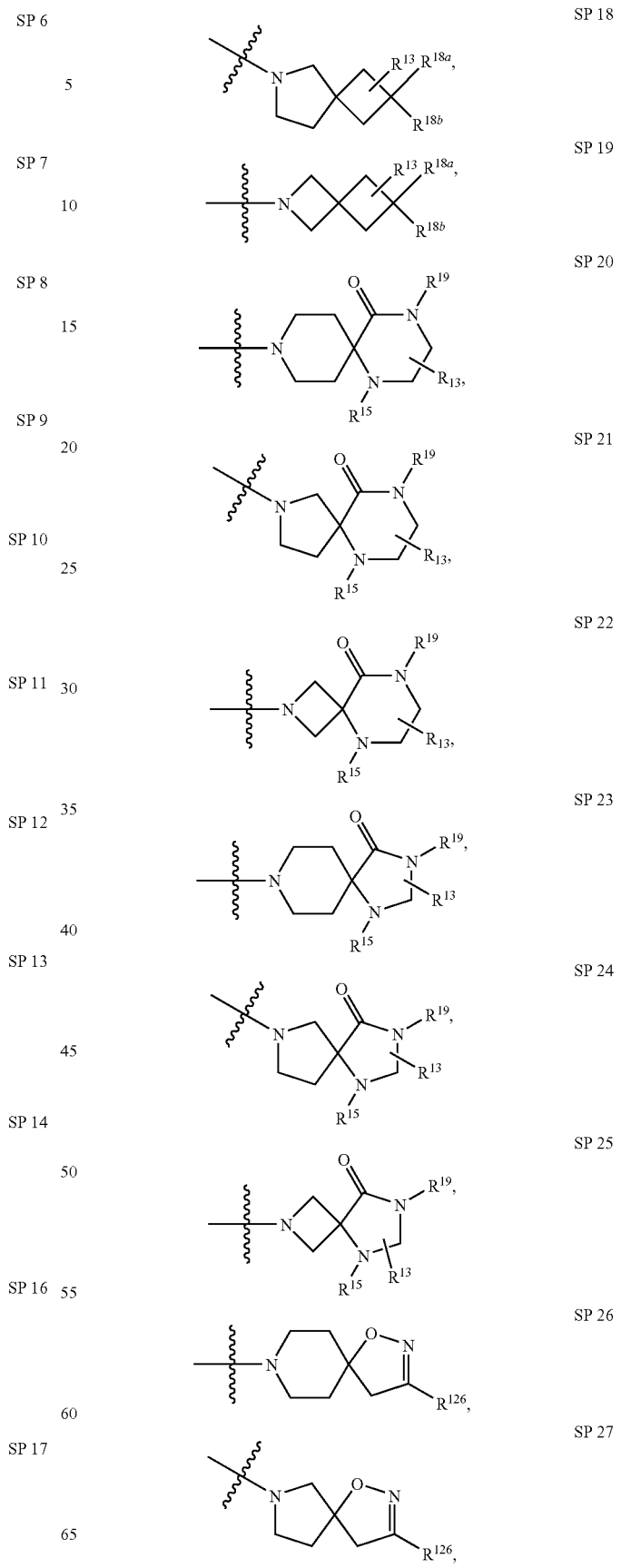

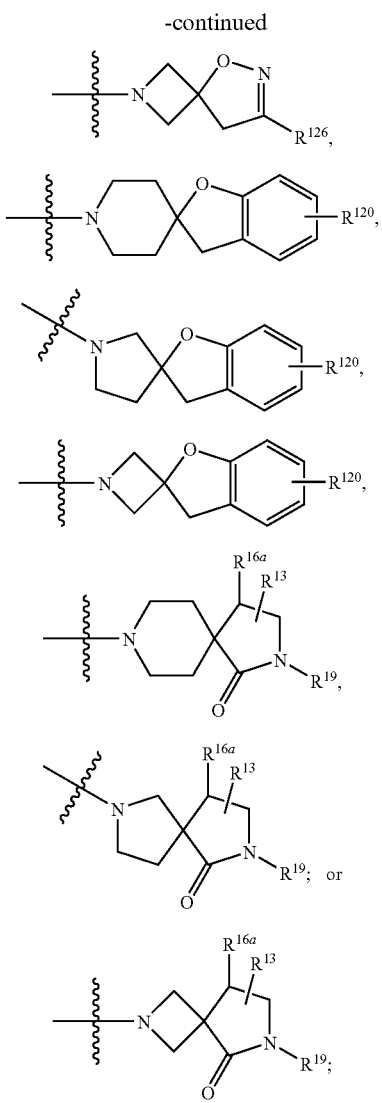

wherein
R$^{13}$ stands for H or phenyl, unsubstituted or mono- or polysubstituted with identical or different substituents; and/or two groups R$^{13}$ together form =O; and/or two adjacent groups R$^{13}$ together form an anellated aryl or heteroaryl ring structure, in particular a benzo group, each unsubstituted or mono- or polysubstituted with identical or different substituents;

R$^{15}$ stands for H; C$_{1-6}$ alkyl; C$_{3-8}$ cycloalkyl, phenyl, pyridyl, each unsubstituted or mono- or polysubstituted with identical or different substituents; or for phenyl or pyridyl bound by a C$_{1-6}$ alkylene group, each unsubstituted or mono- or polysubstituted with identical or different substituents;

R$^{16a}$ stands for H, C$_{1-6}$ alkyl, phenyl or pyridyl, each unsubstituted or mono- or polysubstituted with identical or different substituents;

R$^{18a}$ stands for H; C$_{1-6}$ alkyl; C$_{3-8}$ cycloalkyl, N(C$_{1-6}$ alkyl)$_2$; NH(C$_{1-6}$ alkyl), azetidinyl; pyrrolidinyl, piperidinyl, alkyl)-piperazinyl; phenyl or pyridyl, each unsubstituted or mono- or polysubstituted with identical or different substituents; or for N(C$_{1-6}$ alkyl)$_2$, NH(C$_{1-6}$ alkyl), azetidinyl, pyrrolidinyl, piperidinyl, 4-(C$_{1-6}$ alkyl)-piperazinyl, phenyl, imidazolyl, triazolyl or pyridyl bound by an —(O)$_{0/1}$ —C$_{1-6}$ alkylene group, each unsubstituted or mono- or polysubstituted with identical or different substituents;

R$^{18b}$ stands for H; OH; C$_{1-6}$ alkyl; phenyl or pyridyl, each unsubstituted or mono- or polysubstituted with identical or different substituents; or for phenyl or pyridyl bound by a C$_{1-6}$ alkylene group, each unsubstituted or mono- or polysubstituted with identical or different substituents;

R$^{19}$ stands for H; C$_{1-6}$ alkyl; C$_{3-8}$ cycloalkyl, phenyl, pyridyl, thienyl, imidazolyl, thiazolyl or triazolyl, each unsubstituted or mono- or polysubstituted with identical or different substituents; or for phenyl or pyridyl bound by a C$_{1-6}$ alkylene group or (C=O) group, each unsubstituted or mono- or polysubstituted with identical or different substituents;

R$^{120}$ stands for H; F; Cl; OH; OCH$_3$, O—CF$_3$, C$_{1-6}$ alkyl; CF$_3$, or phenyl, unsubstituted or mono- or polysubstituted;

R$^{126}$ stands for H; C$_{1-6}$ alkyl; C$_{3-8}$ cycloalkyl; phenyl or pyridyl; or for C$_{3-8}$ cycloalkyl, phenyl or pyridyl bound by a C$_{1-3}$ alkylene group, each unsubstituted or mono- or polysubstituted with identical or different substituents.

Other preferred embodiments of the compounds according to the invention are compounds in which the following substructure (B) in formula I:

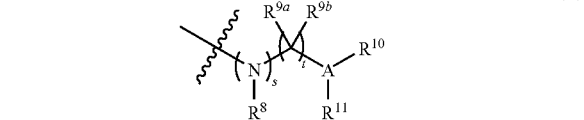

is selected from the group consisting of:

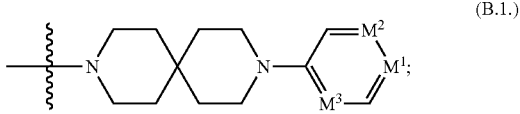

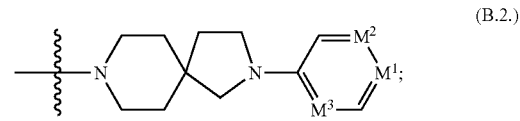

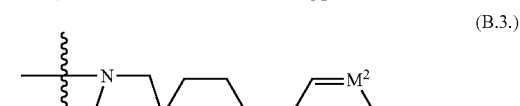

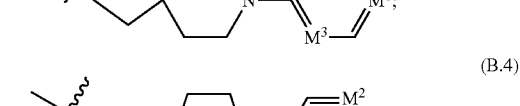

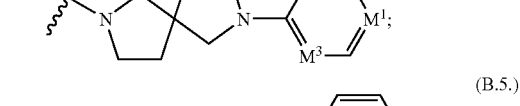

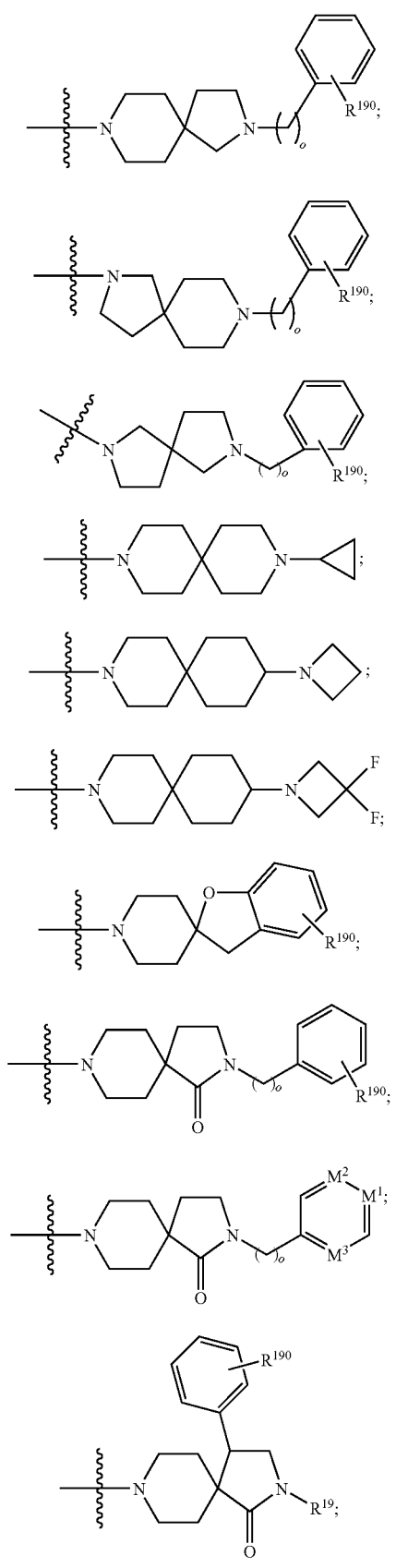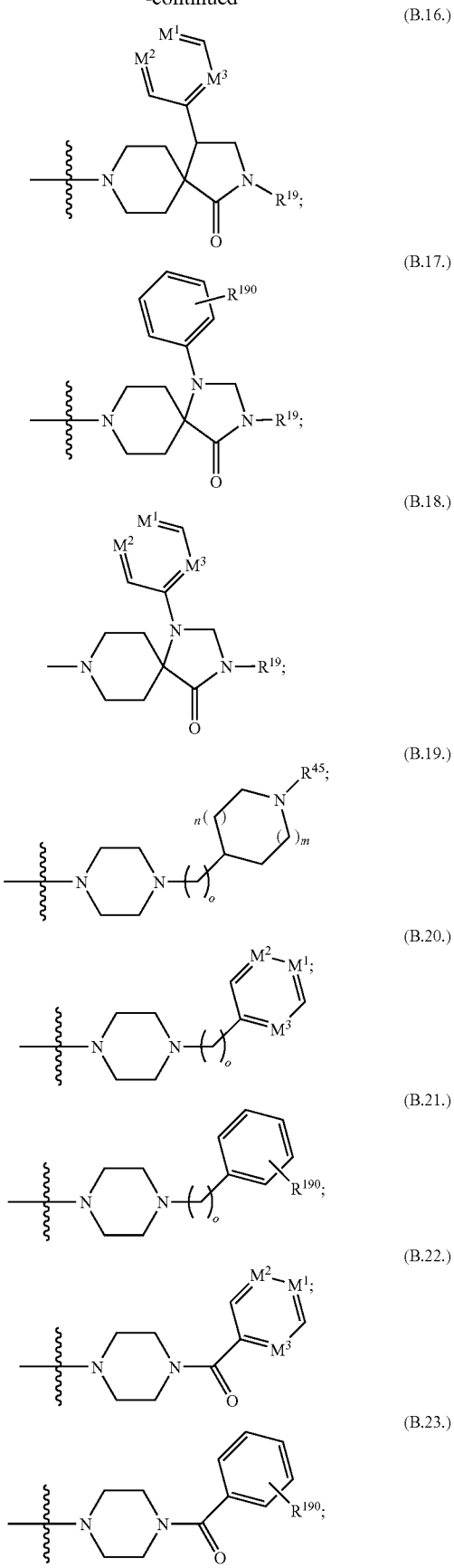

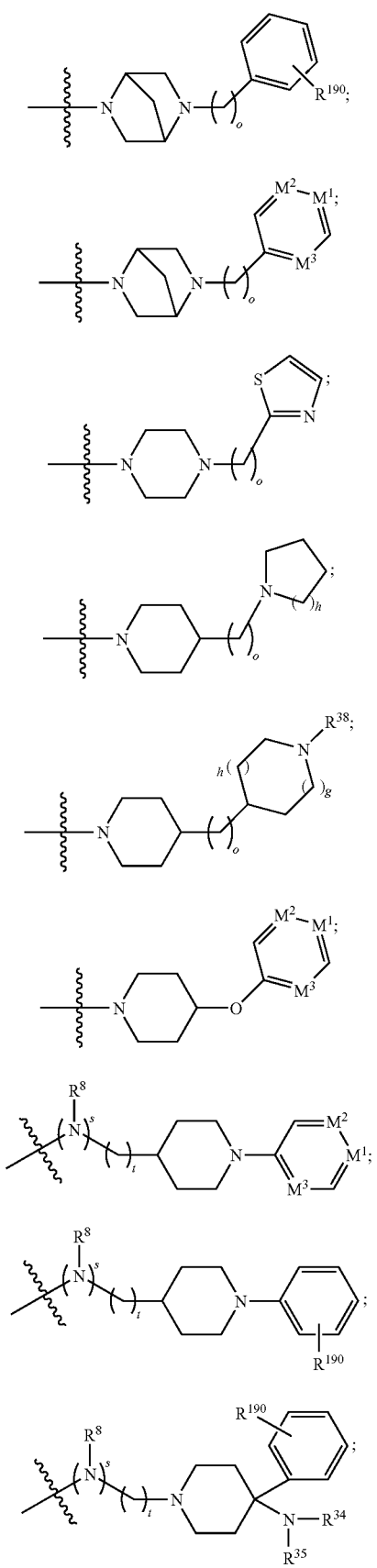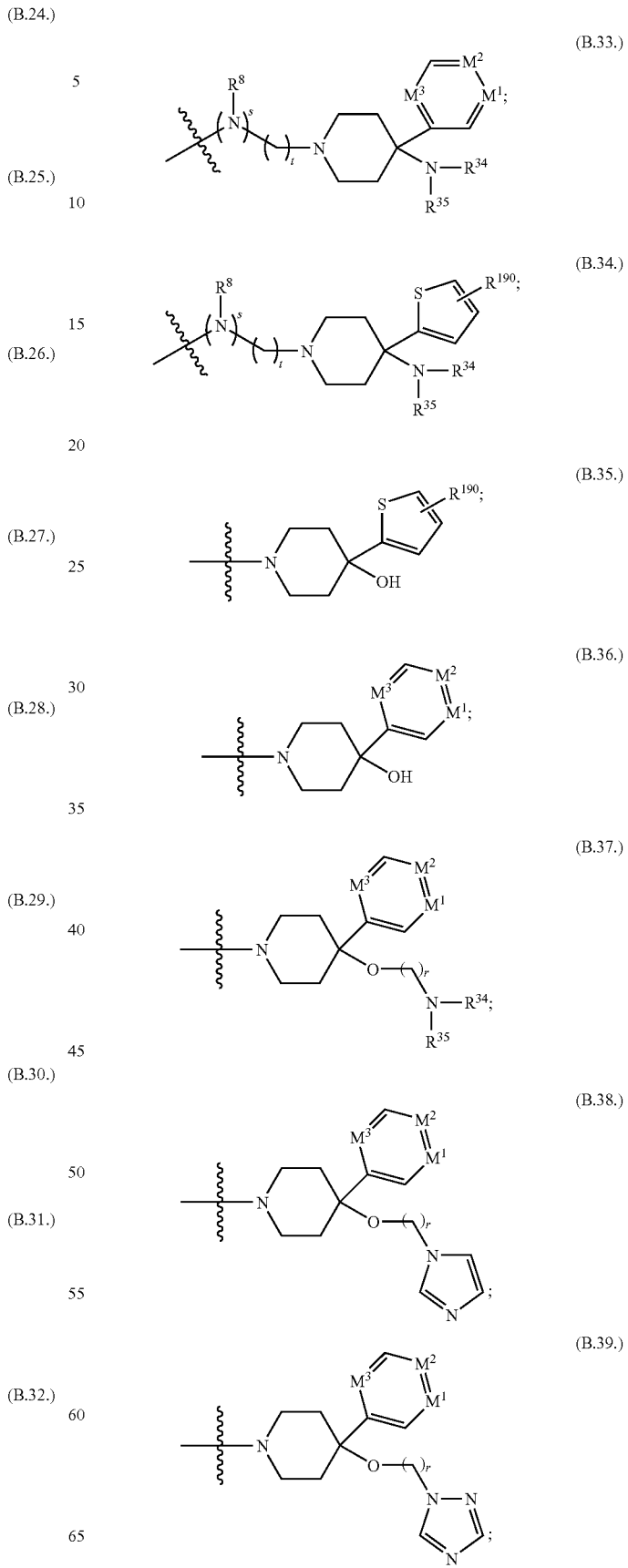

wherein h=0 or 1;
g=0 or 1;
m=0 or 1;
n=0 or 1;
o=0, 1, 2 or 3;
r=1, 2 or 3, in particular 1 or 2;
s=0 or 1;
t=0, 1, 2 or 3, in particular 0, 1 or 2, with the proviso that if s stands for 0, then t likewise stands for 0;

$M^1$, $M^2$ and $M^3$ each stand for N or CH, wherein one variable out of $M^1$, $M^2$ and $M^3$ stands for N and the other two stand for CH;

$R^8$ stands for H; $C_{1-6}$ alkyl, in particular methyl, ethyl, n-propyl, isopropyl, n-butyl, sec-butyl, isobutyl and tert-butyl; $C_{3-6}$ cycloalkyl, in particular cyclopropyl, each unsubstituted or mono- or polysubstituted with identical or different substituents;

$R^{19}$ is selected from H; $C_{1-6}$ alkyl, in particular methyl, ethyl, n-propyl, isopropyl, n-butyl, sec-butyl, isobutyl and tert-butyl; $C_{3-6}$ cycloalkyl, in particular cyclopropyl; each unsubstituted or mono- or polysubstituted with identical or different substituents;

$R^{34}$ and $R^{35}$ are preferably each independently methyl or ethyl or together with the N-atom linking them form an azetidinyl; pyrrolidinyl, piperidinyl, 4-($C_{1-6}$ alkyl)-piperazinyl group, each unsubstituted or mono- or polysubstituted with identical or different substituents;

$R^{38}$ stands for H, $C_{1-6}$ alkyl, $C_{3-6}$ cycloalkyl or pyridyl;

$R^{39}$ is selected from H; $C_{1-6}$ alkyl, in particular methyl, ethyl, n-propyl, isopropyl, n-butyl, sec-butyl, isobutyl and tert-butyl; $C_{3-6}$ cycloalkyl, in particular cyclopropyl, each unsubstituted or mono- or polysubstituted with identical or different substituents;

$R^{45}$ stands for H, $C_{1-6}$ alkyl, $C_{3-6}$ cycloalkyl or pyridyl;

$R^{190}$ represents 0 to 4 substituents independently selected from F, Cl, O—$CF_3$, $CF_3$ and CN;

$R^{271}$ stands for H; and $R^{272}$ stands for $C_{1-4}$ alkyl, $C_{3-6}$ cycloalkyl or a $C_{3-6}$ cycloalkyl bound by a $C_{1-3}$ alkylene group; or $R^{271}$ and $R^{272}$ together form a 4- to 7-membered heterocyclyl ring structure which may be substituted by 0 to 2 substituents selected from the group consisting of F, Cl, O—$CF_3$, —$CF_3$, or CN; or 2 adjacent substituents may together form an anellated aryl or heteroaryl ring structure, preferably an anellated benzo ring.

Other likewise preferred embodiments of the compound according to the invention are those in which in substructure (B) having the general formula I (B)

s stands for 1;
t stands for 0, 1 or 2;
$R^8$ stands for H, $C_{1-6}$ alkyl, $C_{3-8}$ cycloalkyl or a $C_{3-8}$ cycloalkyl bound by a $C_{1-3}$ alkylene group;
A stands for N or CH, with the proviso that if t stands for 0, then A stands for CH, and
$R^{10}$ and $R^{11}$ together with A, to which they are bound, represent a 5- or 6-membered cycloalkyl or heterocycloalkyl group, to which a 5- or 6-membered aryl or heteroaryl ring structure is anellated, wherein the 5- or 6-membered, anellated aryl or heteroaryl ring structure is substituted with a ($C_{1-6}$alkyl)amino, di($C_{1-6}$alkyl)amino group or a 4- to 7-membered N-containing heterocyclyl group, wherein the ($C_{1-6}$ alkyl)amino and di($C_{1-6}$ alkyl)amino groups, the 4- to 7-membered heterocyclyl group and the $C_{1-3}$ alkylene group to which these are bound can be unsubstituted, or mono- or polysubstituted with identical or different substituents selected from the same groups as defined above for the respective types of groups.

In likewise preferred embodiments of the compounds according to the invention the substructure B having the general formula I represents a group corresponding to formula B.50:

(B.50.)

wherein
$R^8$ stands for H, methyl, ethyl, n-propyl, isopropyl, n-butyl, s-butyl, isobutyl, t-butyl, cyclopropyl or a cyclopropyl bound by a $C_{1-3}$ alkylene group, preferably H, methyl or cyclopropyl; wherein in all of these groups at least one C-bound H atom can be replaced by an F atom;
u and v each independently stand for 0, 1 or 2, wherein u+v is greater than 0 and u+v is at most 3; and wherein u and v preferably simultaneously stand for 1;
$\Lambda A$ stands for $CH_2$ or O, with the proviso that if A stands for 0 then u stands for 1;
$\Pi^1$ and $\Pi^2$ each independently stand for CH or N, wherein $\Pi^1$ and $\Pi^2$ preferably both stand for CH or both stand for N;
α stands for 0, 1, 2 or 3, preferably 1; and
$R^x$ and $R^y$, each independently stand for H, $C_{1-6}$ alkyl, preferably methyl, F or $CF_3$;
wherein $R^x$ and $R^y$ are preferably each H;
T stands for $N(R^{271})(R^{272})$, wherein
$R^{271}$ stands for H and
$R^{272}$ stands for $C_{1-4}$ alkyl, $C_{3-6}$ cycloalkyl or a $C_{3-6}$ cycloalkyl bound by a $C_{1-3}$ alkylene group; or
T stands for a heterocyclyl ring selected from the group consisting of:

wherein
$R^{274}$ stands for 0 to 2 substituents independently selected from F, methyl, ethyl, $CF_3$ and $—CH_2—CF_3$, and is preferably absent; or wherein two adjacent substituents $R^{274}$ together form an anellated aryl or heteroaryl ring structure, preferably phenyl, or two substituents $R^{274}$ together form a $C_{1-3}$ alkylen bridge so that the heterocyclyl ring takes on a bicyclically bridged form;
$R^{275}$ represents a group selected from the group consisting of $C_{1-4}$ alkyl,
$C_{3-6}$cycloalkyl or a $C_{3-6}$ cycloalkyl bound by a $C_{1-3}$ alkylene group, wherein $R^{275}$ preferably stands for H or methyl; and
$R^{276}$ stands for F, Cl, methyl or $CF_3$.

The group $—(CR^xR^y)_α-T$ is preferably bound to the position between $\Pi^1$ and $\Pi^2$.

In a preferred embodiment of the compounds according to the invention the substructure represented by formula B.50. is selected from:

B.50.1

-continued

B.50.2.
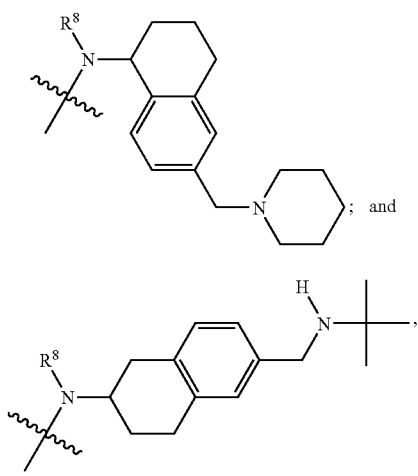
and

B.50.3.
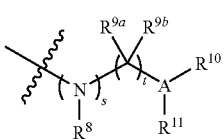

wherein
R$^8$ stands for H, C$_{1-6}$ alkyl, cyclopropyl or a cyclopropyl bound by a C$_{1-3}$ alkylene, preferably for H or methyl, and all of these groups can be substituted in accordance with the definitions given above.

Other preferred embodiments of the compounds according to the invention are compounds in which the following substructure (B) from the formula I shown above (B)

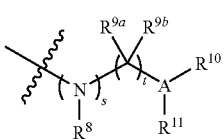

is selected from the group consisting of:

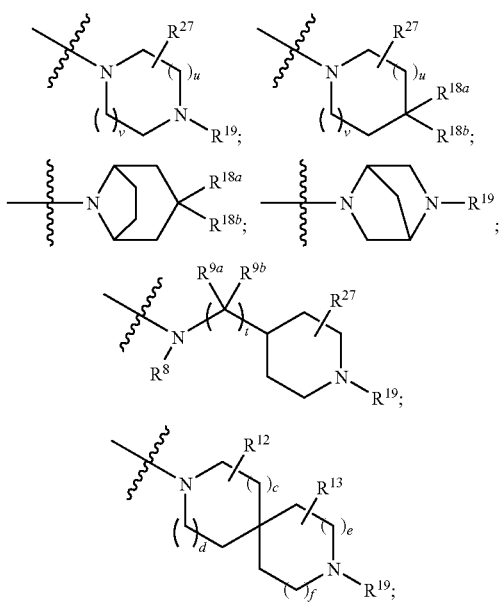

-continued

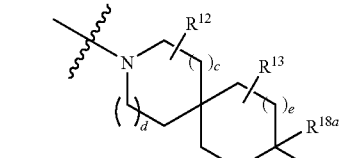

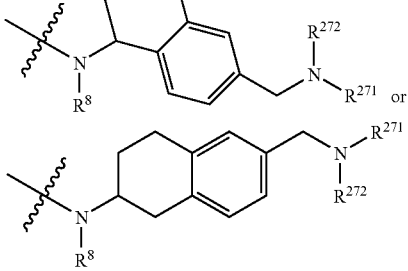

wherein all substituent groups and indices have the meanings given above in connection with the compounds according to the invention and the preferred embodiments thereof, and wherein compounds are preferred in which:

c, d, e and f each independently stand for 0 or 1;
u and v each independently stand for 0 or 1;
t stands for 0, 1, 2 or 3, preferably for 0, 1 or 2;
R$^8$ stands for H; C$_{1-6}$ alkyl, in particular methyl, ethyl, n-propyl, isopropyl, n-butyl, sec-butyl, isobutyl and tert-butyl; C$_{3-6}$ cycloalkyl, in particular cyclopropyl, each unsubstituted or mono- or polysubstituted with identical or different substituents;
R$^{9a}$ and R$^{9b}$ each independently stand for H; F; C$_{1-6}$ alkyl; O—C$_{1-6}$ alkyl; C$_{3-8}$ cycloalkyl; aryl or heteroaryl; a C$_{3-8}$ cycloalkyl, aryl or heteroaryl bound by a C$_{1-6}$ alkylene group; in particular for H, F, C$_{3-6}$ cycloalkyl, phenyl or a C$_{3-6}$ cycloalkyl or phenyl bound by a C$_{1-3}$ alkylene group;
R$^{12}$, R$^{13}$ and R$^{27}$ each independently stand for 0 to 4 substituents independently selected from the group consisting of F; Cl; OH; =O; C$_{1-6}$ alkyl; O—C$_{1-6}$ alkyl; C$_{3-8}$ cycloalkyl; aryl; heteroaryl; C$_{3-8}$ cycloalkyl, aryl or heteroaryl bound by a C$_{1-6}$ alkylene group; preferably for F or C$_{1-6}$ alkyl, or are absent;
R$^{18a}$ stands for H; C$_{1-6}$ alkyl; C$_{3-8}$ cycloalkyl, N(C$_{1-6}$ alkyl)$_2$; NH(C$_{1-6}$ alkyl); azetidinyl; pyrrolidinyl, piperidinyl, 4-(C$_{1-6}$ alkyl)-piperazinyl; phenyl or pyridyl, each unsubstituted or mono- or polysubstituted with identical or different substituents; or N(C$_{1-6}$ alkyl)$_2$, NH(C$_{1-6}$ alkyl), azetidinyl, pyrrolidinyl, piperidinyl, 4-(C$_{1-6}$ alkyl)-piperazinyl, phenyl, imidazolyl, triazolyl or pyridyl, in particular O-pyridyl, bound by an —(O)$_{0-1}$—C$_{1-6}$ alkylene group, each unsubstituted or mono- or polysubstituted with identical or different substituents;
R$^{18b}$ stands for H; OH; C$_{1-6}$ alkyl; phenyl or pyridyl, each unsubstituted or mono- or polysubstituted with identical or different substituents; phenyl or pyridyl bound by a C$_{1-6}$ alkylene group, each unsubstituted or mono- or polysubstituted with identical or different substituents; and
R$^{19}$ stands for H; C$_{1-6}$ alkyl; C$_{3-8}$ cycloalkyl, phenyl, pyridyl, thienyl, imidazolyl, thiazolyl or triazolyl, each unsubstituted or mono- or polysubstituted with identical or different substituents; or for phenyl, pyridyl, thienyl, imidazolyl, thiazolyl or triazolyl bound by a C$_{1-6}$ alkylene group or a (C=O) group, each unsubstituted or mono- or polysubstituted with identical or different substituents; or $R^{19}$ stands for a structure corresponding to formula (VIIIa):

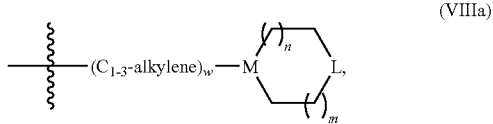
(VIIIa)

wherein w stands for 0 or 1;

n stands for 0 or 1;

m stands for 0 or 1;

M stands for CH or N, with the proviso that if w is 0, then M stands for CH;

L stands for $CR^{44a}R^{44b}$, $NR^{45}$ or O; wherein $R^{44a}$ and $R^{44b}$ each independently stand for H, F or $C_{1-6}$ alkyl, each unsubstituted or mono- or polysubstituted with identical or different substituents; and $R^{45}$ stands for H; $C_{1-6}$ alkyl, $C_{3-6}$ alkyl or pyridyl, each unsubstituted or mono- or polysubstituted with identical or different substituents.

In further preferred embodiments of the compounds according to the invention the substructure Ac II

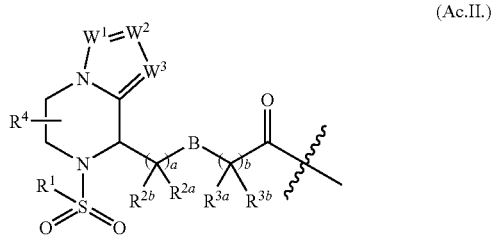
(Ac.II.)

In formula I is selected from the group consisting of:

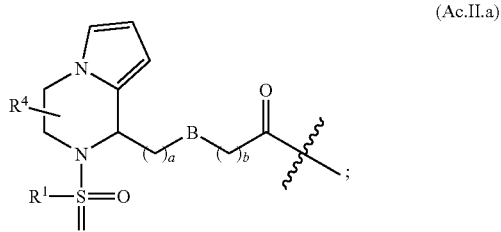
(Ac.II.a)

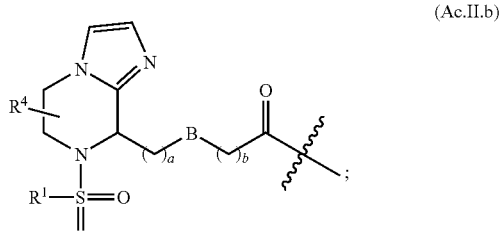
(Ac.II.b)

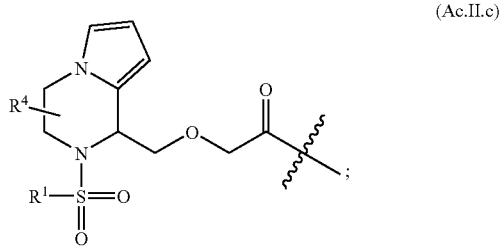
(Ac.II.c)

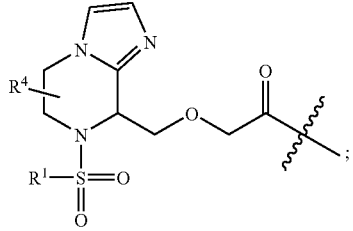
(Ac.II.d)

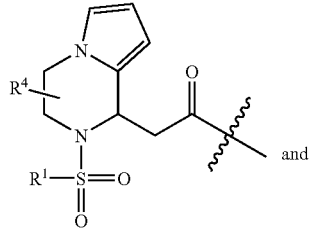
(Ac.II.e)

and

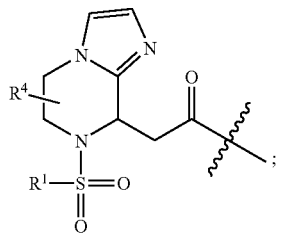
(Ac.II.f)

wherein the various substituent groups, variables and indices have the meanings given above.

In likewise preferred embodiments of the compounds according to the invention the substructure Ac.II. is selected from the structures Ac.II.a-d, in particular Ac.II.c or Ac.II.d, and the substructure B is selected from the structures B.1 to B.49.

In further, likewise preferred embodiments of the compounds according to the invention the substructure Ac.II is selected from one of the structures Ac.II.e. and Ac.II.f., in particular Ac.II.e., and the substructure B is a structure according to the general formula B.50., in particular B.50.1 to B.50.3.

Further preferred embodiments of the compounds according to the invention are those according to one of the following formulas C.1. to C.16:

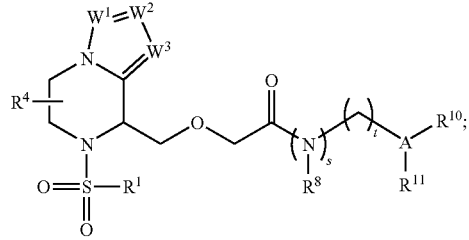
(C.1.)

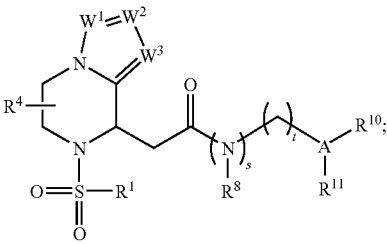
(C.2.)

(C.3.)
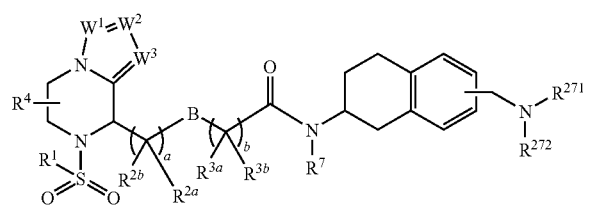
(C.4.)
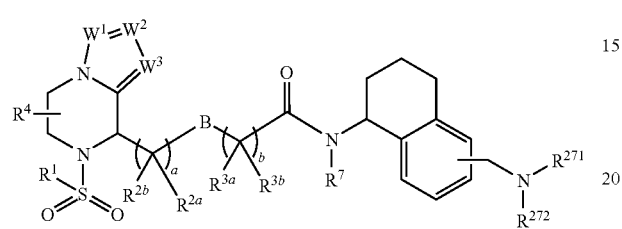
(C.5.)
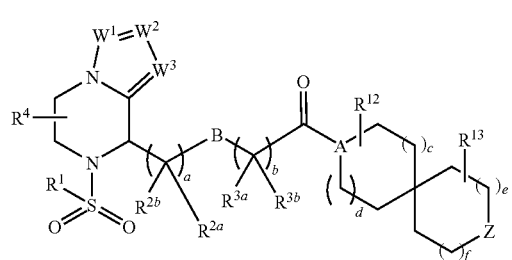
(C.6.)
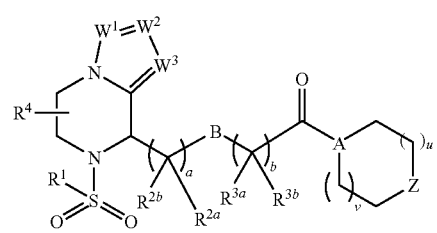
(C.7.)
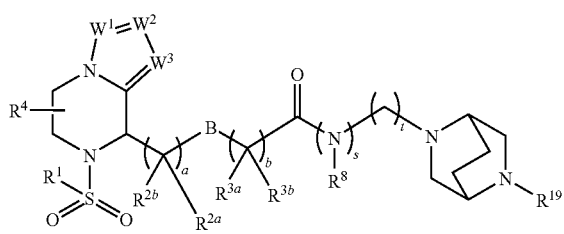
(C.8.)
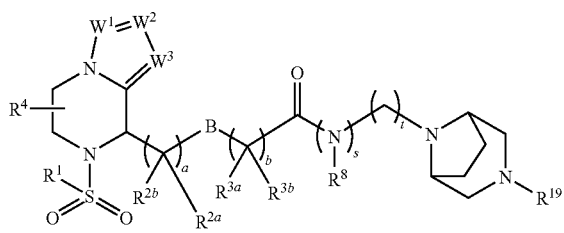
(C.9.)
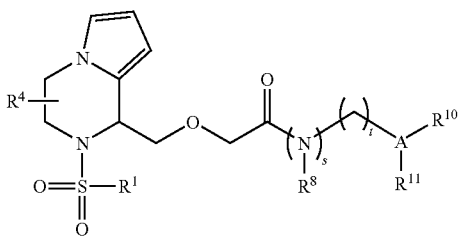
(C.10.)
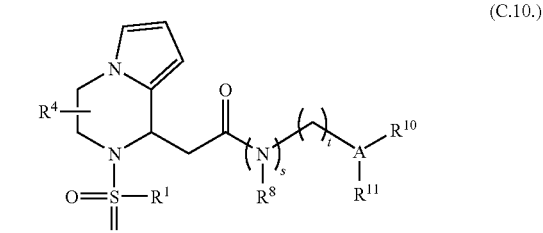
(C.11.)
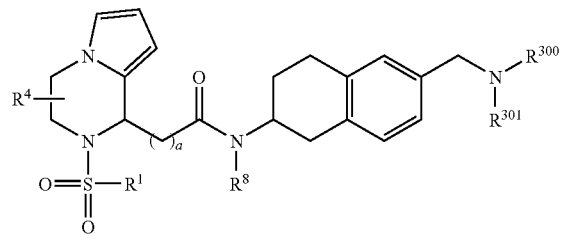
(C.12.)
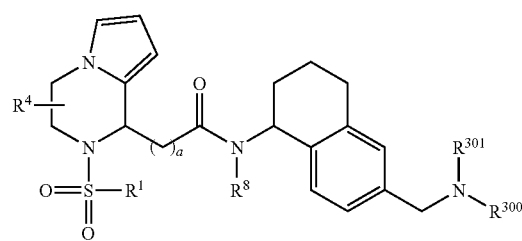
(C.13.)
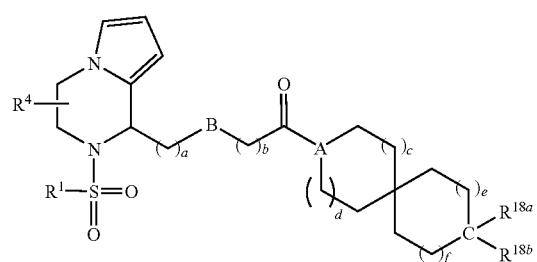
(C.14.)
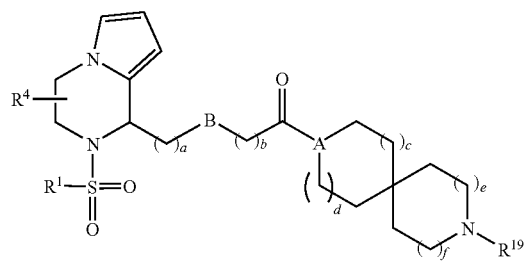

-continued (C.15.)
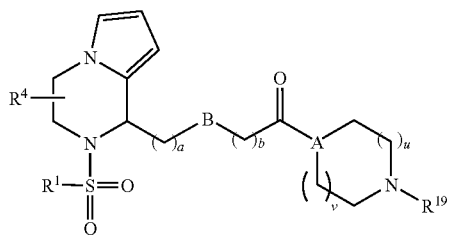

(C.16.)
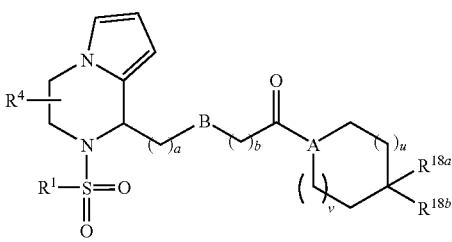

wherein the various substituent groups, variables and indices in formulas C.1. to C.16. have the meanings described above in connection with the compounds according to the invention and the preferred embodiments thereof.

In further preferred embodiments of the compounds according to the invention the compounds are represented by the formula C.9.

(C.9.)
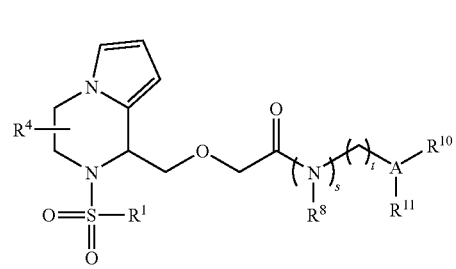

wherein $R^1$ represents a group selected from 4-methoxy-2,6-dimethylphenyl, 2-chloro-6-methylphenyl, 2,4,6-trichlorophenyl, 2,6-dichloro-4-methylphenyl, 2-methyl-1-naphthyl, 2-chloro-1-naphthyl, 2-fluoro-1-naphthyl, and 2-(trifluoromethyl)-1-naphthyl;

$R^4$ is H; and the moiety represented by the formula $B^1$ (B¹)
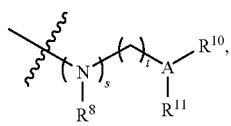

represents

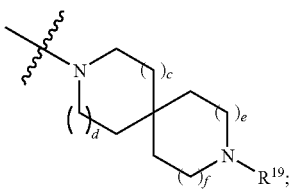

-continued

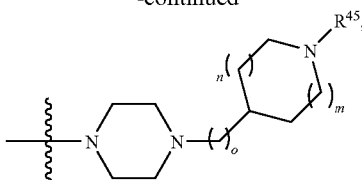

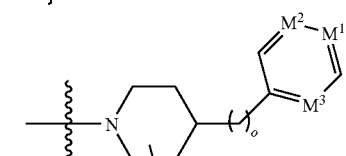

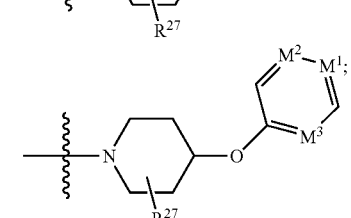

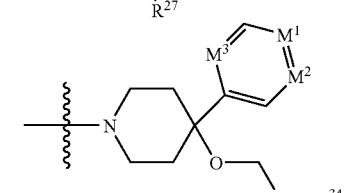

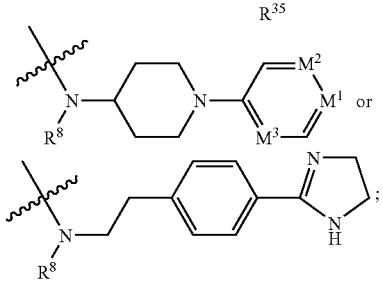

wherein c, d, e and f each independently represent 0 or 1 and preferably, the sum of c+d+e+f is equal or greater than 1, preferably equal or greater than 2;

o represents 0 or 1;

n and m are each independently selected from 0, 1 or 2;

$M^1$, $M^2$ and $M^3$ can each stand for N or CH, wherein one variable out of $M^1$, $M^2$ and $M^3$ stands for N and the other two stand for CH; and wherein preferably M' is N and $M^2$ and $M^3$ are CH;

$R^8$ represents H, Me, cyclopropyl, isopropyl or $CH_2CF_3$;

$R^{19}$ represents H; substituted or unsubstituted $C_{1-6}$-alkyl, $C_{3-6}$-cycloalkyl, aryl or heteroaryl; preferably pyridyl, especially 4-pyridyl, or phenyl, preferably substituted by 1 or 2 substituents each independently selected from F or Cl;

$R^{27}$ represents H or two substituents together forming a $C_{1-3}$-alklylen bridge, such that the piperidinyl group to which the substituents $R^{27}$ are bonded forms a bicyclic group;

$R^{34}$ and $R^{35}$ are preferably each independently methyl or ethyl or together with the N-atom linking them form an azetidinyl; pyrrolidinyl, piperidinyl or 4-($C_{1-6}$ alkyl)-piperazinyl group, each unsubstituted or mono- or polysubstituted with identical or different substituents; and $R^{45}$ stands for H, $C_{1-6}$ alkyl, $C_{3-6}$ cycloalkyl or pyridyl, preferably 4-pyridyl.

In further preferred embodiments of the compounds according to the invention the compounds are represented by the formula D.1. or D.2.

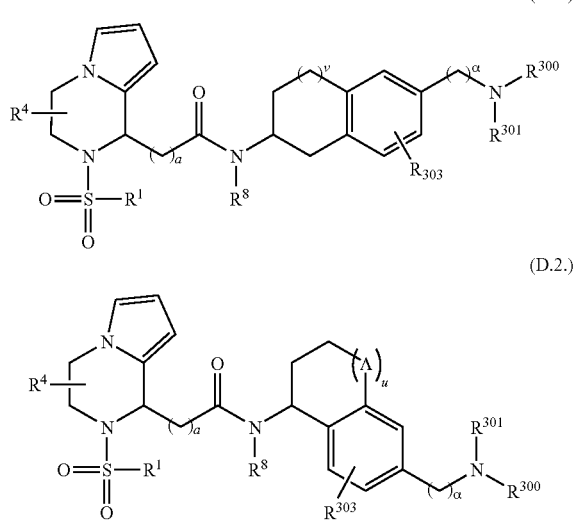

wherein
a represents 1,
u represents 0 or 1, wherein u represents 1 if Λ is 0;
v represents 0 or 1;
α represents 1 or 2;
Π represents $CH_2$ or O;
$R^1$ is selected from 1-naphthyl, 2-naphthyl, 6-methoxy-2-naphthyl, 4-chloro-2,5-dimethylphenyl, 3-methylphenyl, 3-chlorophenyl, 3-(trifluoromethyl)phenyl, 4-methylphenyl, 4-chlorophenyl, 4-(trifluormethyl)phenyl or phenyl independently substituted in 2,3- or 3,4-positions by methyl, chloro or trifluoromethyl;
$R^4$ represents H;
$R^8$ stands for H, $C_{1-6}$ alkyl, cyclopropyl or a cyclopropyl bound by a $C_{1-3}$ alkylene, preferably for H or methyl; and
$R^{300}$ and $R^{301}$ together with the N-atom to which they are bonded form a substituted or unsubstituted 4- to 7-membered heterocycle, preferably piperidine, or
$R^{300}$ and $R^{301}$ each independently stand for H or substituted or unsubstituted $C_{1-6}$ alkyl or $C_{3-6}$-cycloalkyl; preferably, $R^{300}$ and $R^{301}$ are each independently selected from the group consisting of H, Me, Et, t-butyl, cyclopropyl, $CH_2CF_3$; or
$R^{300}$ and $R^{301}$ together with the N-atom to which they are bonded form a substituted or unsubstituted heterocyclic group selected from the group consisting of piperidinyl, N—($C_{1-6}$-alkyl)piperazinyl, morpholinyl, pyrrolidinyl and azetidinyl; and
$R^{303}$ is selected from H, F and $CF_3$.

In further preferred embodiments of the invention, the compounds are selected from the group consisting of:
1 2-(2-(4-Methoxy-2,6-dimethylphenylsulfonyl)-1,2,3,4-tetrahydropyrrolo[1,2-a]pyrazin-1-yl)-1-(4-(1-methylpiperidin-4-yl)piperazin-1-yl)ethanone;
2 2-((2-(4-Methoxy-2,6-dimethylphenylsulfonyl)-1,2,3,4-tetrahydropyrrolo[1,2-a]pyrazin-1-yl)methoxy)-1-(4-(1-methylpiperidin-4-yl)piperazin-1-yl)ethanone;
3 1-(7-Cyclopropyl-2,7-diazaspiro[4.4]nonan-2-yl)-2-(2-(4-methoxy-2,6-dimethylphenylsulfonyl)-1,2,3,4-tetrahydropyrrolo[1,2-a]pyrazin-1-yl)ethanone;
4 2-((2-(4-Methoxy-2,6-dimethylphenylsulfonyl)-1,2,3,4-tetrahydropyrrolo[1,2-a]pyrazin-1-yl)methoxy)-1-(2-(pyridin-4-yl)-2,8-diazaspiro[4.5]decan-8-yl)ethanone;
5 1-(4-(Pyridin-4-yloxy)piperidin-1-yl)-2-((2-(2-(trifluoromethyl)phenylsulfonyl)-1,2,3,4-tetrahydropyrrolo[1,2-a]pyrazin-1-yl)methoxy)ethanone;
6 2-((2-(2-Chloro-6-methylphenylsulfonyl)-1,2,3,4-tetrahydropyrrolo[1,2-a]pyrazin-1-yl)methoxy)-1-(4-(pyridin-4-yloxy)piperidin-1-yl)ethanone;
7 2-((2-(4-Methoxy-2,6-dimethylphenylsulfonyl)-1,2,3,4-tetrahydropyrrolo[1,2-a]pyrazin-1-yl)methoxy)-N-methyl-N-(2-(1-(pyridin-4-yl)piperidin-4-yl)ethyl)acetamide;
8 2-(2-(6-Methoxynaphthalen-2-ylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide;
9 2-(2-(6-Methoxynaphthalen-2-ylsulfonyl)-1,2,3,4-tetrahydropyrrolo[1,2-a]pyrazin-1-yl)-N-(6-(piperidin-1-ylmethyl)-1,2,3,4-tetrahydronaphthalen-1-yl)acetamide;
10 2-((2-(4-Methoxy-2,6-dimethylphenylsulfonyl)-1,2,3,4-tetrahydropyrrolo[1,2-a]pyrazin-1-yl)methoxy)-1-(9-(pyridin-4-yl)-3,9-diazaspiro[5.5]undecan-3-yl)ethanone;
11 1-(9-(Pyridin-4-yl)-3,9-diazaspiro[5.5]undecan-3-yl)-2-((2-(2-(trifluoromethyl)phenylsulfonyl)-1,2,3,4-tetrahydropyrrolo[1,2-a]pyrazin-1-yl)methoxy)ethanone;
12 N-Methyl-N-(2-(1-(pyridin-4-yl)piperidin-4-yl)ethyl)-2-((2-(2-(trifluoromethyl)phenylsulfonyl)-1,2,3,4-tetrahydropyrrolo[1,2-a]pyrazin-1-yl)methoxy)acetamide;
13 2-((2-(4-Methoxy-2,6-dimethylphenylsulfonyl)-1,2,3,4-tetrahydropyrrolo[1,2-a]pyrazin-1-yl)methoxy)-1-(4-(pyridin-4-yloxy)piperidin-1-yl)ethanone;
14 2-((2-(2-Chloro-6-methylphenylsulfonyl)-1,2,3,4-tetrahydropyrrolo[1,2-a]pyrazin-1-yl)methoxy)-1-(2-(pyridin-4-yl)-2,8-diazaspiro[4.5]decan-8-yl)ethanone;
15 2-((2-(2-Chloro-6-methylphenylsulfonyl)-1,2,3,4-tetrahydropyrrolo[1,2-a]pyrazin-1-yl)methoxy)-1-(9-(pyridin-4-yl)-3,9-diazaspiro[5.5]undecan-3-yl)ethanone;
16 2-((2-(2-Chloro-6-methylphenylsulfonyl)-1,2,3,4-tetrahydropyrrolo[1,2-a]pyrazin-1-yl)methoxy)-N-methyl-N-(2-(1-(pyridin-4-yl)piperidin-4-yl)ethyl)acetamide;
17 N-(3,3-Dimethylpiperidin-4-yl)-2-(2-(4-methoxy-2,6-dimethylphenylsulfonyl)-1,2,3,4-tetrahydropyrrolo[1,2-a]pyrazin-1-yl)acetamide;
18 2-(2-(4-Methoxy-2,6-dimethylphenylsulfonyl)-1,2,3,4-tetrahydropyrrolo[1,2-a]pyrazin-1-yl)-1-(2-(pyridin-4-yl)-2,8-diazaspiro[4.5]decan-8-yl)ethanone;
19 2-(2-(2-Chloro-4-(trifluoromethyl)phenylsulfonyl)-1,2,3,4-tetrahydropyrrolo[1,2-a]pyrazin-1-yl)-1-(piperidin-1-yl)ethanone;
20 2-(2-(2-Chloro-4-(trifluoromethyl)phenylsulfonyl)-1,2,3,4-tetrahydropyrrolo[1,2-a]pyrazin-1-yl)-1-(3,4-dihydroisoquinolin-2(1H)-yl)ethanone;
21 1-(2-(Pyridin-4-yl)-2,8-diazaspiro[4.5]decan-8-yl)-2-((2-(2-(trifluoromethypphenylsulfonyl)-1,2,3,4-tetrahydropyrrolo[1,2-a]pyrazin-1-yl)methoxy)ethanone
22 2-((2-(4-Methoxy-2,6-dimethylphenylsulfonyl)-1,2,3,4-tetrahydropyrrolo[1,2-a]pyrazin-1-yl)methoxy)-1-(2,8-diazaspiro[4.5]decan-8-yl)ethanone
23 2-((2-(4-Methoxy-2,6-dimethylphenylsulfonyl)-1,2,3,4-tetrahydropyrrolo[1,2-a]pyrazin-1-yl)methoxy)-1-((1R,3S,5S)-3-(pyridin-4-yloxy)-8-azabicyclo[3.2.1]octan-8-yl)ethanone
24 2-((2-(4-Methoxy-2,6-dimethylphenylsulfonyl)-1,2,3,4-tetrahydropyrrolo[1,2-a]pyrazin-1-yl)methoxy)-1-(4-(pyridin-3-yl)-4-(2-(pyrrolidin-1-yl)ethoxy)piperidin-1-yl)ethanon 25 2-(2-(4-Chloro-2,5-dimethylphenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide 26 2-(2-(3,4-Dichlorophenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide 27 2-(2-(Phenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide 28 2-(2-(2,3-Dichlorophenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide 29 N-(6-(Piperidin-1-ylmethyl)-1,2,3,4-tetrahydronaphthalen-2-yl)-2-(2-tosyl-1,2,3,4-tetrahydropyrrolo[1,2-a]pyrazin-1-yl)acetamide 30 N-(6-(Piperidin-1-ylmethyl)-1,2,3,4-tetrahydronaphthalen-2-yl)-2-(2-(3-(trifluoromethyl)phenylsulfonyl)-1,2,3,4-tetrahydropyrrolo[1,2-a]pyrazin-1-yl)acetamide 31 N-(6-((tert-Butylamino)methyl)-1,2,3,4-tetrahydronaphthalen-2-yl)-2-(2-(6-methoxynaphthalen-2-ylsulfonyl)-1,2,3,4-tetrahydropyrrolo[1,2-a]pyrazin-1-yl)acetamide 32 2-[[2-[(4-Methoxy-2,6-dimethyl-phenyl)sulfonyl]-1,2,3,4-tetrahydro-pyrrolo[1,2-a]pyrazin-1-yl]-methoxy]-N-[1-[5-(trifluoromethyl)-pyridin-2-yl]-piperidin-4-yl]-acetamide 33 2-[[2-[(4-Methoxy-2,6-dimethyl-phenyl)sulfonyl]-1,2,3,4-tetrahydro-pyrrolo[1,2-a]pyrazin-1-yl]-methoxy]-N-[1-[5-(trifluoromethyl)-pyridin-2-yl]-pyrrolidin-3-yl]-acetamide 34 2-[[2-[(4-Methoxy-2,6-dimethyl-phenyl)sulfonyl]-1,2,3,4-tetrahydro-pyrrolo[1,2-a]pyrazin-1-yl]-methoxy]-1-(4-pyridin-4-yl-piperidin-1-yl)-ethanone 35 2-[[2-[(4-Methoxy-2,6-dimethyl-phenyl)sulfonyl]-1,2,3,4-tetrahydro-pyrrolo[1,2-a]pyrazin-1-yl]-methoxy]-1-[4-(pyridin-4-yl-methyl)-piperidin-1-yl]-ethanone 36 2-[[2-[(4-Methoxy-2,6-dimethyl-phenyl)sulfonyl]-1,2,3,4-tetrahydro-pyrrolo[1,2-a]pyrazin-1-yl]-methoxy]-N-(1-pyridin-4-yl-piperidin-4-yl)-acetamide 37 2-[[2-[(4-Methoxy-2,6-dimethyl-phenyl)sulfonyl]-1,2,3,4-tetrahydro-pyrrolo[1,2-a]pyrazin-1-yl]-methoxy]-1-[3-[(4-methyl-piperazin-1-yl)-methyl]-pyrrolidin-1-yl]-ethanone 38 2-[[2-[(4-Methoxy-2,6-dimethyl-phenyl)sulfonyl]-1,2,3,4-tetrahydro-pyrrolo[1,2-a]pyrazin-1-yl]-methoxy]-1-(3-pyridin-4-yloxy-pyrrolidin-1-yl)-ethanone 39 2-[[2-[(4-Methoxy-2,6-dimethyl-phenyl)sulfonyl]-1,2,3,4-tetrahydro-pyrrolo[1,2-a]pyrazin-1-yl]-methoxy]-N-methyl-N-(1-pyridin-4-yl-piperidin-4-yl)-acetamide 40 2-[[2-[(4-Methoxy-2,6-dimethyl-phenyl)sulfonyl]-1,2,3,4-tetrahydro-pyrrolo[1,2-a]pyrazin-1-yl]-methoxy]-1-[4-(3-methyl-3,6-diazabicyclo[2.2.1]heptan-6-yl)-piperidin-1-yl]-ethanone 41 N-[2-[4-(4,5-Dihydro-1H-imidazol-2-yl)-phenyl]-ethyl]-2-[2-[(6-methoxy-naphthalen-2-yl)sulfonyl]-1,2,3,4-tetrahydro-pyrrolo[1,2-a]pyrazin-1-yl]-acetamide 42 N-[(1R)-6-[(tert-Butylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 43 2-[2-[(6-Methoxy-naphthalen-2-yl)sulfonyl]-1,2,3,4-tetrahydro-pyrrolo[1,2-a]pyrazin-1-yl]-N-methyl-N-[6-(piperidin-1-ylmethyl)-1,2,3,4-tetrahydro-naphthalen-2-yl]-acetamide 44 N-[(1R)-6-[(4-Fluoro-piperidin-1-yl)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 45 2-[2-(p-Tolylsulfonyl)-1,2,3,4-tetrahydro-pyrrolo[1,2-a]pyrazin-1-yl]-N-[1R)-6-[(2,2,2-trifluoro-ethylamino)-methyl]-1,2,3,4-tetrahydro-naphthalen-1-yl]-acetamide 46 N-[(1R)-1-[4-[(tert-Butylamino)-methyl]-phenyl]-ethyl]-2-[2-(p-tolylsulfonyl)-1,2,3,4-tetrahydro-pyrrolo[1,2-a]pyrazin-1-yl]-acetamide 47 2-(2-(3-Chlorophenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide 48 2-(2-(6-Methoxynaphthalen-2-ylsulfonyl)-1,2,3,4-tetrahydropyrrolo[1,2-a]pyrazin-1-yl)-N-(5-(piperidin-1-ylmethyl)-2,3-dihydro-1H-inden-2-yl)acetamide 49 2-[2-[(3-Chloro-4-methyl-phenyl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-2-yl]-acetamide 50 2-[2-[(3-Chloro-4-methyl-phenyl)sulfonyl]-1,2,3,4-tetrahydro-pyrrolo[1,2-a]pyrazin-1-yl]-N-[6-(piperidin-1-yl-methyl)-1,2,3,4-tetrahydro-naphthalen-2-yl]-acetamide 51 N-[6-[(Benzylamino)-methyl]-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide 52 2-[2-[(3-Chloro-4-methyl-phenyl)sulfonyl]-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-2-yl]-acetamide 53 N-[6-(Morpholin-4-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 54 N-[6-(Morpholin-4-yl-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 55 2-[2-[(3-Chloro-4-methyl-phenyl)sulfonyl]-1,2,3,4-tetrahydro-pyrrolo[1,2-a]pyrazin-1-yl]-N-[6-[(4-methyl-piperazin-1-yl)-methyl]-1,2,3,4-tetrahydro-naphthalen-1-yl]-acetamide 56 2-[2-[(3-Chloro-4-methyl-phenyl)sulfonyl]-1,2,3,4-tetrahydro-pyrrolo[1,2-a]pyrazin-1-yl]-N-[6-(piperidin-1-yl-methyl)-1,2,3,4-tetrahydro-naphthalen-1-yl]-acetamide 57 2-[2-[(3-Chloro-4-methyl-phenyl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-1-yl]-acetamide 58 N-[6-(Dimethylaminomethyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide 59 N-[6-[(4-Methyl-piperazin-1-yl)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 60 N-[6-[(tert-Butylamino)-methyl]-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide 61 2-[2-[(3-Chloro-4-methyl-phenyl)sulfonyl]-1,2,3,4-tetrahydro-pyrrolo[1,2-a]pyrazin-1-yl]-N-[6-[(4-methyl-piperazin-1-yl)-methyl]-1,2,3,4-tetrahydro-naphthalen-2-yl]-acetamide 62 N-[6-[(1-Methyl-propylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 63 2-[2-[(3-Chloro-4-methyl-phenyl)sulfonyl]-1,2,3,4-tetrahydro-pyrrolo[1,2-a]pyrazin-1-yl]-N-[6-[(1-methyl-propylamino)-methyl]-1,2,3,4-tetrahydro-naphthalen-2-yl]-acetamide 64  N-[6-[(tert-Butylamino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 65  N-[6-[(1-Methyl-propylamino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 66  2-[2-[(3-Chloro-4-methyl-phenyl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-2-yl]-acetamide 67  N-[6-(Morpholin-4-yl-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 68  N-[6-[(4-Methyl-piperazin-1-yl)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 69  N-[6-(1,2,3,4-Tetrahydro-quinolin-1-yl-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 70  N-[6-[(tert-Butylamino)-methyl]-1,2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide 71  N-[6-(8-Azabicyclo[3.2.1]octan-8-yl-methyl)-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide 72  N-[6-[(tert-Butylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 73  N-[6-[(tert-Butyl-methyl-amino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide 74  N-[6-[(tert-Butyl-methyl-amino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 75  N-[6-[(tert-Butyl-methyl-amino)-methyl]-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide 76  N-[6-[(tert-Butyl-methyl-amino)-methyl]-1,2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide 77  N-[6-(8-Azabicyclo[3.2.1]octan-8-yl-methyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide 78  N-[6-[(4-Methyl-piperazin-1-yl)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 79  2-[2-(p-Tolylsulfonyl)-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-2-yl]-acetamide 80  N-[6-(Piperidin-1-yl-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 81  N-[6-[(4-Methyl-piperazin-1-yl)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide 82  N-[6-[(tert-Butylamino)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 83  N-[6-[(Benzylamino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 84  N-[6-(Pyrrolidin-1-yl-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 85  2-[2-(p-Tolylsulfonyl)-1,2,3,4-tetrahydro-pyrrolo[1,2-a]pyrazin-1-yl]-N-[6-(pyrrolidin-1-yl-methyl)-1,2,3,4-tetrahydro-naphthalen-1-yl]-acetamide 86  N-[6-(Pyrrolidin-1-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 87  N-[6-(Morpholin-4-yl-methyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide 88  N-[6-(8-Azabicyclo[3.2.1]octan-8-yl-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 89  N-[6-(Piperidin-1-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 90  N-[6-(1,2,3,4-Tetrahydro-quinolin-1-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 91  2-[2-[(3-Chloro-4-methyl-phenyl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-1-yl]-acetamide 92  N-[6-(Dimethylaminomethyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 93  N-[6-[(Benzylamino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide 94  2-[2-[(6-Methoxy-naphthalen-2-yl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-2-yl]-acetamide 95  N-[6-(8-Azabicyclo[3.2.1]octan-8-yl-methyl)-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide 96  N-[6-(Dimethylaminomethyl)-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide 97  N-[6-[(tert-Butyl-methyl-amino)-methyl]-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide 98  2-[2-[(6-Methoxy-naphthalen-2-yl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-1-yl]-acetamide 99  2-[2-[(6-Methoxy-naphthalen-2-yl)sulfonyl]-1,2,3,4-tetrahydro-pyrrolo[1,2-a]pyrazin-1-yl]-N-[6-[(4-methyl-piperazin-1-yl)-methyl]-1,2,3,4-tetrahydro-naphthalen-2-yl]-acetamide 100  N-[6-[(Benzylamino)-methyl]-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide 101  N-[6-[(Benzylamino)-methyl]-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide 102 2-[2-[(3-Chloro-4-methyl-phenyl)sulfonyl]-1,2,3,4-tetrahydro-pyrrolo[1,2-a]pyrazin-1-yl]-N-[6-(dimethylaminomethyl)-1,2,3,4-tetrahydro-naphthalen-1-yl]-acetamide 103 N-[6-(8-Azabicyclo[3.2.1]octan-8-yl-methyl)-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide 104 N-[6-[(tert-Butyl-methyl-amino)-methyl]-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide 105 2-[2-[(6-Methoxy-naphthalen-2-yl)sulfonyl]-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-2-yl]-acetamide 106 N-[6-(Dimethylaminomethyl)-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide 107 N-[6-(Dimethylaminomethyl)-1,2,3,4-tetrahydro-naphthalen-1-yl]-2-[2-[2-(p-tolylsulfonyl)-1,2,3,4-tetrahydro-pyrrolo[1,2-a]pyrazin-1-yl]-acetamide 108 N-[6-(8-Azabicyclo[3.2.1]octan-8-yl-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 109 N-[6-(8-Azabicyclo[3.2.1]octan-8-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 110 N-[6-(8-Azabicyclo[3.2.1]octan-8-yl-methyl)-1,2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide 111 N-[6-[(Benzylamino)-methyl]-1,2,3,4-tetrahydro-naphthalen-1-yl]-2-[2-[2-(3-chloro-4-methyl-phenyl)sulfonyl]-1,2,3,4-tetrahydro-pyrrolo[1,2-a]pyrazin-1-yl]-acetamide 112 N-[6-[(Benzylamino)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 113 N-[6-[(tert-Butyl-methyl-amino)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 114 N-[6-[(tert-Butylamino)-methyl]-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide 115 2-[2-[(3-Chloro-4-methyl-phenyl)sulfonyl]-1,2,3,4-tetrahydro-pyrrolo[1,2-a]pyrazin-1-yl]-N-[6-(dimethylaminomethyl)-1,2,3,4-tetrahydro-naphthalen-2-yl]-acetamide 116 N-[6-[(tert-Butyl-methyl-amino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 117 2-[2-[(6-Methoxy-naphthalen-2-yl)sulfonyl]-1,2,3,4-tetrahydro-pyrrolo[1,2-a]pyrazin-1-yl]-N-[6-[(4-methyl-piperazin-1-yl)-methyl]-1,2,3,4-tetrahydro-naphthalen-1-yl]-acetamide 118 2-[2-[(6-Methoxy-naphthalen-2-yl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-2-yl]-acetamide 119 2-[2-[(3-Chloro-4-methyl-phenyl)sulfonyl]-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-1-yl]-acetamide 120 2-[2-[(6-Methoxy-naphthalen-2-yl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-1-yl]-acetamide 121 2-[2-[(6-Methoxy-naphthalen-2-yl)sulfonyl]-1,2,3,4-tetrahydro-pyrrolo[1,2-a]pyrazin-1-yl]-N-[6-[(1-methyl-propylamino)-methyl]-1,2,3,4-tetrahydro-naphthalen-2-yl]-acetamide 122 N-[6-[(tert-Butylamino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide 123 2-[2-(p-Tolylsulfonyl)-1,2,3,4-tetrahydro-pyrrolo[1,2-a]pyrazin-1-yl]-N-[6-(pyrrolidin-1-yl-methyl)-1,2,3,4-tetrahydro-naphthalen-2-yl]-acetamide 124 N-[6-(Dimethylaminomethyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 125 2-[2-[(6-Methoxy-naphthalen-2-yl)sulfonyl]-1,2,3,4-tetrahydro-pyrrolo[1,2-a]pyrazin-1-yl]-N-[6-[(1-methyl-propylamino)-methyl]-1,2,3,4-tetrahydro-naphthalen-1-yl]-acetamide 126 N-[6-[(1-Methyl-propylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 127 N-[6-[(Benzylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 128 2-[2-[(6-Methoxy-naphthalen-2-yl)sulfonyl]-1,2,3,4-tetrahydro-pyrrolo[1,2-a]pyrazin-1-yl]-N-[6-(piperidin-1-yl-methyl)-1,2,3,4-tetrahydro-naphthalen-1-yl]-acetamide 129 2-[2-(p-Tolylsulfonyl)-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-1-yl]-acetamide 130 2-[2-[(6-Methoxy-naphthalen-2-yl)sulfonyl]-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-1-yl]-acetamide 131 N-[6-[(1-Methyl-propylamino)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 132 2-[2-[(3-Chloro-4-methyl-phenyl)sulfonyl]-1,2,3,4-tetrahydro-pyrrolo[1,2-a]pyrazin-1-yl]-N-[6-[(1-methyl-propylamino)-methyl]-1,2,3,4-tetrahydro-naphthalen-1-yl]-acetamide 133 N-[6-(Methylamino-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide 134 2-[2-[(6-Methoxy-naphthalen-2-yl)sulfonyl]-1,2,3,4-tetrahydro-pyrrolo[1,2-a]pyrazin-1-yl]-N-[6-(methylamino-methyl)-1,2,3,4-tetrahydro-naphthalen-1-yl]-acetamide 135 N-[6-(Methylamino-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide 136 2-[2-[(3-Chloro-4-methyl-phenyl)sulfonyl]-1,2,3,4-tetrahydro-pyrrolo[1,2-a]pyrazin-1-yl]-N-[6-(methylamino-methyl)-1,2,3,4-tetrahydro-naphthalen-1-yl]-acetamide 137 2-[2-[(6-Methoxy-naphthalen-2-yl)sulfonyl]-1,2,3,4-tetrahydro-pyrrolo[1,2-a]pyrazin-1-yl]-N-[6-(methylamino-methyl)-1,2,3,4-tetrahydro-naphthalen-2-yl]-acetamide 138 2-[2-[(3-Chloro-4-methyl-phenyl)sulfonyl]-1,2,3,4-tetrahydro-pyrrolo[1,2-a]pyrazin-1-yl]-N-[6-(methylamino-methyl)-1,2,3,4-tetrahydro-naphthalen-2-yl]-acetamide 139 N-[6-(Methylamino-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide 140 N-[6-(Methylamino-methyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide 141 1-(4-Hydroxy-4-pyridin-3-yl-piperidin-1-yl)-2-[2-[(4-methoxy-2,6-dimethyl-phenyl)sulfonyl]-1,2,3,4-tetrahydro-pyrrolo[1,2-a]pyrazin-1-yl]-ethanone 142 2-[2-[(4-Methoxy-2,6-dimethyl-phenyl)sulfonyl]-1,2,3,4-tetrahydro-pyrrolo[1,2-a]pyrazin-1-yl]-N-(3-morpholin-4-yl-propyl)-acetamide 143 N-[3-(2,6-Dimethyl-piperidin-1-yl)-propyl]-2-[2-[(4-methoxy-2,6-dimethyl-phenyl)sulfonyl]-1,2,3,4-tetrahydro-pyrrolo[1,2-a]pyrazin-1-yl]-acetamide 144 1-[4-(2-Fluorophenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone 145 2-[2-[(4-Methoxy-2,6-dimethyl-phenyl)sulfonyl]-1,2,3,4-tetrahydro-pyrrolo[1,2-a]pyrazin-1-yl]-1-(4-phenyl-piperazin-1-yl)-ethanone 146 2-[2-[(4-Methoxy-2,6-dimethyl-phenyl)sulfonyl]-1,2,3,4-tetrahydro-pyrrolo[1,2-a]pyrazin-1-yl]-1-[4-(2-piperidin-1-yl-ethyl)-piperidin-1-yl]-ethanone 147 1-[4-[2-(2,5-Dimethyl-1H-pyrrol-1-yl)-ethyl]-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone 148 2-[2-[(4-Methoxy-2,6-dimethyl-phenyl)sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone 149 2-[2-[(4-Methoxy-2,6-dimethyl-phenyl)sulfonyl]-1,2,3,4-tetrahydro-pyrrolo[1,2-a]pyrazin-1-yl]-1-(4-pyridin-2-yl-piperazin-1-yl)-ethanone 150 2-[4-[2-[2-[(4-Methoxy-2,6-dimethyl-phenyl)sulfonyl]-1,2,3,4-tetrahydro-pyrrolo[1,2-a]pyrazin-1-yl]-acetyl]-[1,4]diazepan-1-yl]-pyridine-3-carbonitrile 151 N-[(1-Benzyl-pyrrolidin-3-yl)-methyl]-2-[2-[(4-methoxy-2,6-dimethyl-phenyl)sulfonyl]-1,2,3,4-tetrahydro-pyrrolo[1,2-a]pyrazin-1-yl]-acetamide 152 2-[2-[(4-Methoxy-2,6-dimethyl-phenyl)sulfonyl]-1,2,3,4-tetrahydro-pyrrolo[1,2-a]pyrazin-1-yl]-1-[4-[5-(trifluoromethyl)-pyridin-2-yl]-piperazin-1-yl]-ethanone 153 2-[2-[(2-Chloro-6-methyl-phenyl)sulfonyl]-1,2,3,4-tetrahydro-pyrrolo[1,2-a]pyrazin-1-yl]-N-(2-pyrrolidin-1-yl-ethyl)-acetamide 154 2-[2-[(2-Chloro-6-methyl-phenyl)sulfonyl]-1,2,3,4-tetrahydro-pyrrolo[1,2-a]pyrazin-1-yl]-N-(3-morpholin-4-yl-propyl)-acetamide 155 2-[2-[(2-Chloro-6-methyl-phenyl)sulfonyl]-1,2,3,4-tetrahydro-pyrrolo[1,2-a]pyrazin-1-yl]-N-[3-(2,6-dimethyl-piperidin-1-yl)-propyl]-acetamide 156 2-[2-[(2-Chloro-6-methyl-phenyl)sulfonyl]-1,2,3,4-tetrahydro-pyrrolo[1,2-a]pyrazin-1-yl]-N-[2-(4-methyl-piperazin-1-yl)-1-phenyl-ethyl]-acetamide 157 N-(1-Benzyl-pyrrolidin-3-yl)-2-[2-[(2-chloro-6-methyl-phenyl)sulfonyl]-1,2,3,4-tetrahydro-pyrrolo[1,2-a]pyrazin-1-yl]-acetamide 158 2-[2-[(2-Chloro-6-methyl-phenyl)sulfonyl]-1,2,3,4-tetrahydro-pyrrolo[1,2-a]pyrazin-1-yl]-1-(4-(2-fluorophenyl)-piperazin-1-yl)-ethanone 159 2-[2-[(2-Chloro-6-methyl-phenyl)sulfonyl]-1,2,3,4-tetrahydro-pyrrolo[1,2-a]pyrazin-1-yl]-1-(4-morpholin-4-yl-piperidin-1-yl)-ethanone 160 2-[2-[(2-Chloro-6-methyl-phenyl)sulfonyl]-1,2,3,4-tetrahydro-pyrrolo[1,2-a]pyrazin-1-yl]-1-(4-piperidin-1-yl-piperidin-1-yl)-ethanone 161 2-[2-[(2-Chloro-6-methyl-phenyl)sulfonyl]-1,2,3,4-tetrahydro-pyrrolo[1,2-a]pyrazin-1-yl]-1-[4-(4-methyl-piperazin-1-yl)-piperidin-1-yl]-ethanone 162 2-[2-[(2-Chloro-6-methyl-phenyl)sulfonyl]-1,2,3,4-tetrahydro-pyrrolo[1,2-a]pyrazin-1-yl]-1-(4-pyrimidin-2-yl-piperazin-1-yl)-ethanone 163 2-[2-[(2-Chloro-6-methyl-phenyl)sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone 164 2-[4-[2-[2-[(2-Chloro-6-methyl-phenyl)sulfonyl]-1,2,3,4-tetrahydro-pyrrolo[1,2-a]pyrazin-1-yl]-acetyl]-[1,4]diazepan-1-yl]-pyridine-3-carbonitrile 165 2-[2-[(2-Chloro-6-methyl-phenyl)sulfonyl]-1,2,3,4-tetrahydro-pyrrolo[1,2-a]pyrazin-1-yl]-1-[4-(2-piperidin-1-yl-ethyl)-piperidin-1-yl]-ethanone 166 N-[(1-Benzyl-pyrrolidin-3-yl)-methyl]-2-[2-[(2-chloro-6-methyl-phenyl)sulfonyl]-1,2,3,4-tetrahydro-pyrrolo[1,2-a]pyrazin-1-yl]-acetamide 167 2-[2-(Benzenesulfonyl)-1,2,3,4-tetrahydro-pyrrolo[1,2-a]pyrazin-1-yl]-1-(4-hydroxy-4-pyridin-3-yl-piperidin-1-yl)-ethanone 168 2-[2-(Benzenesulfonyl)-1,2,3,4-tetrahydro-pyrrolo[1,2-a]pyrazin-1-yl]-N-(2-pyrrolidin-1-yl-ethyl)-acetamide 169 2-[2-(Benzenesulfonyl)-1,2,3,4-tetrahydro-pyrrolo[1,2-a]pyrazin-1-yl]-N-[3-(2,6-dimethyl-piperidin-1-yl)-propyl]-acetamide 170 2-[2-(Benzenesulfonyl)-1,2,3,4-tetrahydro-pyrrolo[1,2-a]pyrazin-1-yl]-N-[2-(4-methyl-piperazin-1-yl)-1-phenyl-ethyl]-acetamide 171 2-[2-(Benzenesulfonyl)-1,2,3,4-tetrahydro-pyrrolo[1,2-a]pyrazin-1-yl]-N-(1-benzyl-pyrrolidin-3-yl)-acetamide 172 2-[2-(Benzenesulfonyl)-1,2,3,4-tetrahydro-pyrrolo[1,2-a]pyrazin-1-yl]-1-[4-(2-fluorophenyl)-piperazin-1-yl]-ethanone 173 2-[2-(Benzenesulfonyl)-1,2,3,4-tetrahydro-pyrrolo[1,2-a]pyrazin-1-yl]-1-(4-ethyl-piperazin-1-yl)-ethanone 174 2-[2-(Benzenesulfonyl)-1,2,3,4-tetrahydro-pyrrolo[1,2-a]pyrazin-1-yl]-1-(4-phenyl-piperazin-1-yl)-ethanone 175 2-[2-(Benzenesulfonyl)-1,2,3,4-tetrahydro-pyrrolo[1,2-a]pyrazin-1-yl]-1-(4-pyrrolidin-1-yl-piperidin-1-yl)-ethanone 176 2-[2-(Benzenesulfonyl)-1,2,3,4-tetrahydro-pyrrolo[1,2-a]pyrazin-1-yl]-1-(4-morpholin-4-yl-piperidin-1-yl)-ethanone 177 2-[2-(Benzenesulfonyl)-1,2,3,4-tetrahydro-pyrrolo[1,2-a]pyrazin-1-yl]-1-[4-(4-methyl-piperazin-1-yl)-piperidin-1-yl]-ethanone 178 2-[2-(Benzenesulfonyl)-1,2,3,4-tetrahydro-pyrrolo[1,2-a]pyrazin-1-yl]-1-[4-[2-(2,5-dimethyl-1H-pyrrol-1-yl)-ethyl]piperazin-1-yl]-ethanone 179 2-[2-(Benzenesulfonyl)-1,2,3,4-tetrahydro-pyrrolo[1,2-a]pyrazin-1-yl]-1-(4-pyrimidin-2-yl-piperazin-1-yl)-ethanone 180 2-[2-(Benzenesulfonyl)-1,2,3,4-tetrahydro-pyrrolo[1,2-a]pyrazin-1-yl]-1-[4-(5-methyl-1H-benzoimidazol-2-yl)-piperidin-1-yl]-ethanone 181 2-[4-[2-[2-(Benzenesulfonyl)-1,2,3,4-tetrahydro-pyrrolo[1,2-a]pyrazin-1-yl]-acetyl][1,4]diazepan-1-yl]-pyridine-3-carbonitrile 182 2-[2-(Benzenesulfonyl)-1,2,3,4-tetrahydro-pyrrolo[1,2-a]pyrazin-1-yl]-N-[(1-benzyl-pyrrolidin-3-yl)-methyl]-acetamide 183 2-[2-(Benzenesulfonyl)-1,2,3,4-tetrahydro-pyrrolo[1,2-a]pyrazin-1-yl]-1-[4-[5-(trifluoromethyl)-pyridin-2-yl]-piperazin-1-yl]-ethanone 184 N-[3-(2,6-Dimethyl-piperidin-1-yl)-propyl]-2-[2-[[3-(trifluoromethyl)phenyl]sulfonyl]-1,2,3,4-tetrahydro-pyrrolo[1,2-a]pyrazin-1-yl]-acetamide 185 N-[2-(4-Methyl-piperazin-1-yl)-1-phenyl-ethyl]-2-[2-[[3-(trifluoromethyl)phenyl]sulfonyl]-1,2,3,4-tetrahydro-pyrrolo[1,2-a]pyrazin-1-yl]-acetamide 186 1-[4-(2-Fluorophenyl)-piperazin-1-yl]-2-[2-[[3-(trifluoromethyl)phenyl]sulfonyl]-1,2,3,4-tetrahydro-pyrrolo[1,2-a]pyrazin-1-yl]-ethanone 187 1-(4-Ethyl-piperazin-1-yl)-2-[2-[[3-(trifluoromethyl)phenyl]sulfonyl]-1,2,3,4-tetrahydro-pyrrolo[1,2-a]pyrazin-1-yl]-ethanone 188 1-(4-Piperidin-1-yl-piperidin-1-yl)-2-[2-[[3-(trifluoromethyl)phenyl]sulfonyl]-1,2,3,4-tetrahydro-pyrrolo[1,2-a]pyrazin-1-yl]-ethanone 189 1-[4-(5-Methyl-1H-benzoimidazol-2-yl)-piperidin-1-yl]-2-[2-[[3-(trifluoromethyl)phenyl]sulfonyl]-1,2,3,4-tetrahydro-pyrrolo[1,2-a]pyrazin-1-yl]-ethanone 190 1-(4-Pyridin-2-yl-piperazin-1-yl)-2-[2-[[3-(trifluoromethyl)phenyl]sulfonyl]-1,2,3,4-tetrahydro-pyrrolo[1,2-a]pyrazin-1-yl]-ethanone 191 2-[4-[2-[2-[[3-(Trifluoromethyl)phenyl]sulfonyl]-1,2,3,4-tetrahydro-pyrrolo[1,2-a]pyrazin-1-yl]-acetyl]-[1,4]diazepan-1-yl]-pyridine-3-carbonitrile 192 N-[(1-Benzyl-pyrrolidin-3-yl)-methyl]-2-[2-[[3-(trifluoromethyl)phenyl]sulfonyl]-1,2,3,4-tetrahydro-pyrrolo[1,2-a]pyrazin-1-yl]-acetamide 193 2-[2-[(4-Chloro-2,5-dimethyl-phenyl)sulfonyl]-1,2,3,4-tetrahydro-pyrrolo[1,2-a]pyrazin-1-yl]-N-[3-(2,6-dimethyl-piperidin-1-yl)-propyl]-acetamide 194 2-[2-[(4-Chloro-2,5-dimethyl-phenyl)sulfonyl]-1,2,3,4-tetrahydro-pyrrolo[1,2-a]pyrazin-1-yl]-N-[2-(4-methyl-piperazin-1-yl)-1-phenyl-ethyl]-acetamide 195 2-[2-[(4-Chloro-2,5-dimethyl-phenyl)sulfonyl]-1,2,3,4-tetrahydro-pyrrolo[1,2-a]pyrazin-1-yl]-1-[4-(2-fluorophenyl)-piperazin-1-yl]-ethanone 196 2-[2-[(4-Chloro-2,5-dimethyl-phenyl)sulfonyl]-1,2,3,4-tetrahydro-pyrrolo[1,2-a]pyrazin-1-yl]-1-[4-(5-methyl-1H-benzoimidazol-2-yl)-piperidin-1-yl]ethanone 197 2-[4-[2-[2-[(4-Chloro-2,5-dimethyl-phenyl)sulfonyl]-1,2,3,4-tetrahydro-pyrrolo[1,2-a]pyrazin-1-yl]-acetyl]-[1,4]diazepan-1-yl]-pyridine-3-carbonitrile 198 N-[(1-Benzyl-pyrrolidin-3-yl)-methyl]-2-[2-[(4-chloro-2,5-dimethyl-phenyl)sulfonyl]-1,2,3,4-tetrahydro-pyrrolo[1,2-a]pyrazin-1-yl]-acetamide 199 2-[2-[[2-Chloro-4-(trifluoromethyl)-phenyl]sulfonyl]-1,2,3,4-tetrahydro-pyrrolo[1,2-a]pyrazin-1-yl]-N-[3-(2,6-dimethyl-piperidin-1-yl)-propyl]-acetamide 200 2-[2-[[2-Chloro-4-(trifluoromethyl)-phenyl]sulfonyl]-1,2,3,4-tetrahydro-pyrrolo[1,2-a]pyrazin-1-yl]-N-[2-(4-methyl-piperazin-1-yl)-1-phenyl-ethyl]-acetamide 201 2-[2-[[2-Chloro-4-(trifluoromethyl)-phenyl]sulfonyl]-1,2,3,4-tetrahydro-pyrrolo[1,2-a]pyrazin-1-yl]-1-[4-(2-fluorophenyl)-piperazin-1-yl]-ethanone 202 2-[2-[[2-Chloro-4-(trifluoromethyl)-phenyl]sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone 203 2-[2-[[2-Chloro-4-(trifluoromethyl)-phenyl]sulfonyl]-1,2,3,4-tetrahydro-pyrrolo[1,2-a]pyrazin-1-yl]-1-(4-pyridin-2-yl-piperazin-1-yl)-ethanone 204 2-[4-[2-[2-[[2-Chloro-4-(trifluoromethyl)-phenyl]sulfonyl]-1,2,3,4-tetrahydro-pyrrolo[1,2-a]pyrazin-1-yl]-acetyl]-[1,4]diazepan-1-yl]-pyridine-3-carbonitrile 205 N-[(1-Benzyl-pyrrolidin-3-yl)-methyl]-2-[2-[[2-chloro-4-(trifluoromethyl)-phenyl]sulfonyl]-1,2,3,4-tetrahydro-pyrrolo[1,2-a]pyrazin-1-yl]-acetamide 206 2-[2-[(4-Methoxy-2,6-dimethyl-phenyl)sulfonyl]-1,2,3,4-tetrahydro-pyrrolo[1,2-a]pyrazin-1-yl]-1-[2-(pyridin-2-yl-methyl)-pyrrolidin-1-yl]-ethanone 207 2-[2-[(4-Methoxy-2,6-dimethyl-phenyl)sulfonyl]-1,2,3,4-tetrahydro-pyrrolo[1,2-a]pyrazin-1-yl]-N-(3-piperidin-1-yl-propyl)-acetamide 208 1-[4-(5-Chloro-2-methyl-phenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone 209 1-[4-(4-Chlorophenyl)-4-hydroxy-piperidin-1-yl]-2-[2-[(4-methoxy-2,6-dimethyl-phenyl)sulfonyl]-1,2,3,4-tetrahydro-pyrrolo[1,2-a]pyrazin-1-yl]-ethanone 210 1-(4-Benzyl-4-hydroxy-piperidin-1-yl)-2-[2-[(4-methoxy-2,6-dimethyl-phenyl)sulfonyl]-1,2,3,4-tetrahydro-pyrrolo[1,2-a]pyrazin-1-yl]-ethanone 211 1-[4-Hydroxy-4-[3-(trifluoromethyl)phenyl]-piperidin-1-yl]-2-[2-[(4-methoxy-2,6-dimethyl-phenyl)sulfonyl]-1,2,3,4-tetrahydro-pyrrolo[1,2-a]pyrazin-1-yl]-ethanone 212 2-[2-[(4-Methoxy-2,6-dimethyl-phenyl)sulfonyl]-1,2,3,4-tetrahydro-pyrrolo[1,2-a]pyrazin-1-yl]-N-methyl-N-(2-piperidin-1-yl-ethyl)-acetamide 213 2-[2-[(4-Methoxy-2,6-dimethyl-phenyl)sulfonyl]-1,2,3,4-tetrahydro-pyrrolo[1,2-a]pyrazin-1-yl]-1-[2-(piperidin-1-yl-methyl)-pyrrolidin-1-yl]-ethanone 214 2-[2-[(4-Methoxy-2,6-dimethyl-phenyl)sulfonyl]-1,2,3,4-tetrahydro-pyrrolo[1,2-a]pyrazin-1-yl]-1-[4-(3-methoxyphenyl)-piperazin-1-yl]-ethanone 215 1-[4-(4-Fluorophenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone 216 1-(4-Isopropyl-piperazin-1-yl)-2-[2-[(4-methoxy-2,6-dimethyl-phenyl)sulfonyl]-1,2,3,4-tetrahydro-pyrrolo[1,2-a]pyrazin-1-yl]-ethanone 217 2-[2-[(2-Chloro-6-methyl-phenyl)sulfonyl]-1,2,3,4-tetrahydro-pyrrolo[1,2-a]pyrazin-1-yl]-1-[2-(pyridin-2-yl-methyl)-pyrrolidin-1-yl]-ethanone 218 2-[2-[(2-Chloro-6-methyl-phenyl)sulfonyl]-1,2,3,4-tetrahydro-pyrrolo[1,2-a]pyrazin-1-yl]-N-(3-piperidin-1-yl-propyl)-acetamide 219 2-[2-[(2-Chloro-6-methyl-phenyl)sulfonyl]-1,2,3,4-tetrahydro-pyrrolo[1,2-a]pyrazin-1-yl]-1-(4-hydroxy-4-phenyl-piperidin-1-yl)-ethanone 220 2-[2-[(2-Chloro-6-methyl-phenyl)sulfonyl]-1,2,3,4-tetrahydro-pyrrolo[1,2-a]pyrazin-1-yl]-1-[4-hydroxy-4-[3-(trifluoromethyl)phenyl]-piperidin-1-yl]-ethanone 221 2-[2-[(2-Chloro-6-methyl-phenyl)sulfonyl]-1,2,3,4-tetrahydro-pyrrolo[1,2-a]pyrazin-1-yl]-N-methyl-N-[2-(4-methyl-piperazin-1-yl)-1-phenyl-ethyl]-acetamide 222 2-[2-[(2-Chloro-6-methyl-phenyl)sulfonyl]-1,2,3,4-tetrahydro-pyrrolo[1,2-a]pyrazin-1-yl]-N-methyl-N-(2-piperidin-1-yl-ethyl)-acetamide 223 2-[2-[(2-Chloro-6-methyl-phenyl)sulfonyl]-1,2,3,4-tetrahydro-pyrrolo[1,2-a]pyrazin-1-yl]-1-[4-(3-methoxyphenyl)-piperazin-1-yl]-ethanone 224 2-[2-[(2-Chloro-6-methyl-phenyl)sulfonyl]-1,2,3,4-tetrahydro-pyrrolo[1,2-a]pyrazin-1-yl]-1-[4-(4-fluorophenyl)-piperazin-1-yl]-ethanone 225 2-[2-[(2-Chloro-6-methyl-phenyl)sulfonyl]-1,2,3,4-tetrahydro-pyrrolo[1,2-a]pyrazin-1-yl]-1-(4-isopropyl-piperazin-1-yl)-ethanone 226 2-[2-(Benzenesulfonyl)-1,2,3,4-tetrahydro-pyrrolo[1,2-a]pyrazin-1-yl]-1-[4-(5-chloro-2-methyl-phenyl)-piperazin-1-yl]-ethanone 227 2-[2-(Benzenesulfonyl)-1,2,3,4-tetrahydro-pyrrolo[1,2-a]pyrazin-1-yl]-1-[4-(4-chlorophenyl)-4-hydroxy-piperidin-1-yl]-ethanone
228 2-[2-(Benzenesulfonyl)-1,2,3,4-tetrahydro-pyrrolo[1,2-a]pyrazin-1-yl]-1-(4-hydroxy-4-phenyl-piperidin-1-yl)-ethanone
229 2-[2-(Benzenesulfonyl)-1,2,3,4-tetrahydro-pyrrolo[1,2-a]pyrazin-1-yl]-1-[4-(4-methoxyphenyl)-piperazin-1-yl]-ethanone
230 2-[2-[(4-Chloro-2,5-dimethyl-phenyl)sulfonyl]-1,2,3,4-tetrahydro-pyrrolo[1,2-a]pyrazin-1-yl]-N-methyl-N-[2-(4-methyl-piperazin-1-yl)-1-phenyl-ethyl]-acetamide
231 2-[2-(Benzenesulfonyl)-1,2,3,4-tetrahydro-pyrrolo[1,2-a]pyrazin-1-yl]-1-[4-(3,4-dichlorophenyl)-piperazin-1-yl]-ethanone
232 2-[2-(Benzenesulfonyl)-1,2,3,4-tetrahydro-pyrrolo[1,2-a]pyrazin-1-yl]-1-[4-(p-tolyl-methyl)-piperazin-1-yl]-ethanone
233 2-[2-(Benzenesulfonyl)-1,2,3,4-tetrahydro-pyrrolo[1,2-a]pyrazin-1-yl]-1-[4-[(4-methoxyphenyl)-methyl]-piperazin-1-yl]-ethanone
234 2-[2-(Benzenesulfonyl)-1,2,3,4-tetrahydro-pyrrolo[1,2-a]pyrazin-1-yl]-1-[4-[(2-fluorophenyl)-methyl]-piperazin-1-yl]-ethanone
235 2-[2-(Benzenesulfonyl)-1,2,3,4-tetrahydro-pyrrolo[1,2-a]pyrazin-1-yl]-N-[(1-benzyl-piperidin-3-yl)-methyl]-acetamide
236 2-[2-[[3-(Trifluoromethyl)phenyl]sulfonyl]-1,2,3,4-tetrahydro-pyrrolo[1,2-a]pyrazin-1-yl]-1-[4-[(2,4,6-trimethyl-phenyl)-methyl]-piperazin-1-yl]-ethanone
237 2-[2-[[2-Chloro-4-(trifluoromethyl)-phenyl]sulfonyl]-1,2,3,4-tetrahydro-pyrrolo[1,2-a]pyrazin-1-yl]-1-[4-(4-methoxyphenyl)-piperazin-1-yl]-ethanone
238 1-[4-(3,4-Dichlorophenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone
239 2-[2-[(4-Methoxy-2,6-dimethyl-phenyl)sulfonyl]-1,2,3,4-tetrahydro-pyrrolo[1,2-a]pyrazin-1-yl]-1-[4-[(2,4,6-trimethyl-phenyl)-methyl]-piperazin-1-yl]-ethanone
240 1-[4-[(4-Chlorophenyl)-methyl]-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone
241 2-[2-[(4-Methoxy-2,6-dimethyl-phenyl)sulfonyl]-1,2,3,4-tetrahydro-pyrrolo[1,2-a]pyrazin-1-yl]-1-[4-(p-tolyl-methyl)-piperazin-1-yl]-ethanone
242 2-[2-[(4-Methoxy-2,6-dimethyl-phenyl)sulfonyl]-1,2,3,4-tetrahydro-pyrrolo[1,2-a]pyrazin-1-yl]-1-[4-[(4-methoxyphenyl)-methyl]-piperazin-1-yl]-ethanone
243 1-[4-[(2-Fluorophenyl)-methyl]-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone
244 2-[2-[(4-Methoxy-2,6-dimethyl-phenyl)sulfonyl]-1,2,3,4-tetrahydro-pyrrolo[1,2-a]pyrazin-1-yl]-1-[2-(pyridin-2-yl-methyl)-piperidin-1-yl]-ethanone
245 2-[2-[(4-Methoxy-2,6-dimethyl-phenyl)sulfonyl]-1,2,3,4-tetrahydro-pyrrolo[1,2-a]pyrazin-1-yl]-1-[2-(pyridin-4-yl-methyl)-piperidin-1-yl]-ethanone
246 1-[4-(1,3-Benzodioxol-5-yl-methyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone
247 3-[4-[2-[2-[(4-Methoxy-2,6-dimethyl-phenyl)sulfonyl]-1,2,3,4-tetrahydro-pyrrolo[1,2-a]pyrazin-1-yl]-acetyl]-piperazin-1-yl]-propionitrile
248 N-[(1-Benzyl-piperidin-3-yl)-methyl]-2-[2-[(4-methoxy-2,6-dimethyl-phenyl)sulfonyl]-1,2,3,4-tetrahydro-pyrrolo[1,2-a]pyrazin-1-yl]-acetamide
249 2-[2-[(2-Chloro-6-methyl-phenyl)sulfonyl]-1,2,3,4-tetrahydro-pyrrolo[1,2-a]pyrazin-1-yl]-1-[4-[(4-chlorophenyl)-methyl]-piperazin-1-yl]-ethanone
250 2-[2-[(2-Chloro-6-methyl-phenyl)sulfonyl]-1,2,3,4-tetrahydro-pyrrolo[1,2-a]pyrazin-1-yl]-1-[2-(pyridin-2-yl-methyl)-piperidin-1-yl]-ethanone
251 2-[2-[(2-Chloro-6-methyl-phenyl)sulfonyl]-1,2,3,4-tetrahydro-pyrrolo[1,2-a]pyrazin-1-yl]-1-[2-(pyridin-4-yl-methyl)-piperidin-1-yl]-ethanone
252 1-[4-(1,3-Benzodioxol-5-yl-methyl)-piperazin-1-yl]-2-[2-[(2-chloro-6-methyl-phenyl)sulfonyl]-1,2,3,4-tetrahydro-pyrrolo[1,2-a]pyrazin-1-yl]-ethanone
253 3-[4-[2-[2-[(2-Chloro-6-methyl-phenyl)sulfonyl]-1,2,3,4-tetrahydro-pyrrolo[1,2-a]pyrazin-1-yl]-acetyl]-piperazin-1-yl]-propionitrile
254 N-[(1-Benzyl-piperidin-3-yl)-methyl]-2-[2-[[2-chloro-4-(trifluoromethyl)-phenyl]sulfonyl]-1,2,3,4-tetrahydro-pyrrolo[1,2-a]pyrazin-1-yl]-acetamide
255 1-[2-(4-Dimethylaminophenyl)-azepan-1-yl]-2-[2-[(4-methoxy-2,6-dimethyl-phenyl)sulfonyl]-1,2,3,4-tetrahydro-pyrrolo[1,2-a]pyrazin-1-yl]-ethanone
256 2-[2-[(4-Methoxy-2,6-dimethyl-phenyl)sulfonyl]-1,2,3,4-tetrahydro-pyrrolo[1,2-a]pyrazin-1-yl]-N-methyl-N-(2-morpholin-4-yl-1-phenyl-ethyl)-acetamide
257 1-(4-Benzyl-piperidin-1-yl)-2-[2-[(4-methoxy-2,6-dimethyl-phenyl)sulfonyl]-1,2,3,4-tetrahydro-pyrrolo[1,2-a]pyrazin-1-yl]-ethanone
258 1-[4-(2-Hydroxy-ethyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone
259 2-[2-[(2-Chloro-6-methyl-phenyl)sulfonyl]-1,2,3,4-tetrahydro-pyrrolo[1,2-a]pyrazin-1-yl]-N-methyl-N-(2-morpholin-4-yl-1-phenyl-ethyl)-acetamide
260 2-[2-[(2-Chloro-6-methyl-phenyl)sulfonyl]-1,2,3,4-tetrahydro-pyrrolo[1,2-a]pyrazin-1-yl]-1-[(2S)-2-(pyrrolidin-1-yl-methyl)-pyrrolidin-1-yl]-ethanone
261 2-[4-[2-[2-[(2-Chloro-6-methyl-phenyl)sulfonyl]-1,2,3,4-tetrahydro-pyrrolo[1,2-a]pyrazin-1-yl]-acetyl]-piperazin-1-yl]-pyridine-3-carbonitrile
262 2-[2-[(2-Chloro-6-methyl-phenyl)sulfonyl]-1,2,3,4-tetrahydro-pyrrolo[1,2-a]pyrazin-1-yl]-1-[4-[3-chloro-5-(trifluoromethyl)-pyridin-2-yl]-piperazin-1-yl]-ethanone
263 2-[2-[(2-Chloro-6-methyl-phenyl)sulfonyl]-1,2,3,4-tetrahydro-pyrrolo[1,2-a]pyrazin-1-yl]-1-[4-(2-hydroxy-ethyl)-piperazin-1-yl]-ethanone
264 2-[2-(Benzenesulfonyl)-1,2,3,4-tetrahydro-pyrrolo[1,2-a]pyrazin-1-yl]-1-[(2S)-2-(pyrrolidin-1-yl-methyl)-pyrrolidin-1-yl]-ethanone
265 2-[2-(Benzenesulfonyl)-1,2,3,4-tetrahydro-pyrrolo[1,2-a]pyrazin-1-yl]-1-[4-[3-chloro-5-(trifluoromethyl)-pyridin-2-yl]-piperazin-1-yl]-ethanone
266 2-[2-(Benzenesulfonyl)-1,2,3,4-tetrahydro-pyrrolo[1,2-a]pyrazin-1-yl]-1-[4-[(3,4-dichlorophenyl)-methyl]-piperazin-1-yl]-ethanone
267 2-[2-(Benzenesulfonyl)-1,2,3,4-tetrahydro-pyrrolo[1,2-a]pyrazin-1-yl]-1-(4-methyl-2-phenyl-piperazin-1-yl)-ethanone
268 2-[2-(Benzenesulfonyl)-1,2,3,4-tetrahydro-pyrrolo[1,2-a]pyrazin-1-yl]-1-(4-phenyl-piperidin-1-yl)-ethanone
269 2-[4-[2-[2-[[3-(Trifluoromethyl)phenyl]sulfonyl]-1,2,3,4-tetrahydro-pyrrolo[1,2-a]pyrazin-1-yl]-acetyl]-piperazin-1-yl]-pyridine-3-carbonitrile
270 2-[2-[[2-Chloro-4-(trifluoromethyl)-phenyl]sulfonyl]-1,2,3,4-tetrahydro-pyrrolo[1,2-a]pyrazin-1-yl]-1-[2-(4-dimethylaminophenyl)-pyrrolidin-1-yl]-ethanone
optionally in the form of an isolated enantiomer or an isolated diastereomer, the racemate, the enantiomers, the diastereomers, mixtures of enantiomers or diastereomers, each in the form of their bases and/or physiologically compatible salts, in particular hydrochloride salts.

The numbering of the individual embodiments of the compounds according to the invention used above is retained in the following explanations of the present invention, particularly in the description of the examples.

According to one aspect of the present invention the compounds according to the invention preferably have an antagonistic action on the human B1R receptor or the B1R receptor of the rat. In a preferred embodiment of the invention the compounds according to the invention have an antagonistic action on both the human B1R receptor (hB1R) and on the B1R receptor of the rat (rB1R).

In a preferred embodiment of the present invention the compounds according to the invention exhibit at least 15%, 25%, 50%, 70%, 80% or 90% inhibition on the human B1R receptor and/or on the B1R receptor of the rat in the FLIPR assay at a concentration of 10 μM. Most particularly preferred are compounds which exhibit at least 70%, in particular at least 80% and particularly preferably at least 90% inhibition on the human B1R receptor and on the B1R receptor of the rat at a concentration of 10 μM.

The agonistic or antagonistic action of substances on the bradykinin 1 receptor (B1R) of the human and rat species can be quantified with ectopically expressing cell lines (CHO K1 cells) and with the aid of a $Ca^{2+}$-sensitive dye (Fluo-4) using a fluorescent imaging plate reader (FLIPR). The value in % activation is based on the $Ca^{2+}$ signal after addition of Lys-Des-Arg$^9$ bradykinin (0.5 nM) or Des-Arg$^9$ bradykinin (100 nM). Antagonists lead to a suppression of the $Ca^{2+}$ influx following administration of the agonist. The % inhibition in comparison with the maximum achievable inhibition is indicated.

The substances according to the invention preferably act, for example, on the relevant B1R in connection with various diseases, such that they are suitable as a pharmaceutical active ingredient in pharmaceutical compositions. The invention therefore also provides pharmaceutical compositions containing at least one sulfonylated tetrahydroazolopyrazine according to the invention, optionally along with suitable additives and/or auxiliary substances and/or optionally further active ingredients.

The pharmaceutical compositions according to the invention are preferably suitable for combating pain, in particular pain selected from the group consisting of acute pain, neuropathic pain, visceral pain, chronic pain and inflammatory pain; or for the treatment of migraine; diabetes; diseases of the respiratory tract; inflammatory bowel diseases; neurological diseases; septic shock; reperfusion syndrome; obesity, and as an angiogenesis inhibitor.

The pharmaceutical compositions according to the invention optionally contain, in addition to at least one sulfonylated tetrahydroazolopyrazine according to the invention, suitable additives and/or auxiliary substances, including carrier materials, fillers, solvents, diluents, dyes and/or binders, and can be administered as liquid dosage forms in the form of injection solutions, drops or juices, as semi-solid dosage forms in the form of granules, tablets, pellets, patches, capsules, plasters/spray plasters or aerosols. The choice of auxiliary substances, etc., and the amounts thereof to use depend on whether the medicinal product is to be administered by oral, peroral, parenteral, intravenous, intraperitoneal, intradermal, intramuscular, nasal, buccal, rectal or topical means, for example on the skin, mucous membranes or in the eyes. Preparations in the form of tablets, pastilles, capsules, granules, drops, juices and syrups are suitable for oral administration. Solutions, suspensions, easily reconstitutable dry preparations and sprays are suitable for parenteral, topical and inhalative administration. Sulfonylated tetrahydroazolopyrazines according to the invention in a depot formulation, in dissolved form or in a plaster, optionally with addition of agents promoting skin penetration, are suitable preparations for percutaneous administration. Preparation forms suitable for oral or percutaneous administration can deliver the sulfonylated tetrahydroazolopyrazines according to the invention on a delayed release basis. The sulfonylated tetrahydroazolopyrazines according to the invention can also be used in parenteral long-term depot forms, such as implants or implanted pumps, for example. Other additional active ingredients known to persons skilled in the art can be added in principle to the pharmaceutical compositions according to the invention.

The amount of active ingredient to be administered to the patient varies according to the weight of the patient, the manner of administration, the indication and the severity of the illness. From 0.00005 to 50 mg/kg, preferably 0.01 to 5 mg/kg, of at least one sulfonylated tetrahydroazolopyrazine according to the invention are conventionally administered. A preferred form of the medicinal product contains a sulfonylated tetrahydroazolopyrazine according to the invention as an isolated diastereomer and/or enantiomer, as a racemate or as a non-equimolar or equimolar mixture of diastereomers and/or enantiomers.

B1R is involved in particular in the pain mechanism. The sulfonylated tetrahydroazolopyrazines according to the invention can accordingly be used for the preparation of a medicinal product for the treatment of pain, in particular acute, visceral, neuropathic or chronic pain.

The invention therefore also provides for the use of a sulfonylated tetrahydroazolopyrazine according to the invention to prepare a medicinal product for the treatment of pain, in particular acute, visceral, neuropathic or chronic pain. A particularly preferred embodiment of the present invention is the use of at least one of the sulfonylated tetrahydroazolopyrazines according to the invention to prepare a medicinal product for the treatment of inflammatory pain.

The invention also provides the use of a sulfonylated tetrahydroazolopyrazine according to the invention to prepare a medicinal product for the treatment of diabetes, diseases of the respiratory tract, for example bronchial asthma, allergies, COPD/chronic obstructive pulmonary disease or cystic fibrosis; inflammatory bowel diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; septic shock; reperfusion syndrome, for example following heart attack or stroke; obesity; and as an angiogenesis inhibitor.

In the above uses it may be preferred if the sulfonylated tetrahydroazolopyrazine that is used is in the form of an isolated diastereomer and/or enantiomer, a racemate or a non-equimolar or equimolar mixture of diastereomers or enantiomers.

The invention also provides a process for treating any of the aforementioned indications, in a non-human mammal or human requiring treatment, by administration of a therapeutically active dose of a sulfonylated tetrahydroazolopyrazine according to the invention or of a pharmaceutical composition according to the invention.

The present invention also provides a process for the preparation of the sulfonylated tetrahydroazolopyrazines according to the invention, in particular as described in the following description, examples and claims. The process according to the invention is represented in scheme 1.

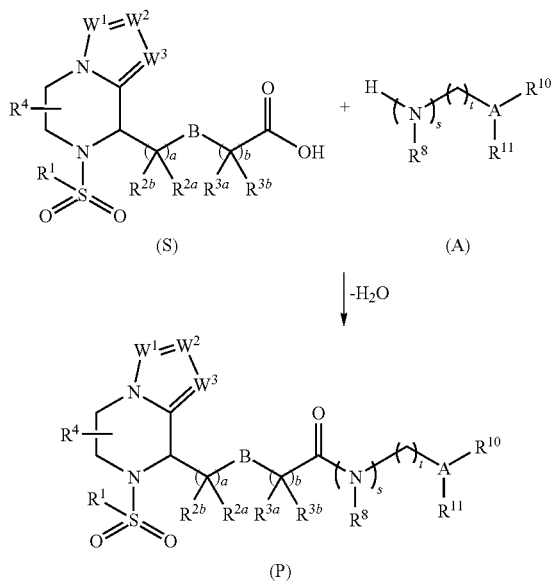

Scheme 1

The free amines (A) and the carboxylic acids (S) are reacted in an amide formation in the presence of at least one dehydrating agent and optionally an organic base in an organic solvent to form the compounds (P) according to the invention. Sodium or magnesium sulfate, phosphorus oxide or reagents such as for example CDI, DCC (optionally polymer-bound), TBTU, EDCl, PyBOP or PFPTFA can be used as dehydrating agents, for example, also in the presence of HOAt or HOBt. Examples of suitable organic bases include triethylamine, DIPEA and pyridine, and examples of useful solvents include THF, dichloromethane, diethylether, dioxane, DMF and acetonitrile. The temperature in the amide formation step is preferably between 0 and 50° C.

The invention is described further hereinafter with reference to general synthesis methods and selected examples. These descriptions serve to further clarify the invention and should not be understood as having a limiting effect.

ABBREVIATIONS

CDI 1,1'-carbonyldiimidazole
d day(s)
DBU 1,8-diazabicyclo[5.4.0]undec-7-ene
DCC N,N'-dicyclohexylcarbodiimide
DCM dichloromethane
DIPEA diisopropylethylamine
DMAP 4-dimethylaminopyridine
DMF dimethyl formamide
DPPA phosphoric acid diphenyl ester azide
EDCl N-(3-dimethylaminopropyl)-N'-ethylcarbodiimide
EtOH ethanol
sat. saturated
h hour(s)
HBTU 0-(benzotriazol-1-yl)-N,N,N',N'-tetramethyluronium hexafluorophosphate
HOAt 1-hydroxy-7-azabenzotriazole
HOBt 1-hydroxybenzotriazole
HATU O-(7-Azabenzotriazol-1-yl)-N,N,N',N'-tetramethyluronium-hexafluorophosphate
LAH lithium aluminium hydride
M molar
MeOH methanol
min minute(s)
RT room temperature
TBACl tetrabutylammonium chloride
TEA triethylamine
TFA trifluoroacetic acid
THF tetrahydrofuran General Synthesis of Acid Structural Units
Method A

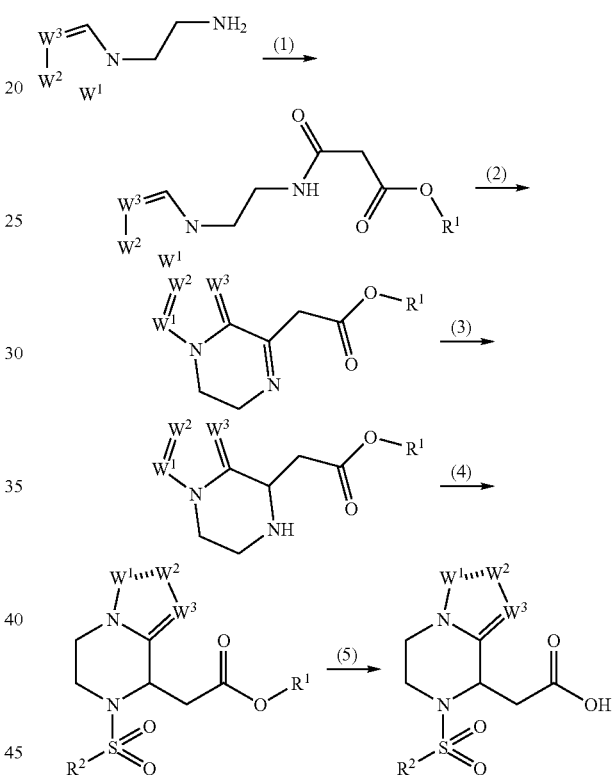

Method A

The acylation with malonic acid monoester (1) can be performed using bases and optionally coupling reagents in solvents such as methanol, DMF or DCM. Sodium methanolate, TEA, DIPEA or N-methylmorpholine, for example, can be used as bases. EDCl, HOBt, DCC, CDl, HBTU, DMAP or pentafluorophenyl diphenyl phosphinate, for example, are suitable as coupling reagents. The reaction time can vary between 1 hour and 3 days. The corresponding malonic acid monoester chloride can also be used in place of the corresponding malonic acid ester.

The subsequent cyclisation (2) to the cyclic imine is performed by reacting $POCl_3$ in solvents such as for example benzene, toluene, ethanol or water or with polyphosphoric acid as solvent.

The reduction of the cyclic imine (3) can be performed using reducing agents such as for example $NaBH_4$ in solvents such as for example ethanol, methanol or water, or by hydrogenolysis with catalysts such as for example Pd on $BaSO_4$ in solvents such as for example ethanol.

The amines obtained are reacted by means of a sulfonylation (4) with sulfonyl chlorides, bromides or pentafluorophenolate R₃SO₂X (X=Cl, Br, OPFP) optionally in the presence of an organic or inorganic base, for example potassium carbonate, sodium hydrogen carbonate, DIPEA, TEA, pyridine, diethylamine or DBU, preferably in an organic solvent, for example acetonitrile, DCM or THF, to form the sulfonylated compounds.

The ester cleavage (5) is converted into the necessary acid structural units using organic acids such as trifluoroacetic acid or aqueous inorganic acids such as hydrochloric acid or using aqueous inorganic bases such as lithium hydroxide, potassium hydroxide, sodium hydroxide, sodium carbonate, sodium hydrogen carbonate, potassium carbonate, in organic solvents such as methanol, dioxane, DCM, THF, diethyl ether or these solvents as blends.

Method B

Method B: Route A and Route B

The acylation (AB1) with oxalic acid monoester can be performed using bases and optionally coupling reagents in solvents such as methanol, DMF or DCM. Examples of suitable bases include sodium methanolate, TEA, DIPEA or N-methylmorpholine. EDCl, HOBt, DCC, CDI, HBTU, DMAP or pentafluorophenyl diphenyl phosphinate are examples of suitable as coupling reagents. The reaction time can vary between 1 hour and 3 days. The corresponding oxalic acid monoester chloride can also be used in place of the corresponding oxalic acid ester.

The subsequent cyclisation (AB2) to the cyclic imine is performed by reacting POCl₃ in solvents such as for example benzene, toluene, ethanol or water or with polyphosphoric acid as solvent.

Route A

The reduction (A1) of the cyclic imine can be performed using reducing agents such as for example lithium aluminium

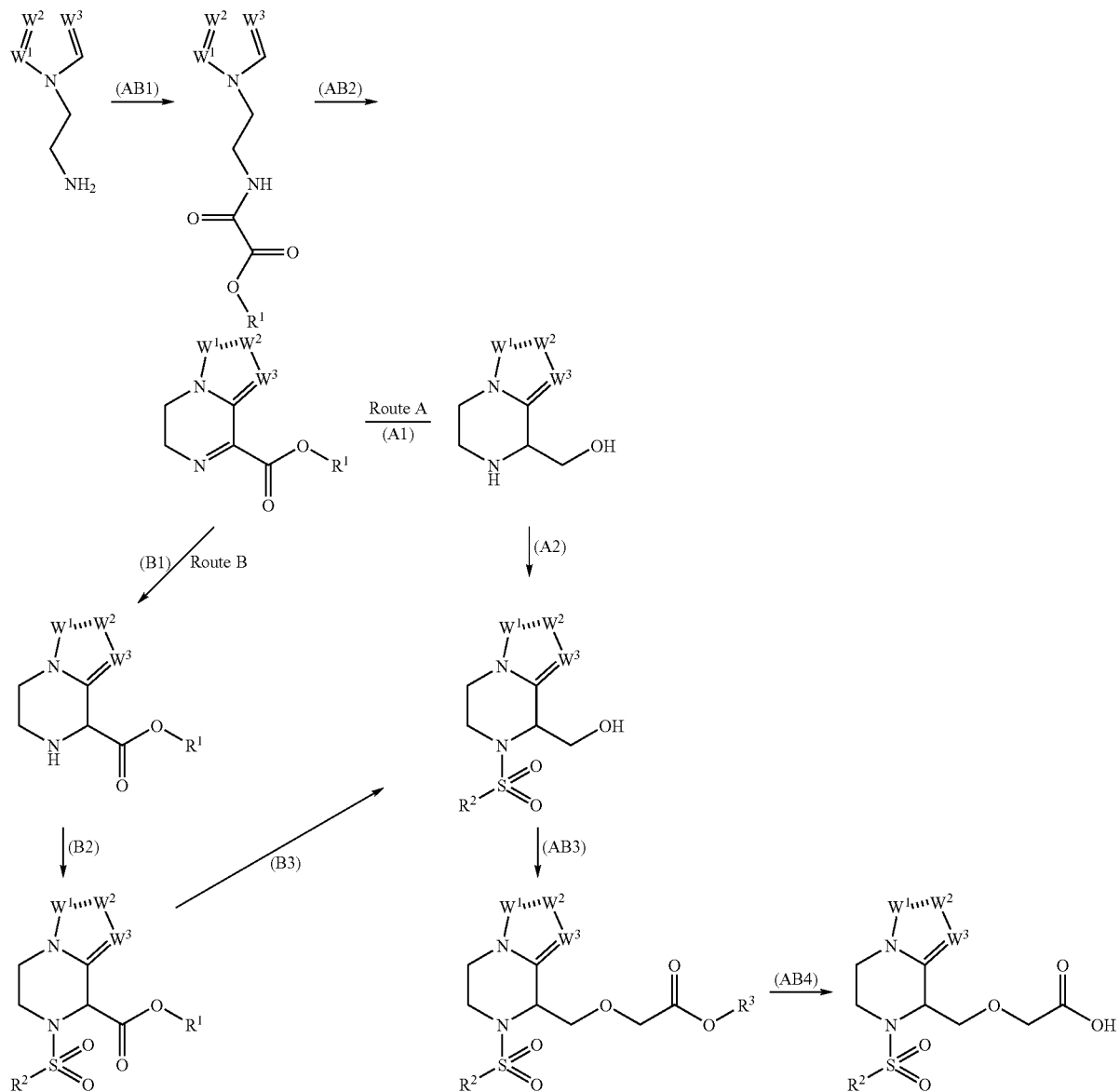

hydride in solvents such as for example diethyl ether or THF. Hydrogenolysis with heterogeneous catalysts such as Pd for example in solvents such as ethanol for example is also possible.

The resulting amino alcohols are reacted by means of a sulfonylation (A2) with sulfonyl chlorides, bromides or pentafluorophenolate $R_3SO_2X$ (X=Cl, Br, OPFP) optionally in the presence of an organic or inorganic base, for example potassium carbonate, sodium hydrogen carbonate, DIPEA, TEA, pyridine, diethylamine or DBU, preferably in an organic solvent, for example acetonitrile, DCM or THF, to form the sulfonylated compounds.

The sulfonylated amino alcohols are converted into the esters in an acylation reaction (AB3) with halogenated ester derivatives using tetrabutylammonium chloride or bromide or tetrabutylammonium hydrogen sulfate, in a phase transfer reaction using an organic solvent such as for example toluene, benzene, DCM or xylene, also blends of these solvents, and an inorganic base such as potassium hydroxide, sodium hydroxide, sodium carbonate, sodium hydrogen carbonate, potassium carbonate or in the presence of an organic or inorganic base, conventional inorganic bases being metal alcoholates such as sodium methanolate, sodium ethanolate, potassium tert-butylate, lithium or sodium bases such as lithium diisopropylamide, butyl lithium, tert-butyl lithium, sodium methylate or metal hydrides such as potassium hydride, lithium hydride, sodium hydride, conventional organic bases being DIPEA, TEA, in an organic solvent such as DCM, THF or diethyl ether. These esters obtained are converted in an ester cleavage (AB4) into the necessary acid structural units using organic acids such as trifluoroacetic acid or aqueous inorganic acids such as hydrochloric acid or using aqueous inorganic bases such as lithium hydroxide, potassium hydroxide, sodium hydroxide, sodium carbonate, sodium hydrogen carbonate, potassium carbonate, in organic solvents such as methanol, dioxane, DCM, THF, diethyl ether or these solvents as blends.

Route B

The reduction (B1) of the cyclic imine can be performed using reducing agents such as, for example, $NaBH_4$ in solvents such as, for example, ethanol, methanol or water. Hydrogenolysis with catalysts such as Pd on $BaSO_4$ for example in solvents such as ethanol for example is also possible.

The resulting amines are reacted by means of a sulfonylation (B2) with sulfonyl chlorides, bromides or pentafluorophenolate $R_3SO_2X$ (X=Cl, Br, OPFP) optionally in the presence of an organic or inorganic base, for example potassium carbonate, sodium hydrogen carbonate, DIPEA, TEA, pyridine, diethylamine or DBU, preferably in an organic solvent, for example acetonitrile, DCM or THF, to form the sulfonylated compounds.

The reduction of the ester (B3) can be performed using reducing agents such as, for example, lithium aluminium hydride in solvents such as, for example, diethyl ether or THF.

The sulfonylated amino alcohols are converted to the necessary acid structural units in an acylation reaction (AB3) with subsequent ester cleavage (AB4) in an analogous manner to that described for Route A.

Synthesis of Sulfonyl Chlorides

4-Methoxy-2,6-dimethylbenzol-1-sulfonyl chloride

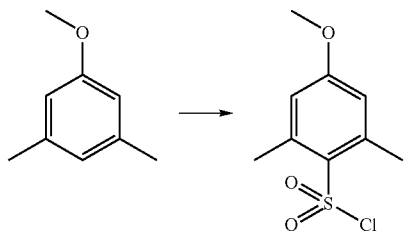

A solution of 3,5-dimethyl anisole (102.5 g, 753 mmol) in DCM (1000 ml) was cooled to 0° C. A solution of chlorosulfonic acid (251 ml, 3763 mmol) in DCM (250 ml) was added dropwise to this solution. After a reaction time of 10 min the reaction solution was poured into an ice bath (1000 ml), the phases were separated and extracted once more with DCM (250 ml). The combined organic phases were washed with water (1000 ml) and saturated sodium chloride solution (1000 ml), dried over $Na_2SO_4$ and concentrated. The product was purified by column chromatography on silica gel (heptane/DCM 5:1). Yield: 63.5 g, 36%

6-Methoxynaphthalene-2-sulfonyl chloride

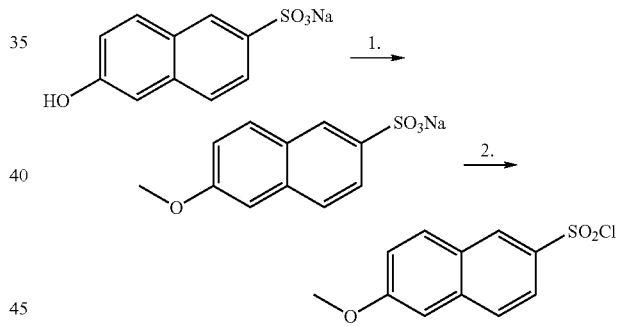

1. Sodium hydroxide (0.7 g) was added to a solution of sodium 6-hydroxynapthalene-2-sulfonate (9 mmol) in water (20 ml). Dimethyl sulfate (1.1 eq.) was added to this solution at 50-55° C. over 1 h, followed by sodium chloride (3.3 g). The solid that was formed was filtered off, washed with saturated NaCl solution and toluene and dried. Yield: 75%

2. Thionyl chloride (0.25 ml) was added to a cooled solution of 6-methoxynaphthalene-2-sulfonate (2 mmol) in dry DMF (1 ml) under $N_2$. The reaction mixture was stirred for 3 h at 0° C. Iced water (20 ml) was added to the mixture, the solid was filtered off and washed with iced water. The solid was taken up in DCM (25 ml), the solution dried over $Na_2SO_4$, filtered and concentrated under reduced pressure. Yield: 75%

Synthesis of the Acid Structural Units Used in the Examples

The acid structural units listed in Table 1 were used for the synthesis of the example compounds.

TABLE 1

| Acid | No. | Name |
|---|---|---|
| | S1 | 2-(2-(4-Methoxy-2,6-dimethylphenylsulfonyl)-1,2,3,4-tetrahydropyrrolo[1,2-a]pyrazin-1-yl)acetic acid |
| | S2 | 2-(2-(6-methoxynaphthalen-2-ylsulfonyl)-1,2,3,4-tetrahydropyrrolo[1,2-a]pyrazin-1-yl)acetic acid |
| | S3 | 2-((2-(4-Methoxy-2,6-dimethylphenylsulfonyl)-1,2,3,4-tetrahydropyrrolo[1,2-a]pyrazin-1-yl)methoxy)acetic acid |
| | S4 | 2-((2-(2-(Trifluoromethyl)phenylsulfonyl)-1,2,3,4-tetrahydropyrrolo[1,2-a]pyrazin-1-yl)methoxy)acetic acid |
| | S5 | 2-((2-(2-Chloro-6-methylphenylsulfonyl)-1,2,3,4-tetrahydropyrrolo[1,2-a]pyrazin-1-yl)methoxy)acetic acid |

TABLE 1-continued

| Acid | No. | Name |
|------|-----|------|
|  | S6 | 2-(2-(2-Chloro-4-(trifluoromethyl)phenylsulfonyl)-1,2,3,4-tetrahydropyrrolo[1,2-a]pyrazin-1-yl)acetic acid |
|  | S7 | 2-(2-(4-Chloro-2,5-dimethylphenylsulfonyl)-1,2,3,4-tetrahydropyrrolo[1,2-a]pyrazin-1-yl)-acetic acid |
|  | S8 | 2-(2-(3,4-Dichlorophenylsulfonyl)-1,2,3,4-tetrahydropyrrolo[1,2-a]pyrazin-1-yl)acetic acid |
|  | S9 | 2-(2-(Phenylsulfonyl)-1,2,3,4-tetrahydropyrrolo[1,2-a]pyrazin-1-yl)acetic acid |
|  | S10 | 2-(2-(2,3-Dichlorophenylsulfonyl)-1,2,3,4-tetrahydropyrrolo[1,2-a]pyrazin-1-yl)acetic acid |

TABLE 1-continued

| Acid | No. | Name |
|---|---|---|
|  | S11 | 2-(2-Tosyl-1,2,3,4-tetrahydropyrrolo[1,2-a]pyrazin-1-yl)acetic acid |
|  | S12 | 2-(2-(3-Trifluoromethyl)phenylsulfonyl)-1,2,3,4-tetrahydropyrrolo[1,2-a]pyrazin-1-yl)acetic acid |
|  | S13 | 2-(2-(3-Chloro-4-methylphenylsulfonyl)-1,2,3,4-tetrahydropyrrolo[1,2-a]pyrazin-1-yl)acetic acid |
|  | S14 | 2-(2-(2-Chloro-6-methylphenylsulfonyl)-1,2,3,4-tetrahydropyrrolo[1,2-a]pyrazin-1-yl)acetic acid |
|  | S15 | 2-(2-(3-chlorophenylsulfonyl)-1,2,3,4-tetrahydropyrrolo[1,2-a]pyrazin-1-yl)acetic acid |

Acid S1

2-(2-(4-Methoxy-2,6-dimethylphenylsulfonyl)-1,2,3,4-tetrahydropyrrolo[1,2-a]pyrazin-1-yl)acetic acid and

Acid S6

2-(2-(2-Chloro-4-(trifluoromethyl)phenylsulfonyl)-1,2,3,4-tetrahydropyrrolo[1,2-a]pyrazin-1-yl)acetic acid

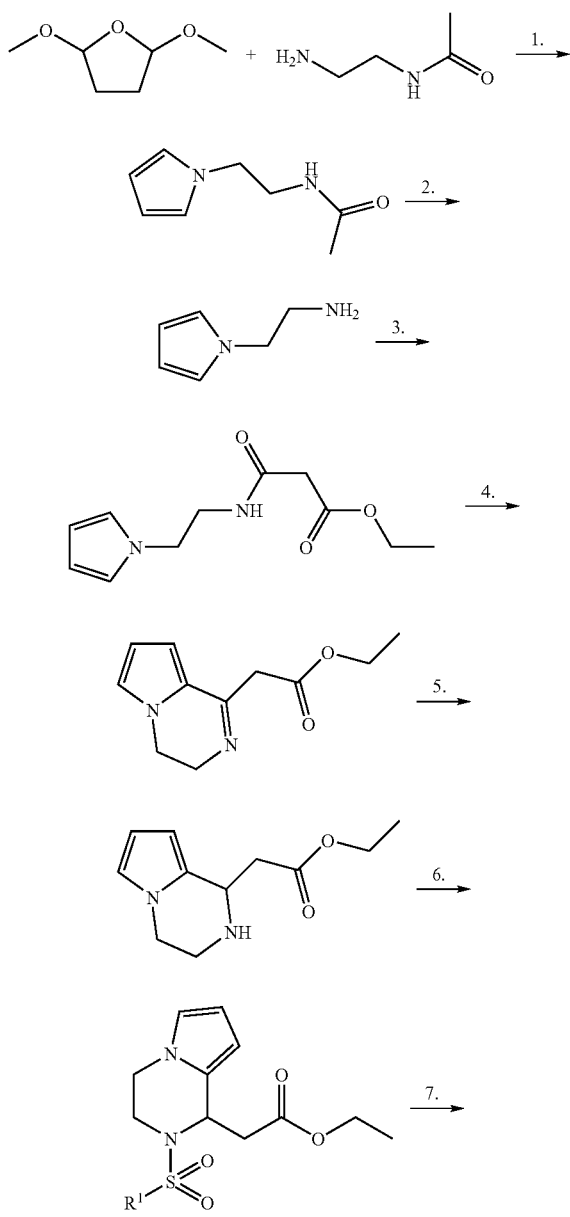

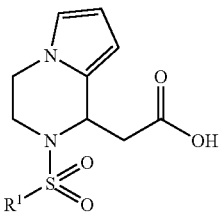

1. A mixture of 2,5-dimethoxytetrahydrofuran (126.7 ml, 0.98 mol) and N-acetylethylenediamine (100 g, 0.98 mol) in acetic acid (600 ml) was refluxed for 2 h. The reaction mixture was cooled to RT and concentrated to small volume. The residue was taken up in DCM and concentrated to small volume again. Purification was performed by column chromatography (silica gel, DCM/MeOH, 95:5).

2. A suspension of N-(2-aminoethyl)acetamide (79.79 g, 0.52 mol) in aqueous KOH (10%, 1200 ml) was refluxed. After cooling to RT the aqueous solution was extracted with DCM (2×800 ml). The combined organic phases were dried over $Na_2SO_4$ and concentrated to dryness.

3. 2-(1H-Pyrrol-1-yl)ethanamine (1.17 g, 10.6 mmol) was dissolved in DCM (30 ml) and mixed with malonic acid monoethyl ester (1.51 ml, 12.8 mmol), HOAt (1.45 g, 10.6 mmol) and EDCl (3.05 g, 15.9 mmol). The reaction solution was stirred overnight at RT and then concentrated to dryness. Purification was performed by column chromatography (silica gel, DCM/7M $NH_3$ in MeOH, 99:1).

4. Polyphosphoric acid (15 ml) was added to the malonic acid amide (1.58 g, 7.1 mmol). The reaction batch was heated to 90° C. After a reaction time of 5 h the hot solution was poured into iced water and carefully made alkaline with solid $NaHCO_3$. The aqueous phase was extracted twice with DCM (30 ml). The combined organic phases were dried over $Na_2SO_4$ and concentrated to dryness. Purification was performed by column chromatography (silica gel, DCM/MeOH, 99:1).

5. The imine (220 mg, 1.11 mmol) was dissolved in ethanol (4 ml). Pd/C (114 mg, 0.11 mmol) was added and the mixture was hydrogenated overnight at RT and under an $H_2$ pressure of 2 bar. The catalyst was then separated off by filtering over celite and the filtrate was concentrated to dryness under reduced pressure. The product was used with no further purification.

6. The amine (231 mg, max. 1.11 mmol) was dissolved in DCM (5 ml). First TEA (0.31 ml, 2.22 mmol) and then the corresponding sulfonyl chloride (338 mg, 1.44 mmol), dissolved in DCM (2 ml), was then added dropwise. The reaction batch was stirred overnight at RT. The solvent was removed under reduced pressure. Purification was performed by column chromatography (silica gel, heptane/ethyl acetate, 3:1).

7. A mixture of sulfonamide (81 mg, 0.2 mmol), methanol (0.4 ml), THF (0.4 ml) and aqueous NaOH solution (4 M, 0.5 ml, 2.0 mmol) was stirred for 3 h at RT. The organic solvent was removed in a rotary evaporator. The suspension obtained was acidified at 0° C. with aqueous $KHSO_4$ solution (0.5 M). DCM (15 ml) was added, the phases were separated and the solvent was removed in a rotary evaporator. The product was used with no further purification.

| R¹ | | Name |
|---|---|---|
| S1 | 4-methoxy-2,6-dimethylphenyl group | 2-(2-(4-Methoxy-2,6-dimethylphenylsulfonyl)-1,2,3,4-tetrahydropyrrolo[1,2-a]pyrazin-1-yl)acetic acid |
| S6 | 2-chloro-4-(trifluoromethyl)phenyl group | 2-(2-(2-Chloro-4-(trifluoromethyl)phenylsulfonyl)-1,2,3,4-tetrahydropyrrolo[1,2-a]pyrazin-1-yl)acetic acid |

Acid S2

2-(2-(6-Methoxynaphthalin-2-ylsulfonyl)-1,2,3,4-tetrahydropyrrolo[1,2-a]pyrazin-1-yl)essigsäure, acid S7: 2-(2-(4-chloro-2,5-dimethylphenylsulfonyl)-1,2,3,4-tetrahydropyrrolo[1,2-a]pyrazin-1-yl)acetic acid, acid S8: 2-(2-(3,4-dichlorophenylsulfonyl)-1,2,3,4-tetrahydropyrrolo[1,2-a]pyrazin-1-yl)acetic acid and acid S12: 2-(2-(3-(trifluoromethyl)phenylsulfonyl)-1,2,3,4-tetrahydropyrrolo[1,2-a]pyrazin-1-yl)acetic acid

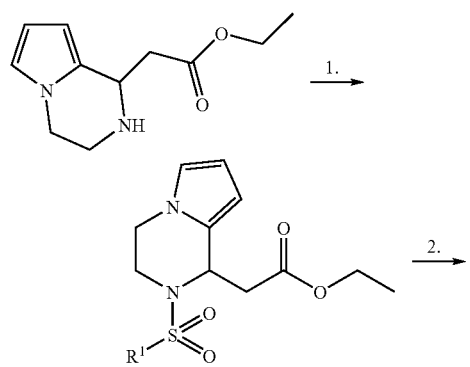

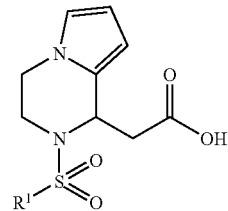

1. The amine (1.11 mmol) was dissolved in DCM (6 ml). First TEA (0.38 ml, 2.76 mmol) and then the sulfonyl chloride (1.11 mmol), dissolved in DCM (2 ml), was then added dropwise. The reaction batch was stirred overnight at RT. The solvent was removed under reduced pressure. Purification was performed by column chromatography (silica gel).

2. The ester cleavage was performed in the manner described for acid S1.

| R1 | | Name |
|---|---|---|
| S2 | 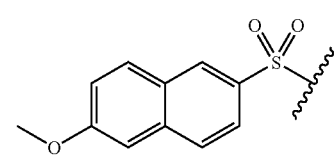 | 2-(2-(6-Methoxynaphthalin-2-ylsulfonyl)-1,2,3,4-tetrahydropyrrolo[1,2-a]pyrazin-1-yl)essigsäure |
| S7 | 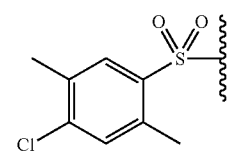 | 2-(2-(4-chloro-2,5-dimethylphenylsulfonyl)-1,2,3,4-tetrahydropyrrolo[1,2-a]pyrazin-1-yl)acetic acid |

-continued

| R1 | | Name |
|---|---|---|
| S8 | [3,4-dichlorophenylsulfonyl structure] | 2-(2-(3,4-Dichlorophenylsulfonyl)-1,2,3,4-tetrahydropyrrolo[1,2-a]pyrazin-1-yl)essigsäure |
| S9 | [phenylsulfonyl structure] | 2-(2-(phenylsulfonyl)-1,2,3,4-tetrahydropyrrrolo[1,2-a]pyrazin-1-yl)acetic acid |
| S12 | [3-(trifluoromethyl)phenylsulfonyl structure] | 2-(2-(3-(trifluoromethyl)phenylsulfonyl)-1,2,3,4-tetrahydropyrrrolo[1,2-a]pyrazin-1-yl)acetic acid |

Acid S3

2-((2-(4-Methoxy-2,6-dimethylphenylsulfonyl)-1,2,3,4-tetrahydropyrrolo[1,2-a]pyrazin-1-yl)methoxy)acetic acid

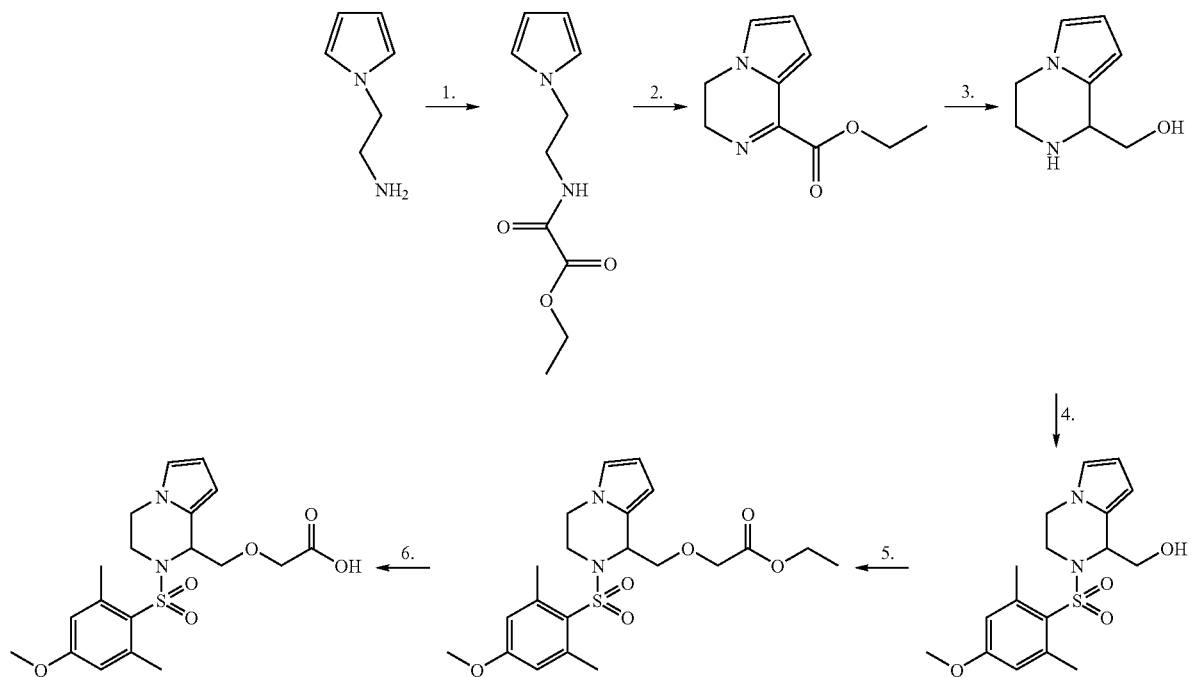

1. Method A: TEA (2 eq.) was added dropwise to a solution of 2-(1H-pyrrol-1-yl)ethanamine (16 g, 145 mmol) in DCM (400 ml) and ethyloxalyl chloride (1.11 eq.) was added at 0° C. The mixture was stirred for 5 h at RT, concentrated to small volume under vacuum and used in the following stage with no further purification.
Method B: To a solution of amine (9.0 g, 68.18 mmol, 1.0 eq.) in DCM (250 ml) was added HOAt (9.2 g, 68.18 mmol, 1.0 eq.), EDCl (19.5 g, 102.27 mmol, 1.5 eq.) and DIPEA (29 ml, 170 mmol, 2.5 eq.) followed by stirred for 30 min at RT. Monoethyl malonate (11.2 g, 102.27 mmol, 1.5 eq.) in DCM (50 ml) was added to the reaction mixture. The reaction mixture was stirred at RT for 12 h. The reaction mixture was diluted with DCM (250 ml) and quenched with saturated NH₄Cl solution (150 ml) and organic layer is separated. Organic layer is washed with saturated NaHCO₃ solution (100 ml), brine (100 ml) and was dried in vacuo to afford solid residue which is purified by column chromatography (silica gel, 40% ethyl acetate/hexanes) to obtain the amide as light yellow oil. Yield: 51% (7.7 g, 34.4 mmol)

2. Method A:Ethyl 2-(2-(1H-pyrrol-1-yl)ethylamino)-2-oxoacetate was heated with polyphosphoric acid (7 eq.) for 4 h at 90° C. and then cooled to RT. Saturated NaHCO$_3$ solution was added to the mixture and it was extracted with DCM. The organic phase was dried (Na$_2$SO$_4$), concentrated to small volume and purified by column chromatography (silica gel). Yield: 16%

Method B: Ethyl 2-(2-(1H-pyrrol-1-yl)ethylamino)-2-oxoacetate (7 g, 33.3 mmol, 1.0 eq.) was taken up in a round bottom flask and cooled with an ice-bath. Pre-cooled TFA (70 ml) was slowly added to the mixture and it was then stirred at RT for 18 h. TFA was evaporated under high-vacuum and the residue taken up in DCM. The resulting mixture was stirred with a saturated aqueous solution of sodium bicarbonate until the pH became neutral. The organic layer was separated and the aqueous layer extracted with DCM (3×150 ml). The combined organic portions were washed with water (2×80 ml), dried over sodium sulfate and concentrated under reduced pressure to yield the crude product. This was purified by column chromatography (silica gel, 25% ethyl acetate/hexanes) to yield the pure title compound as a brown oil. Yield: 62%

3. A suspension of LAH (2 eq.) in THF (4 ml) was added dropwise to a solution of ethyl 3,4-dihydropyrrolo[1,2-a]pyrazine-1-carboxylate (0.52 mmol, 1 eq.) in THF (1 ml) at 0° C. and the mixture was stirred for 1 h. Saturated Na$_2$SO$_4$ solution was added and the mixture was filtered. The solvent was removed and the reaction mixture was taken up in ethyl acetate, dried (Na$_2$SO$_4$) and concentrated to small volume. The crude product was used in the following step without further purification.

4. A solution of 4-methoxy-2,6-dimethylbenzene-1-sulfonyl chloride (1.1 eq.) in DCM (1 ml) was added slowly to a solution of (1,2,3,4-tetrahydropyrrolo[1,2-a]pyrazin-1-yl)methanol (1 eq.) and TEA (2 eq.) in DCM at 0° C. and the mixture was stirred for 1 h. The reaction mixture was concentrated to small volume and purified by column chromatography (silica gel). Yield: 24%

5. Method A: t-Butyl bromoacetate (4.5 eq.) and 35% aqueous KOH solution were added to a solution of (2-(4-methoxy-2,6-dimethylphenylsulfonyl)-1,2,3,4-tetrahydropyrrolo[1,2-a]pyrazin-1-yl)methanol (1 eq.) and TBACl (1 eq.) in toluene (1.5 ml) and the mixture was stirred overnight at RT. The phases were separated and the organic phase was washed with water, dried (Na$_2$SO$_4$) and concentrated to small volume. The crude product was used in the following step without further purification.

Method B: To a cooled (0° C.) suspension of NaH (5.48 g, 22.84 mmol, 2.0 eq.) in THF (50 ml) was added dropwise a solution of (2-(4-methoxy-2,6-dimethylphenyl-sulfonyl)-1,2,3,4-tetrahydropyrrolo[1,2-a]pyrazin-1-yl)methanol (4 g, 11.42 mmol, 1.0 eq.) in THF (50 ml) and the reaction mixture was stirred at RT for 1 h. Then a solution of ethylbromoacetate (1.52 ml, 13.70 mmol, 1.2 eq.) in THF (50 ml) was added dropwise to the reaction mixture at 0° C. and it was stirred at RT for 2 h. The reaction mixture was quenched with ammonium chloride solution (50 ml) and filtered through a bed of celite. The filtrate was concentrated under reduced pressure to give the crude product which was purified by column chromatography (silica gel, 15% ethyl acetate/hexanes) to yield the desired product as a white solid. Yield: 64% (3.2 g, 7.34 mmol)

6. Method A: KOH (2 eq.) was added to a solution of ethyl 2-((2-(4-methoxy-2,6-dimethylphenylsulfonyl)-1,2,3,4-tetrahydropyrrolo[1,2-a]pyrazin-1-yl)methoxy)acetate (1 eq.) in MeOH at RT and the mixture was stirred for 3 h. The reaction mixture was concentrated to small volume and the residue taken up in water and washed with ethyl acetate. The aqueous phase was acidified to pH 3 to 4 and extracted with ethyl acetate. The organic phase was extracted with water and saturated sodium chloride solution, dried (Na$_2$SO$_4$), concentrated to small volume and used in the following step without further purification.

Method B: Ethyl-2-((2-(4-methoxy-2,6-dimethylphenylsulfonyl)-1,2,3,4-tetrahydropyrrolo[1,2-a]pyrazin-1-yl)methoxy)acetate (4.58 mmol, 1 eq.) was dissolved in ethanol (27 ml) and water (6 ml) and potassium hydroxide (1 M in water, 2 eq.) was added. The resulting mixture was stirred at RT for 16 h. Ethanol was removed in vacuo and the residue was taken up in water and diethylether (20 ml each). The aqueous phase was adjusted to pH 3 with 1 M HCl (aq) and extracted with ethyl acetate (3×30 ml). The combined organic layers were dried over MgSO$_4$ and concentrated in vacuo to yield the desired compound. Yield: 1.89 g (>99%)

Acid S4

2-((2-(2-(Trifluoromethyl)phenylsulfonyl)-1,2,3,4-tetrahydropyrrolo[1,2-a]pyrazin-1-yl)methoxy)acetic acid and acid

S5

2-((2-(2-Chloro-6-methylphenylsulfonyl)-1,2,3,4-tetrahydropyrrolo[1,2-a]pyrazin-1-yl)methoxy)acetic acid

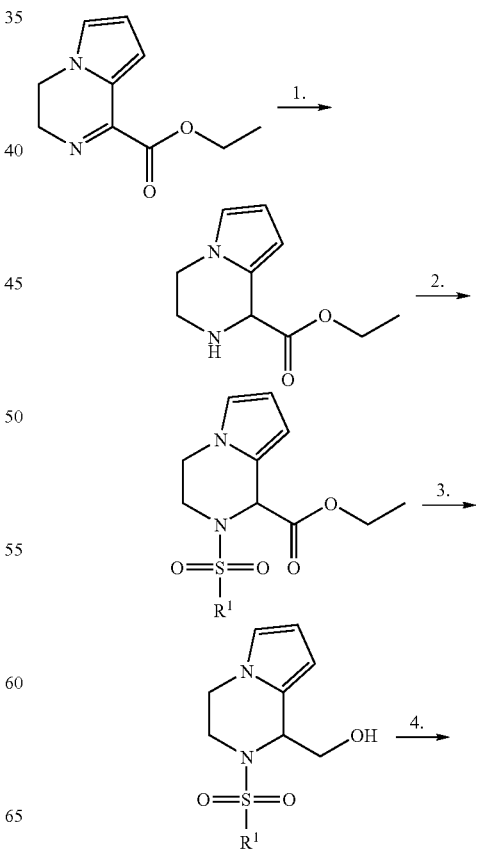

-continued

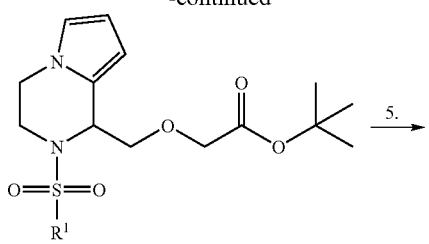

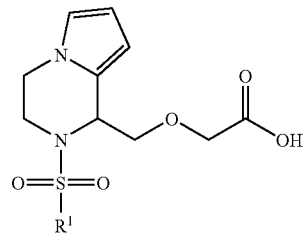

1. A mixture of methanol (45 ml) and water (5 ml) was cooled to 0° C. and added to the imine (2.35 g, 12.23 mmol). NaBH₄ (555 mg, 14.67 mmol) was added in portions over 10 min. The reaction solution was stirred for 1 h at 0° C. The bulk of the organic solvent was removed under reduced pressure. NH₃ solution (10%, 200 ml) and DCM (200 ml) followed by saturated NaCl solution (150 ml) were added to improve the phase separation. The phases were separated and the aqueous phase was extracted twice more with DCM (200 ml each). The combined organic phases were dried over Na₂SO₄ and concentrated to small volume. The crude product obtained was used in the next stage on the same day.

2. The reaction was performed under an N₂ atmosphere. The amine (0.84 g, 4.32 mmol) was dissolved in DCM (10 ml). TEA (1.22 ml, 8.65 mmol) was added and the reaction batch was cooled to 0° C. Sulfonyl chloride (5.19 mmol) was added and the mixture was stirred for 1 h at 0° C. and then overnight at RT. The solvent was removed under reduced pressure. Purification was performed by column chromatography (silica gel, heptane/ethyl acetate, 3:1).

3. The reaction was performed under an N₂ atmosphere. LiBH₄ solution (2 M in THF, 2 ml, 4 mmol) was added to a solution of the ester (0.82 g, 2.038 mmol) in dry THF (50 ml) and the mixture was stirred overnight at RT. Na₂SO₄·10H₂O was added until no further gas evolution was observed. The reaction mixture was stirred for 1 d at RT and then filtered over Na₂SO₄. The residue was washed with THF (approx. 50 ml). The combined organic phases were concentrated to small volume and the crude product used without further purification.

4. Aqueous NaOH solution (35%, 50 ml) followed by tent-butyl bromoacetate (1.62 ml, 11.11 mmol) were added to a solution of the alcohol (0.79 g, max. 2.01 mmol) and n-Bu₄NCl (0.122 g, 0.439 mmol) in DCM (50 ml). The reaction mixture was stirred for 3 h at RT. It was then diluted with DCM (50 ml). The organic phase was washed first with water (3×50 ml) and then with saturated NaCl solution (50 ml). The organic phase was dried (Na₂SO₄), concentrated to small volume and purified by column chromatography (silica gel, heptane/ethyl acetate, 4:1).

5. The tert-butyl ester (440 mg, 0.93 mmol) was dissolved in methanol (9 ml), THF (4 ml) and water (1 ml). NaOH (371 mg, 9.28 mmol) was added and then the mixture was stirred for 2 h at RT. The bulk of the organic solvent was then removed in a rotary evaporator. Ice (100 ml) and DCM (50 ml) were added and then aqueous KHSO₄ solution (0.5 M, 50 ml) was added to the mixture. The phases were separated and the aqueous phase was extracted once more with DCM. The combined organic phases were dried over Na₂SO₄ and concentrated to small volume. The crude product obtained was used with no further purification.

| | R¹ | Name |
|---|---|---|
| S4 | 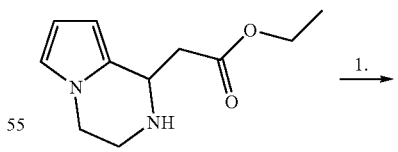 | 2-((2-(2-(Trifluoromethyl)phenylsulfonyl)-1,2,3,4-tetrahydropyrrolo[1,2-a]pyrazin-1-yl)methoxy)acetic acid |
| S5 | 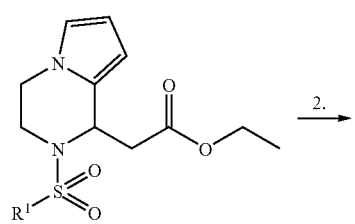 | 2-((2-(2-Chloro-6-methylphenylsulfonyl)-1,2,3,4-tetrahydropyrrolo[1,2-a]pyrazin-1-yl)methoxy)acetic acid |

Acid S10

2-(2-(2,3-Dichlorophenylsulfonyl)-1,2,3,4-tetrahydropyrrolo[1,2-a]pyrazin-1-yl)acetic acid

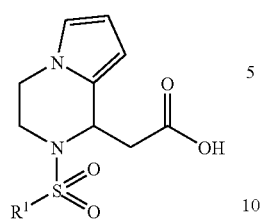

1. The amine (2.4 mmol) was dissolved in THF (30 ml). NaHCO$_3$ (6.0 mmol) was added followed by the addition of sulfonyl chloride (2.88 mmol) in THF (2 ml). The reaction was stirred at 25° C. for 16 h. Reaction mixture is evaporated to dryness under reduced pressure and crude product is purified by silica gel column chromatography (20% ethyl acetate in hexanes) to afford the sulfonamide.

2. A mixture of the sulfonamide (1.2 mmol), MeOH (2.7 ml), THF (5.5 ml) and aqueous LiOH solution (1.8 mmol in 2 ml water) was stirred at 25° C. for 3 h. Organic solvents were removed under reduced pressure. The resulting suspension was acidified with aqueous 1 M HCl while cooling at 0° C. DCM (20 ml) was added. Reaction mixture was extracted with DCM (3×20 ml) and evaporated to dryness under reduced pressure affording carboxylic acid (S10) which was used in the next step without further purification.

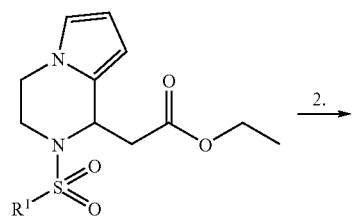

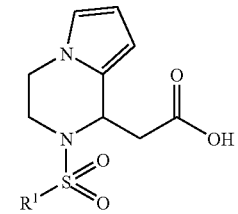

1. The amine (3.36 mmol) was dissolved in THF (5 ml). TEA (5.05 mmol) was added followed by the addition of sulfonyl chloride (4.03 mmol). The reaction was stirred at 25° C. for 16 h. Solvent was evaporated to dryness under reduced pressure and the crude product was purified by silica gel column chromatography (50% ethyl acetate in hexane) to afford sulfonamide.

2. The ester cleavage was performed in the manner described for acid S1.

| | R1 | Name |
|---|---|---|
| S10 | Cl, Cl-phenyl-SO$_2$ | 2-(2-(2,3-Dichlorophenylsulfonyl)-1,2,3,4-tetrahydropyrrolo[1,2-a]pyrazin-1-yl)acetic acid |

Acid S11

2-(2-Tosyl-1,2,3,4-tetrahydropyrrolo[1,2-a]pyrazin-1-yl)acetic acid

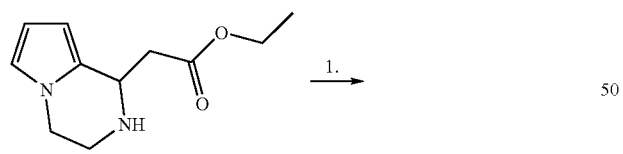

| | R1 | Name |
|---|---|---|
| S11 | tosyl-SO$_2$ | 2-(2-Tosyl-1,2,3,4-tetrahydropyrrolo[1,2-a]pyrazin-1-yl)acetic acid |

Acid S13

2-(2-(3-Chloro-4-methylphenylsulfonyl)-1,2,3,4-tetrahydropyrrolo[1,2-a]pyrazin-1-yl)acetic acid

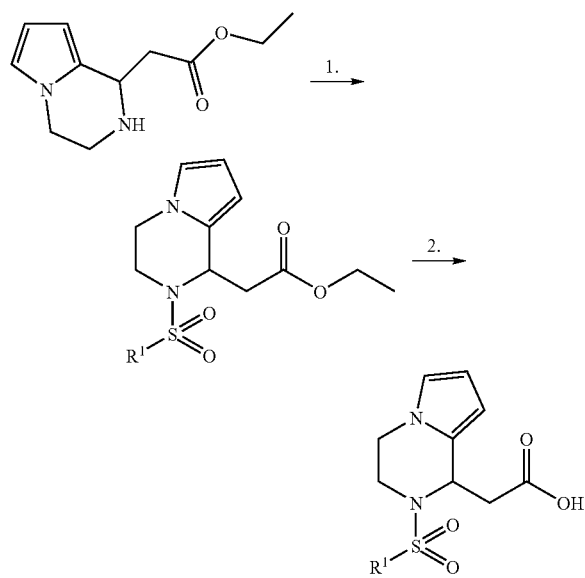

1. TEA (8.4 ml, 0.06 mol) was added to a DCM (5 ml/mmol) solution of the amine (5 g, 0.0240 mol) at 0° C. under nitrogen followed by slow addition of the arylsulfonyl chloride (6.4 g, 0.029 mol). The reaction mixture was stirred at 25° C. for 18 h, diluted with DCM (20 ml), washed with saturated aq. $NaHCO_3$ solution (20 ml), water (10 ml) and organic layer was dried over $Na_2SO_4$, evaporated to dryness under reduced pressure. The crude material was purified on silica gel (100-200 mesh) using 15-25% ethyl acetate in hexanes.

2. Arylsulfonamide (1 g, 0025 mol) was taken in a composite solution of THF/MeOH/$H_2O$ (5:3:1; ~4 ml/mmol) and cooled to 0° C. on an ice bath. Lithium hydroxide monohydrate (0.18 g, 0.0045) was added portion wise and reaction mixture was stirred for 3 to 7 h at 25° C. The solvents were evaporated and the residue was taken in water, washed with ethyl acetate (10 ml). The organic layer was kept aside and the aq. layer was made acidic with 2N aq. HCl solution, extracted with ethyl acetate (3×20 ml), dried over $Na_2SO_4$ and evaporated to dryness under reduced pressure. The crude acid is purified on silica gel (100-200 mesh) using DCM in methanol to obtain pure compound.

|  | R1 | Name |
|---|---|---|
| S13 | 3-chloro-4-methylphenylsulfonyl | 2-(2-Tosyl-1,2,3,4-tetrahydrpyrrolo[1,2-a]pyrazin-1-yl)acetic acid |
| S15 | 3-chlorophenylsulfonyl | 2-(2-(3-Chlorophenylsulfonyl)-1,2,3,4-tetrahydropyrrolo[1,2-a]pyrazin-1-yl)acetic acid |

Synthesis of Amine Structural Units

The amine structural units listed in Table 2 were used for the synthesis of the example compounds.

TABLE 2

| Amine | No. | Name | Supplier |
|---|---|---|---|
| 1-(1-methylpiperidin-4-yl)piperazine structure | A1 | 1-(1-Methylpiperidin-4-yl)piperazine | Fluka |

TABLE 2-continued

| Amine | No. | Name | Supplier |
|---|---|---|---|
| | A2 | 2-Cyclopropyl-2,7-diazaspiro[4.4]nonane | |
| | A3 | 2-(Pyridin-4-yl)-2,8-diazaspiro[4.5]decane | |
| | A4 | 4-(Piperidin-4-yloxy)pyridine | Interchim |
| | A5 | 6-(Piperidin-1-ylmethyl)-1,2,3,4-tetrahydronaphthalen-2-amine | |
| | A6 | 6-(Piperidin-1-ylmethyl)-1,2,3,4-tetrahydronaphthalen-1-amine | |
| | A7 | 3-(Pyridin-4-yl)-3,9-diazaspiro[5.5]undecane | |
| | A8 | N-Methyl-2-(1-(pyridin-4-yl)piperidin-4-yl)ethanamine | |
| | A9 | Piperidine | Aldrich |
| | A10 | 1,2,3,4-Tetrahydroisoquinoline | Aldrich |

TABLE 2-continued

| Amine | No. | Name | Supplier |
|---|---|---|---|
| | A11 | 1-Benzyl-3,3-dimethylpiperidin-4-amine | |
| | A12 | 2,2,2-Trifluoro-1-(2,8-diazaspiro[4.5]decan-2-yl)ethanone | |
| | A13 | 3-(Pyridin-4-yloxy)-8-azabicyclo[3.2.1]octane | |
| | A14 | 3-(4-(2-(Pyrrolidino-1-yl)ethoxy)piperidine-4-yl)pyridine | |
| | A15 | 6-((tert-Butylamino)methyl)-1,2,3,4-tetrahydronaphthalen-2-amine | |
| | A16 | N-[[5-(tert-Butoxycarbonylamino)-5,6,7,8-tetrahydro-naphthalen-2-yl]-methyl]-N-methyl-carbamic acid 9H-fluoren-9-yl-methyl ester | |
| | A17 | N-[6-(Dimethylaminomethyl)-1,2,3,4-tetrahydro-naphthalen-1-yl]-carbamic acid tert-butyl ester | |

TABLE 2-continued

| Amine | No. | Name | Supplier |
|---|---|---|---|
| | A18 | N-[6-[(1-Methyl-propylamino)-methyl]-1,2,3,4-tetrahydro-naphthalen-1-yl]carbamic acid tert-butyl ester | |
| | A19 | N-[6-[(tert-Butylamino)-methyl]-1,2,3,4-tetrahydro-naphthalen-1-yl]-carbamic acid tert-butyl ester | |
| | A20 | N-[6-[(tert-Butyl-methyl-amino)-methyl]-1,2,3,4-tetrahydro-naphthalen-1-yl]-carbamic acid tert-butyl ester | |
| | A21 | N-[6-(Pyrrolidin-1-yl-methyl)-1,2,3,4-tetrahydro-naphthalen-1-yl]-carbamic acid tert-butyl ester | |
| | A22 | N-[6-(Piperidin-1-yl-methyl)-1,2,3,4-tetrahydro-naphthalen-1-yl]carbamic acid tert-butyl ester | |

TABLE 2-continued

| Amine | No. | Name | Supplier |
|---|---|---|---|
|  | A23 | N-[6-(Morpholin-4-yl-methyl)-1,2,3,4-tetrahydro-naphthalen-1-yl]-carbamic acid tert-butyl ester |  |
|  | A24 | N-[6-[(4-Methyl-piperazin-1-yl)-methyl]-1,2,3,4-tetrahydro-naphthalen-1-yl]-carbamic acid tert-butyl ester |  |
|  | A25 | N-[6-(8-Azabicyclo[3.2.1]octan-8-yl-methyl)-1,2,3,4-tetrahydro-naphthalen-1-yl]-carbamic acid tert-butyl ester |  |
|  | A26 | N-[6-[(Benzylamino)-methyl]-1,2,3,4-tetrahydro-naphthalen-1-yl]-carbamic acid tert-butyl ester |  |
|  | A27 | N-[6-(1,2,3,4-Tetrahydro-quinolin-1-yl-methyl)-1,2,3,4-tetrahydro-naphthalen-1-yl]-carbamic acid tert-butyl ester |  |

TABLE 2-continued

| Amine | No. | Name | Supplier |
|---|---|---|---|
| | A28 | N-[[6-(tert-Butoxycarbonylamino)-5,6,7,8-tetrahydro-naphthalen-2-yl]-methyl]-N-methyl-carbamic acid 9H-fluoren-9-yl-methyl ester | |
| | A29 | N-[6-(Dimethylaminomethyl)-naphthalen-2-yl]-carbamic acid tert-butyl ester | |
| | A30 | N-[6-[(1-Methyl-propylamino)-methyl]-1,2,3,4-tetrahydro-naphthalen-2-yl]-carbamic acid tert-butyl ester | |
| | A31 | N-[6-[(tert-Butylamino)-methyl]-1,2,3,4-tetrahydro-naphthalen-2-yl]-carbamic acid tert-butyl ester | |
| | A32 | N-[6-[(tert-Butyl-methyl-amino)-methyl]-1,2,3,4-tetrahydro-naphthalen-2-yl]-carbamic acid tert-butyl ester | |
| | A33 | N-[6-(Pyrrolidin-1-yl-methyl)-1,2,3,4-tetrahydro-naphthalen-2-yl]-carbamic acid tert-butyl ester | |

TABLE 2-continued

| Amine | No. | Name | Supplier |
|---|---|---|---|
| | A34 | N-[6-(Piperidin-1-yl-methyl)-1,2,3,4-tetrahydro-naphthalen-2-yl]-carbamic acid tert-butyl ester | |
| | A35 | N-[6-(Morpholin-4-yl-methyl)-1,2,3,4-tetrahydro-naphthalen-2-yl]-carbamic acid tert-butyl ester | |
| | A36 | N-[6-[(4-Methyl-piperazin-1-yl)-methyl]-1,2,3,4-tetrahydro-naphthalen-2-yl]-carbamic acid tert-butyl ester | |
| | A37 | N-[6-(8-Azabicyclo[3.2.1]octan-8-yl-methyl)-1,2,3,4-tetrahydro-naphthalen-2-yl]-carbamic acid tert-butyl ester | |
| | A38 | N-[6-[(Benzylamino)-methyl]-1,2,3,4-tetrahydro-naphthalen-2-yl]-carbamic acid tert-butyl ester | |
| | A39 | tert-Butyl 6-((3,4-dihydroquinolin-1(2H)-yl)methyl)-1,2,3,4-tetrahydronaphthalen-2-ylcarbamate | |

TABLE 2-continued

| Amine | No. | Name | Supplier |
|---|---|---|---|
| | A40 | 1-(5-(Trifluoromethyl)pyridin-2-yl)piperidin-4-amine | Fluorochem |
| | A41 | 1-(5-(Trifluoromethyl)pyridin-2-yl)pyrrolidin-3-amine | Chinglu Pharmaceuticals |
| | A42 | 4-(Piperidin-4-yl)pyridine | Interchim |
| | A43 | 4-(piperidin-4-ylmethyl)pyridine | Interchim |
| | A44 | 1-(pyridin-4-yl)piperidin-4-amine | ABCR |
| | A45 | 1-methyl-4-(pyrrolidin-3-ylmethyl)piperazine | AKOS |
| | A46 | 4-(pyrrolidin-3-yloxy)pyridine | Amatek Chem |
| | A47 | N-methyl-1-(pyridin-4-yl)piperidin-4-amine | Enamine |
| | A48 | 2-methyl-5-(piperidin-4-yl)-2,5-diazabicyclo[2.2.1]heptane | |
| | A49 | 2-(4-(4,5-Dihydro-1H-imidazol-2-yl)phenyl)ethanamine | |
| | A50 | (R)-6-((tert-Butylamino)methyl)-1,2,3,4-tetrahydronaphthalen-1-amine | |

TABLE 2-continued

| Amine | No. | Name | Supplier |
|---|---|---|---|
| | A51 | N-Methyl-6-(piperidin-1-ylmethyl)-1,2,3,4-tetrahydronaphthalen-2-amine | |
| | A52 | (R)-6-((4-Fluoropiperidin-1-yl)methyl)-1,2,3,4-tetrahydronaphthalen-1-amine | |
| | A53 | (R)-6-((2,2,2-Trifluoroethylamino)methyl)-1,2,3,4-tetrahydronaphthalen-1-amine | |
| | A54 | (R)-N-(4-(1-Aminoethyl)benzyl)-2-methylpropan-2-amine | |
| | A56 | 5-(Piperidin-1-ylmethyl)-2,3-dihydro-1H-inden-2-amine | |
| | A57 | 2-([1,4]Diazepan-1-yl)-pyridine-3-carbonitrile | Maybridge |
| | A58 | 3-(2,6-Dimethyl-piperidin-1-yl)-propyl-amine | Interchim |
| | A59 | [2-(4-Methyl-piperazin-1-yl)-1-phenyl-ethyl]-amine | Interchim |
| | A60 | (1-Benzyl-pyrrolidin-3-yl)-methyl-amine | Akos |
| | A61 | (1-Benzyl-piperidin-3-yl)-methyl-amine | Maybridge |

TABLE 2-continued

| Amine | No. | Name | Supplier |
|---|---|---|---|
| 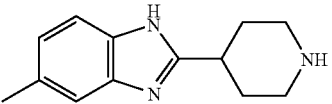 | A62 | 5-Methyl-2-piperidin-4-yl-1H-benzoimidazole | Interchim |
| 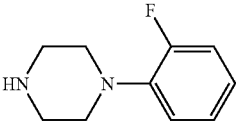 | A63 | 1-(2-Fluorophenyl)-piperazine | Aldrich |
| 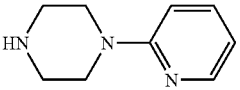 | A64 | 1-Pyridin-2-yl-piperazine | Aldrich |
| 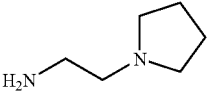 | A65 | 2-Pyrrolidin-1-yl-ethyl-amine | Aldrich |
| 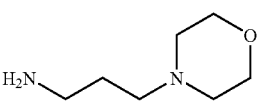 | A66 | 3-Morpholin-4-yl-propyl-amine | Aldrich |
| 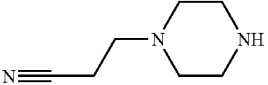 | A67 | 3-Piperazin-1-yl-propionitrile | Aldrich |
| 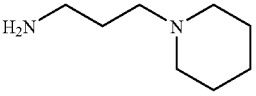 | A68 | 3-Piperidin-1-yl-propyl-amine | Aldrich |
| 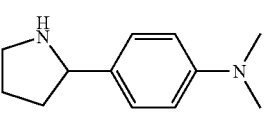 | A69 | Dimethyl-(4-pyrrolidin-2-yl-phenyl)-amine | ASDI |
| 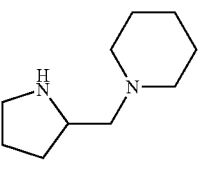 | A70 | 1-(Pyrrolidin-2-yl-methyl)-piperidine | Interchim |
| 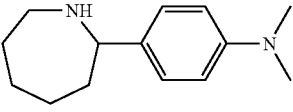 | A71 | [4-(Azepan-2-yl)-phenyl]-dimethyl-amine | ASDI |
| 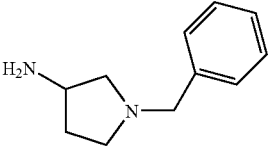 | A73 | (1-Benzyl-pyrrolidin-3-yl)-amine | TCI |

TABLE 2-continued

| Amine | No. | Name | Supplier |
|---|---|---|---|
| | A75 | Methyl-(2-morpholin-4-yl-1-phenyl-ethyl)-amine | Interchim |
| | A76 | 1-(3-Methoxyphenyl)-piperazine | Aldrich |
| | A77 | 1-(4-Fluorophenyl)-piperazine | Aldrich |
| | A78 | 1-(4-Methoxyphenyl)-piperazine | Aldrich |
| | A79 | 1-Ethyl-piperazine | Aldrich |
| | A80 | 1-Phenyl-piperazine | Aldrich |
| | A82 | 1-(1,3-Benzodioxol-5-yl-methyl)-piperazine | Aldrich |
| | A83 | 2-Piperazine-1-yl-pyrimidine | Aldrich |
| | A84 | 4-Pyrrolidin-1-yl-piperidine | Aldrich |
| | A85 | 4-Benzyl-piperidine | Aldrich |
| | A86 | 4-Piperidine-4-yl-morpholine | Aldrich |
| | A87 | 1-Piperidin-4-yl-piperidine | Aldrich |
| | A88 | 1-[[-Pyrrolidin-2-yl]-methyl]-pyrrolidine | Otava |

TABLE 2-continued

| Amine | No. | Name | Supplier |
|---|---|---|---|
| | A89 | 1-(5-Chloro-2-methyl-phenyl)-piperazine | Maybridge |
| | A90 | 2-Piperazin-1-yl-pyridine-3-carbonitrile | Maybridge |
| | A91 | 1-[5-(Trifluoromethyl)-pyridin-2-yl]-piperazine | Maybridge |
| | A92 | 1-[3-Chloro-5-(trifluoromethyl)-pyridin-2-yl]-piperazine | Maybridge |
| | A94 | 2-(Pyrrolidin-2-yl-methyl)-pyridine | Hansa |
| | A95 | 2-(Piperidin-2-yl-methyl)-pyridine | Hansa |
| | A96 | 4-(Piperidin-2-yl-methyl)-pyridine | Hansa |
| | A97 | 4-(4-Chlorophenyl)-piperidin-4-ol | Aldrich |
| | A98 | 4-Phenyl-piperidin-4-ol | Aldrich |
| | A99 | 4-Benzyl-piperidin-4-ol | Alfa |
| | A100 | 4-[3-(Trifluoromethyl)phenyl]-piperidin-4-ol | Alfa |

TABLE 2-continued

| Amine | No. | Name | Supplier |
|---|---|---|---|
| | A101 | 2-Piperazin-1-yl-ethanol | Aldrich |
| | A102 | 1-(3,4-Dichlorophenyl)-piperazine | Aldrich |
| | A103 | 1-[(3,4-Dichlorophenyl)-methyl]-piperazine | Aldrich |
| | A105 | 1-[(4-Chlorophenyl)-methyl]-piperazine | Aldrich |
| | A106 | 1-(p-Tolyl-methyl)-piperazine | Aldrich |
| | A107 | 1-[(4-Methoxyphenyl)-methyl]-piperazine | Aldrich |
| | A108 | 1-[(2-Fluorophenyl)-methyl]-piperazine | Aldrich |
| | A109 | 1-Methyl-3-phenyl-piperazine | Aldrich |
| | A110 | 4-Phenyl-piperidine | Aldrich |
| | A111 | 4-Pyridin-3-yl-piperidin-4-ol | Interchim |
| | A113 | Methyl [2-(4-methyl-piperazin-1-yl)-1-phenyl-ethyl]-amine | Interchim |
| | A114 | 1-Methyl-4-piperidin-4-yl-piperazine | Interchim |

TABLE 2-continued

| Amine | No. | Name | Supplier |
|---|---|---|---|
| | A115 | Methyl-(2-piperidin-1-yl-ethyl)-amine | Chembridge |
| | A116 | 1-(2-Piperidin-4-yl-ethyl)-piperidine | Interchim |
| | A117 | 1-[2-(2,5-Dimethyl-1H-pyrrol-1-yl)-ethyl]-piperazine | Maybridge |

Synthesis of
2-cyclopropyl-2,7-diazaspiro[4.4]nonane A2

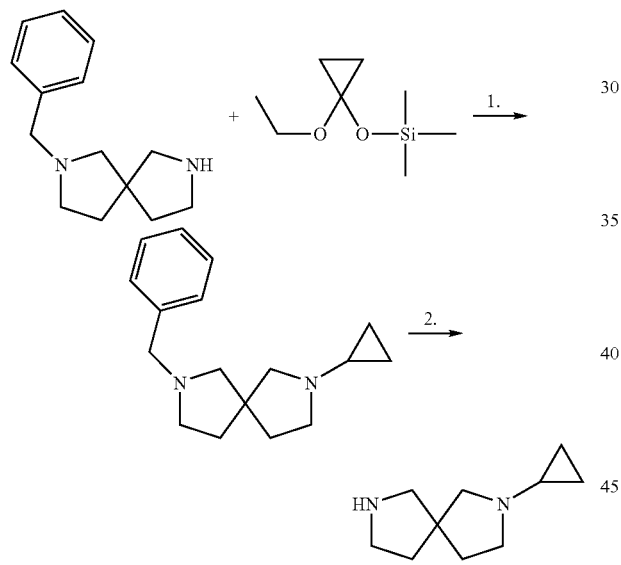

1. NaCNBH$_3$ (654 mg, 10.4 mmol) was added to a solution of 2-benzyl-2,7-diaza-spiro[4.4]nonane (450 mg, 2.08 mmol), acetic acid (1.19 ml, 20.8 mmol), molecular sieve (3 Å, beads) and (1-ethylcyclopropyloxy) trimethylsilane (2.09 ml, 10.4 mmol) in MeOH (45 ml) and the mixture was then refluxed. After 4 h the reaction batch was cooled to RT and filtered. The residue was washed with MeOH (50 ml) and the combined organic phases were concentrated to dryness. The residue was taken up in water (5 ml) and NaOH solution (2 M, 10 ml) and extracted with DCM (2×40 ml). The combined organic phases were dried over Na$_2$SO$_4$ and concentrated to dryness. The crude product was used with no further purification. Yield: 440 mg, 82%

2. A solution of benzylamine (440 mg, 1.72 mmol) in absolute EtOH (10 ml) was gassed for 10 min with N$_2$. Then Pd (10% on carbon, 183 mg, 172 µmol) was added and the mixture was again gassed for 10 min with N$_2$. The reaction batch was stirred overnight at RT under an H$_2$ atmosphere (3 bar). On completion of the reaction the mixture was filtered over celite and rewashed with DCM (30 ml) and MeOH (30 ml). The combined filtrates were concentrated to dryness. The product was used without further purification.

Synthesis of
2-(pyridin-4-yl)-2,8-diazaspiro[4.5]decane A3

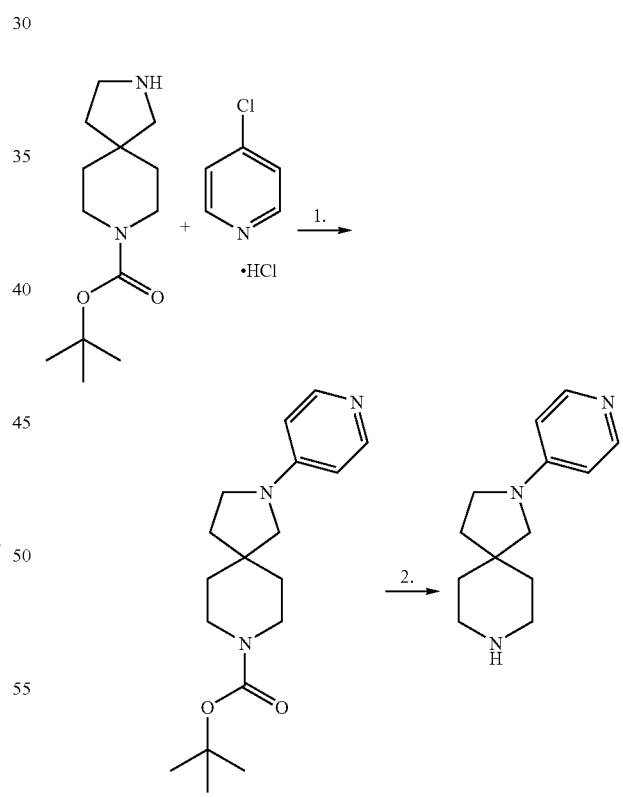

1. The reaction was performed under an N$_2$ atmosphere. tert-Butyl 2,8-diazaspiro[4.5]decane-8-carboxylate (869 mg, 3.62 mmol), 4-chloropyridine hydrochloride (1.08 g, 7.20 mmol) and TEA (2.5 ml, 18 mmol) were suspended in iso-propanol (10 ml). The mixture was heated to 80° C. and stirred overnight at 80° C. Then the solvent was removed in a rotary evaporator. The residue was taken up in DCM and concentrated to small volume again. This process was repeated twice more. The crude product was purified by column chromatography (silica gel, DCM/7M NH₃ in MeOH, 98:2). The product obtained still contained impurities and was used in the next stage in that condition.

2. The reaction was performed under an N₂ atmosphere. The carbamate (1.034 g, max. 3.26 mmol) was dissolved in MeOH (5 ml) and mixed with 4 M HCl in dioxane (5 ml). The reaction batch was stirred for 2 h at RT. Then the solvent was removed. The crude product was purified by column chromatography (silica gel, DCM/7M NH₃ in MeOH, 98:2→95:5→9:1). Yield: 455 mg, 58% over 2 stages.

Synthesis of 6-(piperidin-1-ylmethyl)-1,2,3,4-tetrahydronaphthalen-2-amine A5

6 h at 100° C., then cooled, diluted with water and extracted with ethyl acetate (3×75 ml). The combined organic phases were washed with water (5×20 ml) and saturated sodium chloride solution, dried (Na₂SO₄), filtered and concentrated to small volume. The crude product was purified by column chromatography (100-200 mesh silica gel, 3% ethyl acetate in hexane). Yield: 50% 4.20% DIBAL in toluene (1.72 ml, 2.42 mmol) was added dropwise to a solution of 6-(dibenzylamino)-5,6,7,8-tetrahydronaphthalene-2-carbonitrile (0.57 g, 1.61 mmol) in anhydrous toluene (20 ml) cooled to 0° C. The reaction mixture was slowly heated to 25° C. and stirred for 4 h. Then it was cooled again to 0° C. and 20 ml 10% hydrochloric acid were added dropwise. The reaction mixture was heated to 25° C. and stirred for 2 h. Then it was neutralised with saturated sodium bicarbonate solution and

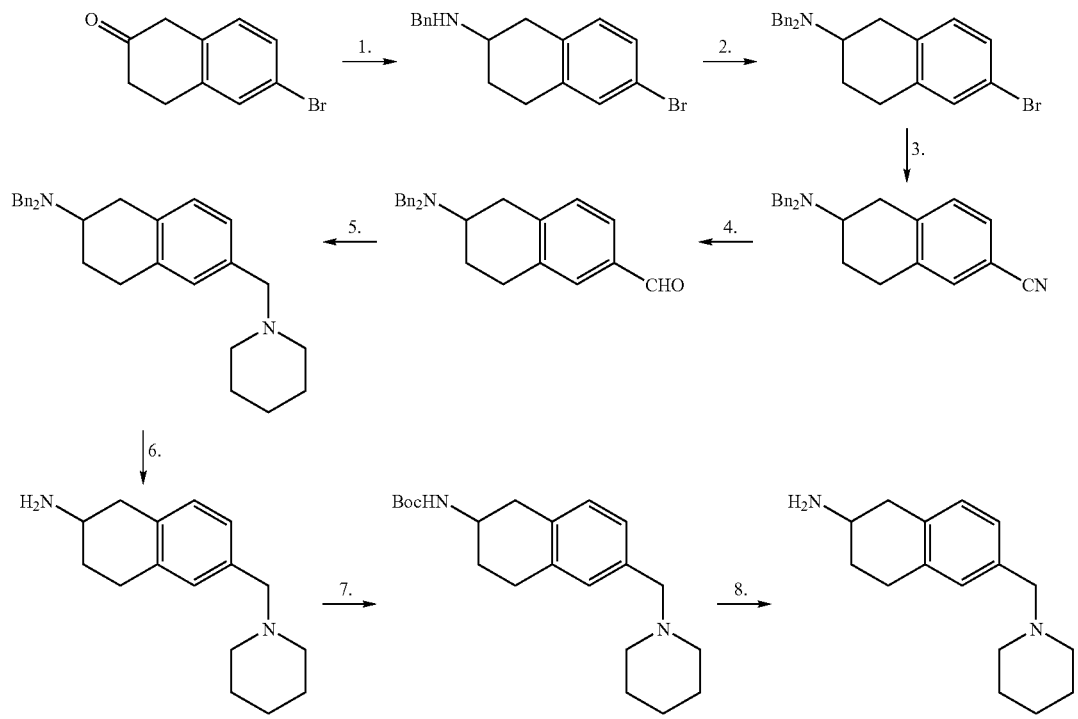

1. Benzylamine (0.72 ml, 6.6 mmol) was added to a solution of 6-bromo-3,4-dihydronaphthalen-2(1H)-one (1 g, 4.4 mmol) in DCM (88 ml), followed by a catalytic amount of acetic acid (0.74 ml). The reaction mixture was stirred for 30 min at 25° C., then Na(OAc)₃BH (3.73 g, 17.6 mmol) was added and the mixture was stirred for 16 h. Then it was diluted with DCM (150 ml) and extracted with saturated bicarbonate solution and saturated sodium chloride solution. The organic phase was dried (Na₂SO₄), filtered and concentrated to small volume. The crude product was purified by column chromatography (100-200 mesh silica gel, 3% methanol in ethyl acetate). Yield: 95%

2. N-Benzyl-6-bromo-1,2,3,4-tetrahydronaphthalen-2-amine was reacted with benzaldehyde under analogous reaction conditions to stage 1. Yield: 50%

3. A mixture of N,N-dibenzyl-6-bromo-1,2,3,4-tetrahydronaphthalen-2-amine (0.9 g, 2.21 mmol) and zinc cyanide (0.39 g, 3.32 mmol) in DMF (20 ml) was degassed with argon for 30 min and then mixed with xanthphos (0.256 g, 0.44 mmol) and tris(dibenzylidene acetone)dipalladium(0) (0.202 g, 0.22 mmol). The resulting reaction mixture was heated for extracted with ethyl acetate. The organic phase was extracted with saturated sodium chloride solution, dried (Na₂SO₄), filtered and concentrated to small volume. The crude product was used in the following stage with no further purification. Yield: 94%

5. 6-(Dibenzylamino)-5,6,7,8-tetrahydronaphthalene-2-carbaldehyde was reacted with piperidine under analogous reaction conditions to stage 1. Yield: 52%

6. Argon was added to a solution of N,N-dibenzyl-6-(piperidin-1-ylmethyl)-1,2,3,4-tetrahydronaphthalen-2-amine (0.5 g, 1.17 mmol) in ethanol (80 ml) for 10 min and then 20% palladium hydroxide (120 mg) was added. The reaction mixture was stirred for 5 h under a hydrogen atmosphere and the progress was monitored hourly via LC-MS. The mixture was filtered over celite and washed with ethanol. The filtrate was concentrated to small volume under reduced pressure and the crude product used in the next stage with no further purification. Yield: quantitative 7. TEA (0.5 ml, 3.73 mmol) was added to a solution of 6-(piperidin-1-ylmethyl)-1,2,3,4-tetrahydronaphthalen-2-amine (0.365 g, 1.49 mmol) in DCM (15 ml), followed by Boc anhydride (0.46 ml, 2.24 mmol) at 0° C. The reaction mixture was stirred for 2 h at 25° C., then iced water was added and the mixture was extracted with DCM (500 ml). The organic phase was extracted with water and saturated sodium chloride solution, dried (Na$_2$SO$_4$), filtered and concentrated to small volume. The crude product was purified by column chromatography (100-200 mesh silica gel, 2% methanol in DCM). Yield: 36%

8. TFA (2 ml/mmol) was added to a solution of tert-butyl 6-(piperidin-1-ylmethyl)-1,2,3,4-tetrahydronaphthalen-2-ylcarbamate (0.19 g, 0.55 mmol) in DCM (10 ml/mmol) at 0° C. and the mixture was stirred for 2 h at 25° C. The solvent was removed and the product was dried under vacuum. The crude product was used in the following stage with no further purification.

Method B

See Synthesis of amine A51 (Step 1-Step 4)

Synthesis of 6-(piperidin-1-ylmethyl)-1,2,3,4-tetrahydronaphthalen-1-amine A6 cooled to −10° C. BH$_3$.SMe$_2$ (0.3 ml, 2.94 mmol) was added slowly to this solution at −10° C., followed by the dropwise addition of methyl 5-oxo-5,6,7,8-tetrahydronaphthalene-2-carboxylate (0.5 g, 2.45 mmol) in THF (2 ml). The reaction mixture was stirred for 30 min and methanol (4 ml) was added at 0° C. Then the mixture was heated to 25° C. and stirred for 16 h. The reaction mixture was concentrated to small volume and the residue diluted with ethyl acetate. The organic phase was extracted with 0.1 N HCl (2×10 ml), 5% sodium bicarbonate solution (2×10 ml) and saturated sodium chloride solution, dried (Na$_2$SO$_4$), filtered and concentrated to small volume. The crude product was purified by column chromatography (20% ethyl acetate in hexane). Yield: 40%

3. DPPA (0.4 ml, 1.61 mmol) was added dropwise to a cold solution of (S)-methyl 5-hydroxy-5,6,7,8-tetrahydronaphthalene-2-carboxylate (0.22 g, 1.07 mmol) in toluene (5 ml), followed by DBU (0.24 ml, 1.61 mmol). The reaction mixture was slowly heated to 25° C. and stirred for 16 h. Then it was diluted with ethyl acetate (15 ml) and extracted with 0.1 N HCl, 5% sodium bicarbonate solution and saturated sodium chloride solution, dried (Na$_2$SO$_4$), filtered and concentrated

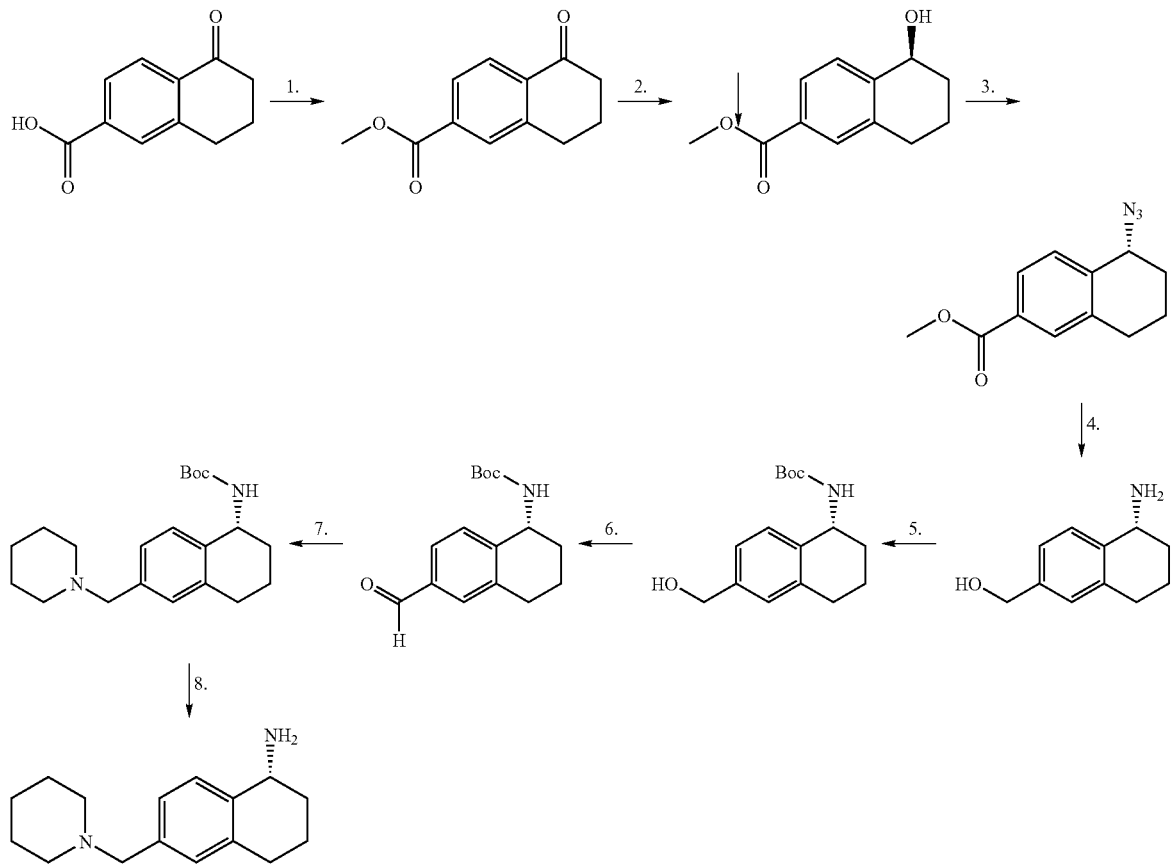

1. 5-Oxo-5,6,7,8-tetrahydronaphthalene-2-carboxylic acid (3 g) was refluxed for 16 h with 30 ml methanol, saturated with HCl gas. The reaction mixture was concentrated to small volume and the residue diluted with DCM. The organic phase was extracted with saturated NaHCO$_3$ solution and saturated sodium chloride solution, dried (Na$_2$SO$_4$) and concentrated to small volume. Yield: quantitative 2. A (1M) solution of (R)-2-methyl-CBS-oxazaborolidine (0.12 ml, 0.12 mmol) was diluted with toluene (10 ml) and to small volume. The crude product was purified by column chromatography (20% ethyl acetate in hexane). Yield: 80%

4. A solution of (R)-methyl 5-azido-5,6,7,8-tetrahydronaphthalene-2-carboxylate (3.39 mmol) in THF (2 ml) was added dropwise to a cold suspension of LAH (0.132 g, 3.46 mmol) in THF (2 ml). The reaction mixture was stirred for 30 min, then heated to 25° C. and stirred for a further 16 h. Then THF/H$_2$O (9:1) was added, the mixture was filtered over celite and concentrated to small volume under reduced pressure. The crude product was used in the following stage without further purification. Yield: quantitative 5. TEA (4 ml, 28.25 mmol) and Boc anhydride (3.7 ml, 16.95 mmol) were added to a solution of (R)-(5-amino-5,6,7,8-tetrahydronaphthalen-2-yl)methanol (2 g, 11.3 mmol) in DCM (20 ml) cooled to 0° C. and the mixture was stirred for 16 h at RT. Then the mixture was diluted with DCM and extracted with water and saturated sodium chloride solution, dried (Na$_2$SO$_4$), filtered and concentrated to small volume. The crude product was purified by column chromatography (30% ethyl acetate in hexane). Yield: 51%

6. Manganese dioxide (2.78 g) was added to a solution of (R)-tert-butyl 6-(hydroxymethyl)-1,2,3,4-tetrahydronaphthalen-1-ylcarbamate (0.8 g, 2.12 mmol) in anhydrous toluene (40 ml) and the mixture was refluxed for 16 h. The solid was filtered over celite, washed with ethyl acetate and the filtrate concentrated to small volume under reduced pressure. The crude product was purified by column chromatography (40% ethyl acetate in hexane). Yield: 44%

7. Sodium cyanoboron hydride (2.5 eq.) was added to a solution of (R)-tert-butyl 6-formyl-1,2,3,4-tetrahydronaphthalen-1-ylcarbamate (0.35 g, 1.27 mmol) and piperazine (1.5 eq.) in methanol (3 ml) at 25° C., followed by acetic acid (catalytic). The mixture was stirred for 16 h. The reaction progress was monitored by thin-layer chromatography. On completion of the reaction the mixture was concentrated under reduced pressure, the residue diluted with DCM and washed with saturated NaHCO$_3$ solution. The organic phase was dried (Na$_2$SO$_4$), filtered and concentrated to small volume under reduced pressure. The crude product was purified by column chromatography (10% methanol in DCM). Yield: 36%

8. TFA (13 eq.) was added to a DCM solution (10 ml/mmol) of (R)-tert-butyl 6-(piperidin-1-ylmethyl)-1,2,3,4-tetrahydronaphthalen-1-ylcarbamate (1 eq.) at 0° C. and the mixture was stirred for 2 h at RT. The solvent was removed and the product was dried under vacuum. The crude product was used in the following stage without further purification.

Synthesis of 3-(pyridin-4-yl)-3,9-diazaspiro[5.5]undecane A7

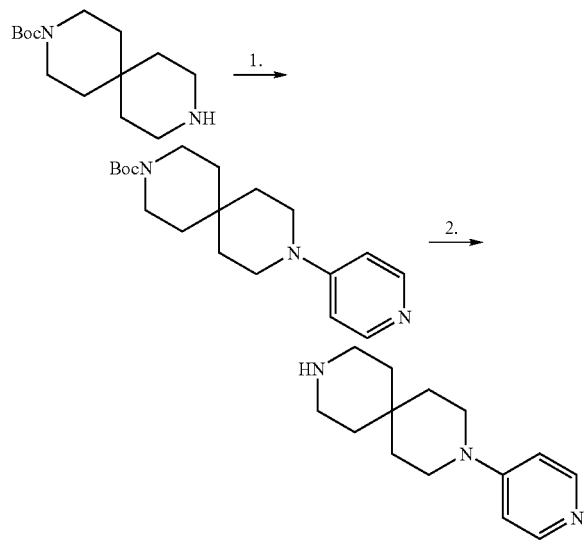

1. Sodium tert-butylate (4 mmol) was added to a solution of 4-bromopyridine hydrochloride (1.9 mmol) in dry toluene (10 ml) under argon, followed by 3,9-diazaspiro[5.5]undecane-3-carboxylic acid tert-butyl ester (1.6 mmol) in toluene (5 ml). Argon was added to the mixture for 15 min, then (S)-(−)-2,2'-bis(diphenylphosphino)-1,1'-binaphthyl (0.123 mmol) and tris(dibenzylidene acetone)dipalladium (0.041 mmol) were added. The mixture was heated at 90° C. for 4 h and the reaction progress was monitored by thin-layer chromatography. On completion of the reaction the mixture was diluted with ethyl acetate (100 ml) and extracted with water and saturated sodium chloride solution, dried (Na$_2$SO$_4$), filtered and concentrated to small volume. The crude product was purified by column chromatography (3% methanol in DCM). Yield: 45%

2. TFA (13 eq.) was added to a DCM solution (10 ml/mmol) of tert-butyl 9-(pyridin-4-yl)-3,9-diazaspiro[5.5]undecane-3-carboxylate (1 eq.) at 0° C. and the mixture was stirred for 2 h at RT. The solvent was removed and the product was dried under vacuum. The crude product was used in the following stage with no further purification. Yield: quantitative Synthesis of N-methyl-2-(1-(pyridin-4-yl)piperidin-4-yl)ethanamine A8

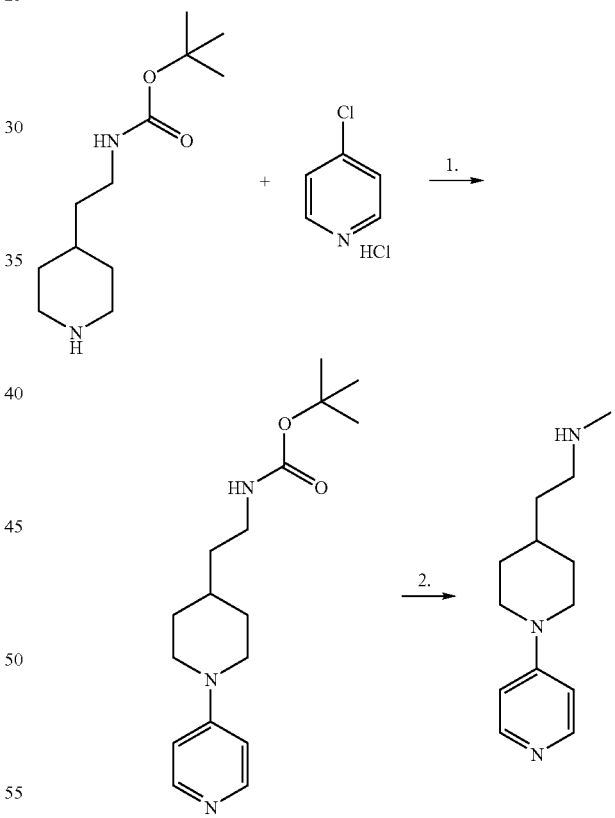

1. (2.00 g, 8.76 mmol), 4-chloropyridine hydrochloride (1.31 g, 8.76 mmol) and TEA (2.44 ml, 17.55 mmol) were in i-PrOH (10 ml) and heated in the microwave for 2 h at 120° C. The solvent was removed under vacuum. The product was purified by column chromatography (silica gel, DCM/(7 M NH$_3$ in MeOH, 99:1→98:2→95:5).

2. The reaction was performed under an argon atmosphere. The amine from stage 1 (1.87 g, 4.56 mmol) was dissolved in dry THF (75 ml) and cooled to 0° C. A solution of LAH (2.4 M in THF, 7.6 ml, 18.25 mmol) was added dropwise. On completion of the addition the mixture was heated to 60° C. After a reaction time of 4.5 h the mixture was cooled to RT and stirred overnight at RT. Na$_2$SO$_4$.10H$_2$O was added to the reaction solution until no further H$_2$ evolution could be detected. The viscous solution was dried by adding Na$_2$SO$_4$ and filtered after approximately 30 min. The residue was rewashed with THF. The combined filtrates were concentrated to dryness and the crude product obtained was purified by column chromatography.

Synthesis of
1-benzyl-3,3-dimethylpiperidin-4-amine A11

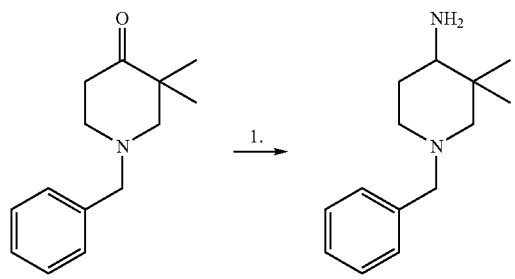

A solution of 1-benzyl-3,3-dimethylpiperidin-4-one (900 mg, 4.14 mmol) and acetic acid (474 µl, 8.28 mmol) in 7 M NH$_3$ in MeOH (35.5 ml, 249 mmol) was first stirred for 30 min at RT. Then NaBH$_4$ (1.57 g, 41.4 mmol) was added at RT. The reaction batch was stirred for 30 min at RT, concentrated and then diluted with DCM (100 ml). The organic phase was washed with saturated aqueous NaHCO$_3$, dried and concentrated to dryness.

Synthesis of 2,2,2-Trifluoro-1-(2,8-diazaspiro[4.5] decan-2-yl)ethanone A12

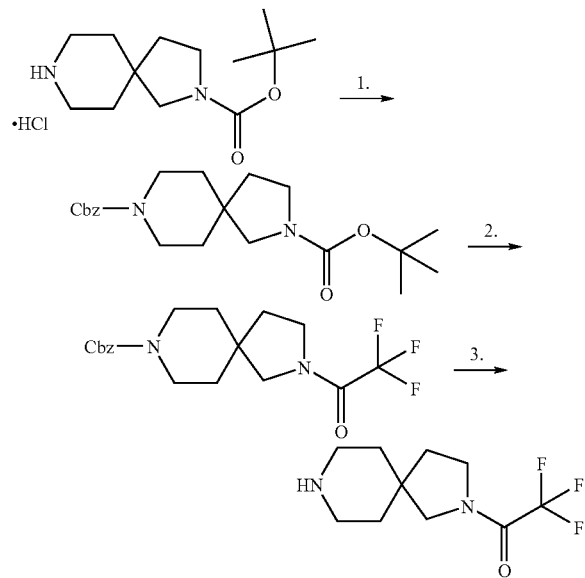

1. To a solution of 1-Boc-diamine hydrochloride (1.0 mmol) and TEA (2.5 mmol) in DCM (15 ml) was added Cbz-Cl (1.4 mmol) and then stirred at ° C. for 1 h. The reaction mixture was diluted with DCM (50 m). The organic layer was washed with water (10 ml), brine (10 ml), dried over anhydrous Na$_2$SO$_4$ and concentrated. The crude product is purified by column chromatography using 40% ethyl acetate in hexanes as eluent.

2. To a solution of step-1 product (1.2 mmol) in DCM (10 ml) was added TFA (2 ml) and stirred for 2 h at 25° C. The reaction mixture was concentrated under reduced pressure and crude mass was dissolved in DCM (10 ml) and then TEA (5 mmol) was added to the reaction mixture. To the solution was added trifluoroacetic anhydride (2.4 mmol) drop wise at 0° C. and stirred for 30 min at 25° C. The reaction mixture was diluted with DCM (50 ml). The organic layer is washed with water, brine, dried over anhydrous Na$_2$SO$_4$ and concentrated. The crude product is purified by column chromatography using 30% ethyl acetate in hexanes as eluent.

3. To a degassed solution of step-2 product (350 mg) in ethanol (30 ml) was added 10% Pd/C (70 mg) and hydrogenated under 2 Kg H$_2$ pressure. The reaction mixture was filtered through celite and the filtrated was concentrated under reduced pressure to give the desired product which was used for amidation without further purification.

Synthesis of (1R,3S,5S)-3-(pyridin-4-yloxy)-8-azabicyclo[3.2.1]octane dihydrochloride [A13]

Stage (i)

(1R,3R,5S)-tert-Butyl 3-hydroxy-8-azabicyclo[3.2.1] octane-8-carboxylate and (1R,3S,5S)-tert-butyl 3-hydroxy-8-azabicyclo[3.2.1]octane-8-carboxylate Boc-nortropinone (2.5 g, 11.097 mmol) was dissolved in methanol (20 ml) and cooled with an ice bath. Sodium boron hydride (1.26 g, 33.291 mmol) was added slowly under protective gas. After stirring for 4 h at RT the mixture was hydrolysed with saturated sodium hydrogen carbonate solution (30 ml), the methanol was removed under vacuum and the aqueous phase extracted with ethyl acetate (3×50 ml). The combined organic phases were dried over magnesium sulfate and concentrated to small volume under vacuum. The crude product was purified by column chromatography (silica gel) with ethyl acetate/methanol/dichloromethane/ammonia (25% eq.) (400:40:40:1). The isomers were separated in this process and they were assigned by NMR analysis. Yield: endo 53% [reacted further in stage (ii)], exo 25%

Stage (ii)

(1R,3S,5S)-tert-Butyl 3-(pyridin-4-yloxy)-8-azabicyclo[3.2.1]octane-8-carboxylate (1R,3R,5S)-tert-Butyl 3-hydroxy-8-azabicyclo[3.2.1]octane-8-carboxylate (1 eq.) was dissolved in tetrahydrofuran (50 eq.) and 4-hydroxypyridine (1 eq.) and triphenylphosphine (1.25 eq.) were added. Diisopropylazodicarboxylate (1.25 eq.) was then added dropwise and the reaction mixture was heated to 55° C. After 15 h tetrahydrofuran was removed under vacuum, the residue was taken up in ethyl acetate (50 ml) and extracted with aqueous hydrogen chloride solution (2×40 ml, 1 mol/l). The aqueous phase was alkalized with sodium hydroxide solution (pH=8) and extracted with ethyl acetate (3×50 ml). These organic phases were combined, dried over Na$_2$SO$_4$ and concentrated to small volume under vacuum. The crude product was purified by column chromatography (silica gel) with ethyl acetate/hexane (3:1). Yield: 65% [The other isomer can be obtained from the corresponding exo product from stage (i) in an analogous manner.]

Stage (iii)

(1R,3S,5S)-3-(Pyridin-4-yloxy)-8-azabicyclo[3.2.1]octane dihydrochloride (1R,3S,5S)-tert-Butyl 3-(pyridin-4-yloxy)-8-azabicyclo[3.2.1]octane-8-carboxylate (1 eq.) was added in hydrogen chloride in methanol (4 eq., 1.25 mol/l) and the reaction mixture was refluxed for 30 min. The solvent was removed under vacuum and the residue taken up in a little ethanol (5 ml) and then mixed with acetone (30 ml). The mixture was stirred for 30 min at RT and then diethyl ether (20 ml) was added. The precipitate was siphoned off, washed with diethyl ether and dried under vacuum. Yield: 90% [The other isomer can be obtained from the corresponding exo product of stage (i) in an analogous manner to stage (ii) and (iii).]

Synthesis of 3-(4-(2-(Pyrrolidino-1-yl)ethoxy)piperidine-4-yl)pyridine A14

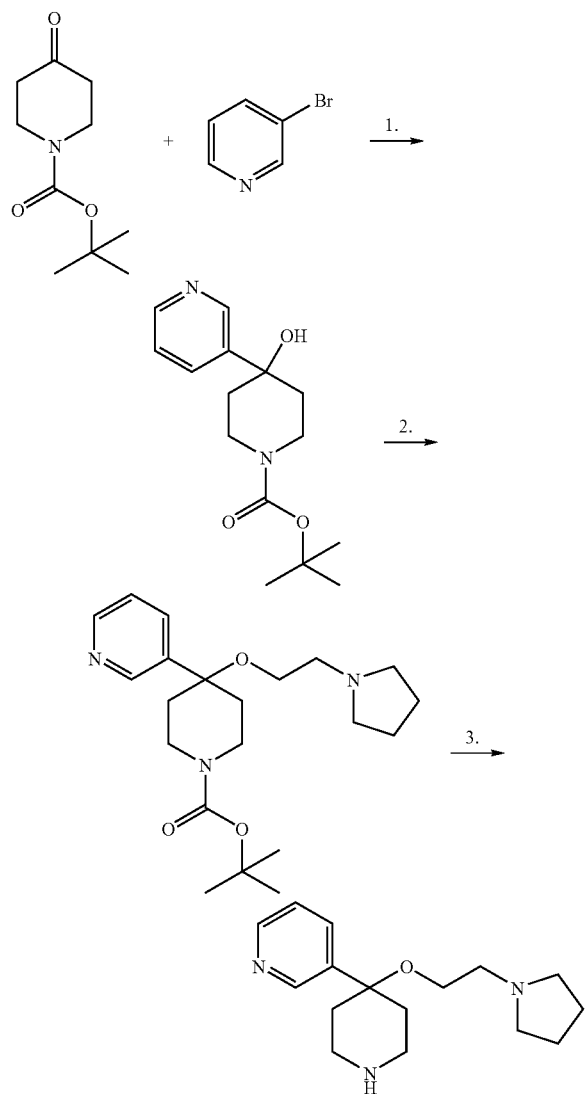

1. 3-Bromo pyridine (22.47 mmol) in anhydrous diethyl ether (10 ml) was added dropwise (10 min) to a stirred solution of n-BuLi (24.7 mmol) in anhydrous diethyl ether (70 ml) under argon at −78° C. and stirred for 30 min. N-Boc-Piperidone (11.23 mol) in ether (10 ml) was then added to this mixture and stirred for additional 1 h at that temperature. The reaction mixture was allowed to warm to 25° C. and partitioned between ethyl acetate (150 ml) and water (80 ml). The aqueous phase was extracted with ethyl acetate (2×70 ml), combined organic phase was dried over $MgSO_4$ and the solvent was removed under reduced pressure to give a yellow liquid residue. The residue is then purified by flash chromatography (2% MeOH:DCM) to give the desired product.

2. Anhydrous potassium hydroxide (11.25 mmol) was added to a mixture of the alcohol (2.25 mmol) and the bromide (3.375 mmol) in degassed toluene (25 ml), followed by 18-Crown-6 (catalytic amount). The reaction mixture was then heated at reflux for 12 h after which toluene was evaporated and water was added to the residue. The aqueous layer was then extracted with DCM (3×60 ml). The organic washings were combined, washed with brine and dried over anhydrous sodium sulfate. Finally, the organic layer was dried in vacuo to yield a solid residue which is purified on silica gel (100-200 mesh) eluting with 4% methanol in DCM to get the product 3. To a cooled (0° C.) solution Boc-compound (0.33 mmol) in DCM (3.5 ml) was added TFA (0.7 ml) and the reaction mixture was stirred at 25° C. for 1 h. After completion of the reaction, the solvent was evaporated under reduced pressure to get crude product which is directly used in the next step.

Synthesis of 6-((tert-Butylamino)methyl)-1,2,3,4-tetrahydronaphthalen-2-amine A15

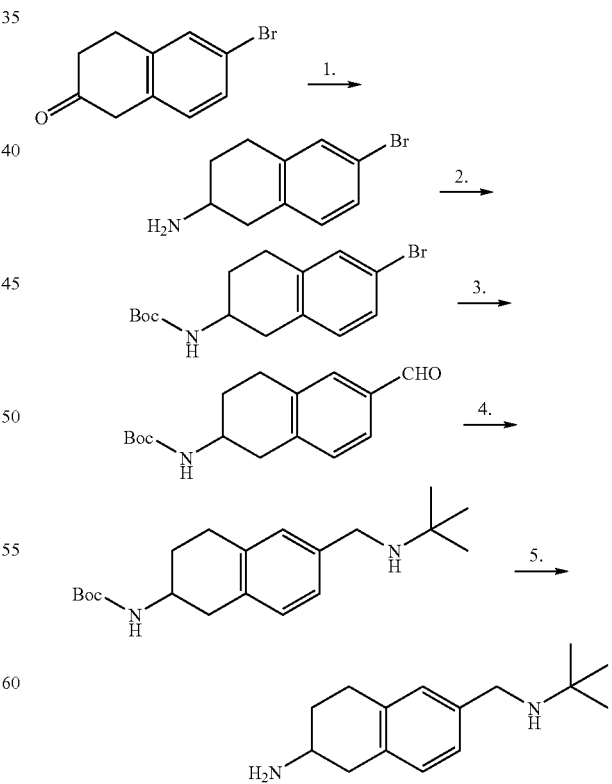

1. $NH_4OAc$ (10.19 g, 0.13 mol, 10 eq.) was added to a solution of 6-bromo-3,4-dihydronaphthalen-2(1H)-one (3 g, 0.13 mol, 1 eq.) in MeOH (100 ml) and the mixture was stirred for 2 h at RT. NaBH₃CN (990 mg, 0.015 mol, 1.2 eq.) was added to the reaction mixture and it was stirred for another 16 h at RT. The reaction mixture was concentrated under reduced pressure, diluted with water (100 ml) and acidified with 1 N HCl solution. The mixture was extracted with DCM (2×100 ml) and the aqueous part basified with 1 N NaOH solution. Then the aqueous part was extracted with DCM (4×200 ml). The organic part was washed with brine (100 ml), dried over Na₂SO₄ and concentrated under reduced pressure. The reddish crude liquid thus obtained was used for the next step without further purification. Yield: 2.6 g 2. To a mixture of 6-bromo-1,2,3,4-tetrahydronaphthalen-2-amine (5.5 g, 24.3 mmol, 1 eq.) in DCM (120 ml) and TEA (10.24 ml, 72 mmol, 3 eq.) was added dropwise boc-anhydride (6 ml, 26 mmol, 1.1 eq.) at 0° C. and the mixture was then stirred at RT for 16 h. After completion of the reaction (monitored by TLC) the mixture was diluted with DCM (100 ml), the organic layer washed with water (100 ml) and brine (100 ml), and dried over anhydrous Na₂SO₄. The solvent was then evaporated to yield the desired compound as an off-white solid which was used in the next step without further purification. Yield: 7 g 3. BuLi (1.5 M, 15 ml, 22.5 mmol, 2 eq.) was added dropwise to a stirred solution of tert-butyl 6-bromo-1,2,3,4-tetrahydronaphthalen-2-ylcarbamate (3.5 g, 10.73 mmol, 1 eq.) in THF (100 ml) at −78° C. and the reaction mixture was stirred for 45 min at the same temperature. Then DMF (3 ml, 32.1 mmol, 3 eq.) was added to the reaction mixture very slowly at −78° C. and it was stirred for 1 h. After completion of the reaction (monitored by TLC) the mixture was quenched with saturated NH₄Cl solution (20 ml) and diluted with ethyl acetate (100 ml). The organic part was separated, washed with water (100 ml) and brine (100 ml), and dried over Na₂SO₄. It was concentrated under reduced pressure to yield the crude product which was purified by column chromatography (silica gel, 20% EtOAc/hexanes) to give the desired compound as a yellowish liquid. Yield: 75% (2.2 g, 8 mmol)

4. A solution of t-BuNH₂ (0.8 ml, 7.6 mmol, 1 eq.) in DCM (3 ml) was added to a solution of tert-butyl 6-formyl-1,2,3,4-tetrahydronaphthalen-2-ylcarbamate (2.1 g, 7.6 mmol, 1 eq.) in dry DCM (100 ml) at 0° C. and resulting reaction mixture was stirred at 25° C. for 2 h. The reaction mixture was cooled to 0° C., then NaBH₃CN (4.45 g, 20.9 mmol, 3.0 eq.) was added portionwise and the mixture was then stirred at 25° C. for 16 h. The mixture was diluted with DCM (200 ml), washed with water (2×50 ml) and brine (2×50 ml) and the organics were dried over Na₂SO₄. The solvent was evaporated under reduced pressure and the residue purified by column chromatography (silica gel; 5% EtOAc/hexanes) to yield the desired product as a white solid. Yield: 72% (1.8 g, 5.4 mmol)

5. TFA (14 ml, 0.192 mol, 40 eq.) was added to a solution of tert-butyl 6-((tert-butylamino)methyl)-1,2,3,4-tetrahydronaphthalen-2-ylcarbamate (1.6 g, 4.8 mmol, 1.0 eq.) in DCM (100 ml) at 0° C. and resulting reaction mixture was stirred at 25° C. for 30 min. The solvent was evaporated under reduced pressure and the residue obtained was diluted with EtOH (50 ml). The mixture was basified with Amberlyst (A-21, ~6 g) to pH 9-10 and then stirred for 1 h. The reaction mixture was filtered and concentrated under reduced pressure to give a yellowish solid which was used for the next step without further purification. Yield: quantitative Synthesis of N-[[5-(tert-Butoxycarbonylamino)-5,6,7,8-tetrahydro-naphthalen-2-yl]-methyl]-N-methyl-carbamic acid 9H-fluoren-9-yl-methyl ester A16

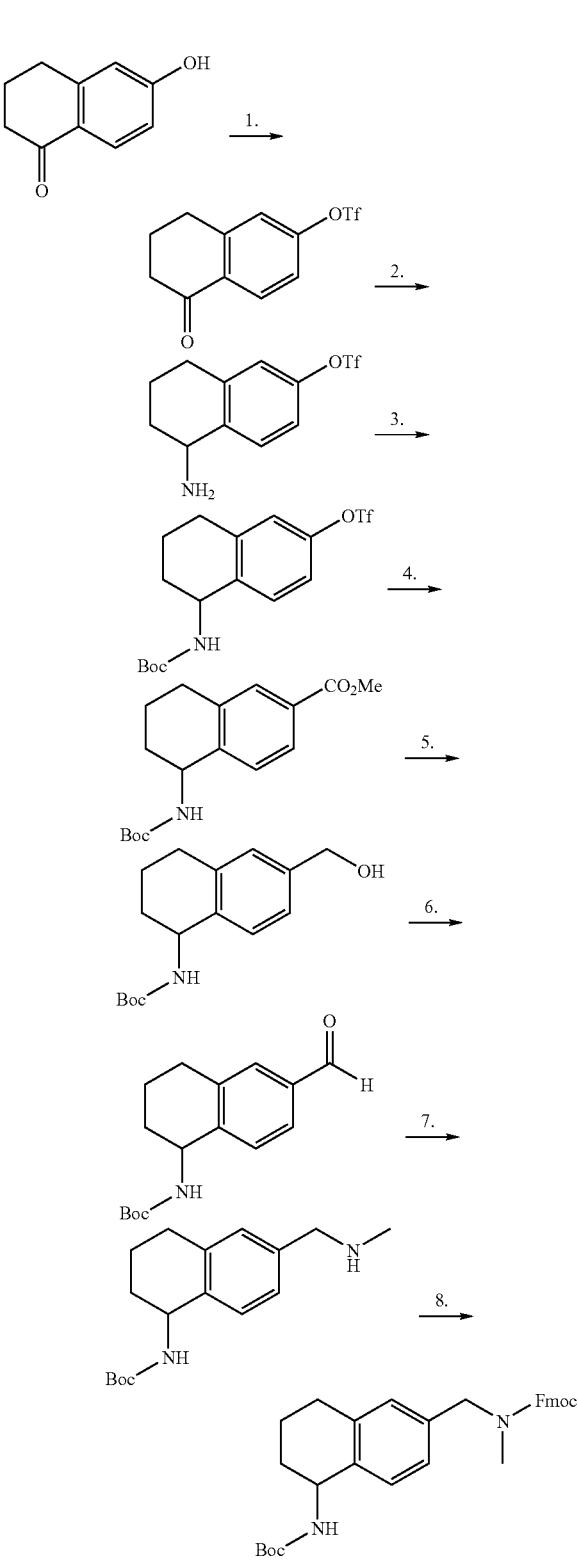

1. To a stirred solution of 6-hydroxy-1-tetralone (3 g, 0.0184 mol) and 2,6-Lutidine (9.6 ml, 0.082 mol, 4.5 eq.) in DCM (48 ml) at 0° C. was added slowly Triflic anhydride (4.5 ml, 0.0274 mol, 1.5 eq.) and the reaction mixture was stirred for 1 h at 0° C. Water (48 ml) was added to quench the reaction. After stirring for 15 min at RT the mixture was diluted with DCM (96 ml) and the layer were separated. The organic layer was washed with 10% aqueous NaHCO₃ solution (100 ml), water (100 ml) and then brine (50 ml). The organic layer was dried over anhydrous Na₂SO₄ and concentrated under reduced pressure. The crude product was purified by column chromatography (silica gel 100-200). The product is eluted in 2% ethyl acetate/hexane.

2. To a stirred solution of step 1 product (2 g, 0.0068 mol) and NH₄OAc (5.23 g, 0.0068 mol, 1.0 eq.) in MeOH (30 ml) was added slowly NaBH₃CN (0.512 g, 0.0082 mol, 1.2 eq.) at RT and the reaction mixture was stirred for 20 h. The reaction mixture was concentrated under reduced pressure, diluted with water (10 ml), acidified 0.1 M HCl to pH~2 and extracted with DCM (20 ml). The aqueous layer was basified with 0.1 N NaOH and extracted with DCM (3×20 ml). The combined organic layers were dried over anhydrous Na₂SO₄ and concentrated under reduced pressure to yield the title compound.

3. To the stirred solution of step-3 product (0.8 g, 0.003 mol) in DCM (10 ml) was added TEA (2 ml, 0.009 mol, 3.0 eq.) at 0° C. Boc anhydride (0.7 ml, 0.0036 mol, 1.2 eq.) was added and the reaction mixture is stirred overnight at RT. The reaction mixture was diluted with DCM (20 ml) and washed with water, then brine. The DCM layer was dried over anhydrous Na₂SO₄ and concentrated under reduced pressure. The crude was purified by column chromatography on silica gel (100-200 mesh). The pure product is eluted in 2% Ethyl acetate/Hexane.

4. To a stirred solution of step 3 product (0.395 g, 0.001 mol) in methanol (10 ml) was added Pd (OAc)₂ (3.0 mol %) and dppf (6 mol %) and the reaction mixture was purged with carbon monoxide for 30 min. The reaction was stirred at 70° C. for 14 h. After completion of the reaction, the reaction mixture was filtered and the filtrate was concentrated to give the crude product. The crude product was purified by column chromatography (silica gel 100-200). The pure product was eluted with 10% Ethyl acetate in hexane.

5. To the stirred suspension of LAH (1.08 g. 0.23 mol, 1.2 eq.) in THF (50 ml) was added a solution of step 4 compound (7.0 g, 0.023 mol) in THF (50 ml) at 0° C. and the reaction mixture was stirred for 30 min at 0° C. After completion of the reaction the reaction mixture was quenched with Na₂SO₄.10H₂O (20 g) and the reaction mixture was filtered, the filtrate was concentrated under reduced pressure to afford the colorless solid compound.

6. To the stirred solution of oxalyl chloride (0.149 g, 0.001 mol, 2 eq.) in DCM (2 ml) was added DMSO (0.168 g, 0.002 mol, 4 eq.) in DCM (2 ml) at −78° C. and stirred for 10 min. Then a solution of step-5 compound (0.15 g, 0.0005 mol) in DCM (2 ml) was added to the reaction mixture. The reaction mixture is stirred at −78° C. for 30 min. TEA (0.5 ml, 0.002 mol, 5.0 eq.) was added and the reaction mixture was stirred for additional 30 min. The reaction mixture was warmed to RT, added water and extracted with DCM (2×10 ml). The combined DCM layer was washed with brine, dried over Na₂SO₄ and concentrated under reduced pressure to yield the solid compound.

7. To a stirring solution of step-6 compound (1.0 g, 0.003636 mol, 1 eq) in DCM (20 ml) was added methylamine hydrochloride (0.3558 g, 0.004363 mol, 1.2 eq.) at RT and then the reaction mixture was stirred for 2 h at RT. Na(OAc)₃BH (2.3125 g, 0.0109 mol, 3 eq.) was then added to the reaction mixture at RT. The final reaction mixture then stirring over 16 h at RT. The reaction mixture was diluted with DCM (50 ml) and organic part washed by water (2×20 ml) and by brine (20 ml). The organic layer then dried over Na₂SO₄, evaporated in reduced pressure to get the crude material, which was purified by column chromatography (silica gel 100-200; 5% methanol/DCM) to desired product.

8. To a solution of step-4 product (0.45 g, 0.0015 mol) in water (9 ml), NaHCO₃ (0.26 g, 0.003 mol, 2 eq.) was added. A solution of Fmoc-Cl (0.6 g, 0.00225 mol, 1.5 eq.) in dioxane (9 ml) was added at 5° C. and then the reaction mixture was stirred at 0° C. for 2 h. The reaction mixture was concentrated under reduced pressure. The concentrated mass was diluted with water and extracted with ethyl acetate (3×50 ml). The combined organic layer was dried with anhydrous Na₂SO₄ and concentrated under reduced pressure to give the crude product. The crude product was purified using column chromatography (silica gel 100-200; 15% ethyl acetate/hexane) to give the desired product.

Synthesis of Amines A17-A27

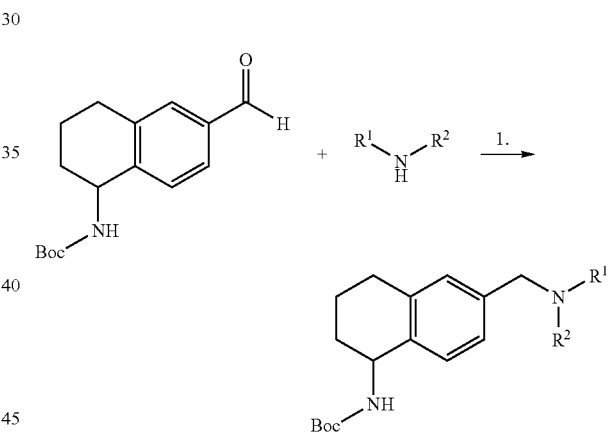

1. To a stirring solution of the aldehyde (1.0 g, 0.003636 mol, 1 eq.) in DCM (20 ml) was added the according amine (for A17 and A25 the amine hydrochloride) (1.2 eq.) at RT. The reaction mixture was stirred for 2 h at RT. Na(OAc)₃BH (2.3125 g, 0.0109 mol, 3 eq.) was then added to the reaction mixture at RT. The final reaction mixture then was stirring over 16 h at RT. The reaction mixture was diluted with DCM (50 ml) and organic part washed by water (2×20 ml) and by brine (20 ml). The organic layer then dried over Na₂SO₄, evaporated under reduced pressure to get the crude material, which was purified by column chromatography (silica gel 100-200; 5% methanol/DCM)

| No. | NR¹R² | Name |
|---|---|---|
| A17 | \N/ N | N-[6-(Dimethylaminomethyl)-1,2,3,4-tetrahydro-naphthalen-1-yl]-carbamic acid tert-butyl ester |

-continued

| No. | NR¹R² | Name |
|---|---|---|
| A18 | H-N-CH(CH₃)-CH₂CH₃ | N-[6-[(1-Methyl-propylamino)-methyl]-1,2,3,4-tetrahydro-naphthalen-1-yl]-carbamic acid tert-butyl ester |
| A19 | H-N-C(CH₃)₃ | N-[6-[(tert-Butylamino)-methyl]-1,2,3,4-tetrahydro-naphthalen-1-yl]-carbamic acid tert-butyl ester |
| A20 | CH₃-N-C(CH₃)₃ | N-[6-[(tert-Butyl-methyl-amino)-methyl]-1,2,3,4-tetrahydro-naphthalen-1-yl]-carbamic acid tert-butyl ester |
| A21 | pyrrolidine | N-[6-(Pyrrolidin-1-yl-methyl)-1,2,3,4-tetrahydro-naphthalen-1-yl]-carbamic acid tert-butyl ester |
| A22 | piperidine | N-[6-(Piperidin-1-yl-methyl)-1,2,3,4-tetrahydro-naphthalen-1-yl]-carbamic acid tert-butyl ester |
| A23 | morpholine | N-[6-(Morpholin-4-yl-methyl)-1,2,3,4-tetrahydro-naphthalen-1-yl]-carbamic acid tert-butyl ester |
| A24 | 4-methylpiperazine | N-[6-[(4-Methyl-piperazin-1-yl)-methyl]-1,2,3,4-tetrahydro-naphthalen-1-yl]-carbamic acid tert-butyl ester |
| A25 | 8-azabicyclo[3.2.1]octane | N-[6-(8-Azabicyclo[3.2.1]octan-8-yl-methyl)-1,2,3,4-tetrahydro-naphthalen-1-yl]-carbamic acid tert-butyl ester |
| A26 | H-N-CH₂-Ph | N-[6-[(Benzylamino)-methyl]-1,2,3,4-tetrahydro-naphthalen-1-yl]-carbamic acid tert-butyl ester |
| A27 | 1,2,3,4-tetrahydroquinoline | N-[6-(1,2,3,4-Tetrahydro-quinolin-1-yl-methyl)-1,2,3,4-tetrahydro-naphthalen-1-yl]-carbamic acid tert-butyl ester |

Synthesis of N-[[6-(tert-Butoxycarbonylamino)-5,6,7,8-tetrahydro-naphthalen-2-yl]-methyl]-N-methyl-carbamic acid 9H-fluoren-9-yl-methyl ester A28

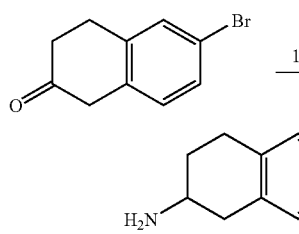

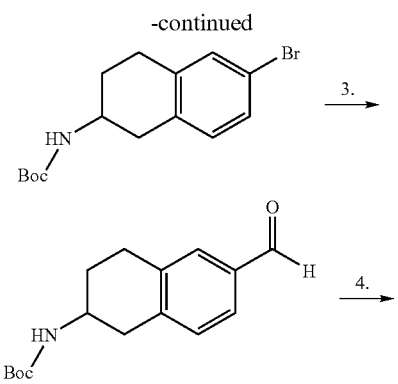

-continued

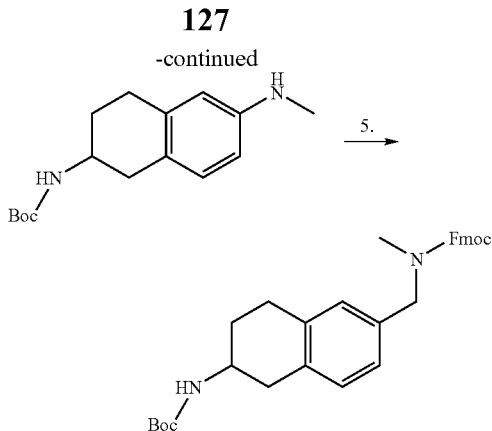

1. To a stirring solution of 6-bromo-2-tetralone (1.0 g, 0.00444 mol, 1 eq.) in methanol (139 ml) was added ammonium acetate (3.4218 g, 0.04444 mol, 10 eq.). The reaction mixture then stirred over 1 h at RT. Sodium cyanoborohydride (0.335 g, 0.00533 mol, 12 eq.) was then added to the reaction mixture at RT and then stirred for 20 h. The solvent of the reaction mixture was evaporated under reduced pressure. The residue then dissolved in water (50 ml) and acidified by 1(N)HCl solution up to PH~2. The aqueous part was extracted with DCM (2×50 ml). The aqueous part was then basified with 1(N) NaOH solution up to PH~10. The aqueous part was extracted with DCM (2×100 ml). The combined organic part was washed with brine (30 ml), dried over Na2SO4, and evaporated under reduced pressure to get the product 6-bromo-1,2,3,4-tetrahydro-2-napthyl amine.

2. To a stirring solution of 6-bromo-1,2,3,4-tetrahydro-2-napthyl amine (0.5 g, 0.00221 mol, 1 eq.) in DCM (15 ml), triethyl amine (0.9 ml, 0.00663 mol, 3 eq.) was added at RT. The reaction mixture was then stirred at RT for 20 min. The reaction mixture was cooled to 0° C. and boc-anhydride (0.578 g, 0.002654 mol, 1.2 eq.) was added slowly. The reaction mixture was stirred for 1 h at RT. The reaction mixture was diluted with DCM (70 ml) and washed by water (2×30 ml) and by brine (20 ml). The organic layer then was dried over $Na_2SO_4$, evaporated in reduced pressure to get the crude material, which is purified by column chromatography (silica gel 100-200; 5% ethyl acetate/hexane).

3. A stirring solution of step-2 compound (0.7 gm, 0.002147 mol, 1 eq) in dry THF (28 ml) was cooled to −78° C. n-Buli (2M) solution (2.147 ml, 0.004294 mol, 2 eq) was added to the reaction mixture drop wise under argon atmosphere. The reaction mixture was then stirred over 45 min at −78° C. DMF (0.6636 ml, 0.008588 mol, 4 eq) was added to the reaction mixture at −78° C. The reaction mixture was slowly warmed to RT over 1 h. The reaction mixture was quenched by saturated ammonium chloride solution (10 ml). The aqueous part was extracted with ethyl acetate (2×30 ml). The combined organic part was washed with brine (20 ml). The organic layer then was dried over $Na_2SO_4$, evaporated in reduced pressure to get the crude material, which is purified by column chromatography (silica gel 100-200; 10% ethyl acetate/hexane).

4. To a stirring solution of step-3 compound (1.0 g, 0.003636 mol, 1 eq.) in DCM (20 ml) was added methylamine hydrochloride (0.3558 g, 0.004363 mol, 1.2 eq) at RT and then the reaction mixture was stirred for 2 h at RT. $Na(OAc)_3BH$ (2.31 g, 0.0109 mol, 3 eq) was then added to the reaction mixture at RT. The reaction mixture was stirred for 16 h at RT. The reaction mixture was diluted with DCM (50 ml) and organic part washed with water (2×20 ml) and brine (20 ml). The organic layer then was dried over $Na_2SO_4$, evaporated under reduced pressure to get the crude material, which is purified by column chromatography (silica gel 100-200; 5% methanol/DCM) to desired product.

5. To a solution of step-4 product (0.45 g, 0.0015 mol) in water (9 ml), $NaHCO_3$ (0.26 g, 0.003 mol, 2 eq.) was added. A solution of Fmoc-Cl (0.6 g, 0.00225 mol, 1.5 eq.) in dioxane (9 ml) was added at 5° C. and then the reaction mixture was stirred at 0° C. for 2 h. The reaction mixture was concentrated under reduced pressure. The concentrated mass was diluted with water and extracted with ethyl acetate (3×50 ml). The combined organic layer was dried with $Na_2SO_4$ and concentrated under reduced pressure to give the crude product. The crude product was purified using column chromatography (silica gel 100-200; 15% ethyl acetate/hexane) to give the desired product.

Synthesis of Amines A29-A39

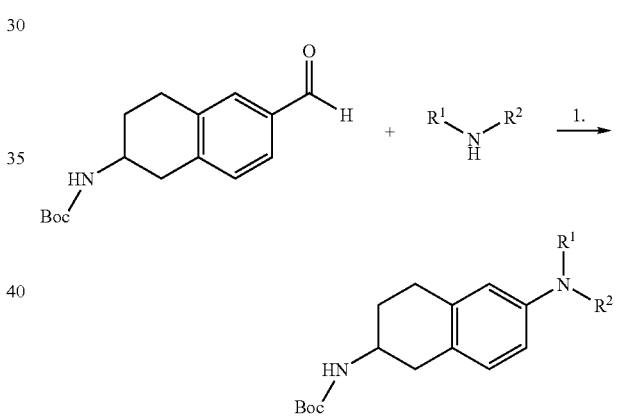

1. To a stirring solution of the aldehyde (1.0 g, 0.003636 mol, 1 eq.) in DCM (20 ml) was added the according amine (for A29 and A37 the amine hydrochloride) (0.3558 g, 0.004363 mol, 1.2 eq) at RT and then the reaction mixture was stirred for 2 h at RT. $Na(OAc)_3BH$ (2.31 g, 0.0109 mol, 3 eq) was then added to the reaction mixture at RT. The reaction mixture was stirred for 16 h at RT. The reaction mixture was diluted with DCM (50 ml) and the organic part was washed with water (2×20 ml) and brine (20 ml). The organic layer was dried with $Na_2SO_4$, evaporated in reduced pressure to get the crude material, which was purified by column chromatography (silica gel 100-200; 5% methanol/DCM).

| No. | $NR^1R^2$ | Name |
|---|---|---|
| A29 | ≻N⁄ | N-[6-(Dimethylaminomethyl)-1,2,3,4-tetrahydro-naphthalen-2-yl]-carbamic acid tert-butyl ester |

-continued

| No. | NR¹R² | Name |
|---|---|---|
| A30 | | N-[6-[(1-Methyl-propylamino)-methyl]-1,2,3,4-tetrahydro-naphthalen-2-yl]-carbamic acid tert-butyl ester |
| A31 | | N-[6-[(tert-Butylamino)-methyl]-1,2,3,4-tetrahydro-naphthalen-2-yl]-carbamic acid tert-butyl ester |
| A32 | | N-[6-[(tert-Butyl-methyl-amino)-methyl]-1,2,3,4-tetrahydro-naphthalen-2-yl]-carbamic acid tert-butyl ester |
| A33 | | N-[6-(Pyrrolidin-1-yl-methyl)-1,2,3,4-tetrahydro-naphthalen-2-yl]-carbamic acid tert-butyl ester |
| A34 | | N-[6-(Piperidin-1-yl-methyl)-1,2,3,4-tetrahydro-naphthalen-2-yl]-carbamic acid tert-butyl ester |
| A35 | | N-[6-(Morpholin-4-yl-methyl)-1,2,3,4-tetrahydro-naphthalen-2-yl]-carbamic acid tert-butyl ester |
| A36 | | N-[6-[(4-Methyl-piperazin-1-yl)-methyl]-1,2,3,4-tetrahydro-naphthalen-2-yl]-carbamic acid tert-butyl ester |
| A37 | | N-[6-(8-Azabicyclo[3.2.1]octan-8-yl-methyl)-1,2,3,4-tetrahydro-naphthalen-2-yl]-carbamic acid tert-butyl ester |
| A38 | | N-[6-[(Benzylamino)-methyl]-1,2,3,4-tetrahydro-naphthalen-2-yl]-carbamic acid tert-butyl ester |
| A39 | | tert-butyl 6-((3,4-dihydroquinolin-1(2H)-yl)methyl)-1,2,3,4-tetrahydronaphthalen-2-ylcarbamate |

Synthesis of 2-Methyl-5-(piperidin-4-yl)-2,5-diazabicyclo[2.2.1]heptane dihydrochloride A48

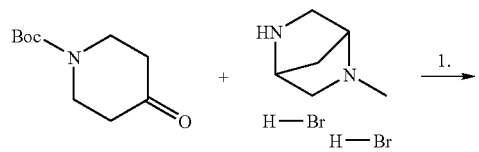

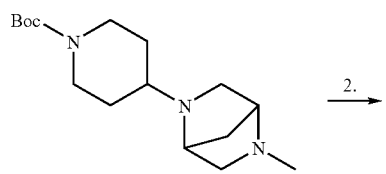

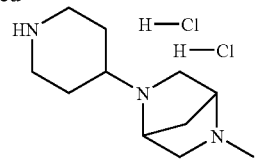

1. tert-Butyl 4-(5-methyl-2,5-diazabicyclo[2.2.1]heptan-2-yl)piperidine-1-carboxylate 2-Methyl-2,5-diazabicyclo[2.2.1]heptane dihydrobromide (1.715 mmol, 1 eq.), tert-butyl 4-oxopiperidine-1-carboxylate (2.401 mmol, 1.4 eq.) and triethylamine (4.288 mmol, 2.5 eq.) were dissolved in dichloromethane (120 mmol, 70 eq.) and the resulting mixture was stirred for 5 min at RT under nitrogen. Subsequently sodium triacetoxy borohydride (2.401 mmol, 1.4 eq.) was added and the mixture stirred for 16 h at RT. Ethyl acetate (30 ml) and sat. aq. sodium hydrogen carbonate solution (30 ml) were added to the reaction mixture and it was stirred for 15 min. The phases were separated and the aqueous phase was extracted with ethyl acetate (3×30 ml). The combined organic layers were dried over MgSO$_4$ and concentrated in vacuo. The crude product was purified by column chromatography (ethyl acetate/methanol/DCM, 10:10:5+25% aq ammonia) to yield the title compound. Yield: 0.35 g (69%)

2. 2-Methyl-5-(piperidin-4-yl)-2,5-diazabicyclo[2.2.1]heptane dihydrochloride Tert-butyl 4-(5-methyl-2,5-diazabicyclo[2.2.1]heptan-2-yl)piperidine-1-carboxylate (1.158 mmol, 1 eq.) was dissolved in Ethanol (7 ml) and acetyl chloride (5.76 mmol, 5 eq.) was added at 0° C. The mixture was stirred at RT for 16 h, at which time a light solid had precipitated. The suspension was diluted with diethyl ether (30 ml) and the solid was collected by filtration and washed with diethyl ether (50 ml). The title compound thus obtained was dried under high vacuum. Yield: 0.34 g (>99%)

Synthesis of 2-(4-(4,5-Dihydro-1H-imidazol-2-yl)phenyl)ethanamine A49

Xanthphos (290 mg, 0.5 mmol, 0.2 eq.) and Pd2(dba)3 (229 mg, 0.25 mmol, 0.1 eq.) were added to the reaction mixture and it was heated to 100° C. for 18 h. The reaction mixture was diluted with water (40 ml) and extracted with ethyl acetate (2×50 ml). The organic layer was washed with brine (50 ml) and dried over Na$_2$SO$_4$. The solvent was evaporated under reduced pressure and the crude product was purified by column chromatography (neutral alumina, 10% ethyl acetate in hexanes) to yield the desired product as a reddish solid. Yield: 73% (450 mg, 1.83 mmol)

3. P$_2$S$_5$ (48 mg) was added to a mixture of tert-butyl 4-cyanophenethylcarbamate (450 mg, 1.83 mmol, 1.0 eq.) and freshly distilled ethylenediamine (2.4 ml, 33.85 mmol, 18.5 eq.) and the resulting reaction mixture was heated to 120° C. for 4 h. The reaction mixture was cooled to 25° C. and poured into ice-cold water (20 ml). It was then extracted with DCM (40 ml). The organic layer was dried over Na$_2$SO$_4$ and the

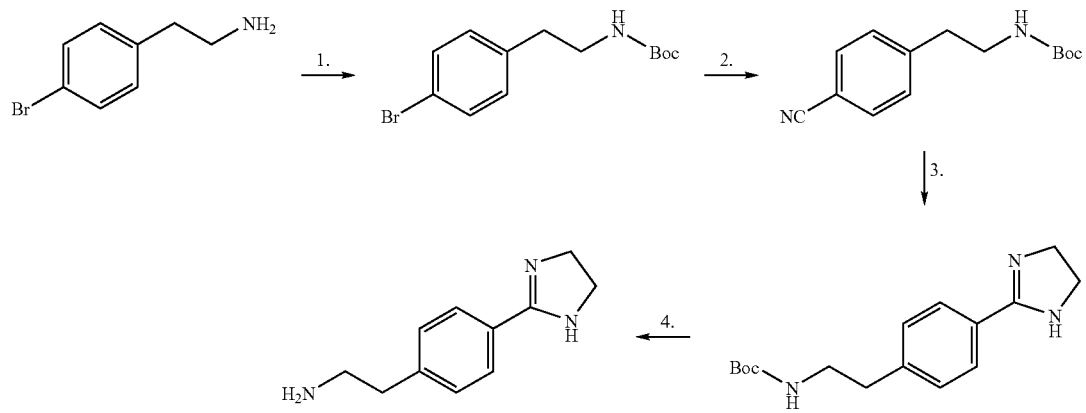

1. Boc$_2$O (818 mg, 3.75 mmol, 1.5 eq.) was added to a stirred solution of 2-(4-bromophenyl)ethanamine (500 mg, 2.5 mmol, 1.0 eq.) and TEA (1.5 ml, 7.5 mmol, 3.0 eq.) in DCM (25 ml) at 0° C. and resulting reaction mixture is stirred at 25° C. for 6 h. The reaction mixture was diluted with DCM (75 ml), washed with water (2×50 ml) and brine (50 ml) and dried over Na$_2$SO$_4$. The solvent was evaporated under reduced pressure and the residue triturated with hexanes to yield the desired product as an off white solid. Yield: 100% (750 mg, 2.5 mmol)

2. A mixture of tert-butyl 4-bromophenethylcarbamate (750 mg, 2.5 mmol, 1.0 eq.) and Zn(CN)$_2$ (439 mg, 3.75 mmol, 1.5 eq.) in dry DMF (15 ml) was degassed with argon for 15 min.

solvent was evaporated under reduced pressure to yield the desired product. Yield: 94% (500 mg, 1.73 mmol)

4. TFA (1 ml) was added to a solution of tert-butyl 4-(4,5-dihydro-1H-imidazol-2-yl)phenethylcarbamate (214 mg, 0.74 mmol, 1.0 eq.) in DCM (3 ml) at 0° C. and the resulting reaction mixture was stirred at RT for 2 h. The reaction mixture was concentrated under reduced pressure to give the crude product which was directly used in the next step.

Synthesis of amine (R)-6-((tert-Butylamino)methyl)-1,2,3,4-tetrahydronaphthalen-1-amine A50

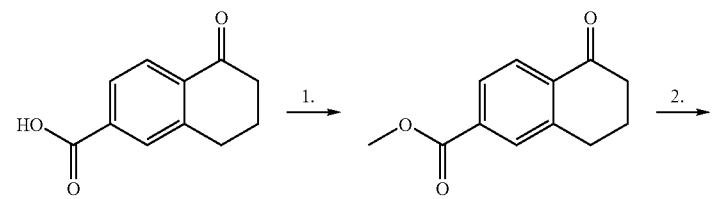

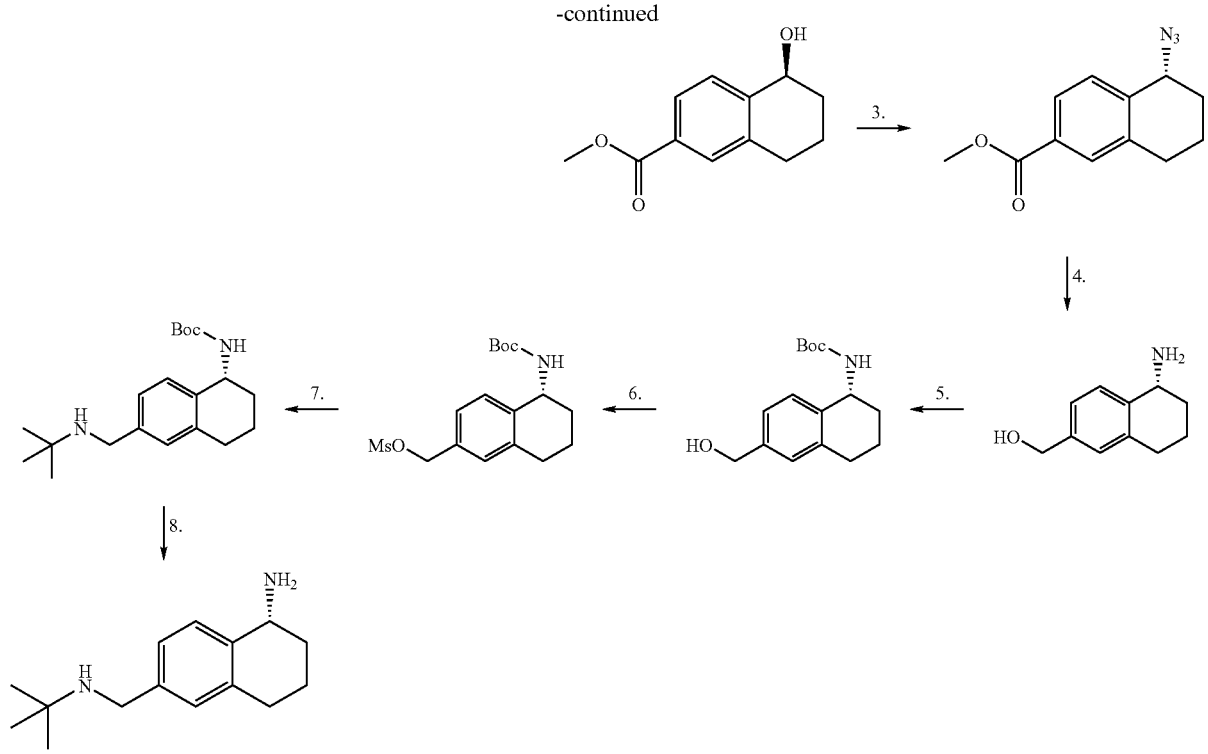

1. A solution of 5-oxo-5,6,7,8-tetrahydronaphthalene-2-carboxylic acid (5.0 g, 26.3 mmol, 1.0 eq.) in MeOH (50 ml) was saturated with HCl gas and then heated at reflux for 16 h. The reaction mixture was concentrated and the residue was diluted with DCM (250 ml). The organic layer was washed with saturated NaHCO$_3$ solution (100 ml) and brine (100 ml), and dried over Na$_2$SO$_4$. The solvent was evaporated under reduced pressure to yield the desired product. Yield: 95% (5.1 g, 25.0 mmol)

2. A 1 M solution of (R)-2-methyl-CBS-oxazaborolidine (1.25 ml, 1.25 mmol, 0.05 eq.) in toluene was diluted with toluene (100 ml) and cooled to −10° C. BH3.DMS (2.9 ml, 30 mmol, 1.2 eq.) was added dropwise, followed by a solution of methyl 5-oxo-5,6,7,8-tetrahydronaphthalene-2-carboxylate (5.1 g, 25 mmol) in THF (20 ml), which was also added dropwise. The bath temperature was kept at −10° C. throughout the addition. The reaction mixture was stirred for 1 h, at which point methanol (40 ml) was added at the same temperature. The reaction mixture was slowly brought to RT and stirred for 16 h. The mixture was then concentrated under reduced pressure and the residue obtained was diluted with ethyl acetate (200 ml). The organic layer was washed with 0.1 N HCl (100 ml), 5% NaHCO$_3$ solution (100 ml) and brine (100 ml), and dried over Na$_2$SO$_4$. The solvent was evaporated under reduced pressure to give the crude product which was purified by column chromatography (silica gel; 20% ethyl acetate/hexanes) to yield the title compound as a light yellow semi-solid. Yield: 57% (2.95 g, 14.3 mmol)

3. DPPA (4.61 ml, 21.4 mmol, 1.5 eq.) and DBU (3.2 ml, 21.4 mmol, 1.5 eq.) were added dropwise to a solution of (S)-methyl 5-hydroxy-5,6,7,8-tetrahydronaphthalene-2-carboxylate (2.95 g, 14.3 mmol, 1.0 eq.) in toluene (70 ml) at 0° C. The reaction mixture was warmed to RT and stirred for 16 h. The reaction mixture was diluted with ethyl acetate (70 ml) and washed with 0.1 N HCl (70 ml), 5% NaHCO$_3$ (70 ml) and brine (70 ml), and dried over Na$_2$SO$_4$. The solvent was evaporated under reduced pressure to yield the crude product which was purified by column chromatography (silica gel; 20% ethyl acetate/hexanes) to yield the title compound as a yellow semi solid. Yield: 97% (3.22 g, 13.9 mmol)

4. A solution of (R)-methyl 5-azido-5,6,7,8-tetrahydronaphthalene-2-carboxylate (3.22 g, 13.9 mmol, 1.0 eq.) in THF (50 ml) was added dropwise to a suspension of LAH (1.06, 3.46 mmol, 2.0 eq.) in THF (50 ml) at 0° C. and the reaction mixture was stirred at same temperature for 30 min. and then for 16 h at RT. After completion of the reaction (monitored by LCMS), the reaction mixture was quenched with THF—H2O (9:1, 10 ml) and filtered through celite. The filtrate was concentrated under reduced pressure to give the desired compound as a yellow semi-solid which was used in the next step without further purification. Yield: 99.5% (2.45 g, 13.84 mmol)

5. Boc-anhydride (10.2 ml, 46.68 mmol, 1.5 eq.) was added to a solution of (R)-(5-amino-5,6,7,8-tetrahydronaphthalen-2-yl)methanol (6.9 g, 38.9 mmol, 1.0 eq.) in DCM (150 ml) at 0° C. and the reaction mixture was stirred at RT for 16 h. The reaction mixture was then diluted with DCM (150 ml) and washed with water (150 ml) and brine (150 ml). The organic layer was dried over Na$_2$SO$_4$ and concentrated. The crude product was purified by column chromatography (silica gel; 30% ethyl acetate/hexanes) to get the desired compound as a white solid. Yield: 65% (7.0 g, 25.27 mmol)

6. Methanesulfonyl chloride (1.7 ml, 21.66 mmol, 2.0 eq.) was added dropwise to a solution of (R)-tert-butyl 6-(hydroxymethyl)-1,2,3,4-tetrahydronaphthalen-1-ylcarbamate (3.0 g, 10.83 mmol, 1.0 eq.) and TEA (5.27 ml, 37.9 mmol, 3.5 eq.) in DCM (100 ml) at 0° C. and the resulting reaction mixture was allowed to stir at RT for 16 h. The reaction mixture was diluted with DCM (100 ml) and washed with water (100 ml) and brine (100 ml), and dried over Na$_2$SO$_4$. The solvent was evaporated under reduced pressure to get the crude product which was used in the next step without further purification. Yield: 73% (2.8 g, 7.89 mmol, crude)
7. A mixture of (R)-(5-(tert-butoxycarbonylamino)-5,6,7,8-tetrahydronaphthalen-2-yl)methyl methanesulfonate (2.8 g, 7.89 mmol, 1.0 eq.), tert-butyl amine (8.4 ml, 78.9 mmol, 10.0 eq.) and K2CO3 (2.72 g, 19.72 mmol, 2.5 eq.) in THF (80 ml) was heated at reflux for 16 h. After completion of the reaction (monitored by TLC) the solvent was evaporated under reduced pressure and the residue was diluted with water (80 ml), extracted with DCM (100 ml) and dried over $Na_2SO_4$. The solvent was evaporated under reduced pressure to get the crude product which was purified by column chromatography (silica gel; 2% MeOH/DCM) to yield the title compound as light yellow semi-solid. Yield: 26% (700 mg, 2.11 mmol)
8. TFA (1 ml) was added to a solution of (R)-tert-butyl 6-((tert-butylamino)methyl)-1,2,3,4-tetrahydronaphthalen-1-ylcarbamate (300 mg, 0.898 mmol, 1.0 eq.) in DCM (4 ml) at 0° C. and the resulting reaction mixture was stirred at 25° C. for 4 h. The solvent was evaporated under reduced pressure and the residue was azeotroped with toluene to get the desired product which is used in the next step.

Synthesis N-Methyl-6-(piperidin-1-ylmethyl)-1,2,3,4-tetrahydronaphthalen-2-amine A51 dropwise to the reaction mixture at 0° C. and the resulting mixture was stirred at RT for 16 h. The reaction mixture was diluted with ethyl acetate (300 ml), washed with sat. $NaHCO_3$ solution (200 ml), sat. $NH_4Cl$ solution (200 ml), water (200 ml) and brine (200 ml), and dried over $Na_2SO_4$. The solvent was evaporated under reduced pressure to obtain the crude material which was purified by column chromatography (silica gel; 1-3% MeOH/DCM) to yield the desired product as a brownish sticky solid. Yield: 90% (19.93 g, 55.67 mmol)
3. TFA (25 ml) was added to a cooled (0° C.) solution of tert-butyl 6-(piperidine-1-carbonyl)-1,2,3,4-tetrahydronaphthalen-2-ylcarbamate (8.33 g, 23.26 mmol, 1.0 eq.) in DCM (25 ml) and the reaction mixture was stirred at RT for 4 h. After completion of the reaction (monitored by TLC) the solvent was evaporated under reduced pressure. The residue was dissolved in MeOH (225 ml), basified with Amberlyst (A-21) ion exchange resin up to pH≈9-10 and filtered. The filtrate was concentrated to dryness to obtain the desired product as a light yellow solid which was employed in the next step.
4. (6-Amino-5,6,7,8-tetrahydronaphthalen-2-yl)(piperidin-1-yl)methanone (23.26 mmol, 1.0 eq.) was added portionwise to a stirred suspension of LAH (4.42 g, 116.3 mmol, 5.0 eq.)

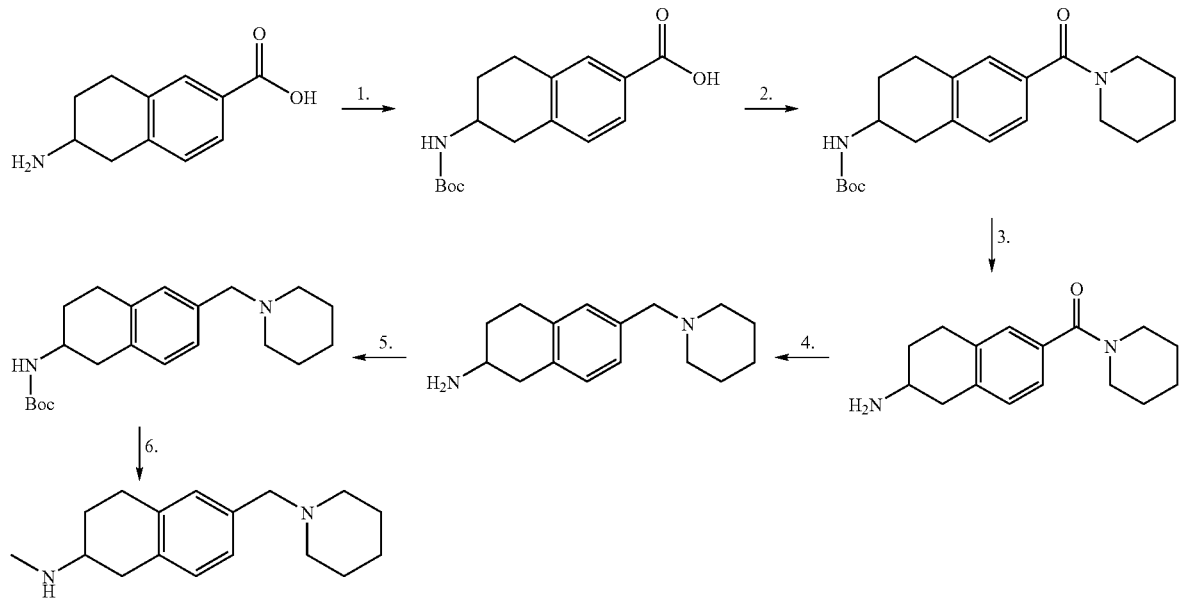

1. 1N NaOH solution (40 ml) was added to a suspension of 6-amino-5,6,7,8-tetrahydronaphthalene-2-carboxylic acid (15.0 g, 79.0 mmol, 1.0 eq.) in dioxane-water (4:1, 100 ml) and then (Boc)2O (25.83 ml, 118.5 mmol, 1.5 eq.) was added dropwise to the reaction mixture at 0° C. and it was stirred at RT for 4 h. Dioxane was evaporated under reduced pressure and the residual aqueous layer was diluted with water (200 ml) and acidified with KHSO4 solution. The solid product was collected by filtration and dried to yield the desired compound as a white solid. Yield: 96% (22.0 g, 75.6 mmol)
2. To a suspension of 6-(tert-butoxycarbonylamino)-5,6,7,8-tetrahydronaphthalene-2-carboxylic acid (18.0 g, 61.86 mmol, 1.0 eq.) in THF (200 ml) was added HATU (23.5 g, 61.86 mmol, 1.0 eq.) and DIPEA (30.62 ml, 185.6 mmol, 3.0 eq.) at 0° C. and the reaction mixture was allowed to stir for 15 min. Piperidine (18.3 ml, 185.6 mmol, 3.0 eq.) was added in dry THF (60 ml) under a N2 atmosphere at 0° C. and the resulting reaction mixture was stirred at RT for 16 h. The reaction mixture was quenched with a THF-water mixture (9:1, 60 ml) and the diluted with THF (300 ml). 10% NaOH solution (12 ml) was added to the mixture at −10° C. and it was stirred for 2 h. The reaction mixture was filtered through celite and the filtrate was evaporated to dryness to yield the desired product as a light brown sticky oil. Yield: 90% (5.10 g, 20.9 mmol)
5. $(Boc)_2O$ (6.54 ml, 30.0 mmol, 1.5 eq.) was added dropwise to a mixture of 6-(piperidin-1-ylmethyl)-1,2,3,4-tetrahydronaphthalen-2-amine (4.88 g, 20.0 mmol, 1.0 eq.) and TEA (5.55 ml, 40.0 mmol, 2.0 eq.) in DCM (50 ml) at 0° C. and the resulting reaction mixture was stirred at RT for 14 h. The reaction mixture was diluted with DCM (50 ml), washed with sat. $NH_4Cl$ solution (2×50 ml) and brine (50 ml), and dried over Na$_2$SO$_4$. The solvent was evaporated under reduced pressure to yield the crude product which was purified by column chromatography (silica gel; 2% MeOH/DCM) to obtain the desired product as an off white solid. Yield: 80% (5.5 g, 15.98 mmol)

6. A solution of tert-butyl 6-(piperidin-1-ylmethyl)-1,2,3,4-tetrahydronaphthalen-2-ylcarbamate (500 mg, 1.45 mmol, 1.0 eq.) in THF (5 ml) was added dropwise to a stirred suspension of LAH (552 mg, 14.5 mmol, 10.0 eq.) in THF (10 ml) at 0° C. After complete addition, the reaction mixture was warmed to RT and stirred for 10 min. Then the reaction mixture was heated at reflux for 2 h. The reaction mixture was cooled to RT and quenched with THF-water (9:1, 4.5 ml) and then 20% NaOH solution was added at 0° C. The reaction mixture was diluted with THF (50 ml) and stirred at RT for 1 h. The mixture was then filtered through celite and the filtrate was concentrated to dryness to yield desired product which was employed in the next step without further purification. Yield: 85% (320 mg, 1.24 mmol)

Synthesis (R)-6-((4-Fluoropiperidin-1-yl)methyl)-1,2,3,4-tetrahydronaphthalen-1-amine A52

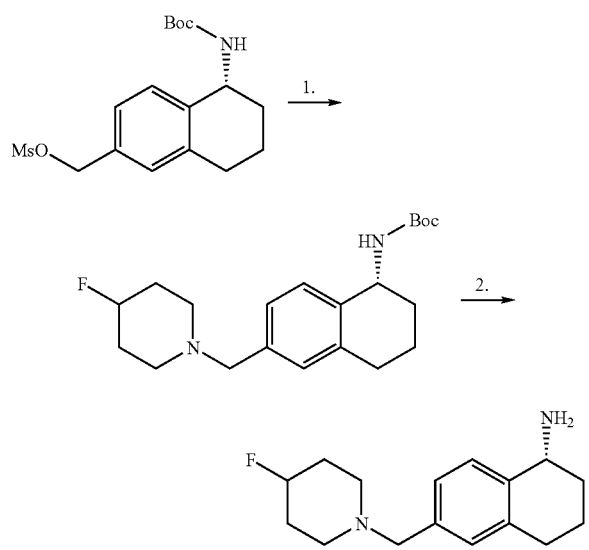

1. A mixture of (R)-(5-(tert-butoxycarbonylamino)-5,6,7,8-tetrahydronaphthalen-2-yl)methyl methanesulfonate (2.0 g, 5.633 mmol, 1.0 eq.), 4-fluoropiperidine.HCl (0.78 g, 5.633 mmol, 1.0 eq.) and K2CO3 (2.33 g, 16.9 mmol, 3.0 eq.) in THF (25 ml) was heated at reflux for 16 h. After completion of the reaction (monitored by TLC), the solvent was evaporated under reduced pressure and the residue was dissolved in ethyl acetate (150 ml), washed with water (100 ml) and brine (100 ml), and dried over Na$_2$SO$_4$. The solvent was evaporated under reduced pressure to give the crude product which was purified by column chromatography (silica gel; 40% ethyl acetate/hexanes) to yield the title compound as a light yellow solid. Yield: 60% (1.22 g, 3.37 mmol)

2. TFA (1 ml) was added to a solution of (R)-tert-butyl 6-((4-fluoropiperidin-1-yl)methyl)-1,2,3,4-tetrahydronaphthalen-1-ylcarbamate (325 mg, 0.898 mmol, 1.0 eq.) in DCM (4 ml) at 0° C. and the resulting reaction mixture was stirred at 25° C. for 4 h. The solvent was evaporated under reduced pressure and the residue was azeotroped with toluene to yield the desired product which was employed in the next step.

Synthesis (R)-6-((2,2,2-Trifluoroethylamino)methyl)-1,2,3,4-tetrahydronaphthalen-1-amine A53

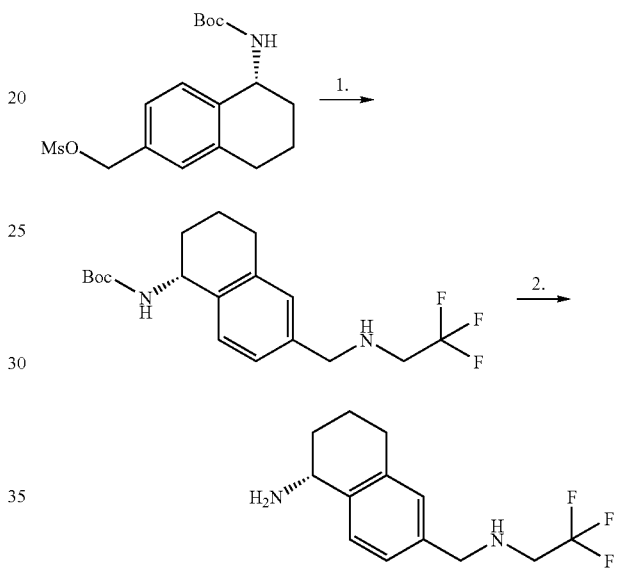

1. A mixture of (R)-(5-(tert-butoxycarbonylamino)-5,6,7,8-tetrahydronaphthalen-2-yl)methyl methanesulfonate (400 mg, 1.13 mmol, 1.0 eq.), 2,2,2-trifluoroethanamine (360 µl, 4.52 mmol, 4.0 eq.) and K$_2$CO$_3$ (470 mg, 3.39 mmol, 3.0 eq.) in THF (10 ml) was heated at 100° C. in sealed tube for 16 h. After completion of the reaction (monitored by TLC), the mixture was diluted with ethyl acetate (50 ml), washed with water (20 ml) and brine (20 ml), and dried over Na$_2$SO$_4$. The solvent was evaporated under reduced pressure to give the crude product which was purified by column chromatography (silica gel; 20% ethyl acetate/hexanes) to yield the title compound as an off-white solid. Yield: 37% (150 mg, 0.412 mmol)

2. (R)-6-((2,2,2-Trifluoroethylamino)methyl)-1,2,3,4-tetrahydronaphthalen-1-amine TFA (1 ml) was added to a solution of (R)-tert-butyl 6-((2,2,2-trifluoroethylamino)-methyl)-1,2,3,4-tetrahydronaphthalen-1-ylcarbamate (230 mg, 0.64 mmol, 1.0 eq.) in DCM (4 ml) at 0° C. and the resulting reaction mixture was stirred at RT for 2 h. The solvent was evaporated under reduced pressure and the residue was azeotroped with toluene to yield the desired product which was used in the next step.

Synthesis of (R)—N-(4-(1-Aminoethyl)benzyl)-2-methylpropan-2-amine A54

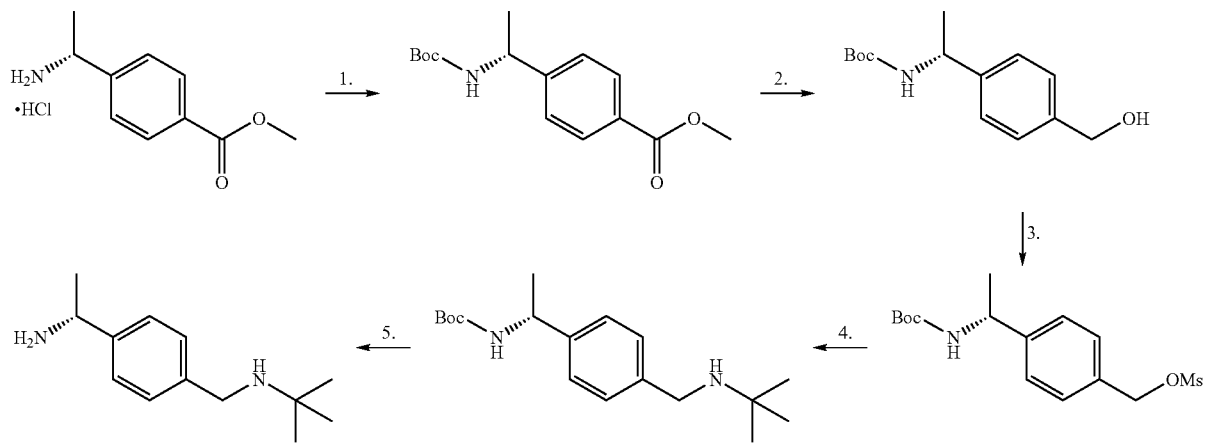

1. Boc-anhydride (2.2 ml, 11.1 mmol, 1.2 eq.) was added to a solution of (R)-methyl 4-(1-aminoethyl)benzoate hydrochloride (2.0 g, 9.2 mmol, 1.0 eq.) and TEA (2.4 ml, 18.4 mmol, 2.0 eq.) in DCM (50 ml) at 0° C. and the reaction mixture was stirred at RT for 16 h. The mixture was diluted with DCM (75 ml) and washed with water (50 ml) and brine (50 ml). The organic layer was dried over $Na_2SO_4$ and concentrated to give the crude product which was purified by column chromatography (silica gel; 20% ethyl acetate/hexanes) to yield the desired compound as a white solid. Yield: 64% (2.0 g, 7.16 mmol)

2. A solution of (R)-methyl 4-(1-(tert-butoxycarbonylamino)ethyl)benzoate (2.0 g, 7.16 mmol, 1.0 eq.) in THF (50 ml) was added dropwise to a suspension of LAH (326 mg, 8.6 mmol, 1.2 eq.) in THF (50 ml) at 0° C. and the reaction mixture was stirred at RT for 2 h. After completion of the reaction (monitored by LCMS) the reaction mixture was quenched with THF—$H_2O$ (9:1, 20 ml) and filtered through celite. The filtrate was concentrated under reduced pressure to give the crude product which was purified by column chromatography (silica gel; 30% ethyl acetate/hexanes) to yield the title compound as a yellow semi solid. Yield: 83% (1.5 g, 5.97 mmol)

3. Methanesulfonyl chloride (360 μl, 4.78 mmol, 1.2 eq.) was added to a solution of (R)-tert-butyl 1-(4-(hydroxymethyl)phenyl)ethylcarbamate (1.0 g, 3.98 mmol, 1.0 eq.) and TEA (1 ml, 7.96 mmol, 2.0 eq.) in DCM (30 ml) at 0° C. and the resulting reaction mixture was stirred at RT for 2 h. The reaction mixture was diluted with DCM (50 ml) and washed with water (20 ml) and brine (20 ml), and dried over $Na_2SO_4$. The solvent was evaporated under reduced pressure to yield the crude product which was used in the next step without further purification.

4. A mixture of (R)-4-(1-(tert-butoxycarbonylamino)ethyl)benzyl methanesulfonate (1.0 g, 3.03 mmol, 1.0 eq.), tert-butyl amine (1.6 ml, 15.15 mmol, 5.0 eq.) and $K_2CO_3$ (1.04 g, 7.59 mmol, 2.5 eq.) in THF (30 ml) was heated at reflux for 20 h. After completion of the reaction (monitored by TLC) the solvent was evaporated under reduced pressure and the residue was diluted with water (50 ml), extracted with DCM (100 ml) and dried over $Na_2SO_4$. The solvent was evaporated under reduced pressure to give the crude product which was purified by column chromatography (neutral alumina; 0.5% MeOH/DCM) to yield the title compound as a light yellow sticky solid. Yield: 32% (300 mg, 0.98 mmol)

5. TFA (1 ml) was added to a solution of (R)-tert-butyl 1-(4-((tert-butylamino)methyl)-phenyl)ethylcarbamate (370 mg, 1.2 mmol, 1.0 eq.) in DCM (4 ml) at 0° C. and the resulting reaction mixture was stirred at RT for 2 h. The solvent was evaporated under reduced pressure and the residue was azeotroped with toluene to yield the desired product which was used in the next step.

Synthesis of 5-(piperidin-1-ylmethyl)-2,3-dihydro-1H-inden-2-amine A56

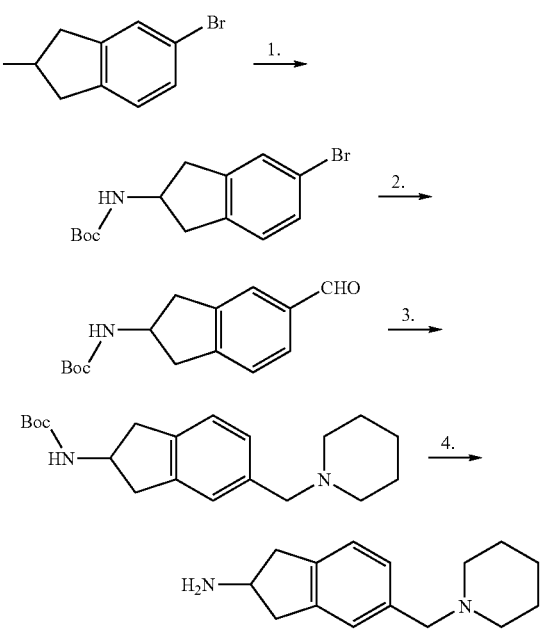

1. Boc-anhydride (1.8 ml, 8.23 mmol, 1.2 eq.) was added drop wise to a mixture the amine (2.0 g, 6.85 mmol, 1.0 eq.) and DIPEA (3.3 ml, 17.12 mmol, 2.5 eq.) in DCM (20 ml) at 0° C. and the resulting reaction mixture was stirred at RT for 14 h. After completion of reaction (monitored by TLC), the reaction mixture was diluted with DCM (100 ml) and washed with water (60 ml), brine (60 ml), dried over anhydrous $Na_2SO_4$.

The solvent was evaporated under reduced pressure to get the Boc-protected compound, which was used in the next step without further purification. Yield: 94% (2.0 g, 6.41 mmol).

2. BuLi (1.5 M, 10.7 ml, 16.05 mmol, 2.5 eq.) was added drop wise to a stirred solution of the Boc-protected compound (2.0 g, 6.41 mmol, 1.0 eq.) in THF (80 ml) at −78° C. and the reaction mixture was stirred for 30 min at same temperature. Then DMF (2.5 ml, 32.1 mmol, 5.0 eq.) was added to the reaction mixture at −78° C. The reaction mixture was slowly warmed to RT and stirred for 15 min. After completion of reaction (monitored by TLC), the mixture was quenched with saturated $NH_4Cl$ (50 ml) and diluted with ethyl acetate (100 ml). Organic layer is separated and dried over $Na_2SO_4$. the solvent was evaporated under reduced pressure to get crude product which was purified by column chromatography (silica gel, 15% EtOAc/hexanes) to get pure aldehyde as a white solid. Yield: 60% (1.0 g, 3.83 mmol).

3. A mixture of the aldehyde (1.0 g, 3.83 mmol, 1.0 eq.) and piperidine (0.52 ml, 5.36 mmol, 1.4 eq.) in dry DCM (100 ml) was stirred at RT for 1 h. The reaction mixture was cooled to 0° C. and then $Na(OAc)_3BH$ (1.21 g, 5.74 mmol, 1.5 eq.) was added portion-wise and stirred at RT for 14 h. The reaction mixture was diluted with DCM (150 ml) and washed with water (2×70 ml), brine (2×70 ml) and dried over $Na_2SO_4$. The solvent was evaporated under reduced pressure and residue was purified by column chromatography (silica gel; 2% MeOH/DCM) to get desired product as a light yellow sticky solid. Yield: 35% (450 mg, 1.36 mmol).

4. TFA (1 ml) was added to a solution of the diamine (248 mg, 0.75 mmol, 1.0 eq.) in DCM (4 ml) at 0° C. and the resulting reaction mixture was stirred at RT for 1 h. The solvent was evaporated under reduced pressure and residue was azeotroped twice with toluene to get desired amine which was used for the next step without further purification.

SYNTHESIS OF EXAMPLES 1-48

Example 1

2-(2-(4-Methoxy-2,6-dimethylphenylsulfonyl)-1,2,3,4-tetrahydro-pyrrolo[1,2-a]pyrazin-1-yl)-1-(4-(1-methylpiperidin-4-yl)piperazin-1-yl)ethanone

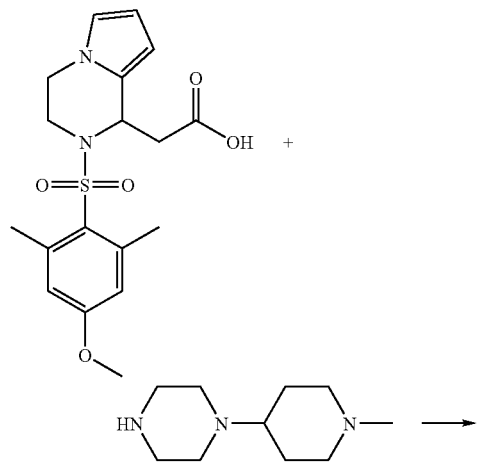

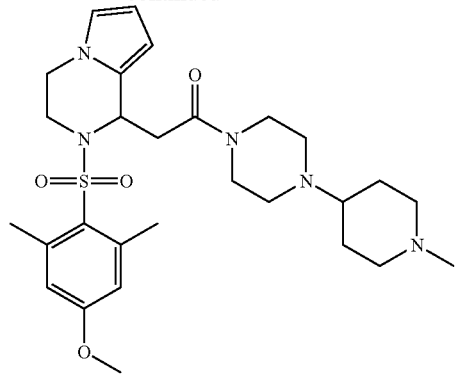

Acid S1 (85 mg, 0.2 mmol) was dissolved in DCM (5 ml) and cooled to 0° C. 1-(1-Methylpiperidin-4-yl)piperazine A1 (45 mg, 0.25 mmol), DIPEA (0.043 ml, 0.25 mmol), EDCl (47 mg, 0.25 mmol) and HOAt (3 mg, 0.02 mmol) were added and the reaction batch was stirred overnight at RT. Then the solvent was removed in a rotary evaporator and the crude product obtained was purified by column chromatography (silica gel, heptane/ethyl acetate, 4:1→DCM/7 M $NH_3$ in MeOH, 95:5).

m/z 544.7 $[MH]^+$.

Example 2

2-((2-(4-Methoxy-2,6-dimethylphenylsulfonyl)-1,2,3,4-tetrahydropyrrolo[1,2-a]pyrazin-1-yl)methoxy)-1-(4-(1-methylpiperidin-4-yl)piperazin-1-yl)ethanone

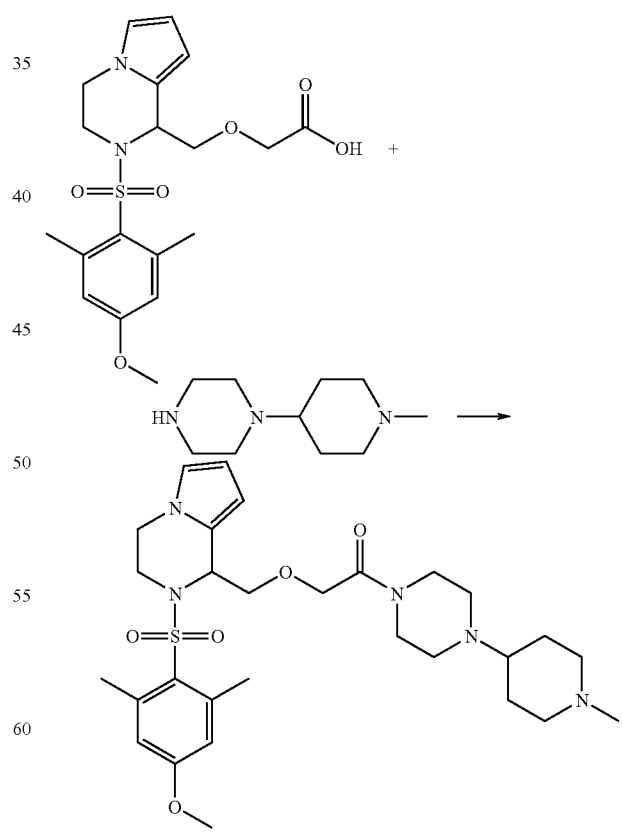

The reaction was performed under an $N_2$ atmosphere. A solution of acid S3 (0.42 mmol), 1-(1-methylpiperidin-4-yl)

piperazine A1 (92 mg, 0.5 mmol) and HOAt (5.7 mg, 0.042 mmol) in DCM (5 ml) was cooled to 0° C. EDCl (89 mg, 0.46 mmol) was added and the reaction batch was stirred for 1 h at 0° C. and overnight at RT. Then further 1-(1-methylpiperidin-4-yl)piperazine A1 (38 mg, 0.21 mmol), EDCl (40 mg, 0.21 mmol) and HOAt (5.7 mg, 0.042 mmol) were added and the mixture was stirred for 3 days at RT. Then the solvent was removed in a rotary evaporator and the crude product obtained was purified by column chromatography (silica gel, DCM/7 M NH$_3$ in MeOH, 98:2→95:5). m/z=574.8 [MH]$^+$ Example 3

1-(7-Cyclopropyl-2,7-diazaspiro[4.4]nonan-2-yl)-2-(2-(4-methoxy-2,6-dimethylphenylsulfonyl)-1,2,3,4-tetrahydropyrrolo[1,2-a]pyrazin-1-yl)ethanone

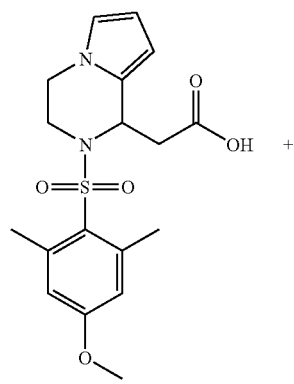

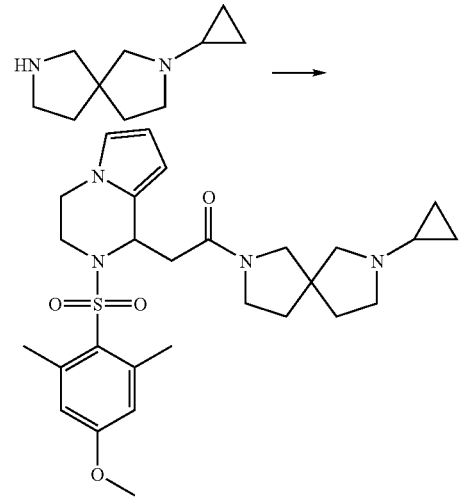

Acid S1 (70 mg, 0.185 mmol) was dissolved in DCM (5 ml) and cooled to 0° C. Amine A2 (36.9 mg, 0.218 mmol), DIPEA (0.061 ml, 0.37 mmol), EDCl (53 mg, 0.277 mmol) and HOAt (2.5 mg, 0.018 mmol) were added and the reaction batch was stirred for 3 h at RT. The reaction batch was washed with HCl (0.5 M, 20 ml) and saturated NaCl solution. The organic phase was dried over Na$_2$SO$_4$ and concentrated to small volume. The crude product obtained was purified by column chromatography (silica gel, DCM/7M NH$_3$ in MeOH, 99:1→98:2) and then by preparative HPLC. m/z=527.7 [MH]$^+$ Example 4

2-((2-(4-Methoxy-2,6-dimethylphenylsulfonyl)-1,2,3,4-tetrahydropyrrolo[1,2-a]pyrazin-1-yl)methoxy)-1-(2-(pyridin-4-yl)-2,8-diazaspiro[4.5]decan-8-yl)ethanone

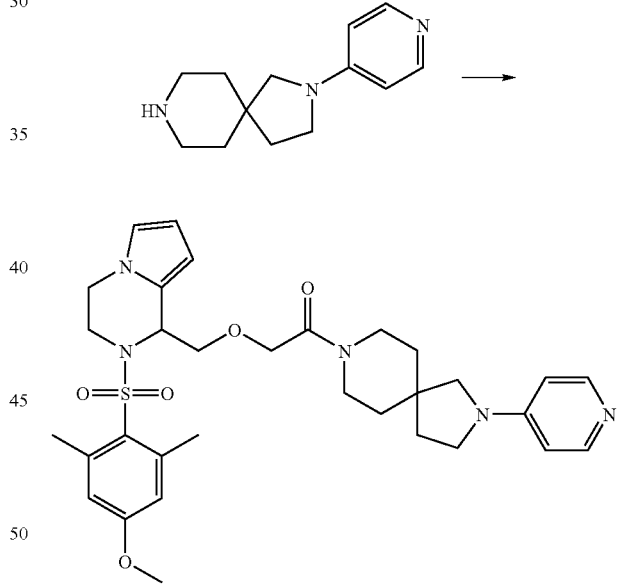

The reaction was performed under an N$_2$ atmosphere. A solution of acid S3 (90 mg, 0.22 mmol) and amine A3 (58 mg, 0.264 mmol) in DCM (10 ml) was cooled to 0° C. HOAt (3 mg, 0.022 mmol) and EDCl (51 mg, 0.26 mmol) were added and the reaction batch was stirred for 1 h at 0° C. and then for 1 h at RT. DIPEA (0.058 ml, 0.331 mmol) was added and the mixture was stirred overnight at RT. Then the solvent was removed in a rotary evaporator and the crude product obtained was purified by column chromatography (silica gel, DCM/7 M NH$_3$ in methanol, 98:2→97:3). m/z=608.8 [MH]$^+$

Example 5

1-(4-(Pyridin-4-yloxy)piperidin-1-yl)-2-((2-(2-(trifluoromethyl)phenylsulfonyl)-1,2,3,4-tetrahydropyrrolo[1,2-a]pyrazin-1-yl)methoxy)ethanone

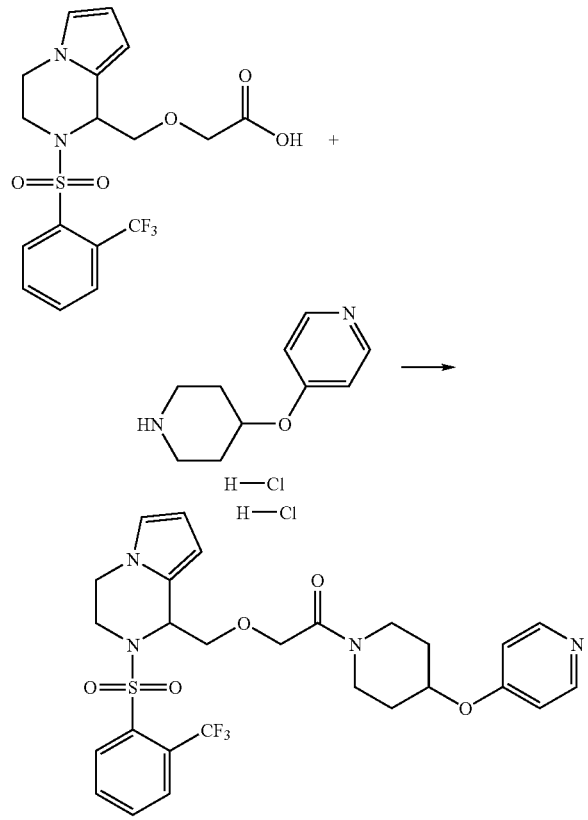

The reaction was performed under an $N_2$ atmosphere. A solution of acid S4 (0.27 g, 0.645 mmol), 4-(piperidin-4-yloxy)pyridine dihydrochloride A4 (243 mg, 0.968 mmol) and DIPEA (0.338 ml, 1.935 mmol) in DCM (10 ml) was cooled to 0° C. HOAt (9 mg, 0.066 mmol) and EDCl (186 mg, 0.97 mmol) were added and the reaction batch was stirred overnight at RT. Then the solvent was removed in a rotary evaporator and the crude product obtained was purified by column chromatography (silica gel, DCM/7 M $NH_3$ in MeOH, 99:1). m/z=579.6 [MH]$^+$

Example 8

2-(2-(6-Methoxynaphthalen-2-ylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide

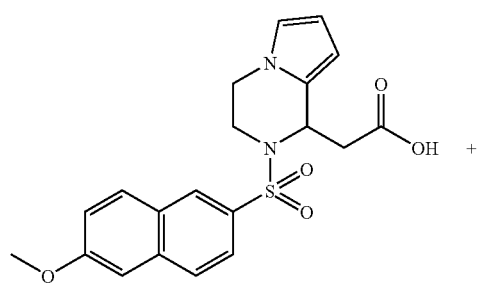

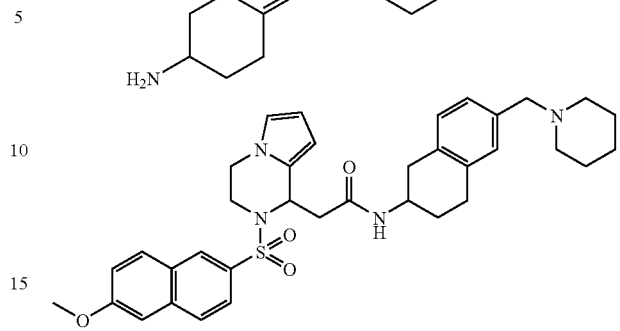

DIPEA (2.5 eq.), HOAt (1.0 eq.) and EDCl (1.5 eq.) were added to a solution of 2-(2-(6-methoxynaphthalen-2-ylsulfonyl)-1,2,3,4-tetrahydropyrrolo[1,2-a]pyrazin-1-yl)acetic acid S2 (0.2325 mmol, 1.0 eq.) in DCM (3 ml) at 0° C. and the mixture was stirred for 15 min at RT. Then 6-(piperidin-1-ylmethyl)-1,2,3,4-tetrahydronaphthalen-2-amine A5 (0.2325 mmol, 1.0 eq.) in DCM (2 ml) was added at 0° C. and the mixture was stirred overnight at RT. The reaction mixture was diluted with DCM and extracted with aqueous $NaHCO_3$ solution, aqueous $NH_4Cl$ solution, water and saturated sodium chloride solution. The organic phase was dried ($Na_2SO_4$), concentrated to small volume and purified by column chromatography (alox). Yield: 58%; m/z=627.4 [MH]$^+$

Example 9

2-(2-(6-Methoxynaphthalen-2-ylsulfonyl)-1,2,3,4-tetrahydropyrrolo[1,2-a]pyrazin-1-yl)-N—((R)-6-(piperidin-1-ylmethyl)-1,2,3,4-tetrahydronaphthalen-1-yl)acetamide

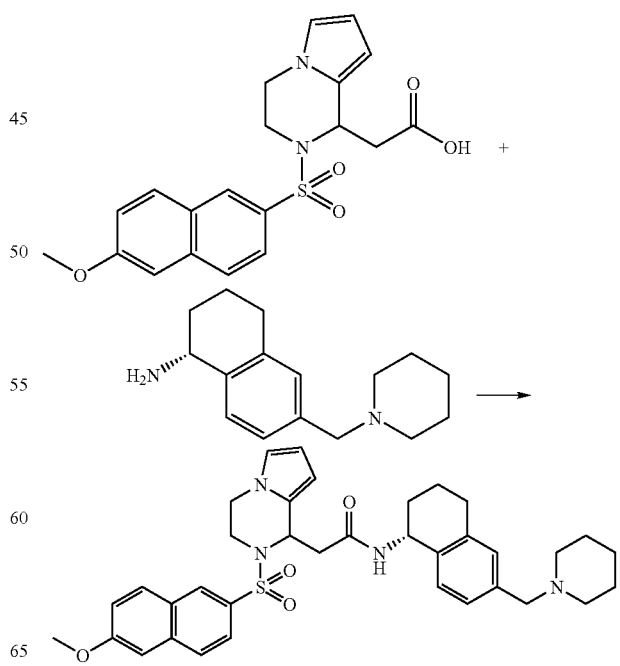

DIPEA (2.5 eq.), HOAt (1.0 eq.) and EDCl (1.5 eq.) were added to a solution of 2-(2-(6-methoxynaphthalen-2-ylsulfonyl)-1,2,3,4-tetrahydropyrrolo[1,2-a]pyrazin-1-yl)-acetic acid S2 (0.195 mmol, 1.0 eq.) in DCM (3 ml) at 0° C. and the mixture was stirred for 15 min at RT. Then (R)-6-(piperidin-1-ylmethyl)-1,2,3,4-tetrahydro-naphthalen-1-amine A6 (0.234 mmol, 1.2 eq.) in DCM (2 ml) was added at 0° C. and the mixture was stirred overnight at RT. The reaction mixture was diluted with DCM and extracted with aqueous NaHCO$_3$ solution, aqueous NH$_4$Cl solution, water and saturated NaCl solution. The organic phase was dried (Na$_2$SO$_4$), concentrated to small volume and purified by column chromatography (alox). Yield: 55%; m/z=627.4 [MH]$^+$

Example 10

2-((2-(4-Methoxy-2,6-dimethylphenylsulfonyl)-1,2,3,4-tetrahydropyrrolo[1,2-a]pyrazin-1-yl)methoxy)-1-(9-(pyridin-4-yl)-3,9-diazaspiro[5.5]undecan-3-yl)ethanone

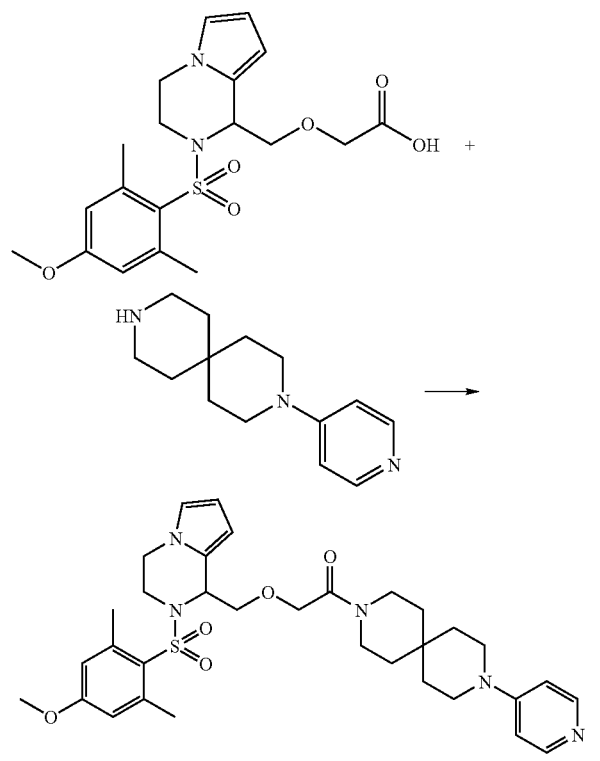

DIPEA (9 eq.), HOBt (3 eq.) and EDCl (3 eq.) were added to a solution of acid S3 (1 eq.) in DCM (5 ml) at 0° C. and the mixture was stirred for 10 min. Then 3-(pyridin-4-yl)-3,9-diazaspiro[5.5]undecane A7 (1.2 eq.) was added and the mixture was stirred for 16 h at RT. The reaction mixture was diluted with DCM and extracted with aqueous NH$_4$Cl and aqueous NaHCO$_3$ solution. The crude product was concentrated to small volume and purified by column chromatography (alox). Yield: 30%; m/z=622.4 [MH]$^+$

Example 11

1-(9-(Pyridin-4-yl)-3,9-diazaspiro[5.5]undecan-3-yl)-2-((2-(2-(trifluoromethyl)phenylsulfonyl)-1,2,3,4-tetrahydropyrrolo[1,2-a]pyrazin-1-yl)methoxy)ethanone

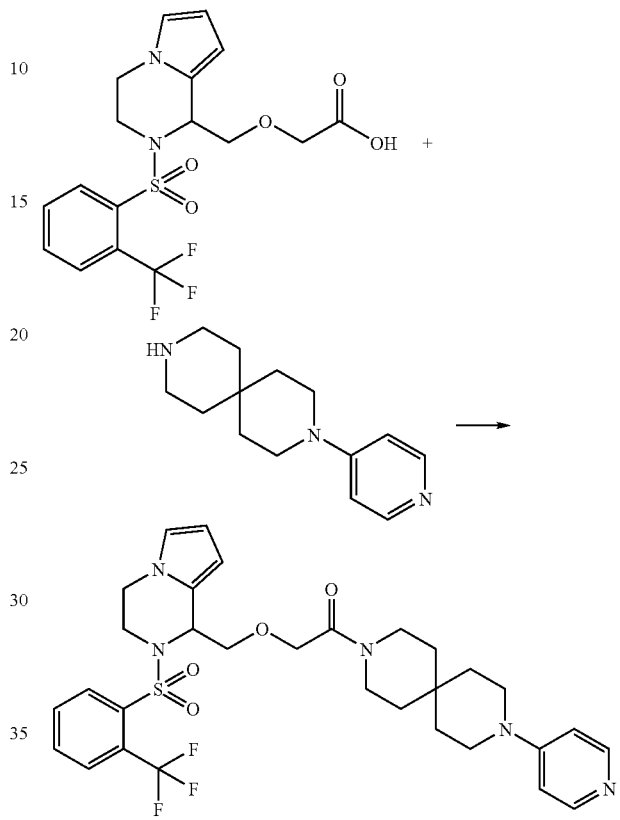

A solution of acid S4 (160 mg, 0.382 mmol), amine A7 (128 mg, 0.421 mmol), DIPEA (0.2 ml, 1.147 mmol) and EDCl (88 mg, 0.459 mmol) in DCM (5 ml) was cooled to 0° C. and mixed with HOAt (5.21 mg, 0.038 mmol). The reaction batch was heated to RT and stirred at this temperature for 16 h. The solvent was removed in a rotary evaporator and the crude product was purified twice by column chromatography (silica gel, DCM/(7 M NH$_3$ in MeOH, 99:1→98:2→95:5). m/z=632.7 [MH]$^+$

Example 14

2-((2-(2-Chloro-6-methylphenylsulfonyl)-1,2,3,4-tetrahydropyrrolo[1,2-a]pyrazin-1-yl)methoxy)-1-(2-(pyridin-4-yl)-2,8-diazaspiro[4.5]decan-8-yl)ethanone

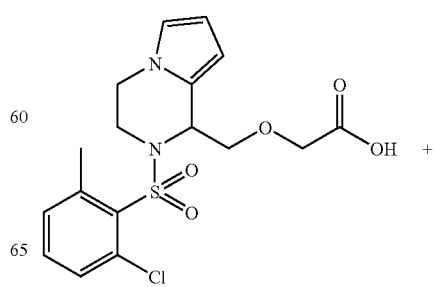

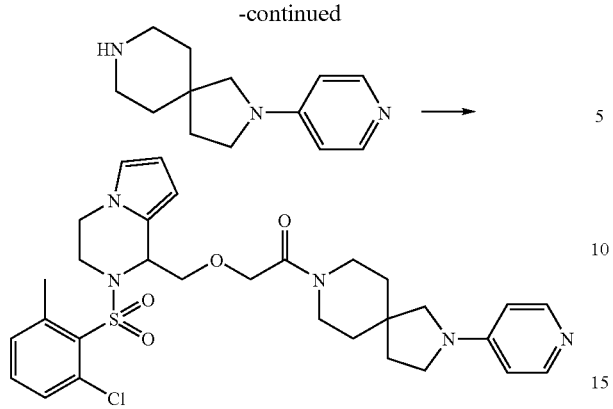

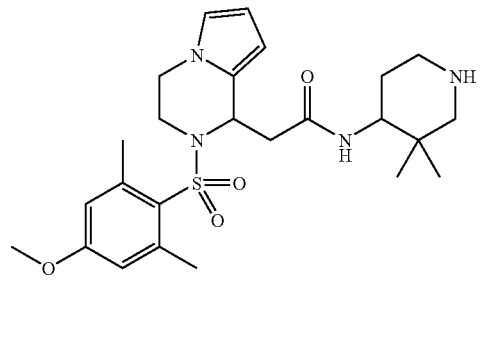

A solution of acid S5 (200 mg, 0.501 mmol), amine A3 (175 mg, 0.602 mmol), DIPEA (0.219 ml, 1.254 mmol) and EDCl (106 mg, 0.552 mmol) in dry DMF (5 ml) was stirred at 0° C. and mixed with HOAt (6.83 mg, 0.050 mmol). The reaction batch was heated to RT and stirred at this temperature for 16 h. The solvent was removed in a rotary evaporator and the crude product was purified by column chromatography (silica gel, DCM/(7 M NH$_3$ in MeOH, 99:1→98:2→95:5). m/z=599.2 [MH]$^+$ Example 17

N-(3,3-Dimethylpiperidin-4-yl)-2-(2-(4-methoxy-2,6-dimethylphenylsulfonyl)-1,2,3,4-tetrahydropyrrolo[1,2-a]pyrazin-1-yl)acetamide

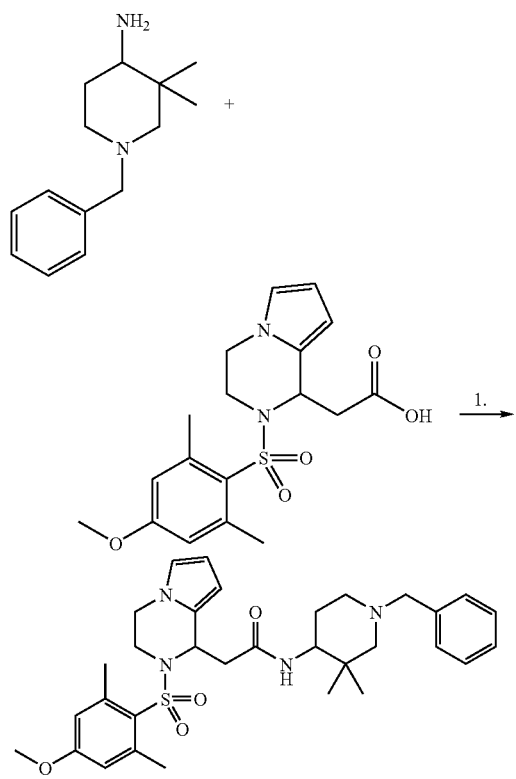

1. Amine A11 (159 mg, 633 μmol), HOAt (14.39 mg, 106 μmol) and EDCl (152 mg, 793 μmol) were added to a solution of acid S1 (200 mg, 528 μmol) in DCM (5 ml). After 3 h further amine A11 (108 mg, 430 μmol) was added and the mixture was stirred overnight at RT. The solvent was then siphoned off completely and the crude product obtained was purified by column chromatography (silica gel, DCM/(7 M NH$_3$ in MeOH), 99:1).

2. A solution of the product from stage 1 (213 mg, 368 μmol) in dry THF was first rinsed with N$_2$ for 10 min, then Pd/C (39.2 mg, 37 μmol) was added and the solution was rinsed again with N$_2$ for 10 min. The reaction batch was stirred overnight at RT under an H$_2$ atmosphere (9 bar) and then filtered over diatomaceous earth. The diatomaceous earth was washed repeatedly with DCM. The combined organic phases were concentrated to small volume and the product was purified by preparative HPLC. The solvent was removed by freeze drying. m/z=489.7 [MH]$^+$ Example 18

2-(2-(4-Methoxy-2,6-dimethylphenylsulfonyl)-1,2,3,4-tetrahydro-pyrrolo[1,2-a]pyrazin-1-yl)-1-(2-(pyridin-4-yl)-2,8-diazaspiro[4.5]decan-8-yl)-ethanone

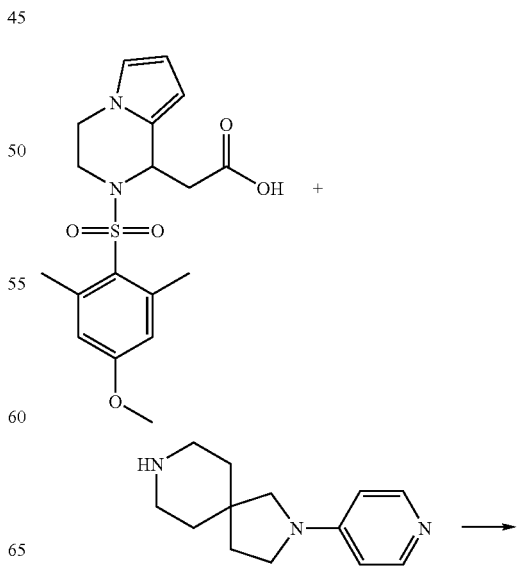

-continued

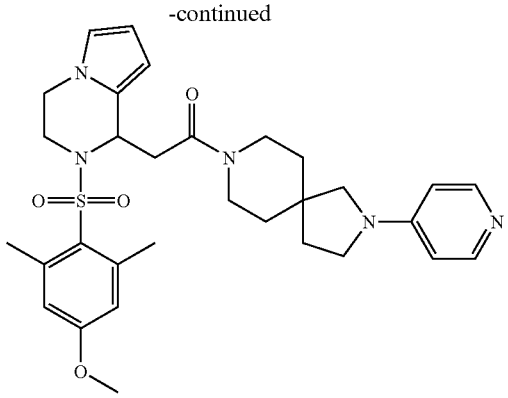

Amine A3 (107 mg, 0.49 mmol) and HOAt (12.2 mg, 0.09 mmol) were added to a solution of acid S1 (170 mg, 0.45 mmol) in DCM (5 ml), followed by EDCl (129 mg, 0.67 mmol). The reaction mixture was stirred for 3 h at RT and then concentrated to dryness. The product was purified by preparative HPLC. The solvent was removed by freeze drying. m/z=578.7 [MH]+

Example 19

2-(2-(2-Chloro-4-(trifluoromethyl)phenylsulfonyl)-1,2,3,4-tetrahydropyrrolo[1,2-a]pyrazin-1-yl)-1-(piperidin-1-yl)ethanone

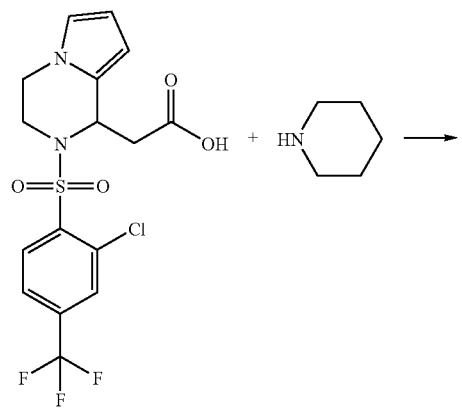

Carboxylic acid S6 (400 mg, 0.947 mmol) was suspended in THF (10 ml) and TEA (0.15 ml, 1.136 mmol), EDCl (181.5 mg, 0.947 mmol) and HOBt (150 mg, 0.947 mmol) were added in succession. The reaction batch was stirred for 1 h at RT and then piperidine A9 (0.947 mmol) was added. The reaction mixture was stirred for a further hour and then diluted with ethyl acetate (40 ml). The organic phase was washed successively with water and saturated NaCl solution, dried over $Na_2SO_4$ and concentrated to small volume. The crude product was processed by column chromatography. m/z=490.9 [MH]+

Example 22

2-((2-(4-Methoxy-2,6-dimethylphenylsulfonyl)-1,2,3,4-tetrahydro-pyrrolo[1,2-a]pyrazin-1-yl)methoxy)-1-(2,8-diazaspiro[4.5]decan-8-yl)ethanone

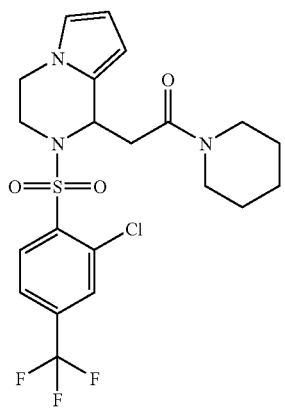

1. To an ice-cold solution of acid S3 (0.612 mmol) and DIPEA (1.3 mmol) in THF (2.5 ml) was added HATU (0.612 mmol) and the reaction mixture was stirred for 15 min. Then a solution of amine A12 (0.735 mmol) in THF (1 ml) was added slowly and allowed to stir at 25° C. for 16 h. The reaction mixture was concentrated under reduced pressure and diluted with water (50 ml) and extracted with ethyl acetate (2×50 ml). The organic layer was washed with water, brine, dried over anhydrous $Na_2SO_4$ and concentrated. The crude product was purified by column chromatography using 1-5% MeOH in DCM as eluent. Yield: 50%
2. To a solution of step-1 product (180 mg) in MeOH (5 ml) was added 1N NaOH solution (5 ml) at 0° C. Then the reac-

Example 23

2-((2-(4-Methoxy-2,6-dimethylphenylsulfonyl)-1,2,3,4-tetrahydropyrrolo[1,2-a]pyrazin-1-yl)methoxy)-1-((1R,3S,5S)-3-(pyridin-4-yloxy)-8-azabicyclo[3.2.1]octan-8-yl)ethanone

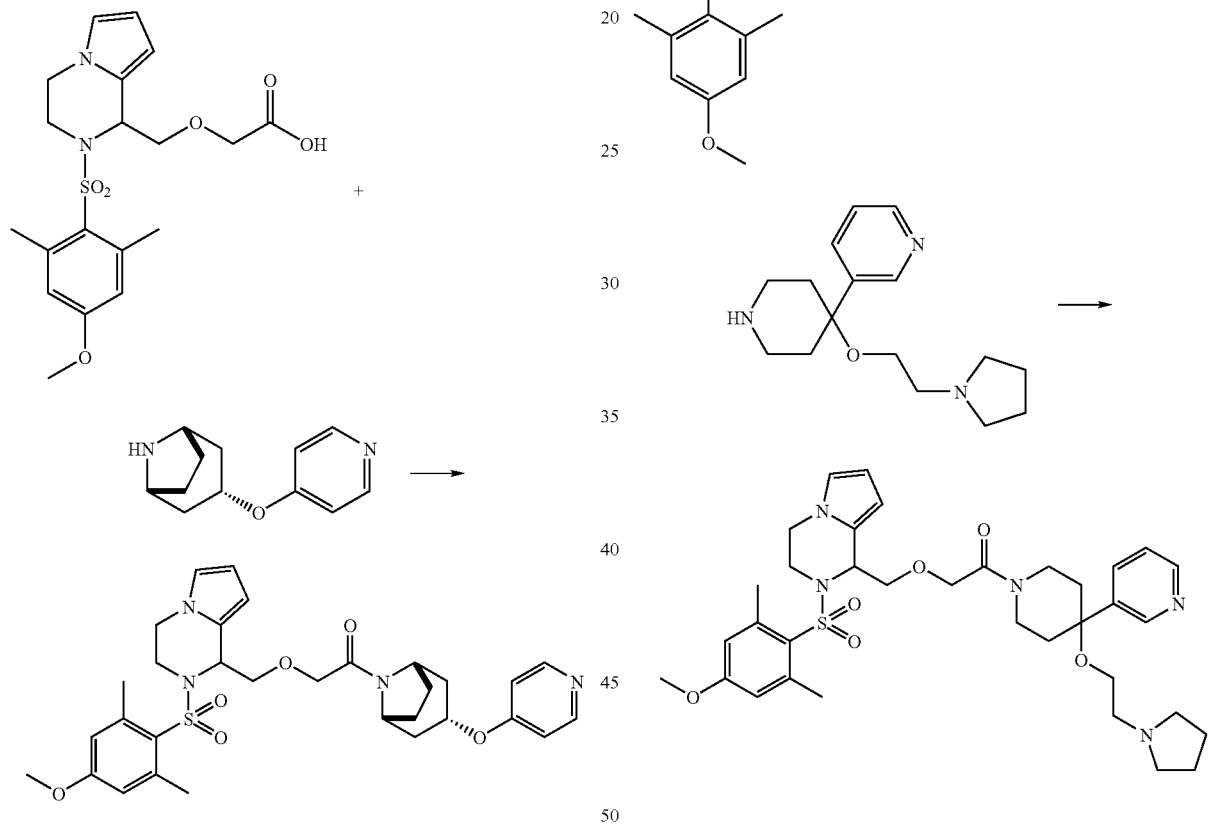

DIPEA (3.96 mmol) and HATU (1.49 mmol) were added to a cooled (0° C.) solution of S3 (0.99 mmol) in THF (10 ml) and reaction mixture was stirred for 15 min. A solution of amine A13 (0.99 mmol) in THF (5 ml) was added drop wise and the reaction mixture was stirred at 25° C. for 14 h. the solvent was evaporated under reduced pressure and the residue was dissolved in DCM (50 ml), washed with saturated NH$_4$Cl solution (20 ml), saturated NaHCO$_3$ solution (20 ml), brine (20 ml). the organic layer was dried over Na$_2$SO$_4$ and concentrated. The crude material was purified by silica gel column chromatography to yield the desired compound. m/z=594.7 [MH]$^+$

Example 24

2-((2-(4-Methoxy-2,6-dimethylphenylsulfonyl)-1,2,3,4-tetrahydropyrrolo[1,2-a]pyrazin-1-yl)methoxy)-1-(4-(pyridin-3-yl)-4-(2-(pyrrolidin-1-yl)ethoxy)piperidin-1-yl)ethanone

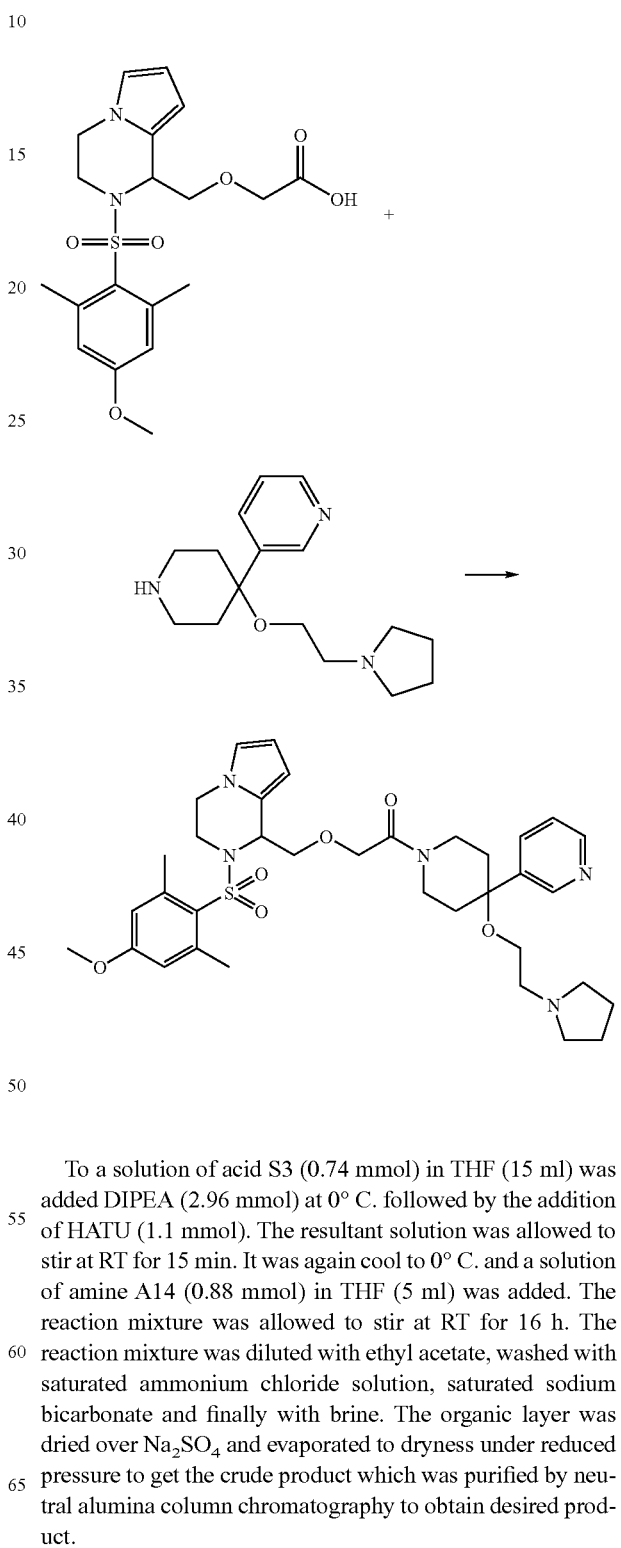

To a solution of acid S3 (0.74 mmol) in THF (15 ml) was added DIPEA (2.96 mmol) at 0° C. followed by the addition of HATU (1.1 mmol). The resultant solution was allowed to stir at RT for 15 min. It was again cool to 0° C. and a solution of amine A14 (0.88 mmol) in THF (5 ml) was added. The reaction mixture was allowed to stir at RT for 16 h. The reaction mixture was diluted with ethyl acetate, washed with saturated ammonium chloride solution, saturated sodium bicarbonate and finally with brine. The organic layer was dried over Na$_2$SO$_4$ and evaporated to dryness under reduced pressure to get the crude product which was purified by neutral alumina column chromatography to obtain desired product.

tion mixture was stirred at 25° C. for 16 h. The reaction mixture was diluted with water and extracted with ethyl acetate. The organic layer was washed with water, brine, dried over anhydrous Na$_2$SO$_4$ and concentrated. The crude product was purified by column chromatography on neutral alumina using 1-10% MeOH in DCM as eluent. m/z=530.7 [MH]$^+$

Example 25

2-(2-(4-chloro-2,5-dimethylphenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide

Example 31

N-(6-((tert-Butylamino)methyl)-1,2,3,4-tetrahydronaphthalen-2-yl)-2-(2-(6-methoxynaphthalen-2-ylsulfonyl)-1,2,3,4-tetrahydropyrrolo[1,2-a]-pyrazin-1-yl)acetamide

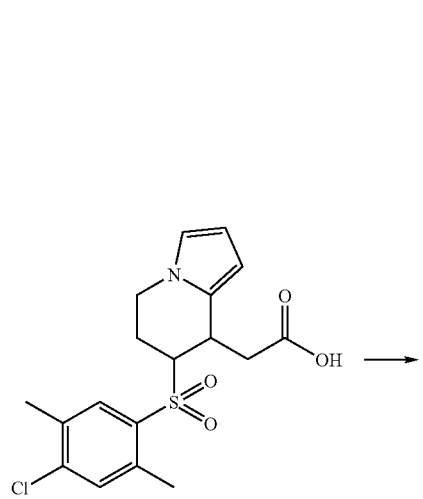

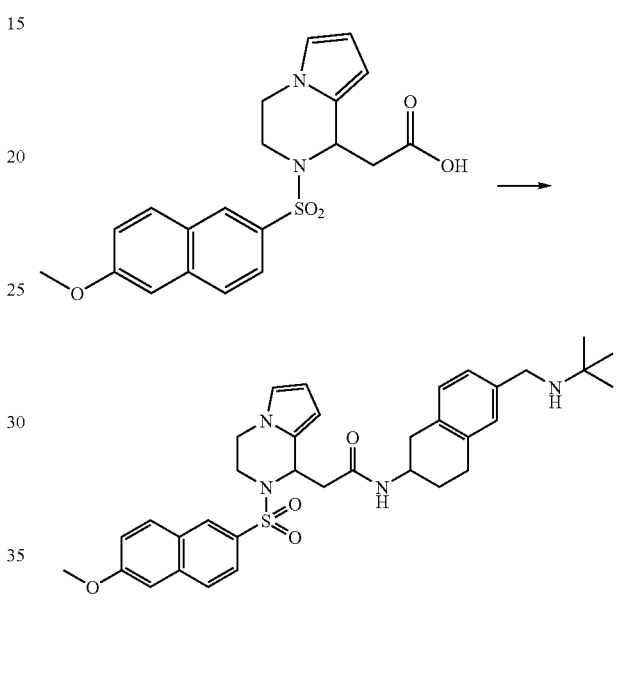

The carboxylic acid S7 (0.486 mmol) was dissolved in DCM (5 ml) and cooled to 0° C. followed by the addition of DIPEA (1.215 mmol), EDCl (0.729 mmol) and HOAt (0.486 mmol) and then reaction mixture was stirred at 25° C. for 15 min. The reaction mixture was again cooled down to 0° C. and a solution of amine A5 (0.486 mmol) in DCM (5 ml) was added. Reaction mixture was stirred at 25° C. for 16 h and then diluted with DCM. Reaction mixture was successively washed with sodium bicarbonate (10 ml), ammonium chloride solution (10 ml), water (10 ml) and brine (10 ml). Organic layer is dried over $Na_2SO_4$ and concentrated to dryness to afford crude product which is purified by silica gel column chromatography (3% methanol-DCM) to afford the product as white solid. m/z=609.4 [MH+]

To a cooled (0° C.) suspension of 2-(2-(6-methoxynaphthalen-2-ylsulfonyl)-1,2,3,4-tetrahydropyrrolo[1,2-a]pyrazin-1-yl)acetic acid (S2) (310 mg, 0.77 mmol, 1.0 eq.) in DCM (20 ml) was added HATU (600 mg, 1.54 mmol, 2 eq.) and DIPEA (0.4 ml, 2.31 mmol, 3 eq.) and the reaction mixture was allowed to stir for 30 min. Finally, 6-((tert-Butylamino)methyl)-1,2,3,4-tetrahydronaphthalen-2-amine (A15) (180 mg, 0.77 mmol, 1.0 eq.) was added and the reaction mixture and it was stirred at RT for 16 h. The mixture was diluted with DCM (100 ml) and successively washed with ammonium chloride solution (50 ml), sodium bicarbonate solution (50 ml), water (10 ml) and brine (10 ml). The organics were dried over $Na_2SO_4$ and the solvent was evaporated under reduced pressure to give the crude product which was purified by column chromatography (silica gel, 6% MeOH/DCM) to yield the pure title compound as a white solid. Yield: 34% (160 mg, 0.26 mmol); MS, Rt=3.6 min; m/z=615.1 [MH]+

The synthesis of further example compounds took place by the methods already described. The following Table 3 shows the method used to prepare each of these further compounds.

| Example no. | Acid | Amine | Product | As per example no. | m/z MH+ |
|---|---|---|---|---|---|
| 6 | S5 | A4 * 2 HCl | 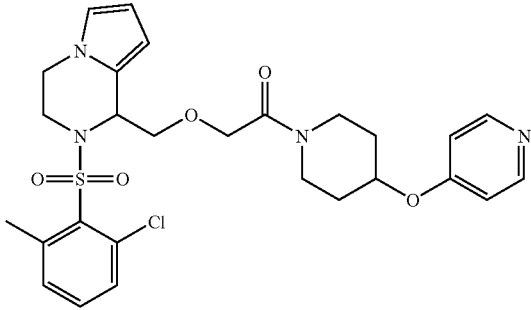 2-((2-(2-Chloro-6-methylphenylsulfonyl)-1,2,3,4-tetrahydropyrrolo[1,2-a]pyrazin-1-yl)methoxy)-1-(4-(pyridin-4-yloxy)piperidin-1-yl)ethanone | 5 | 560.1 |
| 7 | S3 | A8 | 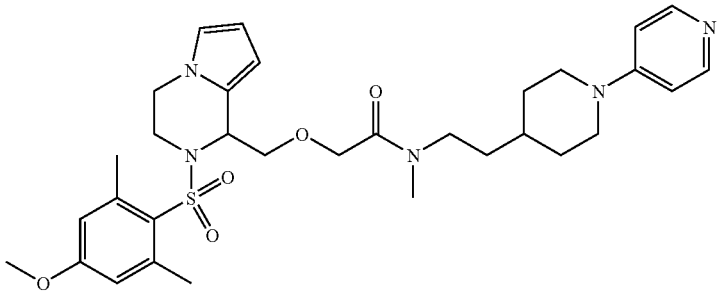 2-((2-(4-Methoxy-2,6-dimethylphenylsulfonyl)-1,2,3,4-tetrahydropyrrolo[1,2-a]pyrazin-1-yl)methoxy)-N-methyl-N-(2-(1-pyridin-4-yl)piperidin-4-yl)ethyl)acetamide | 4 (silica gel, DCM/7 M NH$_3$ in methanol, 98:2) | 610.8 |
| 12 | S4 | A8 | 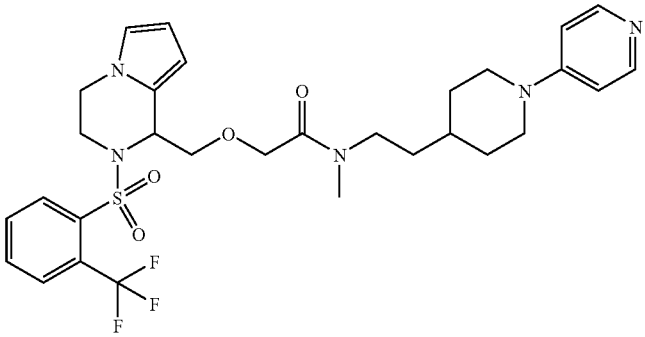 N-Methyl-N-(2-(1-(pyridin-4-yl)piperidin-4-yl)ethyl)-2-((2-(2-(trifluoromethyl)phenylsulfonyl)-1,2,3,4-tetrahydropyrrolo[1,2-a]pyrazin-1-yl)methoxy)acetamide | 4 (silica gel, DCM/7 M NH$_3$ in methanol, 99:1 → 98:2 → 95:5). | 620.7 |

| Example no. | Acid | Amine | Product | As per example no. | m/z MH+ |
|---|---|---|---|---|---|
| 13 | S3 | A4 * 2 HCl | 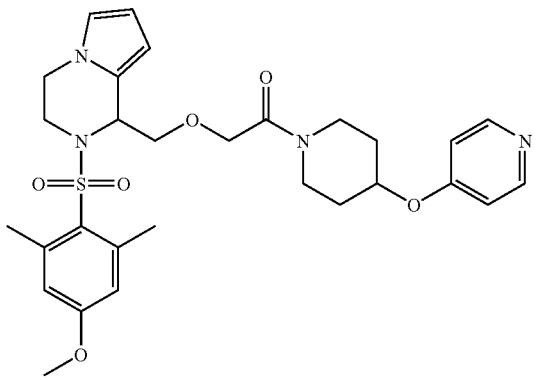<br>2-((2-(4-Methoxy-2,6-dimethylphenylsulfonyl)-1,2,3,4-tetrahydropyrrolo[1,2-a]pyrazin-1-yl)methoxy)-1-(4-(pyridin-4-yloxy)piperidin-1-yl)ethanone | 5 | 569.7 |
| 15 | S5 | A7 | 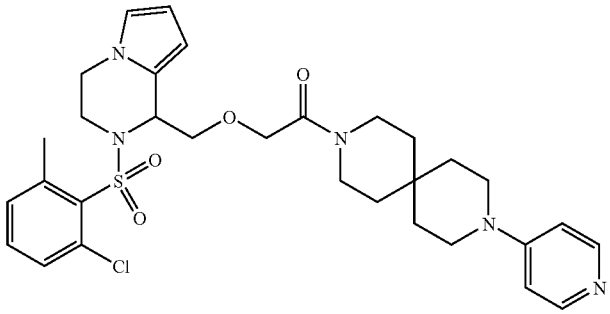<br>2-((2-(2-Chloro-6-methylphenylsulfonyl)-1,2,3,4-tetrahydropyrrolo[1,2-a]pyrazin-1-yl)methoxy)-1-(9-(pyridin-4-yl)-3,9-diazaspiro[5.5]undecan-3-yl)ethanone | 14 | 613.2 |
| 16 | S5 | A8 | 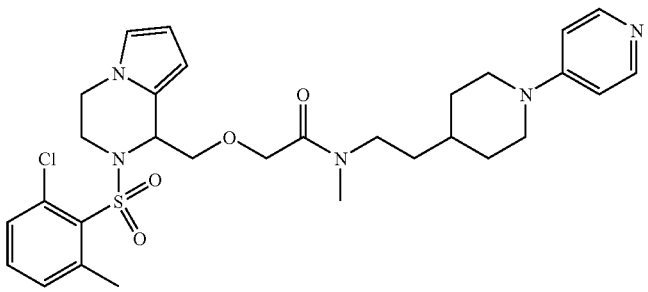<br>2-((2-(2-Chloro-6-methylphenylsulfonyl)-1,2,3,4-tetrahydropyrrolo[1,2-a]pyrazin-1-yl)methoxy)-N-methyl-N-(2-(1-(pyridin-4-yl)piperidin-4-yl)ethyl)acetamide | 4 (silica gel, DCM/7 M NH₃ in methanol, 99:1 → 98:2 → 95:5). | 601.2 |

-continued

| Example no. | Acid | Amine | Product | As per example no. | m/z MH+ |
|---|---|---|---|---|---|
| 20 | S6 | A10 | 2-(2-(2-Chloro-4-(trifluoromethyl)phenylsulfonyl)-1,2,3,4-tetrahydropyrrolo[1,2-a]pyrazin-1-yl)-1-(3,4-dihydroisoquinolin-2(1H)-yl)ethanone | 19 | 539.0 |
| 21 | S4 | A3 * 2 HCl | 1-(2-(Pyridin-4-yl)-2,8-diazaspiro[4.5]decan-8-yl)-2-((2-(2-(trifluoromethyl)phenylsulfonyl)-1,2,3,4-tetrahydropyrrolo[1,2-a]pyrazin-1-yl)methoxy)ethanone | 11 | 617.7 |
| 26 | S8 | A5 | 2-(2-(3,4-dichlorophenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide | 25 | 615.3 |
| 27 | S9 | A5 | 2-(2-(phenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide | 25 | 547.4 |

-continued

| Example no. | Acid | Amine | Product | As per example no. | m/z MH+ |
|---|---|---|---|---|---|
| 28 | S10 | A5 | 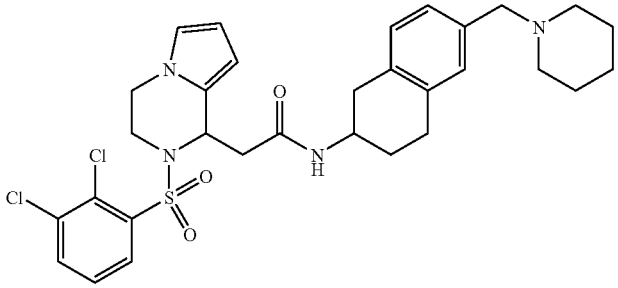<br>2-(2-(2,3-dichlorophenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide | 25 | 615.3 |
| 29 | S11 | A5 | 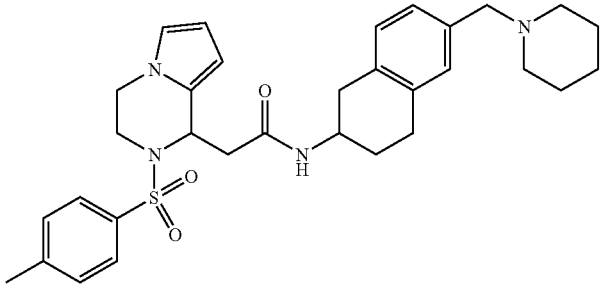<br>N-(6-(piperidin-1-ylmethyl)-1,2,3,4-tetrahydronaphthalen-2-yl)-2-(2-tosyl-1,2,3,4-tetrahydropyrrolo[1,2-a]pyrazin-1-yl)acetamide | 25 | 561.4 |
| 30 | S12 | A5 | 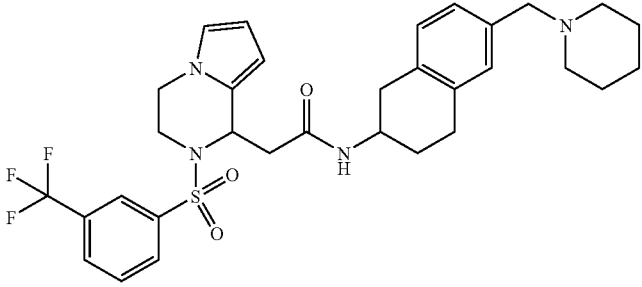<br>N-(6-(piperidin-1-ylmethyl)-1,2,3,4-tetrahydronaphthalen-2-yl)-2-(2-(3-(trifluoromethyl)-phenylsulfonyl)-1,2,3,4-tetrahydropyrrolo-[1,2-a]pyrazin-1-yl)acetamide | 25 | 615.4 |

Synthesis of Examples 32-40

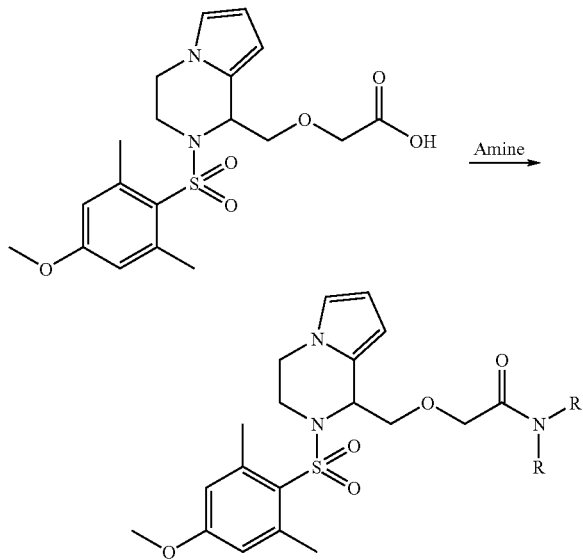

To a solution of 2-((2-(4-methoxy-2,6-dimethylphenylsulfonyl)-1,2,3,4-tetrahydro-pyrrolo[1,2-a]pyrazin-1-yl)methoxy)acetic acid (S-3) (0.367 mmol, 1 eq.) and N-ethyl-diisopropylamine (0.734 mmol, 2 eq.) in DCM (7 ml) were added N-ethyl-N'-3-(dimethylamino)-propyl-carbodiimide hydrochloride (0.44 mmol, 1.2 eq.) and 1-hydroxybenzotriazole hydrate (0.073 mmol, 0.2 eq.) at 0° C. and the resulting mixture was stirred for 15 min at RT. The solution was cooled to 0° C. and the Amine (1 eq., see table) was added. The mixture was stirred at RT for 16 h. The solvent was evaporated in vacuo and the residue taken up in ethyl acetate and extracted with 10% aq. ammonium chloride solution (1×), sat. aq. sodium hydrogen carbonate solution (1×) and sat. aq. NaCl-solution (1×). The organic layer was dried over MgSO$_4$ and concentrated in vacuo. The crude product was purified by column chromatography (ethyl acetate/ethanol/25% aq ammonia (1000:100:5), ethyl acetate/methanol/25% aq ammonia (100:100:1) or ethyl acetate/cyclohexane (100:400).

(i) In the case of amine hydrochloride salts the amount of N-ethyl-diisopropylamine employed was adjusted according to the stoichiometry of the hydrochloride salts.

| Example Nr. | Structure | Name | Amine Structure | Yield | Analysis (LC/MS) |
|---|---|---|---|---|---|
| 32 | 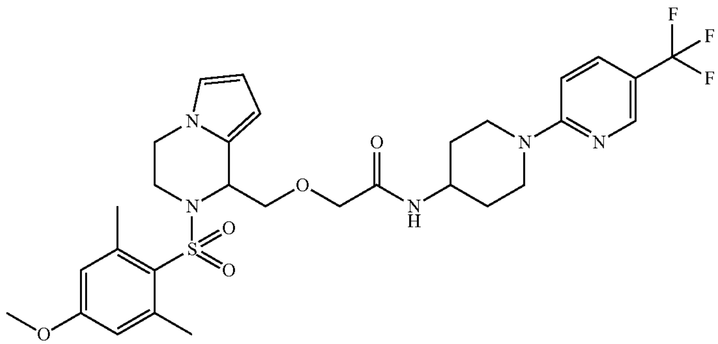 | 2-[[2-[(4-Methoxy-2,6-dimethyl-phenyl)sulfonyl]-1,2,3,4-tetrahydro-pyrrolo[1,2-a]pyrazin-1-yl]-methoxy]-N-[1-[5-(trifluoromethyl)-pyridin-2-yl]-piperidin-4-yl]-acetamide | | 60% (0.14 g) | Rt = 4.8 min; m/z = 636.31 [MH]+ |
| 33 | 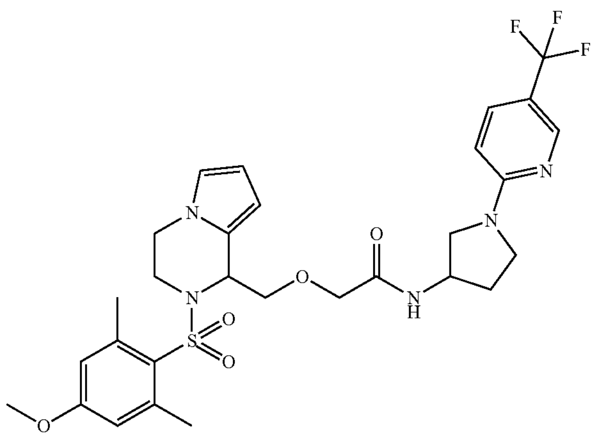 | 2-[[2-[(4-Methoxy-2,6-dimethyl-phenyl)sulfonyl]-1,2,3,4-tetrahydro-pyrrolo[1,2-a]pyrazin-1-yl]-methoxy]-N-[1-[5-(trifluoromethyl)-pyridin-2-yl]-pyrrolidin-3-yl]-acetamide | | 35% (0.08 g) | Rt = 4.1 min; m/z = 622.0 [MH]+ |

-continued
| Example Nr. | Structure | Name | Amine Structure | Yield | Analysis (LC/MS) |
|---|---|---|---|---|---|
| 34 | 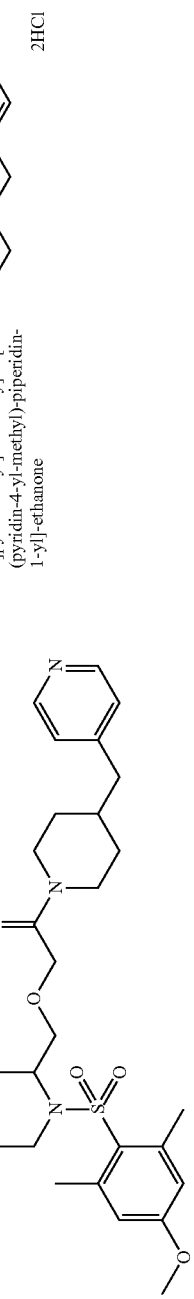 | 2-[[2-[(4-Methoxy-2,6-dimethyl-phenyl)sulfonyl]-1,2,3,4-tetrahydro-pyrrolo[1,2-a]pyrazin-1-yl]-methoxy]-1-(4-pyridin-4-yl-piperidin-1-yl)-ethanone |  | 69% (0.14 g) | Rt = 3.0 min; m/z = 553.1 [MH]$^+$ |
| 35 | 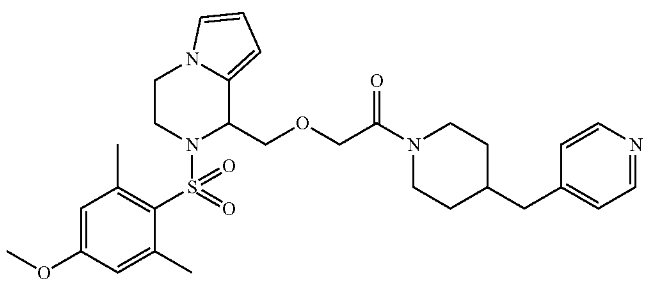 | 2-[[2-[(4-Methoxy-2,6-dimethyl-phenyl)sulfonyl]-1,2,3,4-tetrahydro-pyrrolo[1,2-a]pyrazin-1-yl]-methoxy]-1-[4-(pyridin-4-yl-methyl)-piperidin-1-yl]-ethanone | 2HCl | 72% (0.15 g) | Rt = 3.1 min; m/z = 567.1 [MH]$^+$ |

-continued

| Example Nr. | Structure | Name | Amine Structure | Yield | Analysis (LC/MS) |
|---|---|---|---|---|---|
| 36 | 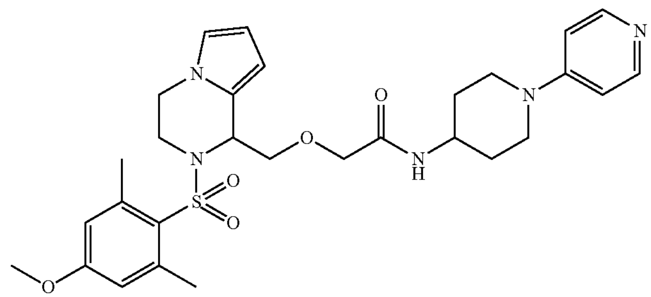 | 2-[[2-[(4-Methoxy-2,6-dimethyl-phenyl)sulfonyl]-1,2,3,4-tetrahydro-pyrrolo[1,2-a]pyrazin-1-yl]-methoxy]-N-(1-pyridin-4-yl-piperidin-4-yl)-acetamide | 2HCl | 77% (0.16 g) | Rt = 3.3 min; m/z = 568.1 [MH]+ |
| 37 | 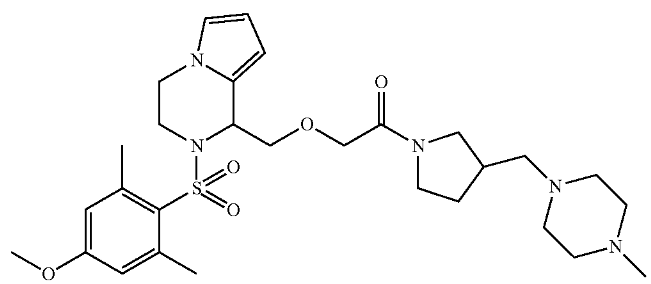 | 2-[[2-[(4-Methoxy-2,6-dimethyl-phenyl)sulfonyl]-1,2,3,4-tetrahydro-pyrrolo[1,2-a]pyrazin-1-yl]-methoxy]-1-[3-[(4-methyl-piperazin-1-yl)methyl]-pyrrolidin-1-yl]-ethanone | | 52% (0.11 g) | Rt = 2.7 min; m/z = 574.1 [MH]+ |
| 38 | 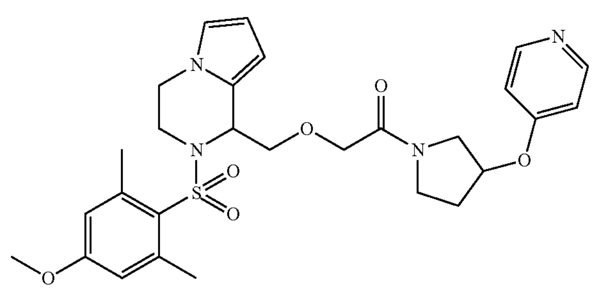 | 2-[[2-[(4-Methoxy-2,6-dimethyl-phenyl)sulfonyl]-1,2,3,4-tetrahydro-pyrrolo[1,2-a]pyrazin-1-yl]-methoxy]-1-(3-pyridin-4-yloxy-pyrrolidin-1-yl)-ethanone | | 74% 0.15 g | Rt = 2.9 min; m/z = 555.1 [MH]+ |

-continued

| Example Nr. | Structure | Name | Amine Structure | Yield | Analysis (LC/MS) |
|---|---|---|---|---|---|
| 39 | 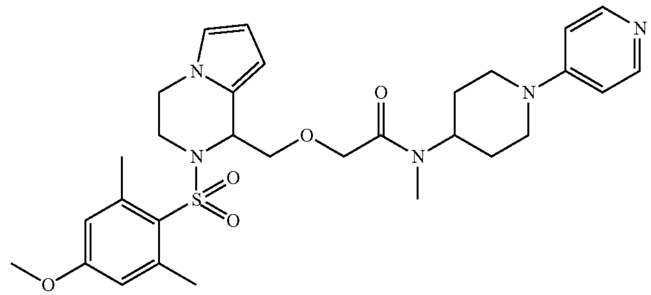 | 2-[[2-[(4-Methoxy-2,6-dimethyl-phenyl)sulfonyl]-1,2,3,4-tetrahydro-pyrrolo[1,2-a]pyrazin-1-yl]-methoxy]-N-methyl-N-(1-pyridin-4-yl-piperidin-4-yl)-acetamide | | 75% (0.16 g) | Rt = 3.2 min; m/z = 582.1 [MH]$^+$ |
| 40 | 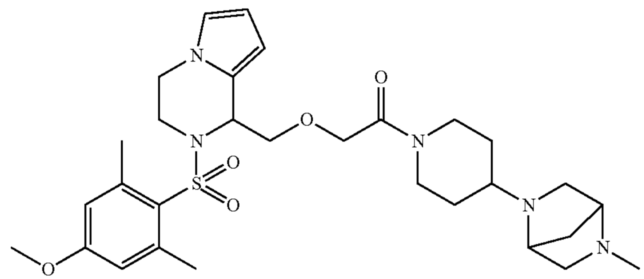 | 2-[[2-[(4-Methoxy-2,6-dimethyl-phenyl)sulfonyl]-1,2,3,4-tetrahydro-pyrrolo[1,2-a]pyrazin-1-yl]-methoxy]-1-[4-(3-methyl-3,6-diazabicyclo[2.2.1]heptan-6-yl)-piperidin-1-yl]-ethanone | 2HCl | 23% (0.05 g) | Rt 2.4 min; m/z 586.1 [MH]$^+$ |

Example 41

N-[2-[4-(4,5-Dihydro-1H-imidazol-2-yl)-phenyl]-ethyl]-2-[2-[(6-methoxy-naphthalen-2-yl)sulfonyl]-1,2,3,4-tetrahydro-pyrrolo[1,2-a]pyrazin-1-yl]-acetamide

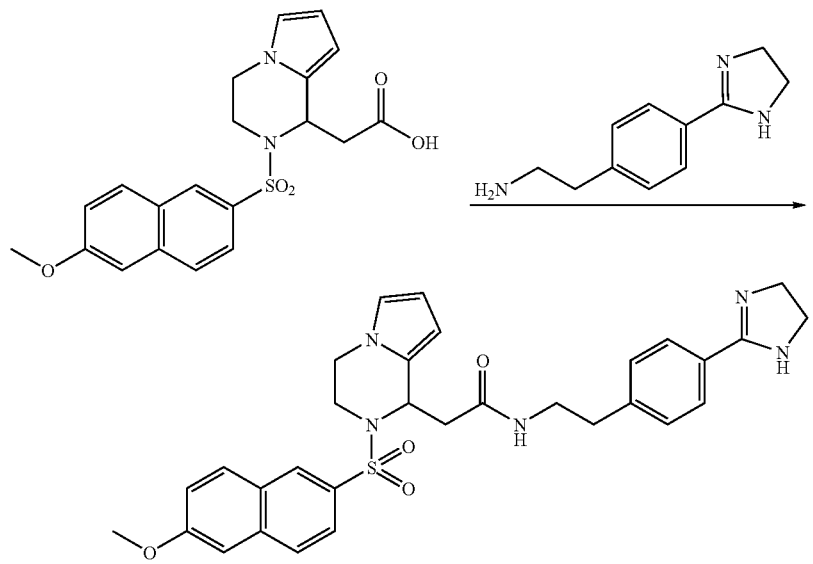

HATU (563 mg, 1.48 mmol, 2.0 eq.) was added to a mixture of 2-(2-(6-methoxynaphthalen-2-ylsulfonyl)-1,2,3,4-tetrahydropyrrolo[1,2-a]pyrazin-1-yl)acetic acid (S-2) (297 mg, 0.74 mmol, 1.0 eq.), 2-(4-(4,5-Dihydro-1H-imidazol-2-yl)phenyl)ethanamine (A49) (140 mg, 0.74 mmol, 1.0 eq.), and DIPEA (0.39 ml, 2.22 mmol, 3.0 eq.) in THF (10 ml) at 0° C. and the resulting reaction mixture was stirred at RT for 14 h. The solvent was evaporated under reduced pressure, the residue dissolved in DCM (30 ml) and washed with saturated ammonium chloride solution (15 ml), saturated sodium bicarbonate solution (15 ml), water (15 ml) and brine (15 ml). The organic layer was dried over $Na_2SO_4$ and concentrated under reduced pressure to yield the crude product which was purified by column chromatography (neutral alumina; 1% MeOH/DCM) to afford the desired product as an off-white solid. Yield: 35% (140 mg, 0.245 mmol); MS, Rt=3.3 min; m/z=572.5 [MH]+

Example 42

N-[(1R)-6-[(tert-Butylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide

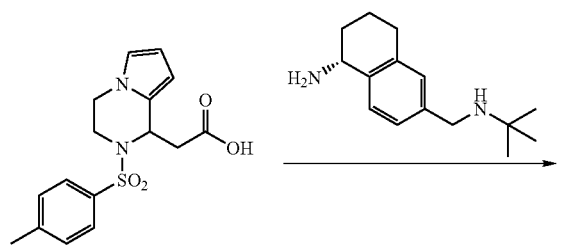

-continued

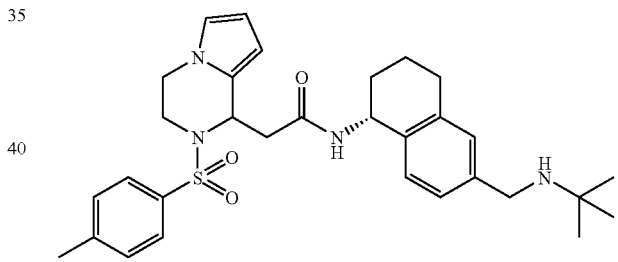

To a solution of 2-(2-tosyl-1,2,3,4-tetrahydropyrrolo[1,2-a]pyrazin-1-yl)acetic acid (S11) (300 mg, 0.898 mmol, 1.0 eq.) in THF (5 ml) were added DIPEA (0.47 ml, 2.694 mmol, 3.0 eq.) and HATU (410 mg, 1.08 mmol, 1.2 eq.) at 0° C. and the mixture was stirred for 15 min at the same temperature. A solution of (R)-6-((tert-butylamino)methyl)-1,2,3,4-tetrahydronaphthalen-1-amine (A50) (0.898 mmol, 1.0 eq.) in THF (5 ml) was added to the reaction mixture and it was stirred at RT for 16 h. The reaction mixture was diluted with ethyl acetate (50 ml) and washed with sat. $NH_4Cl$ solution (20 ml), sat. $NaHCO_3$ solution (20 ml), water (20 ml) and brine (20 ml). The organic layer was dried over $Na_2SO_4$ and concentrated under reduced pressure to get the crude product which was purified by column chromatography (silica gel; 1.5% MeOH/DCM) to yield the desired product as an off-white solid. Yield: 19% (94 mg, 0.171 mmol); MS, Rt=3.2 min; m/z=549.1 [MH]+

Example 43

2-[2-[(6-Methoxy-naphthalen-2-yl)sulfonyl]-1,2,3,4-tetrahydro-pyrrolo[1,2-a]pyrazin-1-yl]-N-methyl-N-[6-(piperidin-1-yl-methyl)-1,2,3,4-tetrahydro-naphthalen-2-yl]-acetamide

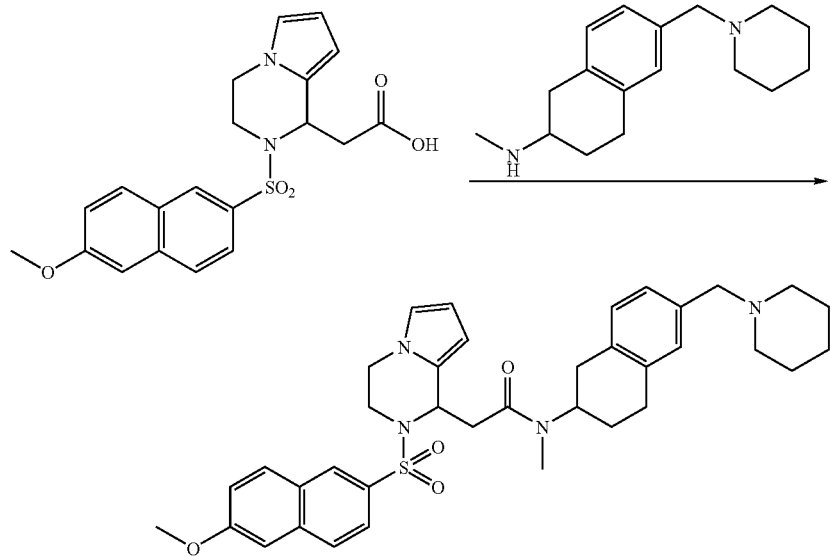

To a solution of 2-(2-(6-methoxynaphthalen-2-ylsulfonyl)-1,2,3,4-tetrahydropyrrolo-[1,2-a]pyrazin-1-yl)acetic acid (S2) (200 mg, 0.5 mmol, 1.0 eq.) in THF (6 ml) were added DIPEA (300 μl, 2.0 mmol, 4.0 eq.) and HATU (190 mg, 0.5 mmol, 1.0 eq.) at 0° C. and the resulting mixture was stirred for 15 min at same temperature. A solution of N-methyl-6-(piperidin-1-ylmethyl)-1,2,3,4-tetrahydronaphthalen-2-amine (A51) (0.6 mmol, 1.2 eq.) in THF (4 ml) was added to the reaction mixture and it was allowed to stir at RT for 16 h. The reaction mixture was diluted with ethyl acetate (30 ml) and washed with sat. NH$_4$Cl solution (20 ml), sat. NaHCO$_3$ solution (20 ml), water (20 ml) and brine (20 ml). The organic layer was dried over Na$_2$SO$_4$ and concentrated under reduced pressure to obtain the crude product which was purified by column chromatography (silica gel; 2-4% MeOH/DCM) to yield the desired product as a white solid. Yield: 47% (150 mg, 0.234 mmol); MS, Rt=3.7 min; m/z=641.1 [MH]+

Example 44

N-[(1R)-6-[(4-Fluoro-piperidin-1-yl)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide

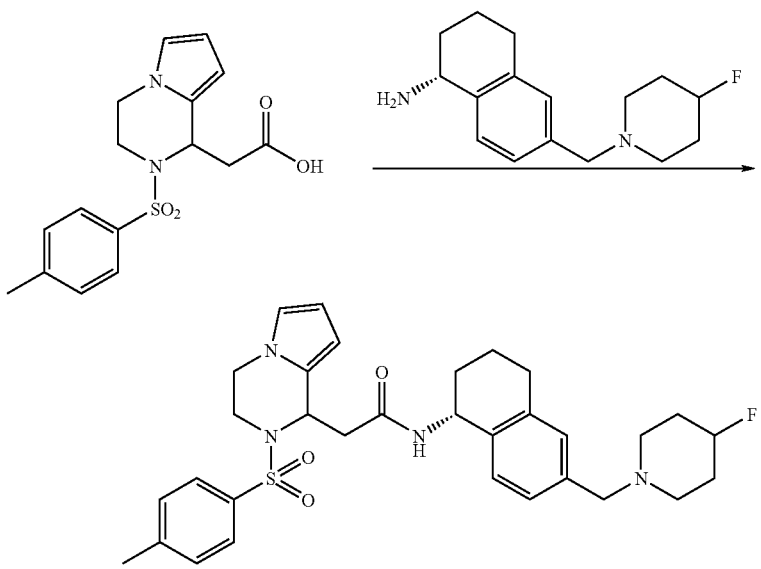

DIPEA (630 µl, 3.592 mmol, 4.0 eq.) was added to a stirred solution of 2-(2-tosyl-1,2,3,4-tetrahydropyrrolo[1,2-a]pyrazin-1-yl)acetic acid (S11) (300 mg, 0.898 mmol, 1.0 eq.) in DCM (15 ml), followed by EDCl (260 mg, 1.347 mmol, 1.5 eq.) and HOBT (183 mg, 1.347 mmol, 1.5 eq.) which were added at 0° C. The reaction mixture was allowed to stir for 30 min. A solution of R)-6-((4-fluoropiperidin-1-yl)methyl)-1,2,3,4-tetrahydronaphthalen-1-amine (A52) (0.898 mmol, 1.0 eq.) in DCM (5 ml) was added to the reaction mixture and it was stirred at RT for 16 h. The reaction mixture was diluted with DCM (50 ml) and washed with sat. NH₄Cl solution (50 ml), sat. NaHCO₃ solution (50 ml), water (50 ml) and brine (50 ml), and dried over Na₂SO₄. The solvent was evaporated under reduced pressure to give crude product which was purified by column chromatography (silica gel; 2% MeOH/DCM) to yield the desired compound as an off white solid. Yield: 38% (197 mg, 0.34 mmol); MS, Rt=3.2 min; m/z=579.1 [M H]+

Example 45

2-(2-Tosyl-1,2,3,4-tetrahydropyrrolo[1,2-a]pyrazin-1-yl)-N—((R)-6-((2,2,2-trifluoroethylamino)methyl)-1,2,3,4-tetrahydronaphthalen-1-yl)acetamide

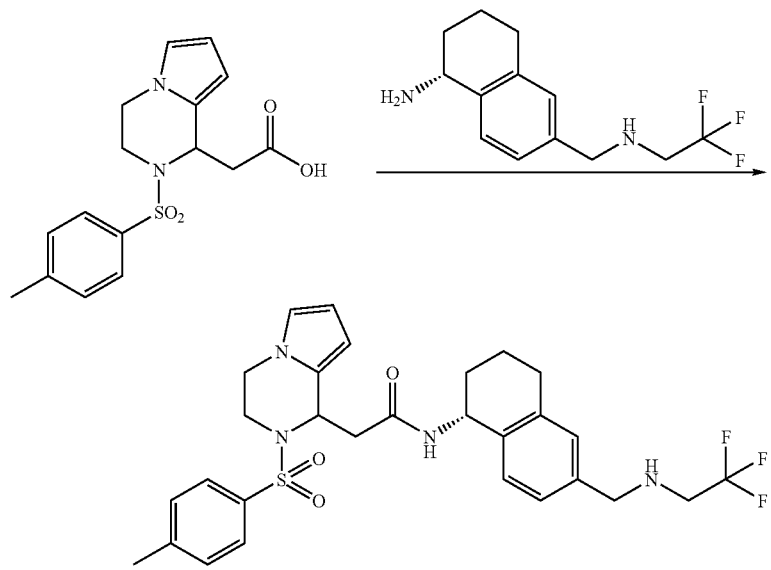

To a solution of 2-(2-tosyl-1,2,3,4-tetrahydropyrrolo[1,2-a]pyrazin-1-yl)acetic acid (S11) (214 mg, 0.64 mmol, 1.0 eq.) in THF (5 ml) were added DIPEA (340 µl, 1.92 mmol, 3.0 eq.) and HATU (292 mg, 0.77 mmol, 1.2 eq.) at 0° C. and the mixture was stirred for 15 min at the same temperature. A solution of (R)-6-((2,2,2-trifluoroethylamino)methyl)-1,2,3,4-tetrahydronaphthalen-1-amine (A53) (0.64 mmol, 1.0 eq.) in THF (5 ml) was added to the reaction mixture and it was stirred at RT for 16 h. The reaction mixture was concentrated and the residue was diluted with DCM (50 ml) and washed with sat. NH₄Cl solution (20 ml), sat. NaHCO₃ solution (20 ml), water (20 ml) and brine (20 ml). The organic layer was dried over Na₂SO₄ and concentrated under reduced pressure to give the crude product which was purified by column chromatography (silica gel; 0.7% MeOH/DCM) to yield the desired product as an off-white solid. Yield: 22% (80 mg, 0.14 mmol); MS, Rt=3.2 min; m/z=575.0 [MH]+

Example 46

N-[(1R)-1-[4-[(tert-Butylamino)-methyl]-phenyl]-ethyl]-2-[2-(p-tolylsulfonyl)-1,2,3,4-tetrahydro-pyrrolo[1,2-a]pyrazin-1-yl]-acetamide

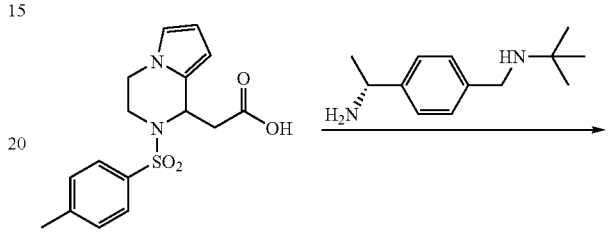

-continued

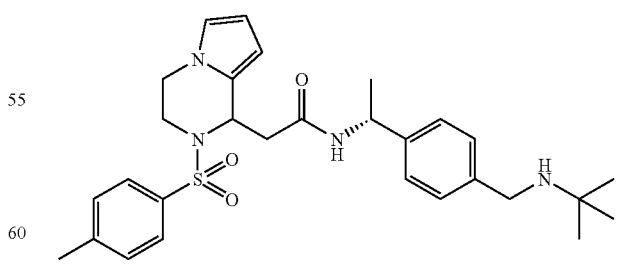

To a suspension of 2-(2-tosyl-1,2,3,4-tetrahydropyrrolo[1,2-a]pyrazin-1-yl)acetic acid (S11) (405 mg, 1.2 mmol, 1.0 eq.) in THF (5 ml) were added DIPEA (1.0 ml, 6.0 mmol, 5.0 eq.) and HATU (547 mg, 1.4 mmol, 1.2 eq.) at 0° C. and the mixture was stirred for 15 min at the same temperature. A solution of (R)—N-(4-(1-aminoethyl)-benzyl)-2-methylpropan-2-amine (A54) (1.2 mmol, 1.0 eq.) in THF (3 ml) was added to the reaction mixture and it was stirred at RT for 16 h. The mixture was diluted with DCM (70 ml) and washed with sat. NH$_4$Cl solution (25 ml), sat. NaHCO$_3$ solution (25 ml), water (25 ml) and brine (25 ml). The organic layer was dried over Na$_2$SO$_4$ and concentrated under reduced pressure to give the crude product which was purified by column chromatography (silica gel; 3% MeOH/DCM) to yield the desired product as a light brown solid. Yield: 29% (180 mg, 0.334 mmol); MS, Rt=2.9 min; m/z=523.1 [M H]+

Example 47

2-(2-(3-chlorophenylsulfonyl)-1,2,3,4-tetrahydropyrrolo[1,2-a]-pyrazin-1-yl)-N-(6-(piperidin-1-ylmethyl)-1,2,3,4-tetrahydronaphthalen-2-yl)-acetamide

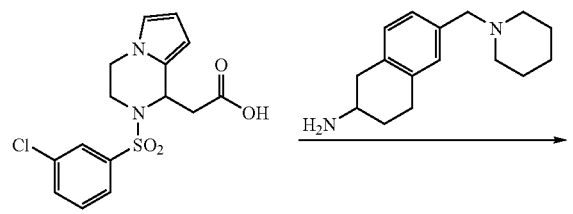

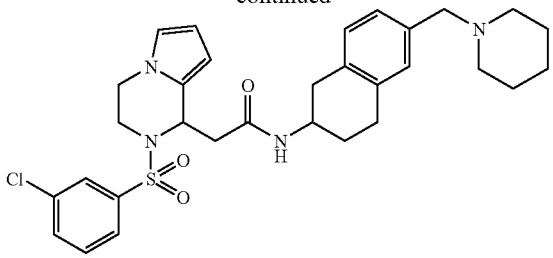

To a solution of acid S15 (300 mg, 0.847 mmol, 1.0 eq.) in THF (8 ml) were added DIPEA (0.5 ml, 2.542 mmol, 3.0 eq.) and HATU (642 mg, 1.695 mmol, 2.0 eq.) at 0° C. and stirred for 15 min at same temperature. A solution of amine A5 (1.27 mmol, 1.2 eq.) in THF (5 ml) was added to the reaction mixture and stirred at RT for 16 h. The reaction mixture was diluted with ethyl acetate (60 ml) and washed with sat. NH$_4$Cl solution (10 ml), sat. NaHCO$_3$ solution (10 ml), water (10 ml), brine (10 ml). Organic layer is dried over Na$_2$SO$_4$ and concentrated under reduced pressure to get crude product which is purified by column chromatography (silica gel; 2-4% MeOH/DCM) to yield desired product as white solid. Yield: 30% (150 mg, 0.258 mmol); MS, Rt=3.2 min; m/z=581.0 [MH]+

Example 48

2-(2-(6-methoxynaphthalen-2-ylsulfonyl)-1,2,3,4-tetrahydropyrrolo-[1,2-a]pyrazin-1-yl)-N-(5-(piperidin-1-ylmethyl)-2,3-dihydro-1H-inden-2-yl)-acetamide

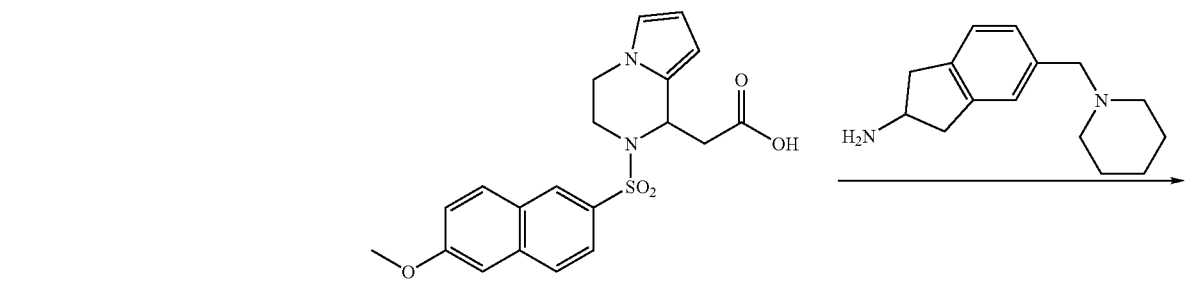

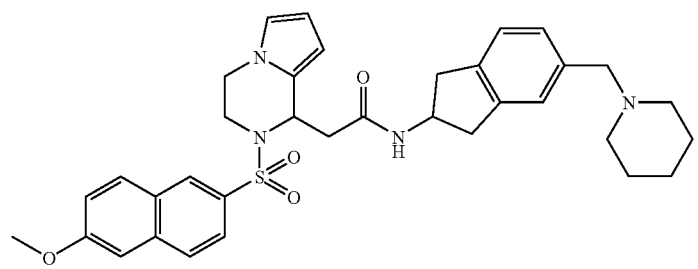

To a suspension of acid S2 (250 mg, 0.625 mmol, 1.0 eq.) in DCM (5 ml) were added DIPEA (250 µl, 1.25 mmol, 2.0 eq.) and HATU (332 mg, 0.875 mmol, 1.4 eq.) at 0° C. and stirred for 15 min at same temperature. A solution of amine A56 (0.75 mmol, 1.2 eq.) in DCM (3 ml) was added to the reaction mixture and stirred at RT for 16 h. The reaction mixture was diluted with DCM (75 ml) and washed with sat. NH$_4$Cl solution (30 ml), sat. NaHCO$_3$ solution (30 ml), water (30 ml), brine (30 ml). The organic layer was dried over Na$_2$SO$_4$ and concentrated under reduced pressure to get crude product which was purified by column chromatography (neutral alumina; 0.5% MeOH/DCM) to yield desired product as off white solid. Yield: 31% (120 mg, 0.196 mmol); MS, Rt=3.4 min; m/z=613.0 [MH]+

Synthesis of the examples 49-132 (Method A)

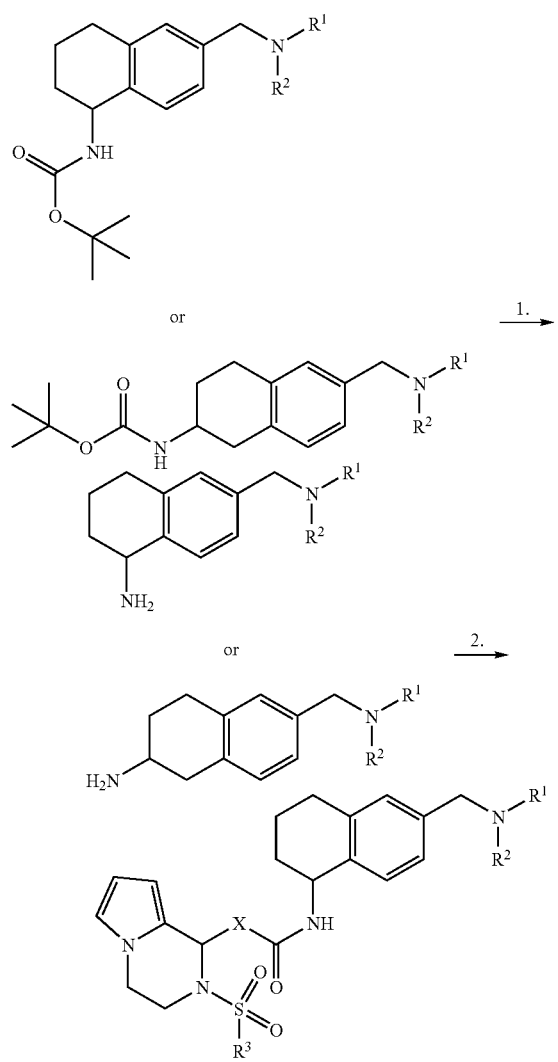

1. The Boc-protected amine (A17-A27 or A29-A39) (0.00019 mol) was treated with TFA (2 ml) in DCM (8 ml) at 0° C. and the resulting reaction mixture was allowed to stir at 25° C. for 4 h (monitored by TLC). The solvent was completely evaporated, dried properly to remove traces of TFA and the residue was directly used in library synthesis.

2. To a solution of acid Building Block (0.00023 mol, 1.2 eq.) in DCM (4 ml) was added EDCl.HCl (0.00046 mol, 2 eqv), HOBt (0.00023 mol) at 0° C. and reaction mixture was stirred at the same temperature for another 15 mins. In another round-bottom flask, the Boc-deprotected amine BB (0.00019 mol, 1 eqv) in DCM (2 ml) was cooled in ice bath, treated with DIPEA (0.00069 mol, 3 eqv) and was added to the reaction mixture at 0° C. Reaction mixture was stirred at RT for 16 h and diluted with DCM. The organic layer was successively washed with aqueous ammonium chloride, sodium bicarbonate and brine and finally dried over Na$_2$SO$_4$. Evaporation of organic layer under reduced pressure gave the crude product which was purified by prep.HPLC using aqueous ammonia method Synthesis of the examples 133-140 (Method B)

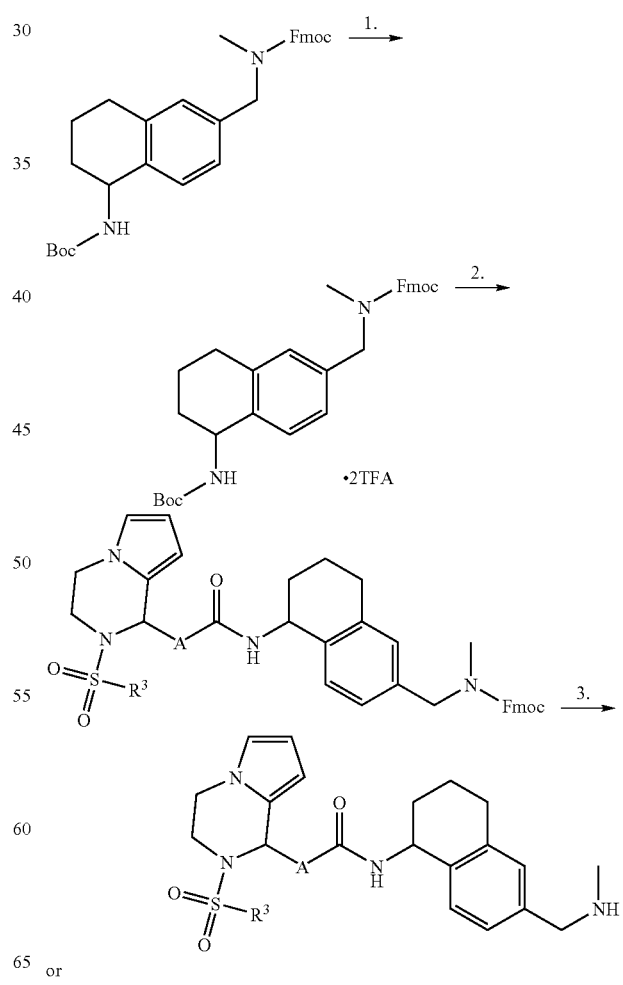

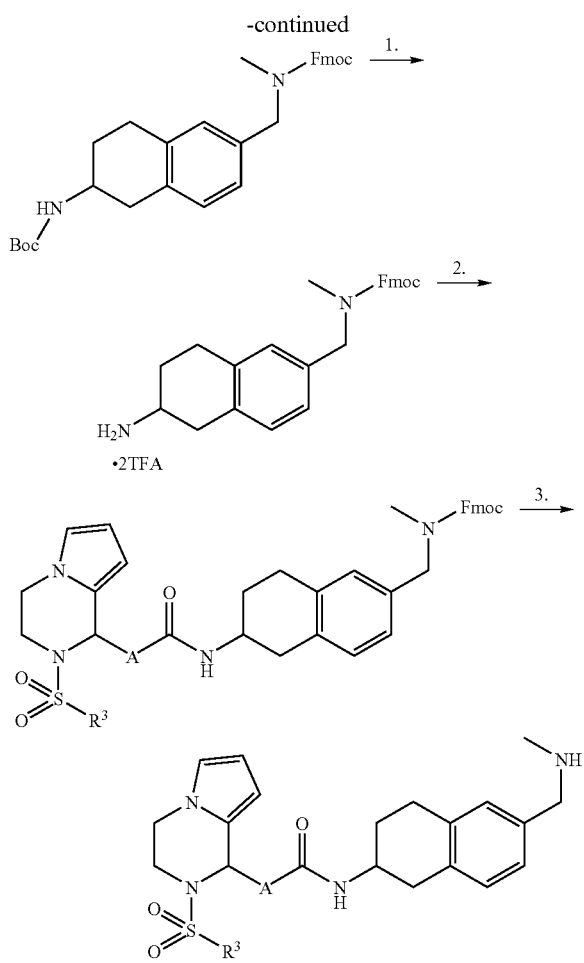

1. The Boc-protected amine A16 or A28 (0.00019 mol) was treated with TFA (2 ml) in DCM (8 ml) at 0° C. and the resulting reaction mixture was allowed to stir at 25° C. for 4 h (monitored by TLC). The solvent was completely evaporated, dried properly to remove traces of TFA and the residue was directly used in library synthesis.

2. To a solution of acid (0.00023 mol, 1.2 eq.) in DCM (4 ml) was added EDCl.HCl (0.00046 mol, 2 eqv), HOBt (0.00023 mol) at 0° C. and reaction mixture was stirred at the same temperature for another 15 mins. In another round-bottom flask, the Boc-deprotected amine BB (0.00019 mol, 1 eqv) in DCM (2 ml) was cooled in ice bath, treated with DIPEA (0.00069 mol, 3 eqv) and was added to the reaction mixture at 0° C. The reaction mixture was stirred at RT for 16 h and diluted with DCM. The organic layer was successively washed with aqueous ammonium chloride, sodium bicarbonate and brine and finally dried over $Na_2SO_4$. Evaporation of the organic layer under reduced pressure gave the crude product which is purified by column chromatography to give the pure desired product.

3. The step-2 product (0.0001 mol) was stirred at RT with 20% piperidine in acetonitrile (6 ml) for 3 h. The reaction mixture was concentrated under reduced pressure to give the crude product. The crude is purified by prep.HPLC purification using aqueous ammonia method.

Synthesis of the Examples 141-270 (Method C)

To a solution of CDI (0.105 M in DCM, 1 ml) a solution of the acid (0.05 M in DCM, 2 ml) was added. The reaction mixture was stirred for 1 h at RT. A solution of the amine (0.1 M in DCM, 1 ml) was added and the reaction mixture was stirred for additional 16 h. After that time water (3 ml) was added, the mixture was shaken for 15 min. and the organic layer was separated. Brine was added and after separation of the organic layer the products were evaporated and purified by HPLC.

The following compounds were synthesized:

|    | Acid | Amine | Method | M+ |    |
|----|------|-------|--------|------|-----|
| 49 | S13  | A33   | A      | 581.2 | 2-[2-[(3-Chloro-4-methyl-phenyl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-2-yl]-acetamide |
| 50 | S13  | A34   | A      | 595.2 | 2-[2-[(3-Chloro-4-methyl-phenyl)sulfonyl]-1,2,3,4-tetrahydro-pyrrolo[1,2-a]pyrazin-1-yl]-N-[6-(piperidin-1-yl-methyl)-1,2,3,4-tetrahydro-naphthalen-2-yl]-acetamide |
| 51 | S13  | A38   | A      | 617.2 | N-[6-[(Benzylamino)-methyl]-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide |
| 52 | S13  | A39   | A      | 643.2 | 2-[2-[(3-Chloro-4-methyl-phenyl)sulfonyl]-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-2-yl]-acetamide |
| 53 | S12  | A23   | A      | 617.2 | N-[6-(Morpholin-4-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 54 | S11  | A23   | A      | 563.1 | N-[6-(Morpholin-4-yl-methyl)-1,2,3,4-tetrahydro-naphthalen-1-yl]-2-[2-[(p-tolylsulfonyl)-1,2,3,4-tetrahydro-pyrrolo[1,2-a]pyrazin-1-yl]-acetamide |
| 55 | S13  | A24   | A      | 610.2 | 2-[2-[(3-Chloro-4-methyl-phenyl)sulfonyl]-1,2,3,4-tetrahydro-pyrrolo[1,2-a]pyrazin-1-yl]-N-[6-[(4-methyl-piperazin-1-yl)-methyl]-1,2,3,4-tetrahydro-naphthalen-1-yl]-acetamide |
| 56 | S13  | A22   | A      | 595.1 | 2-[2-[(3-Chloro-4-methyl-phenyl)sulfonyl]-1,2,3,4-tetrahydro-pyrrolo[1,2-a]pyrazin-1-yl]-N-[6-(piperidin-1-yl-methyl)-1,2,3,4-tetrahydro-naphthalen-1-yl]-acetamide |

-continued

| | Acid | Amine | Method | M+ | |
|---|---|---|---|---|---|
| 57 | S13 | A23 | A | 597.3 | 2-[2-[(3-Chloro-4-methyl-phenyl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-1-yl]-acetamide |
| 58 | S11 | A29 | A | 521.3 | N-[6-(Dimethylaminomethyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide |
| 59 | S12 | A24 | A | 630.3 | N-[6-[(4-Methyl-piperazin-1-yl)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 60 | S13 | A31 | A | 583.4 | N-[6-[(tert-Butylamino)-methyl]-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide |
| 61 | S13 | A36 | A | 610.2 | 2-[2-[(3-Chloro-4-methyl-phenyl)sulfonyl]-1,2,3,4-tetrahydro-pyrrolo[1,2-a]pyrazin-1-yl]-N-[6-[(4-methyl-piperazin-1-yl)-methyl]-1,2,3,4-tetrahydro-naphthalen-2-yl]-acetamide |
| 62 | S11 | A30 | A | 549.3 | N-[6-[(1-Methyl-propylamino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide |
| 63 | S13 | A30 | A | 583.4 | 2-[2-[(3-Chloro-4-methyl-phenyl)sulfonyl]-1,2,3,4-tetrahydro-pyrrolo[1,2-a]pyrazin-1-yl]-N-[6-[(1-methyl-propylamino)-methyl]-1,2,3,4-tetrahydro-naphthalen-2-yl]-acetamide |
| 64 | S12 | A31 | A | 603.4 | N-[6-[(tert-Butylamino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 65 | S12 | A30 | A | 603.4 | N-[6-[(1-Methyl-propylamino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 66 | S13 | A35 | A | 597.4 | 2-[2-[(3-Chloro-4-methyl-phenyl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-2-yl]-acetamide |
| 67 | S12 | A35 | A | 617.3 | N-[6-(Morpholin-4-yl-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 68 | S12 | A36 | A | 630.5 | N-[6-[(4-Methyl-piperazin-1-yl)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 69 | S12 | A39 | A | 663.5 | N-[6-(1,2,3,4-Tetrahydro-quinolin-1-yl-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 70 | S13 | A19 | A | 583.4 | N-[6-[(tert-Butylamino)-methyl]-1,2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide |
| 71 | S13 | A37 | A | 621.4 | N-[6-(8-Azabicyclo[3.2.1]octan-8-yl-methyl)-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide |
| 72 | S11 | A19 | A | 549.4 | N-[6-[(tert-Butylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide |
| 73 | S11 | A32 | A | 563.3 | N-[6-[(tert-Butyl-methyl-amino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide |
| 74 | S11 | A20 | A | 563.4 | N-[6-[(tert-Butyl-methyl-amino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide |
| 75 | S13 | A32 | A | 597.3 | N-[6-[(tert-Butyl-methyl-amino)-methyl]-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide |
| 76 | S13 | A20 | A | 597.3 | N-[6-[(tert-Butyl-methyl-amino)-methyl]-1,2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide |

-continued

| | Acid | Amine | Method | M+ | |
|---|---|---|---|---|---|
| 77 | S11 | A37 | A | 587.5 | N-[6-(8-Azabicyclo[3.2.1]octan-8-yl-methyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide |
| 78 | S11 | A24 | A | 576.2 | N-[6-[(4-Methyl-piperazin-1-yl)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide |
| 79 | S11 | A39 | A | 609.2 | 2-[2-(p-Tolylsulfonyl)-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-2-yl]-acetamide |
| 80 | S11 | A22 | A | 561.4 | N-[6-(Piperidin-1-yl-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide |
| 81 | S11 | A36 | A | 576.2 | N-[6-[(4-Methyl-piperazin-1-yl)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide |
| 82 | S12 | A19 | A | 603.4 | N-[6-[(tert-Butylamino)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 83 | S12 | A38 | A | 637.4 | N-[6-[(Benzylamino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 84 | S12 | A33 | A | 601.4 | N-[6-(Pyrrolidin-1-yl-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 85 | S11 | A21 | A | 547.2 | 2-[2-(p-Tolylsulfonyl)-1,2,3,4-tetrahydro-pyrrolo[1,2-a]pyrazin-1-yl]-N-[6-(pyrrolidin-1-yl-methyl)-1,2,3,4-tetrahydro-naphthalen-1-yl]-acetamide |
| 86 | S12 | A21 | A | 601.2 | N-[6-(Pyrrolidin-1-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 87 | S11 | A35 | A | 563.2 | N-[6-(Morpholin-4-yl-methyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide |
| 88 | S12 | A37 | A | 641.2 | N-[6-(8-Azabicyclo[3.2.1]octan-8-yl-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 89 | S12 | A22 | A | 615.4 | N-[6-(Piperidin-1-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 90 | S12 | A27 | A | 663.4 | N-[6-(1,2,3,4-Tetrahydro-quinolin-1-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 91 | S13 | A21 | A | 581.2 | 2-[2-[(3-Chloro-4-methyl-phenyl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-1-yl]-acetamide |
| 92 | S12 | A29 | A | 575.2 | N-[6-(Dimethylaminomethyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 93 | S11 | A38 | A | 583.4 | N-[6-[(Benzylamino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide |
| 94 | S2 | A33 | A | 613.4 | 2-[2-[(6-Methoxy-naphthalen-2-yl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-2-yl]-acetamide |
| 95 | S2 | A25 | A | 653.4 | N-[6-(8-Azabicyclo[3.2.1]octan-8-yl-methyl)-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide |
| 96 | S2 | A29 | A | 587.5 | N-[6-(Dimethylaminomethyl)-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide |

-continued

| | Acid | Amine | Method | M+ | |
|---|---|---|---|---|---|
| 97 | S2 | A32 | A | 629.5 | N-[6-[(tert-Butyl-methyl-amino)-methyl]-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide |
| 98 | S2 | A21 | A | 613.3 | 2-[2-[(6-Methoxy-naphthalen-2-yl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-1-yl]-acetamide |
| 99 | S2 | A36 | A | 642.5 | 2-[2-[(6-Methoxy-naphthalen-2-yl)sulfonyl]-1,2,3,4-tetrahydro-pyrrolo[1,2-a]pyrazin-1-yl]-N-[6-[(4-methyl-piperazin-1-yl)-methyl]-1,2,3,4-tetrahydro-naphthalen-2-yl]-acetamide |
| 100 | S2 | A26 | A | 649.3 | N-[6-[(Benzylamino)-methyl]-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide |
| 101 | S2 | A38 | A | 649.3 | N-[6-[(Benzylamino)-methyl]-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide |
| 102 | S13 | A17 | A | 555.2 | 2-[2-[(3-Chloro-4-methyl-phenyl)sulfonyl]-1,2,3,4-tetrahydro-pyrrolo[1,2-a]pyrazin-1-yl]-N-[6-(dimethylaminomethyl)-1,2,3,4-tetrahydro-naphthalen-1-yl]-acetamide |
| 103 | S2 | A37 | A | 653.4 | N-[6-(8-Azabicyclo[3.2.1]octan-8-yl-methyl)-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide |
| 104 | S2 | A20 | A | 629.4 | N-[6-[(tert-Butyl-methyl-amino)-methyl]-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide |
| 105 | S2 | A39 | A | 675.4 | 2-[2-[(6-Methoxy-naphthalen-2-yl)sulfonyl]-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-2-yl]-acetamide |
| 106 | S2 | A17 | A | 587.4 | N-[6-(Dimethylaminomethyl)-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide |
| 107 | S11 | A17 | A | 521.4 | N-[6-(Dimethylaminomethyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide |
| 108 | S11 | A25 | A | 587.4 | N-[6-(8-Azabicyclo[3.2.1]octan-8-yl-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide |
| 109 | S12 | A25 | A | 641.4 | N-[6-(8-Azabicyclo[3.2.1]octan-8-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 110 | S13 | A25 | A | 621.4 | N-[6-(8-Azabicyclo[3.2.1]octan-8-yl-methyl)-1,2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide |
| 111 | S13 | A26 | A | 617.4 | N-[6-[(Benzylamino)-methyl]-1,2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide |
| 112 | S12 | A26 | A | 637.5 | N-[6-[(Benzylamino)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 113 | S12 | A20 | A | 617.3 | N-[6-[(tert-Butyl-methyl-amino)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 114 | S2 | A19 | A | 615.4 | N-[6-[(tert-Butylamino)-methyl]-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide |
| 115 | S13 | A29 | A | 555.2 | 2-[2-[(3-Chloro-4-methyl-phenyl)sulfonyl]-1,2,3,4-tetrahydro-pyrrolo[1,2-a]pyrazin-1-yl]-N-[6-(dimethylaminomethyl)-1,2,3,4-tetrahydro-naphthalen-2-yl]-acetamide |

-continued

| | Acid | Amine | Method | M+ | |
|---|---|---|---|---|---|
| 116 | S12 | A32 | A | 617.4 | N-[6-[(tert-Butyl-methyl-amino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 117 | S2 | A24 | A | 642.4 | 2-[2-[(6-Methoxy-naphthalen-2-yl)sulfonyl]-1,2,3,4-tetrahydro-pyrrolo[1,2-a]pyrazin-1-yl]-N-[6-[(4-methyl-piperazin-1-yl)-methyl]-1,2,3,4-tetrahydro-naphthalen-1-yl]-acetamide |
| 118 | S2 | A35 | A | 629.5 | 2-[2-[(6-Methoxy-naphthalen-2-yl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-2-yl]-acetamide |
| 119 | S13 | A27 | A | 643.3 | 2-[2-[(3-Chloro-4-methyl-phenyl)sulfonyl]-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-1-yl]-acetamide |
| 120 | S2 | A23 | A | 629.4 | 2-[2-[(6-Methoxy-naphthalen-2-yl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-1-yl]-acetamide |
| 121 | S2 | A30 | A | 615.3 | 2-[2-[(6-Methoxy-naphthalen-2-yl)sulfonyl]-1,2,3,4-tetrahydro-pyrrolo[1,2-a]pyrazin-1-yl]-N-[6-[(1-methyl-propylamino)-methyl]-1,2,3,4-tetrahydro-naphthalen-2-yl]-acetamide |
| 122 | S11 | A31 | A | 549.3 | N-[6-[(tert-Butylamino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide |
| 123 | S11 | A33 | A | 547.5 | 2-[2-(p-Tolylsulfonyl)-1,2,3,4-tetrahydro-pyrrolo[1,2-a]pyrazin-1-yl]-N-[6-(pyrrolidin-1-yl-methyl)-1,2,3,4-tetrahydro-naphthalen-2-yl]-acetamide |
| 124 | S12 | A17 | A | 575.2 | N-[6-(Dimethylaminomethyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 125 | S2 | A18 | A | 615.3 | 2-[2-[(6-Methoxy-naphthalen-2-yl)sulfonyl]-1,2,3,4-tetrahydro-pyrrolo[1,2-a]pyrazin-1-yl]-N-[6-[(1-methyl-propylamino)-methyl]-1,2,3,4-tetrahydro-naphthalen-1-yl]-acetamide |
| 126 | S11 | A18 | A | 549.4 | N-[6-[(1-Methyl-propylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide |
| 127 | S11 | A26 | A | 583.4 | N-[6-[(Benzylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide |
| 128 | S2 | A22 | A | 627.3 | 2-[2-[(6-Methoxy-naphthalen-2-yl)sulfonyl]-1,2,3,4-tetrahydro-pyrrolo[1,2-a]pyrazin-1-yl]-N-[6-(piperidin-1-yl-methyl)-1,2,3,4-tetrahydro-naphthalen-1-yl]-acetamide |
| 129 | S11 | A27 | A | 609.2 | 2-[2-(p-Tolylsulfonyl)-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-1-yl]-acetamide |
| 130 | S2 | A27 | A | 675.4 | 2-[2-[(6-Methoxy-naphthalen-2-yl)sulfonyl]-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-1-yl]-acetamide |
| 131 | S12 | A18 | A | 603.3 | N-[6-[(1-Methyl-propylamino)-methyl]-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |
| 132 | S13 | A18 | A | 583.2 | 2-[2-[(3-Chloro-4-methyl-phenyl)sulfonyl]-1,2,3,4-tetrahydro-pyrrolo[1,2-a]pyrazin-1-yl]-N-[6-[(1-methyl-propylamino)-methyl]-1,2,3,4-tetrahydro-naphthalen-1-yl]-acetamide |
| 133 | S11 | A16 | B | 507.4 | N-[6-(Methylamino-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide |
| 134 | S2 | A16 | B | 573.4 | 2-[2-[(6-Methoxy-naphthalen-2-yl)sulfonyl]-1,2,3,4-tetrahydro-pyrrolo[1,2-a]pyrazin-1-yl]-N-[6-(methylamino-methyl)-1,2,3,4-tetrahydro-naphthalen-1-yl]-acetamide |
| 135 | S12 | A16 | B | 561.2 | N-[6-(Methylamino-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide |

-continued

| | Acid | Amine | Method | M+ | |
|---|---|---|---|---|---|
| 136 | S13 | A16 | B | 541.4 | 2-[2-[(3-Chloro-4-methyl-phenyl)sulfonyl]-1,2,3,4-tetrahydro-pyrrolo[1,2-a]pyrazin-1-yl]-N-[6-(methylamino-methyl)-1,2,3,4-tetrahydro-naphthalen-1-yl]-acetamide |
| 137 | S2 | A28 | B | 573.4 | 2-[2-[(6-Methoxy-naphthalen-2-yl)sulfonyl]-1,2,3,4-tetrahydro-pyrrolo[1,2-a]pyrazin-1-yl]-N-[6-(methylamino-methyl)-1,2,3,4-tetrahydro-naphthalen-2-yl]-acetamide |
| 138 | S13 | A28 | B | 541.4 | 2-[2-[(3-Chloro-4-methyl-phenyl)sulfonyl]-1,2,3,4-tetrahydro-pyrrolo[1,2-a]pyrazin-1-yl]-N-[6-(methylamino-methyl)-1,2,3,4-tetrahydro-naphthalen-2-yl]-acetamide |
| 139 | S12 | A28 | B | 561.2 | N-[6-(Methylamino-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide |
| 140 | S11 | A28 | B | 507.4 | N-[6-(Methylamino-methyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide |
| 141 | S1 | A111 | C | 538.7 | 1-(4-Hydroxy-4-pyridin-3-yl-piperidin-1-yl)-2-[2-[(4-methoxy-2,6-dimethyl-phenyl)sulfonyl]-1,2,3,4-tetrahydro-pyrrolo[1,2-a]pyrazin-1-yl]ethanone |
| 142 | S1 | A66 | C | 504.6 | 2-[2-[(4-Methoxy-2,6-dimethyl-phenyl)sulfonyl]-1,2,3,4-tetrahydro-pyrrolo[1,2-a]pyrazin-1-yl]-N-(3-morpholin-4-yl-propyl)-acetamide |
| 143 | S1 | A58 | C | 530.7 | N-[3-(2,6-Dimethyl-piperidin-1-yl)-propyl]-2-[2-[(4-methoxy-2,6-dimethyl-phenyl)sulfonyl]-1,2,3,4-tetrahydro-pyrrolo[1,2-a]pyrazin-1-yl]-acetamide |
| 144 | S1 | A63 | C | 540.7 | 1-[4-(2-Fluorophenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 145 | S1 | A81 | C | 522.7 | 2-[2-[(4-Methoxy-2,6-dimethyl-phenyl)sulfonyl]-1,2,3,4-tetrahydro-pyrrolo[1,2-a]pyrazin-1-yl]-1-(4-phenyl-piperazin-1-yl)-ethanone |
| 146 | S1 | A116 | C | 556.8 | 2-[2-[(4-Methoxy-2,6-dimethyl-phenyl)sulfonyl]-1,2,3,4-tetrahydro-pyrrolo[1,2-a]pyrazin-1-yl]-1-[4-(2-piperidin-1-yl-ethyl)-piperidin-1-yl]-ethanone |
| 147 | S1 | A117 | C | 567.8 | 1-[4-[2-(2,5-Dimethyl-1H-pyrrol-1-yl)-ethyl]-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 148 | S1 | A62 | C | 575.7 | 2-[2-[(4-Methoxy-2,6-dimethyl-phenyl)sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone |
| 149 | S1 | A64 | C | 523.7 | 2-[2-[(4-Methoxy-2,6-dimethyl-phenyl)sulfonyl]-1,2,3,4-tetrahydro-pyrrolo[1,2-a]pyrazin-1-yl]-1-(4-pyridin-2-yl-piperazin-1-yl)-ethanone |
| 150 | S1 | A57 | C | 562.7 | 2-[4-[2-[2-[(4-Methoxy-2,6-dimethyl-phenyl)sulfonyl]-1,2,3,4-tetrahydro-pyrrolo[1,2-a]pyrazin-1-yl]-acetyl]-[1,4]diazepan-1-yl]-pyridine-3-carbonitrile |
| 151 | S1 | A60 | C | 550.7 | N-[(1-Benzyl-pyrrolidin-3-yl)-methyl]-2-[2-[(4-methoxy-2,6-dimethyl-phenyl)sulfonyl]-1,2,3,4-tetrahydro-pyrrolo[1,2-a]pyrazin-1-yl]-acetamide |
| 152 | S1 | A91 | C | 591.7 | 2-[2-[(4-Methoxy-2,6-dimethyl-phenyl)sulfonyl]-1,2,3,4-tetrahydro-pyrrolo[1,2-a]pyrazin-1-yl]-1-[4-[5-(trifluoromethyl)-pyridin-2-yl]-piperazin-1-yl]-ethanone |
| 153 | S14 | A65 | C | 465.0 | 2-[2-[(2-Chloro-6-methyl-phenyl)sulfonyl]-1,2,3,4-tetrahydro-pyrrolo[1,2-a]pyrazin-1-yl]-N-(2-pyrrolidin-1-yl-ethyl)-acetamide |
| 154 | S14 | A66 | C | 495.0 | 2-[2-[(2-Chloro-6-methyl-phenyl)sulfonyl]-1,2,3,4-tetrahydro-pyrrolo[1,2-a]pyrazin-1-yl]-N-(3-morpholin-4-yl-propyl)-acetamide |
| 155 | S14 | A58 | C | 521.1 | 2-[2-[(2-Chloro-6-methyl-phenyl)sulfonyl]-1,2,3,4-tetrahydro-pyrrolo[1,2-a]pyrazin-1-yl]-N-[3-(2,6-dimethyl-piperidin-1-yl)-propyl]-acetamide |
| 156 | S14 | A59 | C | 570.2 | 2-[2-[(2-Chloro-6-methyl-phenyl)sulfonyl]-1,2,3,4-tetrahydro-pyrrolo[1,2-a]pyrazin-1-yl]-N-[2-(4-methyl-piperazin-1-yl)-1-phenyl-ethyl]-acetamide |
| 157 | S14 | A73 | C | 527.1 | N-(1-Benzyl-pyrrolidin-3-yl)-2-[2-[(2-chloro-6-methyl-phenyl)sulfonyl]-1,2,3,4-tetrahydro-pyrrolo[1,2-a]pyrazin-1-yl]-acetamide |
| 158 | S14 | A63 | C | 531.0 | 2-[2-[(2-Chloro-6-methyl-phenyl)sulfonyl]-1,2,3,4-tetrahydro-pyrrolo[1,2-a]pyrazin-1-yl]-1-[4-(2-fluorophenyl)-piperazin-1-yl]-ethanone |

-continued

| | Acid | Amine | Method | M+ | |
|---|---|---|---|---|---|
| 159 | S14 | A86 | C | 521.1 | 2-[2-[(2-Chloro-6-methyl-phenyl)sulfonyl]-1,2,3,4-tetrahydro-pyrrolo[1,2-a]pyrazin-1-yl]-1-(4-morpholin-4-yl-piperidin-1-yl)-ethanone |
| 160 | S14 | A87 | C | 519.1 | 2-[2-[(2-Chloro-6-methyl-phenyl)sulfonyl]-1,2,3,4-tetrahydro-pyrrolo[1,2-a]pyrazin-1-yl]-1-(4-piperidin-1-yl-piperidin-1-yl)-ethanone |
| 161 | S14 | A114 | C | 534.1 | 2-[2-[(2-Chloro-6-methyl-phenyl)sulfonyl]-1,2,3,4-tetrahydro-pyrrolo[1,2-a]pyrazin-1-yl]-1-[4-(4-methyl-piperazin-1-yl)-piperidin-1-yl]-ethanone |
| 162 | S14 | A83 | C | 515.0 | 2-[2-[(2-Chloro-6-methyl-phenyl)sulfonyl]-1,2,3,4-tetrahydro-pyrrolo[1,2-a]pyrazin-1-yl]-1-(4-pyrimidin-2-yl-piperazin-1-yl)-ethanone |
| 163 | S14 | A62 | C | 566.1 | 2-[2-[(2-Chloro-6-methyl-phenyl)sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone |
| 164 | S14 | A57 | C | 553.1 | 2-[4-[2-[2-[(2-Chloro-6-methyl-phenyl)sulfonyl]-1,2,3,4-tetrahydro-pyrrolo[1,2-a]pyrazin-1-yl]-acetyl]-[1,4]diazepan-1-yl]-pyridine-3-carbonitrile |
| 165 | S14 | A116 | C | 547.2 | 2-[2-[(2-Chloro-6-methyl-phenyl)sulfonyl]-1,2,3,4-tetrahydro-pyrrolo[1,2-a]pyrazin-1-yl]-1-[4-(2-piperidin-1-yl-ethyl)-piperidin-1-yl]-ethanone |
| 166 | S14 | A60 | C | 541.1 | N-[(1-Benzyl-pyrrolidin-3-yl)-methyl]-2-[2-[(2-chloro-6-methyl-phenyl)sulfonyl]-1,2,3,4-tetrahydro-pyrrolo[1,2-a]pyrazin-1-yl]-acetamide |
| 167 | S9 | A111 | C | 480.6 | 2-[2-(Benzenesulfonyl)-1,2,3,4-tetrahydro-pyrrolo[1,2-a]pyrazin-1-yl]-1-(4-hydroxy-4-pyridin-3-yl-piperidin-1-yl)-ethanone |
| 168 | S9 | A65 | C | 416.5 | 2-[2-(Benzenesulfonyl)-1,2,3,4-tetrahydro-pyrrolo[1,2-a]pyrazin-1-yl]-N-(2-pyrrolidin-1-yl-ethyl)-acetamide |
| 169 | S9 | A58 | C | 472.7 | 2-[2-(Benzenesulfonyl)-1,2,3,4-tetrahydro-pyrrolo[1,2-a]pyrazin-1-yl]-N-[3-(2,6-dimethyl-piperidin-1-yl)-propyl]-acetamide |
| 170 | S9 | A59 | C | 521.7 | 2-[2-(Benzenesulfonyl)-1,2,3,4-tetrahydro-pyrrolo[1,2-a]pyrazin-1-yl]-N-[2-(4-methyl-piperazin-1-yl)-1-phenyl-ethyl]-acetamide |
| 171 | S9 | A74 | C | 478.6 | 2-[2-(Benzenesulfonyl)-1,2,3,4-tetrahydro-pyrrolo[1,2-a]pyrazin-1-yl]-N-(1-benzyl-pyrrolidin-3-yl)-acetamide |
| 172 | S9 | A63 | C | 482.6 | 2-[2-(Benzenesulfonyl)-1,2,3,4-tetrahydro-pyrrolo[1,2-a]pyrazin-1-yl]-1-[4-(2-fluorophenyl)-piperazin-1-yl]-ethanone |
| 173 | S9 | A79 | C | 416.5 | 2-[2-(Benzenesulfonyl)-1,2,3,4-tetrahydro-pyrrolo[1,2-a]pyrazin-1-yl]-1-(4-ethyl-piperazin-1-yl)-ethanone |
| 174 | S9 | A81 | C | 464.6 | 2-[2-(Benzenesulfonyl)-1,2,3,4-tetrahydro-pyrrolo[1,2-a]pyrazin-1-yl]-1-(4-phenyl-piperazin-1-yl)-ethanone |
| 175 | S9 | A84 | C | 456.6 | 2-[2-(Benzenesulfonyl)-1,2,3,4-tetrahydro-pyrrolo[1,2-a]pyrazin-1-yl]-1-(4-pyrrolidin-1-yl-piperidin-1-yl)-ethanone |
| 176 | S9 | A86 | C | 472.6 | 2-[2-(Benzenesulfonyl)-1,2,3,4-tetrahydro-pyrrolo[1,2-a]pyrazin-1-yl]-1-(4-morpholin-4-yl-piperidin-1-yl)-ethanone |
| 177 | S9 | A114 | C | 485.7 | 2-[2-(Benzenesulfonyl)-1,2,3,4-tetrahydro-pyrrolo[1,2-a]pyrazin-1-yl]-1-[4-(4-methyl-piperazin-1-yl)-piperidin-1-yl]-ethanone |
| 178 | S9 | A117 | C | 509.7 | 2-[2-(Benzenesulfonyl)-1,2,3,4-tetrahydro-pyrrolo[1,2-a]pyrazin-1-yl]-1-[4-[2-(2,5-dimethyl-1H-pyrrol-1-yl)-ethyl]-piperazin-1-yl]-ethanone |
| 179 | S9 | A83 | C | 466.6 | 2-[2-(Benzenesulfonyl)-1,2,3,4-tetrahydro-pyrrolo[1,2-a]pyrazin-1-yl]-1-(4-pyrimidin-2-yl-piperazin-1-yl)-ethanone |
| 180 | S9 | A62 | C | 517.7 | 2-[2-(Benzenesulfonyl)-1,2,3,4-tetrahydro-pyrrolo[1,2-a]pyrazin-1-yl]-1-[4-(5-methyl-1H-benzoimidazol-2-yl)-piperidin-1-yl]-ethanone |
| 181 | S9 | A57 | C | 504.6 | 2-[4-[2-[2-(Benzenesulfonyl)-1,2,3,4-tetrahydro-pyrrolo[1,2-a]pyrazin-1-yl-acetyl]-[1,4]diazepan-1-yl]-pyridine-3-carbonitrile |
| 182 | S9 | A60 | C | 492.6 | 2-[2-(Benzenesulfonyl)-1,2,3,4-tetrahydro-pyrrolo[1,2-a]pyrazin-1-yl]-N-[(1-benzyl-pyrrolidin-3-yl)-methyl]-acetamide |
| 183 | S9 | A91 | C | 533.6 | 2-[2-(Benzenesulfonyl)-1,2,3,4-tetrahydro-pyrrolo[1,2-a]pyrazin-1-yl]-1-[4-[5-(trifluoromethyl)-pyridin-2-yl]-piperazin-1-yl]-ethanone |
| 184 | S12 | A58 | C | 540.6 | N-[3-(2,6-Dimethyl-piperidin-1-yl)-propyl]-2-[2-[[3-(trifluoromethyl)phenyl]sulfonyl]-1,2,3,4-tetrahydro-pyrrolo[1,2-a]pyrazin-1-yl]-acetamide |

-continued

| | Acid | Amine | Method | M+ | |
|---|---|---|---|---|---|
| 185 | S12 | A59 | C | 589.7 | N-[2-(4-Methyl-piperazin-1-yl)-1-phenyl-ethyl]-2-[2-[[3-(trifluoromethyl)phenyl]sulfonyl]-1,2,3,4-tetrahydro-pyrrolo[1,2-a]pyrazin-1-yl]-acetamide |
| 186 | S12 | A63 | C | 550.6 | 1-[4-(2-Fluorophenyl)-piperazin-1-yl]-2-[2-[[3-(trifluoromethyl)phenyl]sulfonyl]-1,2,3,4-tetrahydro-pyrrolo[1,2-a]pyrazin-1-yl]-ethanone |
| 187 | S12 | A79 | C | 484.5 | 1-(4-Ethyl-piperazin-1-yl)-2-[2-[[3-(trifluoromethyl)phenyl]sulfonyl]-1,2,3,4-tetrahydro-pyrrolo[1,2-a]pyrazin-1-yl]-ethanone |
| 188 | S12 | A87 | C | 538.6 | 1-(4-Piperidin-1-yl-piperidin-1-yl)-2-[2-[[3-(trifluoromethyl)phenyl]sulfonyl]-1,2,3,4-tetrahydro-pyrrolo[1,2-a]pyrazin-1-yl]-ethanone |
| 189 | S12 | A62 | C | 585.6 | 1-[4-(5-Methyl-1H-benzoimidazol-2-yl)-piperidin-1-yl]-2-[2-[[3-(trifluoromethyl)phenyl]sulfonyl]-1,2,3,4-tetrahydro-pyrrolo[1,2-a]pyrazin-1-yl]-ethanone |
| 190 | S12 | A64 | C | 533.6 | 1-(4-Pyridin-2-yl-piperazin-1-yl)-2-[2-[[3-(trifluoromethyl)phenyl]sulfonyl]-1,2,3,4-tetrahydro-pyrrolo[1,2-a]pyrazin-1-yl]-ethanone |
| 191 | S12 | A57 | C | 572.6 | 2-[4-[2-[2-[[3-(Trifluoromethyl)phenyl]sulfonyl]-1,2,3,4-tetrahydro-pyrrolo[1,2-a]pyrazin-1-yl]-acetyl]-[1,4]diazepan-1-yl]-pyridine-3-carbonitrile |
| 192 | S12 | A60 | C | 560.6 | N-[(1-Benzyl-pyrrolidin-3-yl)-methyl]-2-[2-[[3-(trifluoromethyl)phenyl]sulfonyl]-1,2,3,4-tetrahydro-pyrrolo[1,2-a]pyrazin-1-yl]-acetamide |
| 193 | S7 | A58 | C | 535.2 | 2-[2-[(4-Chloro-2,5-dimethyl-phenyl)sulfonyl]-1,2,3,4-tetrahydro-pyrrolo[1,2-a]pyrazin-1-yl]-N-[3-(2,6-dimethyl-piperidin-1-yl)-propyl]-acetamide |
| 194 | S7 | A59 | C | 584.2 | 2-[2-[(4-Chloro-2,5-dimethyl-phenyl)sulfonyl]-1,2,3,4-tetrahydro-pyrrolo[1,2-a]pyrazin-1-yl]-N-[2-(4-methyl-piperazin-1-yl)-1-phenyl-ethyl]-acetamide |
| 195 | S7 | A63 | C | 545.1 | 2-[2-[(4-Chloro-2,5-dimethyl-phenyl)sulfonyl]-1,2,3,4-tetrahydro-pyrrolo[1,2-a]pyrazin-1-yl]-1-[4-(2-fluorophenyl)-piperazin-1-yl]-ethanone |
| 196 | S7 | A62 | C | 580.2 | 2-[2-[(4-Chloro-2,5-dimethyl-phenyl)sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone |
| 197 | S7 | A57 | C | 567.1 | 2-[4-[2-[2-[(4-Chloro-2,5-dimethyl-phenyl)sulfonyl]-1,2,3,4-tetrahydro-pyrrolo[1,2-a]pyrazin-1-yl-acetyl]-[1,4]diazepan-1-yl]-pyridine-3-carbonitrile |
| 198 | S7 | A60 | C | 555.1 | N-[(1-Benzyl-pyrrolidin-3-yl)-methyl]-2-[2-[(4-chloro-2,5-dimethyl-phenyl)sulfonyl]-1,2,3,4-tetrahydro-pyrrolo[1,2-a]pyrazin-1-yl]-acetamide |
| 199 | S6 | A58 | C | 575.1 | 2-[2-[[2-Chloro-4-(trifluoromethyl)-phenyl]sulfonyl]-1,2,3,4-tetrahydro-pyrrolo[1,2-a]pyrazin-1-yl]-N-[3-(2,6-dimethyl-piperidin-1-yl)-propyl]-acetamide |
| 200 | S6 | A59 | C | 624.1 | 2-[2-[[2-Chloro-4-(trifluoromethyl)-phenyl]sulfonyl]-1,2,3,4-tetrahydro-pyrrolo[1,2-a]pyrazin-1-yl]-N-[2-(4-methyl-piperazin-1-yl)-1-phenyl-ethyl]-acetamide |
| 201 | S6 | A63 | C | 585.0 | 2-[2-[[2-Chloro-4-(trifluoromethyl)-phenyl]sulfonyl]-1,2,3,4-tetrahydro-pyrrolo[1,2-a]pyrazin-1-yl]-1-[4-(2-fluorophenyl)-piperazin-1-yl]-ethanone |
| 202 | S6 | A62 | C | 620.1 | 2-[2-[[2-Chloro-4-(trifluoromethyl)-phenyl]sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone |
| 203 | S6 | A64 | C | 568.0 | 2-[2-[[2-Chloro-4-(trifluoromethyl)-phenyl]sulfonyl]-1,2,3,4-tetrahydro-pyrrolo[1,2-a]pyrazin-1-yl]-1-(4-pyridin-2-yl-piperazin-1-yl)-ethanone |
| 204 | S6 | A57 | C | 607.1 | 2-[4-[2-[2-[[2-Chloro-4-(trifluoromethyl)-phenyl]sulfonyl]-1,2,3,4-tetrahydro-pyrrolo[1,2-a]pyrazin-1-yl]-acetyl]-[1,4]diazepan-1-yl]-pyridine-3-carbonitrile |
| 205 | S6 | A60 | C | 595.1 | N-[(1-Benzyl-pyrrolidin-3-yl)-methyl]-2-[2-[[2-chloro-4-(trifluoromethyl)-phenyl]-sulfonyl]-1,2,3,4-tetrahydro-pyrrolo[1,2-a]pyrazin-1-yl]-acetamide |
| 206 | S1 | A94 | C | 522.7 | 2-[2-[(4-Methoxy-2,6-dimethyl-phenyl)sulfonyl]-1,2,3,4-tetrahydro-pyrrolo[1,2-a]pyrazin-1-yl]-1-[2-(pyridin-2-yl-methyl)-pyrrolidin-1-yl]-ethanone |
| 207 | S1 | A68 | C | 502.7 | 2-[2-[(4-Methoxy-2,6-dimethyl-phenyl)sulfonyl]-1,2,3,4-tetrahydro-pyrrolo[1,2-a]pyrazin-1-yl]-N-(3-piperidin-1-yl-propyl)-acetamide |
| 208 | S1 | A89 | C | 571.1 | 1-[4-(5-Chloro-2-methyl-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 209 | S1 | A97 | C | 572.1 | 1-[4-(4-Chlorophenyl)-4-hydroxy-piperidin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |

|   | Acid | Amine | Method | M+ |   |
|---|---|---|---|---|---|
| 210 | S1 | A99 | C | 551.7 | 1-(4-Benzyl-4-hydroxy-piperidin-1-yl)-2-[2-[(4-methoxy-2,6-dimethyl-phenyl)sulfonyl]-1,2,3,4-tetrahydro-pyrrolo[1,2-a]pyrazin-1-yl]-ethanone |
| 211 | S1 | A100 | C | 605.7 | 1-[4-Hydroxy-4-[3-(trifluoromethyl)phenyl]-piperidin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 212 | S1 | A115 | C | 502.7 | 2-[2-[(4-Methoxy-2,6-dimethyl-phenyl)sulfonyl]-1,2,3,4-tetrahydro-pyrrolo[1,2-a]pyrazin-1-yl]-N-methyl-N-(2-piperidin-1-yl-ethyl)-acetamide |
| 213 | S1 | A70 | C | 528.7 | 2-[2-[(4-Methoxy-2,6-dimethyl-phenyl)sulfonyl]-1,2,3,4-tetrahydro-pyrrolo[1,2-a]pyrazin-1-yl]-1-[2-(piperidin-1-yl-methyl)-pyrrolidin-1-yl]-ethanone |
| 214 | S1 | A76 | C | 552.7 | 2-[2-[(4-Methoxy-2,6-dimethyl-phenyl)sulfonyl]-1,2,3,4-tetrahydro-pyrrolo[1,2-a]pyrazin-1-yl]-1-[4-(3-methoxyphenyl)-piperazin-1-yl]-ethanone |
| 215 | S1 | A77 | C | 540.7 | 1-[4-(4-Fluorophenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 216 | S1 | A80 | C | 488.7 | 1-(4-Isopropyl-piperazin-1-yl)-2-[2-[(4-methoxy-2,6-dimethyl-phenyl)sulfonyl]-1,2,3,4-tetrahydro-pyrrolo[1,2-a]pyrazin-1-yl]-ethanone |
| 217 | S14 | A94 | C | 513.1 | 2-[2-[(2-Chloro-6-methyl-phenyl)sulfonyl]-1,2,3,4-tetrahydro-pyrrolo[1,2-a]pyrazin-1-yl]-1-[2-(pyridin-2-yl-methyl)-pyrrolidin-1-yl]-ethanone |
| 218 | S14 | A68 | C | 493.1 | 2-[2-[(2-Chloro-6-methyl-phenyl)sulfonyl]-1,2,3,4-tetrahydro-pyrrolo[1,2-a]pyrazin-1-yl]-N-(3-piperidin-1-yl-propyl)-acetamide |
| 219 | S14 | A98 | C | 528.1 | 2-[2-[(2-Chloro-6-methyl-phenyl)sulfonyl]-1,2,3,4-tetrahydro-pyrrolo[1,2-a]pyrazin-1-yl]-1-(4-hydroxy-4-phenyl-piperidin-1-yl)-ethanone |
| 220 | S14 | A100 | C | 596.1 | 2-[2-[(2-Chloro-6-methyl-phenyl)sulfonyl]-1,2,3,4-tetrahydro-pyrrolo[1,2-a]pyrazin-1-yl]-1-[4-hydroxy-4-[3-(trifluoromethyl)phenyl]-piperidin-1-yl]-ethanone |
| 221 | S14 | A113 | C | 584.2 | 2-[2-[(2-Chloro-6-methyl-phenyl)sulfonyl]-1,2,3,4-tetrahydro-pyrrolo[1,2-a]pyrazin-1-yl]-N-methyl-N-[2-(4-methyl-piperazin-1-yl)-1-phenyl-ethyl]-acetamide |
| 222 | S14 | A115 | C | 493.1 | 2-[2-[(2-Chloro-6-methyl-phenyl)sulfonyl]-1,2,3,4-tetrahydro-pyrrolo[1,2-a]pyrazin-1-yl]-N-methyl-N-(2-piperidin-1-yl-ethyl)-acetamide |
| 223 | S14 | A76 | C | 543.1 | 2-[2-[(2-Chloro-6-methyl-phenyl)sulfonyl]-1,2,3,4-tetrahydro-pyrrolo[1,2-a]pyrazin-1-yl]-1-[4-(3-methoxyphenyl)-piperazin-1-yl]-ethanone |
| 224 | S14 | A77 | C | 531.0 | 2-[2-[(2-Chloro-6-methyl-phenyl)sulfonyl]-1,2,3,4-tetrahydro-pyrrolo[1,2-a]pyrazin-1-yl]-1-[4-(4-fluorophenyl)-piperazin-1-yl]-ethanone |
| 225 | S14 | A80 | C | 479.0 | 2-[2-[(2-Chloro-6-methyl-phenyl)sulfonyl]-1,2,3,4-tetrahydro-pyrrolo[1,2-a]pyrazin-1-yl]-1-(4-isopropyl-piperazin-1-yl)-ethanone |
| 226 | S9 | A89 | C | 513.1 | 2-[2-(Benzenesulfonyl)-1,2,3,4-tetrahydro-pyrrolo[1,2-a]pyrazin-1-yl]-1-[4-(5-chloro-2-methyl-phenyl)-piperazin-1-yl]-ethanone |
| 227 | S9 | A97 | C | 514.0 | 2-[2-(Benzenesulfonyl)-1,2,3,4-tetrahydro-pyrrolo[1,2-a]pyrazin-1-yl]-1-[4-(4-chlorophenyl)-4-hydroxy-piperidin-1-yl]-ethanone |
| 228 | S9 | A98 | C | 479.6 | 2-[2-(Benzenesulfonyl)-1,2,3,4-tetrahydro-pyrrolo[1,2-a]pyrazin-1-yl]-1-(4-hydroxy-4-phenyl-piperidin-1-yl)-ethanone |
| 229 | S9 | A78 | C | 494.6 | 2-[2-(Benzenesulfonyl)-1,2,3,4-tetrahydro-pyrrolo[1,2-a]pyrazin-1-yl]-1-[4-(4-methoxyphenyl)-piperazin-1-yl]-ethanone |
| 230 | S7 | A113 | C | 598.2 | 2-[2-[(4-Chloro-2,5-dimethyl-phenyl)sulfonyl]-1,2,3,4-tetrahydro-pyrrolo[1,2-a]pyrazin-1-yl]-N-methyl-N-[2-(4-methyl-piperazin-1-yl)-1-phenyl-ethyl]-acetamide |
| 231 | S9 | A102 | C | 533.5 | 2-[2-(Benzenesulfonyl)-1,2,3,4-tetrahydro-pyrrolo[1,2-a]pyrazin-1-yl]-1-[4-(3,4-dichlorophenyl)-piperazin-1-yl]-ethanone |
| 232 | S9 | A106 | C | 492.6 | 2-[2-(Benzenesulfonyl)-1,2,3,4-tetrahydro-pyrrolo[1,2-a]pyrazin-1-yl]-1-[4-(p-tolyl-methyl)-piperazin-1-yl]-ethanone |
| 233 | S9 | A107 | C | 508.6 | 2-[2-(Benzenesulfonyl)-1,2,3,4-tetrahydro-pyrrolo[1,2-a]pyrazin-1-yl]-1-[4-[(4-methoxyphenyl)-methyl]-piperazin-1-yl]-ethanone |
| 234 | S9 | A108 | C | 496.6 | 2-[2-(Benzenesulfonyl)-1,2,3,4-tetrahydro-pyrrolo[1,2-a]pyrazin-1-yl]-1-[4-[(2-fluorophenyl)-methyl]-piperazin-1-yl]-ethanone |

| | Acid | Amine | Method | M+ | |
|---|---|---|---|---|---|
| 235 | S9 | A61 | C | 506.7 | 2-[2-(Benzenesulfonyl)-1,2,3,4-tetrahydro-pyrrolo[1,2-a]pyrazin-1-yl]-N-[(1-benzyl-piperidin-3-yl)-methyl]-acetamide |
| 236 | S12 | A104 | C | 588.7 | 2-[2-[[3-(Trifluoromethyl)phenyl]sulfonyl]-1,2,3,4-tetrahydro-pyrrolo[1,2-a]pyrazin-1-yl]-1-[4-[(2,4,6-trimethyl-phenyl)-methyl]-piperazin-1-yl]-ethanone |
| 237 | S6 | A78 | C | 597.1 | 2-[2-[[2-Chloro-4-(trifluoromethyl)-phenyl]sulfonyl]-1,2,3,4-tetrahydro-pyrrolo[1,2-a]pyrazin-1-yl]-1-[4-(4-methoxyphenyl)-piperazin-1-yl]-ethanone |
| 238 | S1 | A102 | C | 591.6 | 1-[4-(3,4-Dichlorophenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 239 | S1 | A104 | C | 578.8 | 2-[2-[(4-Methoxy-2,6-dimethyl-phenyl)sulfonyl]-1,2,3,4-tetrahydro-pyrrolo[1,2-a]pyrazin-1-yl]-1-[4-[(2,4,6-trimethyl-phenyl)-methyl]-piperazin-1-yl]-ethanone |
| 240 | S1 | A105 | C | 571.1 | 1-[4-[(4-Chlorophenyl)-methyl]-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 241 | S1 | A106 | C | 550.7 | 2-[2-[(4-Methoxy-2,6-dimethyl-phenyl)sulfonyl]-1,2,3,4-tetrahydro-pyrrolo[1,2-a]pyrazin-1-yl]-1-[4-(p-tolyl-methyl)-piperazin-1-yl]-ethanone |
| 242 | S1 | A107 | C | 566.7 | 2-[2-[(4-Methoxy-2,6-dimethyl-phenyl)sulfonyl]-1,2,3,4-tetrahydro-pyrrolo[1,2-a]pyrazin-1-yl]-1-[4-[(4-methoxyphenyl)-methyl]-piperazin-1-yl]-ethanone |
| 243 | S1 | A108 | C | 554.7 | 1-[4-[(2-Fluorophenyl)-methyl]-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 244 | S1 | A95 | C | 536.7 | 2-[2-[(4-Methoxy-2,6-dimethyl-phenyl)sulfonyl]-1,2,3,4-tetrahydro-pyrrolo[1,2-a]pyrazin-1-yl]-1-[2-(pyridin-2-yl-methyl)-piperidin-1-yl]-ethanone |
| 245 | S1 | A96 | C | 536.7 | 2-[2-[(4-Methoxy-2,6-dimethyl-phenyl)sulfonyl]-1,2,3,4-tetrahydro-pyrrolo[1,2-a]pyrazin-1-yl]-1-[2-(pyridin-4-yl-methyl)-piperidin-1-yl]-ethanone |
| 246 | S1 | A82 | C | 580.7 | 1-[4-(1,3-Benzodioxol-5-yl-methyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 247 | S1 | A67 | C | 499.6 | 3-[4-[2-[2-[(4-Methoxy-2,6-dimethyl-phenyl)sulfonyl]-1,2,3,4-tetrahydro-pyrrolo[1,2-a]pyrazin-1-yl]-acetyl]-piperazin-1-yl]-propionitrile |
| 248 | S1 | A61 | C | 564.7 | N-[(1-Benzyl-piperidin-3-yl)-methyl]-2-[2-[(4-methoxy-2,6-dimethyl-phenyl)sulfonyl]-1,2,3,4-tetrahydro-pyrrolo[1,2-a]pyrazin-1-yl]-acetamide |
| 249 | S14 | A105 | C | 561.5 | 2-[2-[(2-Chloro-6-methyl-phenyl)sulfonyl]-1,2,3,4-tetrahydro-pyrrolo[1,2-a]pyrazin-1-yl]-1-[4-[(4-chlorophenyl)-methyl]-piperazin-1-yl]-ethanone |
| 250 | S14 | A95 | C | 527.1 | 2-[2-[(2-Chloro-6-methyl-phenyl)sulfonyl]-1,2,3,4-tetrahydro-pyrrolo[1,2-a]pyrazin-1-yl]-1-[2-(pyridin-2-yl-methyl)-piperidin-1-yl]-ethanone |
| 251 | S14 | A96 | C | 527.1 | 2-[2-[(2-Chloro-6-methyl-phenyl)sulfonyl]-1,2,3,4-tetrahydro-pyrrolo[1,2-a]pyrazin-1-yl]-1-[2-(pyridin-4-yl-methyl)-piperidin-1-yl]-ethanone |
| 252 | S14 | A82 | C | 571.1 | 1-[4-(1,3-Benzodioxol-5-yl-methyl)-piperazin-1-yl]-2-[2-[(2-chloro-6-methyl-phenyl)sulfonyl]-1,2,3,4-tetrahydro-pyrrolo[1,2-a]pyrazin-1-yl]-ethanone |
| 253 | S14 | A67 | C | 490.0 | 3-[4-[2-[2-[(2-Chloro-6-methyl-phenyl)sulfonyl]-1,2,3,4-tetrahydro-pyrrolo[1,2-a]pyrazin-1-yl-acetyl]-piperazin-1-yl]-propionitrile |
| 254 | S6 | A61 | C | 609.1 | N-[(1-Benzyl-piperidin-3-yl)-methyl]-2-[2-[[2-chloro-4-(trifluoromethyl)-phenyl]sulfonyl]-1,2,3,4-tetrahydro-pyrrolo[1,2-a]pyrazin-1-yl]-acetamide |
| 255 | S1 | A71 | C | 578.8 | 1-[2-(4-Dimethylaminophenyl)-azepan-1-yl]-2-[2-[(4-methoxy-2,6-dimethyl-phenyl)sulfonyl]-1,2,3,4-tetrahydro-pyrrolo[1,2-a]pyrazin-1-yl]-ethanone |
| 256 | S1 | A75 | C | 580.7 | 2-[2-[(4-Methoxy-2,6-dimethyl-phenyl)sulfonyl]-1,2,3,4-tetrahydro-pyrrolo[1,2-a]pyrazin-1-yl]-N-methyl-N-(2-morpholin-4-yl-1-phenyl-ethyl)-acetamide |
| 257 | S1 | A85 | C | 535.7 | 1-(4-Benzyl-piperidin-1-yl)-2-[2-[(4-methoxy-2,6-dimethyl-phenyl)sulfonyl]-1,2,3,4-tetrahydro-pyrrolo[1,2-a]pyrazin-1-yl]-ethanone |
| 258 | S1 | A101 | C | 490.6 | 1-[4-(2-Hydroxy-ethyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone |

-continued

| | Acid | Amine | Method | M+ | |
|---|---|---|---|---|---|
| 259 | S14 | A75 | C | 571.1 | 2-[2-[(2-Chloro-6-methyl-phenyl)sulfonyl]-1,2,3,4-tetrahydro-pyrrolo[1,2-a]pyrazin-1-yl]-N-methyl-N-(2-morpholin-4-yl-1-phenyl-ethyl)-acetamide |
| 260 | S14 | A88 | C | 505.1 | 2-[2-[(2-Chloro-6-methyl-phenyl)sulfonyl]-1,2,3,4-tetrahydro-pyrrolo[1,2-a]pyrazin-1-yl]-1-[(2S)-2-(pyrrolidin-1-yl-methyl)-pyrrolidin-1-yl]-ethanone |
| 261 | S14 | A90 | C | 539.1 | 2-[4-[2-[2-[(2-Chloro-6-methyl-phenyl)sulfonyl]-1,2,3,4-tetrahydro-pyrrolo[1,2-a]pyrazin-1-yl]-acetyl]-piperazin-1-yl]-pyridine-3-carbonitrile |
| 262 | S14 | A92 | C | 616.5 | 2-[2-[(2-Chloro-6-methyl-phenyl)sulfonyl]-1,2,3,4-tetrahydro-pyrrolo[1,2-a]pyrazin-1-yl]-1-[4-[3-chloro-5-(trifluoromethyl)-pyridin-2-yl]-piperazin-1-yl]-ethanone |
| 263 | S14 | A101 | C | 481.0 | 2-[2-[(2-Chloro-6-methyl-phenyl)sulfonyl]-1,2,3,4-tetrahydro-pyrrolo[1,2-a]pyrazin-1-yl]-1-[4-(2-hydroxy-ethyl)-piperazin-1-yl]-ethanone |
| 264 | S9 | A88 | C | 456.6 | 2-[2-(Benzenesulfonyl)-1,2,3,4-tetrahydro-pyrrolo[1,2-a]pyrazin-1-yl]-1-[(2S)-2-(pyrrolidin-1-yl-methyl)-pyrrolidin-1-yl]-ethanone |
| 265 | S9 | A92 | C | 568.0 | 2-[2-(Benzenesulfonyl)-1,2,3,4-tetrahydro-pyrrolo[1,2-a]pyrazin-1-yl]-1-[4-[3-chloro-5-(trifluoromethyl)-pyridin-2-yl]-piperazin-1-yl]-ethanone |
| 266 | S9 | A103 | C | 547.5 | 2-[2-(Benzenesulfonyl)-1,2,3,4-tetrahydro-pyrrolo[1,2-a]pyrazin-1-yl]-1-[4-[(3,4-dichlorophenyl)-methyl]-piperazin-1-yl]-ethanone |
| 267 | S9 | A109 | C | 478.6 | 2-[2-(Benzenesulfonyl)-1,2,3,4-tetrahydro-pyrrolo[1,2-a]pyrazin-1-yl]-1-(4-methyl-2-phenyl-piperazin-1-yl)-ethanone |
| 268 | S9 | A110 | C | 463.6 | 2-[2-(Benzenesulfonyl)-1,2,3,4-tetrahydro-pyrrolo[1,2-a]pyrazin-1-yl]-1-(4-phenyl-piperidin-1-yl)-ethanone |
| 269 | S12 | A90 | C | 558.6 | 2-[4-[2-[2-[[3-(Trifluoromethyl)phenyl]sulfonyl]-1,2,3,4-tetrahydro-pyrrolo[1,2-a]pyrazin-1-yl]-acetyl]-piperazin-1-yl]-pyridine-3-carbonitrile |
| 270 | S6 | A69 | C | 595.1 | 2-[2-[[2-Chloro-4-(trifluoromethyl)-phenyl]sulfonyl]-1,2,3,4-tetrahydro-pyrrolo[1,2-a]pyrazin-1-yl]-1-[2-(4-dimethylaminophenyl)-pyrrolidin-1-yl]-ethanone |

1. Functional Investigation on the Bradykinin 1 Receptor (B1R)

The agonistic or antagonistic action of substances can be determined on the bradykinin 1 receptor (B1R) of the human and rat species with the following assay. According to this assay, the $Ca^{2+}$ inflow through the channel is quantified with the aid of a $Ca^{2+}$-sensitive dye (Fluo-4 type, Molecular Probes Europe BV, Leiden, Netherlands) in a fluorescent imaging plate reader (FLIPR, Molecular Devices, Sunnyvale, USA).

2. Method:

Chinese hamster ovary cells (CHO K1 cells) which are stably transfected with the human B1R gene (hB1R cells) or the B1R gene of the rat (rB1R cells) are used. For functional investigations these cells are plated-out onto black 96-well plates with a clear base (BD Biosciences, Heidelberg, Germany or Greiner, Frickenhausen, Germany) in a density of 20,000-35,000 cells/well. Overnight the cells are incubated at 37° C. and 5% $CO_2$ in culture medium (hB1R cells: Ham's Nutrient Mixture F12, Gibco Invitrogen GmbH, Karlsruhe, Germany or DMEM, Sigma-Aldrich, Taufkirchen, Germany; rB1R cells: D-MEM/F12, Gibco Invitrogen, Karlsruhe, Germany) with 10 vol. % FBS (foetal bovine serum, Gibco Invitrogen GmbH, Karlsruhe, Germany or PAN Biotech GmbH, Aidenbach, Germany).

On the following day the cells are loaded with 2.13 µM Fluo-4 (Molecular Probes Europe BV, Leiden, Netherlands) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany) for 60 min at 37° C. The plates are subsequently washed twice with HBSS buffer, and HBSS buffer which additionally contains 0.1% BSA (bovine serum albumin; Sigma-Aldrich, Taufkirchen, Germany), 5.6 mM glucose and 0.05% gelatine (Merck KGaA, Darmstadt, Germany) is added. After a further incubation of 20 minutes at RT, the plates are inserted into the FLIPR for $Ca^{2+}$ measurement. Alternatively they are washed with buffer A (15 mM HEPES, 80 mM NaCl, 5 mM KCl, 1.2 mM $CaCl_2$, 0.7 mM $MgSO_4$, 2 g/l glucose, 2.5 mM probenecid) and loaded with buffer A with added 2.5 µM Fluo-4 and 0.025% Pluronic F127 (Sigma-Aldrich, Taufkirchen, Germany). The cells are then washed twice with buffer A and incubated for 30 minutes with buffer A, which additionally contains 0.05% BSA and 0.05% gelatine, at RT and then used for $Ca^{2+}$ measurement in the FLIPR. The $Ca^{2+}$-dependent fluorescence is measured here before and after addition of substances ($\lambda_{ex}$=488 nm, $\lambda_{em}$=540 nm). The quantification is performed by measuring the highest fluorescence intensity (FC, fluorescence counts) over time.

3. FLIPR Assay:

The FLIPR protocol comprises two additions of substance. Test substances (10 µM) are first pipetted onto the cells and the $Ca^{2+}$ inflow is compared with the control (hB1R: Lys-Des-Arg$^9$ bradykinin >=50 nM; rB1R: Des-Arg$^9$ bradykinin 10 µM). The value in % activation based on the $Ca^{2+}$ signal after addition of Lys-Des-Arg$^9$ bradykinin (>=50 nM) or Des-Arg$^9$ bradykinin (10 µM) is obtained therefrom. After incubation for 10-20 minutes, Lys-Des-Arg$^9$ bradykinin (hB1R) or Des-Arg$^9$ bradykinin (rB1R) is applied in the $EC_{80}$ concentration and the inflow of $Ca^{2+}$ is likewise determined.

Antagonists lead to a suppression of the $Ca^{2+}$ inflow. The % inhibition in comparison with the maximum achievable inhibition is calculated.

The substances are added in varying concentrations in order to determine the $IC_{50}$ value. Double or triple determinations (n=2 or n=3) are performed and these are repeated in at least one further independent experiment (N>=2).

The compounds preferably exhibit a B1R antagonistic action on the human receptor and/or on the rat receptor. The following data is provided in Table 8 below by way of example: ("% Inh. (rat B1R) 10 μM" stands for "% inhibition rat B1R at 10 μM" and "% Inh. (hum. B1R) 10 μM" stands for "% inhibition human B1R at 10 μM").

| Example | B1R antagonism. human [10 μM] % inhibition | B1R antagonism. rat [10 μM] % inhibition |
|---|---|---|
| 1 | 94.8 | 100.34 |
| 2 | 99.93 | 98.91 |
| 3 | 69.58 | 58.81 |
| 4 | 99.76 | 103.71 |
| 5 | 99.81 | 101.52 |
| 6 | 99.61 | 100.12 |
| 7 | 99.93 | 102.03 |
| 8 | 99.93 | 103.7 |
| 9 | 99.49 | 102.71 |
| 10 | 99.78 | 103.32 |
| 11 | 99.87 | 98.12 |
| 12 | 99.51 | 99.28 |
| 13 | 100.11 | 100.21 |
| 14 |  | 108.86 |
| 15 | 99.91 | 98.26 |
| 16 | 99.89 | 98.54 |
| 17 | 97.44 | 99.21 |
| 18 | 99.88 | 94.79 |
| 19 |  | −7.98 |
| 20 |  | 30.705 |
| 21 | 99.95 | 113.24 |
| 22 | 99.59 | 113.09 |
| 23 | 100.18 | 107.92 |
| 24 | 99.94 | 113.51 |
| 25 | 95.99 | 103.03 |
| 26 | 98.94 | 101.67 |
| 27 | 99.96 | 101.83 |
| 28 | 99.55 | 100.48 |
| 29 | 99.84 | 101.89 |
| 30 | 99.82 | 102.38 |
| 31 | 100.19 | 103.50 |
| 32 | 8.84 | 65.45 |
| 33 | 15.73 | 58.08 |
| 34 | 99.21 | 103.42 |
| 35 | 97.66 | 101.49 |
| 36 | 97.50 | 103.44 |
| 37 | 97.84 | 104.35 |
| 38 | 98.11 | 104.44 |
| 39 | 99.56 | 105.20 |
| 40 | 99.6 | 94.9 |
| 41 | 100.08 | 103.30 |
| 42 | 99.86 | 107.37 |
| 43 | 99.48 | 103.42 |
| 44 | 99.28 | 103.51 |
| 45 | 50.62 | 64.04 |
| 46 | 55.80 | 29.01 |
| 47 | 99.86 | 106.11 |
| 48 | 99.59 | 104.69 |
| 49 | 99.86 | 99.99 |
| 50 | 99.72 | 99.51 |
| 51 | 99.53 | 103.05 |
| 52 | 96.04 | 102.55 |
| 53 | 99.01 | 102.22 |
| 54 | 99.02 | 100.20 |
| 55 | 99.78 | 99.42 |
| 56 | 99.73 | 97.97 |
| 57 | 98.55 | 101.21 |
| 58 | 99.96 | 103.23 |
| 59 | 99.75 | 76.24 |
| 60 | 99.77 | 99.49 |
| 61 | 99.70 | 100.00 |
| 62 | 99.21 | 98.41 |
| 63 | 99.72 | 91.12 |
| 64 | 99.87 | 101.98 |
| 65 | 99.08 | 98.74 |
| 66 | 99.89 | 100.32 |
| 67 | 99.73 | 101.07 |
| 68 | 99.72 | 98.87 |
| 69 | 62.82 | 90.72 |
| 70 | 99.87 | 101.58 |
| 71 | 99.85 | 101.63 |
| 72 | 99.90 | 101.12 |
| 73 | 99.85 | 103.21 |
| 74 | 99.73 | 91.19 |
| 75 | 99.87 | 101.55 |
| 76 | 99.81 | 100.94 |
| 77 | 99.25 | 103.44 |
| 78 | 99.84 | 86.20 |
| 79 | 57.86 | 99.32 |
| 80 | 99.78 | 100.74 |
| 81 | 99.14 | 102.32 |
| 82 | 99.92 | 100.55 |
| 83 | 99.35 | 101.37 |
| 84 | 99.77 | 100.50 |
| 85 | 99.88 | 101.43 |
| 86 | 99.81 | 97.46 |
| 87 | 99.42 | 101.97 |
| 88 | 99.89 | 96.48 |
| 89 | 100.02 | 99.10 |
| 90 | 54.58 | 51.42 |
| 91 | 99.91 | 99.05 |
| 92 | 99.87 | 102.08 |
| 93 | 99.87 | 96.83 |
| 94 | 99.88 | 100.99 |
| 95 | 99.69 | 99.78 |
| 96 | 99.93 | 102.36 |
| 97 | 99.84 | 102.50 |
| 98 | 99.86 | 99.70 |
| 99 | 99.76 | 100.79 |
| 100 | 99.85 | 102.95 |
| 101 | 99.93 | 102.87 |
| 102 | 99.86 | 100.64 |
| 103 | 99.98 | 102.01 |
| 104 | 99.90 | 103.08 |
| 105 | 99.80 | 102.66 |
| 106 | 99.96 | 100.99 |
| 107 | 99.33 | 98.43 |
| 108 | 99.91 | 101.09 |
| 109 | 99.83 | 99.85 |
| 110 | 99.90 | 98.83 |
| 111 | 99.95 | 102.77 |
| 112 | 99.79 | 102.31 |
| 113 | 99.81 | 97.08 |
| 114 | 100.01 | 99.57 |
| 115 | 99.84 | 101.81 |
| 116 | 99.75 | 101.87 |
| 117 | 99.96 | 98.80 |
| 118 | 99.99 | 101.75 |
| 119 | 23.42 | 62.23 |
| 120 | 97.85 | 101.68 |
| 121 | 99.90 | 99.49 |
| 122 | 99.57 | 100.67 |
| 123 | 99.99 | 101.26 |
| 124 | 99.67 | 97.31 |
| 125 | 99.63 | 99.14 |
| 126 | 99.94 | 101.86 |
| 127 | 97.40 | 101.17 |
| 128 | 99.77 | 103.12 |
| 129 | 46.07 | 74.72 |
| 130 | 73.58 | 98.78 |
| 131 | 99.83 | 100.99 |
| 132 | 99.81 | 101.63 |
| 133 | 99.44 | 103.88 |
| 134 | 99.81 | 103.33 |

| Example | B1R antagonism. human [10 μM] % inhibition | B1R antagonism. rat [10 μM] % inhibition |
|---|---|---|
| 135 | 99.58 | 104.28 |
| 136 | 99.70 | −29.23 |
| 137 | 99.72 | 103.80 |
| 138 | 99.76 | 102.59 |
| 139 | 99.14 | 102.59 |
| 140 | 96.09 | 101.77 |
| 141 | | 37.775 |
| 142 | | 37.915 |
| 143 | | 37.35 |
| 144 | | 70.29 |
| 145 | | 57.67 |
| 146 | | 73.45 |
| 147 | | 86.49 |
| 148 | | 70.445 |
| 149 | | 68.93 |
| 150 | | 50.33 |
| 151 | | 104.35 |
| 152 | | 50.925 |
| 153 | | 15.82 |
| 154 | | 41.85 |
| 155 | | 61.5 |
| 156 | | 95.1 |
| 157 | | 69.5 |
| 158 | | 32.045 |
| 159 | | 3.48 |
| 160 | | 42.775 |
| 161 | | 10.5 |
| 162 | | 25.205 |
| 163 | | 39.715 |
| 164 | | 44.065 |
| 165 | | 55.765 |
| 166 | | 99.115 |
| 167 | | 0.145 |
| 168 | | 40.095 |
| 169 | | 7.565 |
| 170 | | 68.405 |
| 171 | | 24.36 |
| 172 | | 14.07 |
| 173 | | 9.74 |
| 174 | | 27.99 |
| 175 | | 9.54 |
| 176 | | 26.725 |
| 177 | | −1.9 |
| 178 | | 17.245 |
| 179 | | 20.77 |
| 180 | | 32.945 |
| 181 | | 33.865 |
| 182 | | 37.455 |
| 183 | | 56.08 |
| 184 | | 19.43 |
| 185 | | 76.44 |
| 186 | | 24.425 |
| 187 | | 18.32 |
| 188 | | −2.25 |
| 189 | | −1.61 |
| 190 | | 20.44 |
| 191 | | |
| 192 | | |
| 193 | | |
| 194 | | |
| 195 | | |
| 196 | | |
| 197 | | |
| 198 | | |
| 199 | | |
| 200 | | |
| 201 | | |
| 202 | | |
| 203 | | |
| 204 | | |
| 205 | | |
| 206 | | |
| 207 | | |
| 208 | | |
| 209 | | |
| 210 | | |
| 211 | | |
| 212 | | |
| 213 | | |
| 214 | | |
| 215 | | |
| 216 | | |
| 217 | | |
| 218 | | |
| 219 | | |
| 220 | | |
| 221 | | |
| 222 | | |
| 223 | | |
| 224 | | |
| 225 | | |
| 226 | | |
| 227 | | |
| 228 | | |
| 229 | | |
| 230 | | 5.28 |
| 231 | | −0.67 |
| 232 | | 2.94 |
| 233 | | 20.63 |
| 234 | | 17.34 |
| 235 | | −14.02 |
| 236 | | 9.23 |
| 237 | | 9.45 |
| 238 | | 17.61 |
| 239 | | −8.74 |
| 240 | | 55.88 |
| 241 | | 46.81 |
| 242 | | 8.40 |
| 243 | | 29.36 |
| 244 | | −37.61 |
| 245 | | −21.48 |
| 246 | | 6.85 |
| 247 | | −27.36 |
| 248 | | 84.04 |
| 249 | | −12.55 |
| 250 | | −38.00 |
| 251 | | −37.07 |
| 252 | | −10.50 |
| 253 | | −39.06 |
| 254 | | 8.85 |
| 255 | | −7.23 |
| 256 | | 5.54 |
| 257 | | 75.53 |
| 258 | | 9.05 |
| 259 | | 4.54 |
| 260 | | −11.39 |
| 261 | | 29.81 |
| 262 | | −12.50 |
| 263 | | 2.37 |
| 264 | | 1.78 |
| 265 | | 17.92 |
| 266 | | −3.52 |
| 267 | | −4.75 |
| 268 | | 27.96 |
| 269 | | 1.05 |
| 270 | | 3.10 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound corresponding to the formula (I):

(I)

wherein a stands for 1 or 2;

b stands for 0, 1 or 2;

B stands for $C(R^{6a}(R^{6b}))$, $NR^7$, O or a single bond, with the proviso that if b is 0, then B does not stand for $NR^7$;

$W^1$, $W^2$ and $W^3$ each stand for $CR^5$;

$R^1$ stands for aryl, heteroaryl, $CH(aryl)_2$ or an aryl or heteroaryl group bound via a $C_{1-3}$ alkylene group;

$R^{2a}$, $R^{2b}$, $R^{3a}$, $R^{3b}$, $R^{6a}$ and $R^{6b}$ each independently stand for H, F, Cl, Br, I, $-CF_3$, OH, SH, O$-C_{1-6}$ alkyl, $C_{1-6}$ alkyl, $C_{3-8}$ cycloalkyl, aryl or heteroaryl; or for a $C_{3-8}$ cycloalkyl, aryl or heteroaryl group bound via a $C_{1-6}$ alkylene group or $C_{2-6}$ alkenylene group; or $R^{2a}$ and $R^{2b}$ and/or $R^{3a}$ and $R^{3b}$ can together denote =O;

$R^4$ stands for 0 to 4 substituents each independently selected from the group consisting of F; Cl; OH; =O; $C_{1-6}$ alkyl; O$-C_{1-6}$ alkyl; $C_{3-8}$ cycloalkyl; aryl and heteroaryl; or a $C_{3-8}$ cycloalkyl, aryl or heteroaryl group bound via a $C_{1-6}$ alkylene group;

$R^5$ stands for H, $C_{1-6}$ alkyl, halogen, $-CN$ or $CF_3$;

$R^7$ stands for H, $C_{1-6}$ alkyl, $C_{3-8}$ cycloalkyl, aryl, heteroaryl or for a $C_{3-8}$ cycloalkyl, aryl or heteroaryl group bound via a $C_{1-6}$ alkylene group, $C_{2-6}$ alkenylene group or $C_{2-6}$ alkynylene group;

s is 0 or 1, t is 0, 1, 2 or 3, $R^8$ stands for H; $C_{1-6}$ alkyl; $C_{3-8}$ cycloalkyl; aryl or heteroaryl; or a $C_{3-8}$ cycloalkyl, aryl or heteroaryl group bound via a $C_{1-6}$ alkylene group;

$R^{9a}$ and $R^{9b}$ each independently denote H; F; Cl; OH; $C_{1-6}$ alkyl; O$-C_{1-6}$ alkyl; $C_{3-8}$ cycloalkyl; aryl or heteroaryl; or a $C_{3-8}$ cycloalkyl, aryl or heteroaryl group bound via a $C_{1-6}$ alkylene group;

A stands for N or CH, with the proviso that if s is 1 and t is 0, then A stands for CH; and with the proviso that if s is 0, then t is 0, and A stands for N;

$R^{10}$ and $R^{11}$ together with A represent a spirocyclic or cyclic group corresponding to formula (II) or formula (III):

(II)

(III)

wherein c, d, e, f, u and v each independently denote 0, 1 or 2;

$R^{12}$, $R^{13}$ and $R^{27}$ each independently stand for 0 to 4 substituents each independently selected from the group consisting of F; Cl; OH; =O; $C_{1-6}$ alkyl; O$-C_{1-6}$ alkyl; $C_{3-8}$ cycloalkyl; aryl; heteroaryl; and $C_{3-8}$ cycloalkyl, aryl or heteroaryl bound via a $C_{1-6}$ alkylene group; or two substituents $R^{27}$ together represent a $C_{1-3}$ alkylene bridge such that the cyclic group of formula (III) assumes a bicyclically bridged form; or two adjacent substituents $R^{13}$ form an anellated aryl or heteroaryl ring; or two adjacent substituents $R^{27}$ form an anellated aryl or heteroaryl ring which optionally may be substituted by a 4- to 7-membered heterocyclyl group, which in turn can optionally be connected to the anellated aryl or heteroaryl ring by a $C_{1-3}$ alkylene group;

X stands for $CR^{14a}R^{14b}$, $NR^{15}$ or O;

Y stands for $CR^{16a}R^{16b}$, $NR^{17}$ or O;

with the proviso that X does not denote $NR^{15}$ if Y denotes $NR^{17}$; and with the proviso that X and Y do not simultaneously denote O;

wherein $R^{14a}$, $R^{14b}$, $R^{16a}$ and $R^{16b}$ each independently denote H; F; Cl; OH; $C_{1-6}$ alkyl; O$-C_{1-6}$ alkyl; $C_{3-8}$ cycloalkyl; aryl or heteroaryl; or a $C_{3-8}$ cycloalkyl, aryl or heteroaryl group bound via a $C_{1-6}$ alkylene group; or $R^{14a}$ and $R^{14b}$ can together stand for =O; or $R^{16a}$ and $R^{16b}$ can together stand for =O;

$R^{15}$ and $R^{17}$ each independently stand for H; $C_{1-6}$ alkyl; $C_{3-8}$ cycloalkyl, aryl or heteroaryl; or a $C_{3-8}$ cycloalkyl, aryl or heteroaryl group bound via a $C_{1-6}$ alkylene group;

Z in formula (II) stands for $CR^{18a}R^{18b}$, $NR^{19}$ or O; or if X stands for O and f is 0, then Z in formula (II) may denote $-(C(R^{124})-C(R^{125}))-$, wherein $R^{124}$ and $R^{125}$ together with the carbon atoms linking them form a fused aryl or heteroaryl ring; or if X stands for O, and f is for 0, then Z in formula (II) may denote $=(N(CR^{126}))-$, wherein the N atom is singly bound to the O atom, and $R^{126}$ stands for H; $C_{1-6}$ alkyl; $C_{3-8}$ cycloalkyl; aryl or heteroaryl; or a $C_{3-8}$ cycloalkyl, aryl or heteroaryl group bound via a $C_{1-6}$ alkylene group;

Z in formula (III) stands for $CR^{18a}R^{18b}$, $NR^{19}$, O, S, S(=O) or S(=O)$_2$; wherein $R^{18a}$ stands for H; $C_{1-6}$ alkyl; $C_{3-8}$ cycloalkyl; aryl or heteroaryl; or a $C_{3-8}$ cycloalkyl, aryl or heteroaryl group bound via a $C_{1-6}$ alkylene group; or $R^{18a}$ stands for a structure corresponding to formula (IV), (IV)

wherein i and j each independently stand for 0 or 1;

E stands for N or CH, with the proviso that if i is 1 and j is 0, then E stands for CH, $R^{34}$ and $R^{35}$ each independently denote H; $C_{1-6}$ alkyl; $C_{3-8}$ cycloalkyl; aryl or heteroaryl; or an aryl, heteroaryl or $C_{3-8}$ cycloalkyl group bound via a $C_{1-3}$ alkylene group; or $R^{34}$ and $R^{35}$ together with E form a 5- or 6-membered aryl or heteroaryl ring; or $R^{34}$ and $R^{35}$ together with E form a saturated heterocyclic structure corresponding to formula (V),

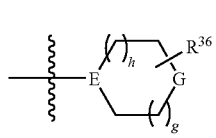

(V)

wherein h and g each independently denote 0, 1 or 2;

G stands for $CR^{37a}R^{37b}$, $NR^{38}$, O, S, S=O or $S(=O)_2$, with the proviso that if E stands for CH, then G does not stand for $CR^{37a}R^{37b}$;

$R^{36}$ stands for 0 to 4 substituents each independently selected from the group consisting of H; F; Cl; Br; I; OH; SH; =O; O—$C_{1-6}$ alkyl; $C_{1-6}$ alkyl; $C_{3-8}$ cycloalkyl; aryl and heteroaryl; or a $C_{3-8}$ cycloalkyl, aryl or heteroaryl group bound by a $C_{1-6}$ alkylene group; or two adjacent substituents $R^{36}$ together represent an anellated aryl or heteroaryl ring; or two substituents $R^{36}$ together represent a $C_{1-3}$-alkylene bridge such that the cyclic structure represented by formula (V) assumes a bicyclically bridged form;

$R^{37a}$ and $R^{37b}$ each independently denote H; F; Cl; Br; I; OH; SH; =O; O—$C_{1-6}$ alkyl; $C_{1-6}$ alkyl; $C_{3-8}$ cycloalkyl; aryl or heteroaryl; or a $C_{3-8}$ cycloalkyl, aryl and heteroaryl group bound via a $C_{1-6}$ alkylene group;

$R^{38}$ stands for H; $C_{1-6}$ alkyl; $C_{3-8}$ cycloalkyl; aryl or heteroaryl; or an aryl, heteroaryl or $C_{3-8}$ cycloalkyl group bound via a $C_{1-3}$ alkylene group;

$R^{18b}$ stands for H; OH; $C_{1-6}$ alkyl; $C_{3-8}$ cycloalkyl; O—$C_{1-6}$ alkyl; O—($C_{3-8}$ cycloalkyl); ($C_{1-6}$ alkylene)-O—$C_{1-6}$ alkyl; ($C_{1-6}$ alkylene)-O—($C_{3-8}$ cycloalkyl); aryl; heteroaryl; O-aryl or O-heteroaryl; or an aryl, O-aryl, heteroaryl or O-heteroaryl group bound via a $C_{1-6}$ alkylene group; or $R^{18b}$ stands for a structure corresponding to formula (VI),

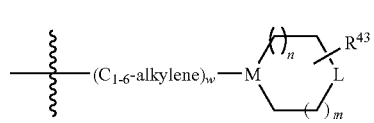

(VI)

wherein k is 0 or 1;

$R^{39}$ stands for H; $C_{1-6}$ alkyl; $C_{3-8}$ cycloalkyl; aryl or heteroaryl; or a $C_{3-8}$ cycloalkyl, aryl or heteroaryl group bound via a $C_{1-3}$ alkylene group;

$R^{40}$ stands for $C_{1-6}$ alkyl; $C_{3-8}$ cycloalkyl; aryl or heteroaryl; or a $C_{3-8}$ cycloalkyl, aryl or heteroaryl group bound via a $C_{1-6}$ alkylene group; or $R^{39}$ and $R^{40}$ together with the N—C(=O) group linking them form a ring corresponding to formula (VII),

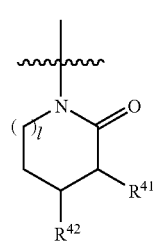

(VII)

wherein l stands for 0, 1 or 2; and $R^{41}$ and $R^{42}$ together with the carbon atoms linking them form an anellated aryl or heteroaryl ring;

$R^{19}$ stands for H; or $(P)_z$—$R^{22}$, wherein z is 0 or 1;

P stands for (C=O), $S(=O)_2$ or C(=O)—$N(R^{24})$; wherein the N atom in the C(=O)—$N(R^{24})$ group is linked to $R^{22}$;

$R^{24}$ stands for H; $C_{1-6}$ alkyl; $C_{3-8}$ cycloalkyl; aryl, heteroaryl or a $C_{3-8}$ cycloalkyl group bound via a $C_{1-3}$ alkylene group;

$R^{22}$ stands for $C_{1-6}$ alkyl; $C_{3-8}$ cycloalkyl; aryl or heteroaryl; or an aryl, heteroaryl or $C_{3-8}$ cycloalkyl group bound via a $C_{1-6}$ alkylene group; or $R^{22}$ stands for a group corresponding to formula (VIII),

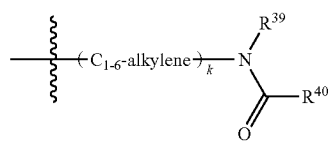

(VIII)

wherein n is 0, 1 or 2;

m is 0, 1 or 2;

w is 0 or 1,

M stands for CH or N; with the proviso that if P stands for C(=O)—$NR^{24}$ and w is 0, then M stands for CH; and with the proviso that if z and w are each 0, then M stands for CH;

L stands for $CR^{44a}R^{44b}$, $NR^{45}$, O, S, S=O or $S(=O)_2$;

$R^{43}$ stands for 0 to 4 substituents each independently selected from the group consisting of F; Cl; OH; =O; $C_{1-6}$ alkyl; O—$C_{1-6}$ alkyl; $C_{3-8}$ cycloalkyl; aryl and heteroaryl; or a $C_{3-8}$ cycloalkyl, aryl or heteroaryl group bound via a $C_{1-6}$ alkylene group; or two adjacent substituents $R^{43}$ together represent an anellated aryl or heteroaryl ring;

$R^{44a}$ and $R^{44b}$ each independently stand for H; F; Cl; Br; I; OH; $C_{1-6}$ alkyl; O—$C_{1-6}$ alkyl; $C_{3-8}$ cycloalkyl; aryl or heteroaryl; or a $C_{3-8}$ cycloalkyl, aryl or heteroaryl group bound via a $C_{1-6}$ alkylene group; or $R^{44a}$ and $R^{44b}$ can together stand for =O;

$R^{45}$ stands for H; $C_{1-6}$ alkyl; $C_{3-8}$ cycloalkyl; aryl or heteroaryl; or an aryl, heteroaryl or $C_{3-8}$ cycloalkyl group bound via a $C_{1-3}$ alkylene group;

or wherein, if s and t in formula (I) each are 0 and A stands for N,

R$^{10}$ stands for H, C$_{1-6}$ alkyl or —C(=O)—R$^{280}$, wherein R$^{280}$ stands for —N(C$_{1-6}$ alkyl)$_2$ or a 4- to 7-membered heterocyclyl group; and R$^{11}$ stands for a phenyl group or a phenyl group bound via a C$_{1-3}$ alkylene group, wherein the C$_{1-3}$ alkylene group optionally may be substituted with a —C(=O)R$^{280}$ group and R$^{280}$ stands for —N(C$_{1-6}$ alkyl)$_2$ or a 4- to 7-membered heterocyclyl group; or wherein the phenyl group optionally may be substituted with an —(NR$^{300}$R$^{301}$) group or a 4- to 8-membered heterocyclyl group, and the —(NR$^{300}$R$^{301}$) group or the 4- to 8-membered heterocyclyl group optionally may be bound to the phenyl group by a C$_{1-3}$ alkylene group and R$^{300}$ and R$^{301}$ each independently stand for H or C$_{1-6}$ alkyl;

wherein the aforementioned C$_{1-6}$ alkyl, C$_{1-3}$ alkylene, C$_{1-6}$ alkylene, C$_{2-6}$ alkenylene, C$_{2-6}$ alkynylene, C$_{3-8}$-cycloalkyl groups can each be unsubstituted or mono- or polysubstituted with identical or different substituents selected from the group consisting of F, Cl, Br, I, CF$_3$, OCF$_3$, CN, NH$_2$, NH—C$_{1-6}$ alkyl, NH—C$_{1-6}$ alkylene-OH, C$_{1-6}$ alkyl, N(C$_{1-6}$ alkyl)$_2$, N(C$_{1-6}$ alkylene-OH)$_2$, NO$_2$, SH, S—C$_{1-6}$ alkyl, C$_{1-6}$ alkyl, S-benzyl, O—C$_{1-6}$ alkyl, OH, O—C$_{1-6}$ alkylene-OH, =O, O-benzyl, C(=O)C$_{1-6}$ alkyl, CO$_2$H, CO$_2$—C$_{1-6}$ alkyl, phenyl, phenoxy, benzyl, naphthyl, furyl, thienyl and pyridinyl;

wherein the aforementioned aryl and heteroaryl groups can each be unsubstituted or mono- or polysubstituted with identical or different substituents selected from the group consisting of F, Cl, Br, I, CN, NH$_2$, NH—C$_{1-6}$ alkyl, NH—C$_{1-6}$ alkylene-OH, N(C$_{1-6}$ alkyl)$_2$, N(C$_{1-6}$ alkylene-OH)$_2$, NH-aryl1, N(aryl1)$_2$, N(C$_{1-6}$ alkyl)aryl1, pyrrolinyl, piperazinyl, morpholinyl, azetidinyl, piperidinyl, thiazolinyl, azepanyl, diazepanyl, (C$_{1-3}$ alkylene)-azetidinyl, (C$_{1-3}$ alkylene)-pyrrolinyl, (C$_{1-3}$ alkylene)-piperidinyl, (C$_{1-3}$ alkylene)-morpholinyl, (C$_{1-3}$ alkylene)-piperazinyl, (C$_{1-3}$ alkylene)-thiazolinyl, (C$_{1-3}$ alkylene)-azepanyl, (C$_{1-3}$ alkylene)-diazepanyl, NO$_2$, SH, S—C$_{1-6}$ alkyl, OH, O—C$_{1-6}$ alkyl, O—C$_{1-6}$ alkyl-OH, C(=O)C$_{1-6}$ alkyl, NHSO$_2$C$_{1-6}$ alkyl, NHCOC$_{1-6}$ alkyl, CO$_2$H, CH$_2$SO$_2$ phenyl, CO$_2$—C$_{1-6}$ alkyl, OCF$_3$, CF$_3$, —O—CH$_2$—O—, —O—CH$_2$—CH$_2$—O—, —O—C(CH$_3$)$_2$—CH$_2$—, unsubstituted C$_{1-6}$ alkyl, pyrrolidinyl, imidazolyl, benzyloxy, phenoxy, phenyl, naphthyl, pyridinyl, —C$_{1-3}$ alkylene-aryl1, benzyl, thienyl, and furyl, wherein aryl1 stands for phenyl, thiazolyl, thienyl or pyridinyl;

wherein the aforementioned heterocyclyl group can be unsubstituted or mono- or polysubstituted with identical or different substituents selected from the group consisting of F, Cl, Br, I, —CN, NH$_2$, NH—C$_{1-6}$ alkyl, NH—C$_{1-6}$ alkylene-OH, C$_{1-6}$ alkyl, N(C$_{1-6}$ alkyl)$_2$, N(C$_{1-6}$ alkylene-OH)$_2$, pyrrolinyl, piperazinyl, morpholinyl, NO$_2$, SH, S—C$_{1-6}$ alkyl, S-benzyl, O—C$_{1-6}$ alkyl, OH, O—C$_{1-6}$ alkylene-OH, =O, O-benzyl, C(=O)C$_{1-6}$ alkyl, CO$_2$H, CO$_2$—C$_{1-6}$ alkyl or benzyl, and wherein the aforementioned C$_{1-6}$ alkyl, C$_{1-3}$ alkylene, C$_{1-6}$ alkylene, C$_{2-6}$ alkenylene and C$_{2-6}$ alkynylene groups may each be branched or unbranched;

or a pharmaceutically acceptable salt thereof.

2. A compound as claimed in claim 1, wherein (a1) formula (II) assumes the following substructure (IIa):

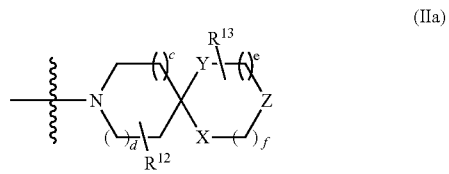

(IIa)

or (a2) formula (III) assumes one of the following substructures (IIIa) or (IIIb):

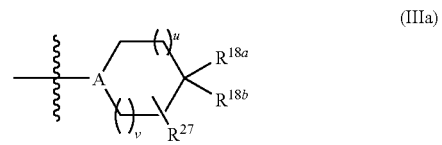

(IIIa)

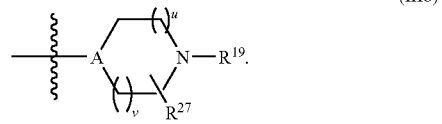

(IIIb)

3. A compound as claimed in claim 2, wherein (a1) the substructure (IIa) assumes the following substructure (IIb):

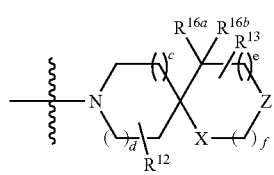

(IIb)

or (a2) the substructures (IIIa) and (IIIb) assume one of the following substructures (IIIc), (IIId) or (IIIe):

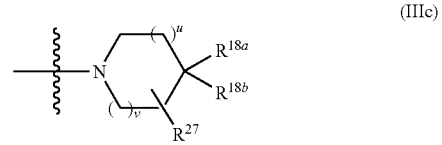

(IIIc)

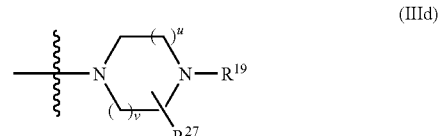

(IIId)

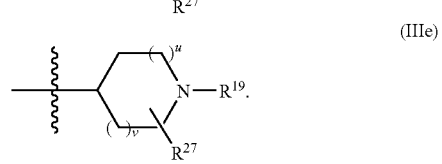

(IIIe)

4. A compound as claimed in claim 3, wherein:

(a1) the substructure (IIa) assumes the substructure (IIb),
 $R^8$ stands for H; $C_{1-6}$ alkyl, or $C_{3-6}$ cycloalkyl, each unsubstituted or mono- or polysubstituted with identical or different substituents, and
 $R^{9a}$ and $R^{9b}$ each stand for H; or (a2) the substructures (IIIa) and (IIIb) assume one of the substructures (IIIc) or (IIId), and
 s and t each stand for 0; or (a3) the substructures (IIIa) and (IIIb) assume one of the substructures (IIIc) or (IIId), and
 two of the substituents $R^{27}$ together represent a $C_{1-3}$ alkylene bridge such that the cyclic structure represented in substructure (IIIc) or (IIId) assumes a bicyclically bridged form, and
 s and t are each o; or (a4) the substructures (IIIa) and (IIIb) assume one of the substructures (IIIc) or (IIIe),
 s stands for 1 and t for 1, 2 or 3; and
 $R^8$ stands for H, $C_{1-6}$ alkyl or $C_{3-6}$ cycloalkyl, each unsubstituted or mono- or polysubstituted with identical or different substituents.

5. A compound as claimed in claim 4, wherein (a1) substructure (IIb) assumes the following substructure (IIc):

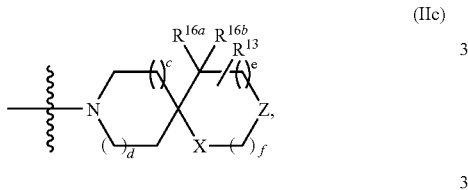
(IIc)

and wherein s and t each denote 0;
or (a2) the substructures (IIIc) or (IIId) assume one of the following substructures (IIIf) or (IIIg),

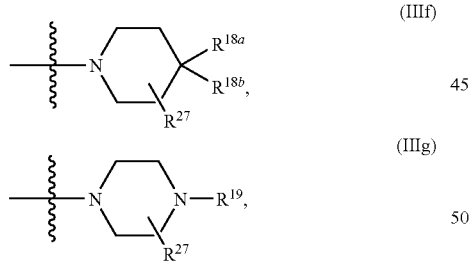
(IIIf)

(IIIg)

wherein
$R^{27}$ stands for H or methyl; or
two adjacent substituents $R^{27}$ form an anellated aryl or heteroaryl ring;
or (a3) the substructures (IIIc) or (IIId) represent one of the following groups (A) to (H):

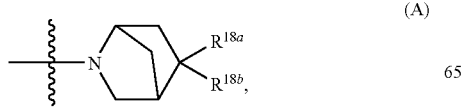
(A)

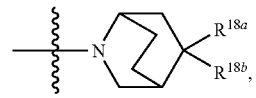
(B)

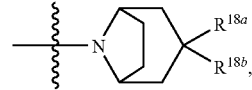
(C)

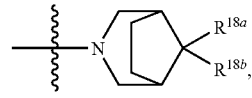
(D)

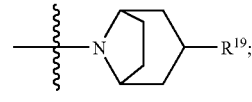
(E)

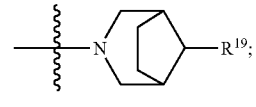
(F)

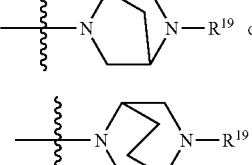
(G)

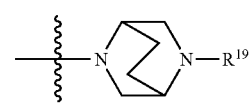
(H)

or (a4) the substructures (IIIc) or (IIIe) represent a group corresponding to one of formulas (IIIh) or (IIIi),

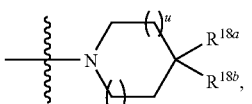
(IIIh)

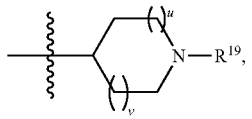
(IIIi)

and $R^{9a}$ and $R^{9b}$ each stand for H.

6. A compound as claimed in claim 5, wherein (a1) in the substructure (IIc),
$R^{16a}$ and $R^{16b}$ each stand for H or together form =O;
$R^{13}$ stands for aryl or heteroaryl; or
two substituents $R^{13}$ together form =O; or
two adjacent substituents $R^{13}$ form an anellated aryl or heteroaryl ring;
or (a2) in the substructures (IIIf) or (IIIg)
$R^{18a}$ stands for H; $C_{1-6}$ alkyl; $C_{3-8}$ cycloalkyl, —NH($C_{1-6}$ alkyl), —N($C_{1-6}$ alkyl)$_2$, phenyl, pyridyl, pyrimidinyl, thiazolyl, imidazolyl, triazolyl or thienyl, each unsubstituted or mono- or polysubstituted; or for phenyl, pyridyl, pyrimidinyl, imidazolyl, triazolyl or thienyl bound via an —$(O)_{0-1}$—$C_{1-6}$ alkylene group, each unsubstituted or mono- or polysubstituted;
or
$R^{18a}$ stands for a structure corresponding to formula (VIIa)

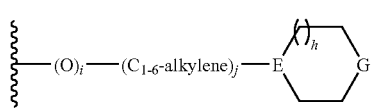
(VIIa)

wherein
i is 0 or 1;
j is 0 or 1;
h is 0 or 1;
E stands for N or CH; with the proviso that if i is 1 and j is 0, then E stands for CH;
G stands for $CR^{37a}R^{37b}$ or $NR^{38}$; wherein
  $R^{37a}$ and $R^{37b}$ each independently stand for H; F or $C_{1-6}$ alkyl, each unsubstituted or mono- or polysubstituted with identical or different substituents; and
  $R^{38}$ stands for H; $C_{1-6}$ alkyl, $C_{3-6}$ cycloalkyl or pyridyl;
$R^{18b}$ stands for H; OH; $C_{1-6}$ alkyl; phenyl, pyridyl, pyrimidinyl, imidazolyl, triazolyl, thienyl or thiazolyl; each unsubstituted or mono- or polysubstituted with identical or different substituents; or for phenyl, pyridyl, pyrimidinyl, O-phenyl, O-pyridyl, imidazolyl, triazolyl, thienyl or thiazolyl bound via a $C_{1-6}$ alkylene group, each unsubstituted or mono- or polysubstituted with identical or different substituents; or for phenyl, pyridyl, pyrimidinyl, imidazolyl, triazolyl, thiazolyl or thienyl bridged by $C_{1-6}$ alkylene-NH(C=O), each unsubstituted or mono- or polysubstituted with identical or different substituents,
$R^{19}$ stands for H; $C_{1-6}$ alkyl; or $C_{3-8}$ cycloalkyl, or for $C_{1-6}$ alkyl; phenyl, pyridyl, thienyl, thiazolyl, triazolyl, pyrimidinyl or imidazolyl bound by $(C=O)_{0-1}$; each unsubstituted or mono- or polysubstituted with identical or different substituents; or for phenyl, pyridyl, thienyl, thiazolyl, pyrimidinyl, triazolyl or imidazolyl bound by a $C_{1-6}$ alkylene group; each unsubstituted or mono- or polysubstituted with identical or different substituents; or
$R^{19}$ stands for a structure corresponding to formula (VIIIa)

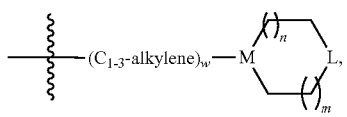
(VIIIa)

wherein
w is 0 or 1;
n is 0 or 1;
m is 0 or 1;
M stands for CH or N, with the proviso that if w is 0, then M stands for CH;
L stands for $CR^{44a}R^{44b}$ or $NR^{45}$; wherein
  $R^{44a}$ and $R^{44b}$ each independently stand for H; F or $C_{1-6}$ alkyl, each unsubstituted or mono- or polysubstituted with identical or different substituents; and $R^{45}$ stands for H; $C_{1-6}$ alkyl, $C_{3-6}$ cycloalkyl or pyridyl;
or
(a3) the substructures (IIIc) or (IIId) represent one of the following groups (A) to (H),

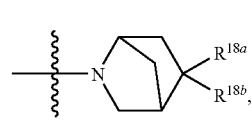
(A)

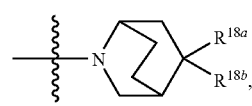
(B)

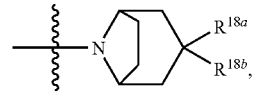
(C)

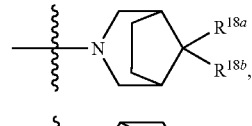
(D)

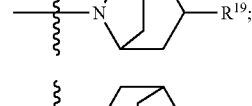
(E)

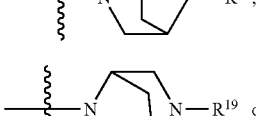
(F)

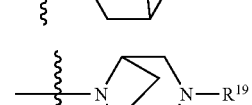
(G)

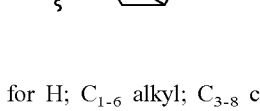
(H)

wherein
$R^{18a}$ stands for H; $C_{1-6}$ alkyl; $C_{3-8}$ cycloalkyl, $N(C_{1-6}$ alkyl$)_2$; $NH(C_{1-6}$ alkyl); azetidinyl; pyrrolidinyl, piperidinyl, 4-($C_{1-6}$ alkyl)-piperazinyl; phenyl, pyridyl, pyrimidinyl, imidazolyl, triazolyl, thiazolyl or thienyl, each unsubstituted or mono- or polysubstituted with identical or different substituents; or for —$N(C_{1-6}$ alkyl$)_2$; —$NH(C_{1-6}$ alkyl); azetidinyl; pyrrolidinyl, piperidinyl, 4-($C_{1-6}$ alkyl)-piperazinyl; phenyl, imidazolyl, triazolyl, thienyl, thiazolyl, pyrimidinyl or pyridyl bound by an —$(O)_{0-1}$—$C_{1-6}$ alkylene group, each unsubstituted or mono- or polysubstituted with identical or different substituents;
$R^{18b}$ stands for H; OH; $C_{1-6}$ alkyl; phenyl, pyridyl, pyrimidinyl, imidazolyl, triazolyl, thiazolyl or thienyl, each unsubstituted or mono- or polysubstituted with identical or different substituents; or for phenyl, pyridyl, pyrimidinyl, imidazolyl, triazolyl, thiazolyl or thienyl bound via a $C_{1-6}$ alkylene group, each unsubstituted or mono- or polysubstituted with identical or different substituents; and
$R^{19}$ stands for H; $C_{1-6}$ alkyl; $C_{3-8}$ cycloalkyl, phenyl, pyridyl, pyrimidinyl, thienyl, imidazolyl, thiazolyl or triazolyl, each unsubstituted or mono- or polysubstituted with identical or different substituents; or for phenyl, pyridyl, pyrimidinyl, thienyl, imidazolyl, thiazolyl or triazolyl bound via a C$_{1-6}$ alkylene group or a (C=O) group, each unsubstituted or mono- or polysubstituted with identical or different substituents;
or
(a4) in the substructures (IIIh) or (IIIi)
R$^{18a}$ stands for H; C$_{1-6}$ alkyl; C$_{3-8}$ cycloalkyl, N(C$_{1-6}$ alkyl)$_2$; NH(C$_{1-6}$ alkyl); azetidinyl; pyrrolidinyl; piperidinyl, 4-(C$_{1-6}$ alkyl)-piperazinyl; phenyl, pyridyl, pyrimidinyl, thienyl, imidazolyl, thiazolyl or triazolyl, each unsubstituted or mono- or polysubstituted with identical or different substituents; or for —N(C$_{1-6}$ alkyl)$_2$; —NH(C$_{1-6}$ alkyl); azetidinyl; pyrrolidinyl; piperidinyl, 4-(C$_{1-6}$ alkyl)-piperazinyl; phenyl, pyridyl, pyrimidinyl, thienyl, imidazolyl, thiazolyl or triazolyl bound via an —O)$_{0/1}$—C$_{1-6}$ alkylene group, each unsubstituted or mono- or polysubstituted with identical or different substituents;
R$^{18b}$ stands for H; OH; C$_{1-6}$ alkyl; phenyl, pyridyl, pyrimidinyl, thienyl, imidazolyl, thiazolyl or triazolyl, each unsubstituted or mono- or polysubstituted with identical or different substituents; or for phenyl, pyridyl, pyrimidinyl, thienyl, imidazolyl, thiazolyl or triazolyl bound via a C$_{1-6}$ alkylene group, each unsubstituted or mono- or polysubstituted with identical or different substituents; and
R$^{19}$ stands for H; C$_{1-6}$ alkyl; C$_{3-8}$ cycloalkyl, phenyl, pyridyl, pyrimidinyl, thienyl, imidazolyl, thiazolyl or triazolyl, each unsubstituted or mono- or polysubstituted with identical or different substituents; or for phenyl, pyridyl, pyrimidinyl, thienyl, imidazolyl, thiazolyl or triazolyl bound by a C$_{1-6}$ alkylene group or a (C=O) group, each unsubstituted or mono- or polysubstituted with identical or different substituents.

7. A compound as claimed in claim 1, wherein in the substructure (B) in formula (I)

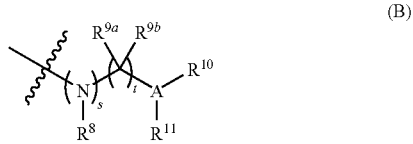

(B)

stands for 1;
t stands for 0, 1 or 2;
R$^8$ stands for H, C$_{1-6}$ alkyl, C$_{3-8}$ cycloalkyl or C$_{3-8}$ cycloalkyl bound via a C$_{1-3}$ alkylene group;
A stands for N or CH, with the proviso that if t is 0, then A stands for CH, and
R$^{10}$ and R$^{11}$ together with A form a 5- or 6-membered cycloalkyl or heterocycloalkyl group to which a 5- or 6-membered aryl or heteroaryl ring is anellated,
wherein the anellated, 5- or 6-membered aryl or heteroaryl ring is substituted with a (C$_{1-6}$ alkyl)amino, di(C$_{1-6}$ alkyl)amino or 4- to 7-membered N-containing heterocyclyl group, and
wherein the (C$_{1-6}$ alkyl)amino, di(C$_{1-6}$ alkyl)amino or 4- to 7-membered N-containing heterocyclyl group optionally may be bound to the anellated aryl or heteroaryl ring via a C$_{1-3}$ alkylene group, and the C$_{1-3}$ alkylene group can be unsubstituted or mono- or polysubstituted with identical or different substituents.

8. A compound as claimed in claim 7, wherein the substructure B in formula (I) represents a group corresponding to formula (B.50):

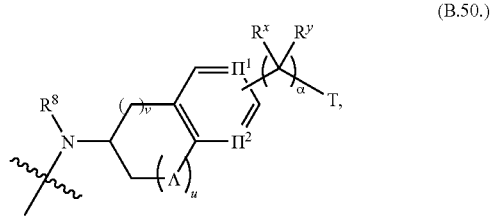

(B.50.)

wherein
R$^8$ stands for H, methyl, ethyl, n-propyl, isopropyl, n-butyl, sec-butyl, isobutyl, t-butyl, cyclopropyl or a cyclopropyl group bound via a C$_{1-3}$ alkylene group, wherein in any of these groups at least one C-bound H atom optionally may be replaced by an F atom;
u and v each independently stand for 0, 1 or 2, with the proviso that u+v is greater than 0, and u+v is at most 3;
Λ stands for CH$_2$ or O, with the proviso that if Λ is 0, then u stands for 1;
Π$^1$ and Π$^2$ each independently stand for CH or N;
α stands for 0, 1, 2 or 3; and
each occurrence of R$^x$ and R$^y$ independently stands for H, C$_{1-6}$ alkyl, F or CF$_3$;
T stands for N(R$^{271}$)(R$^{272}$), wherein
R$^{271}$ stands for H, and
R$^{272}$ stands for C$_{1-4}$ alkyl, C$_{3-6}$ cycloalkyl or a C$_{3-6}$ cycloalkyl group bound via a C$_{1-3}$ alkylene group; or
T stands for a heterocyclyl group selected from the group consisting of:

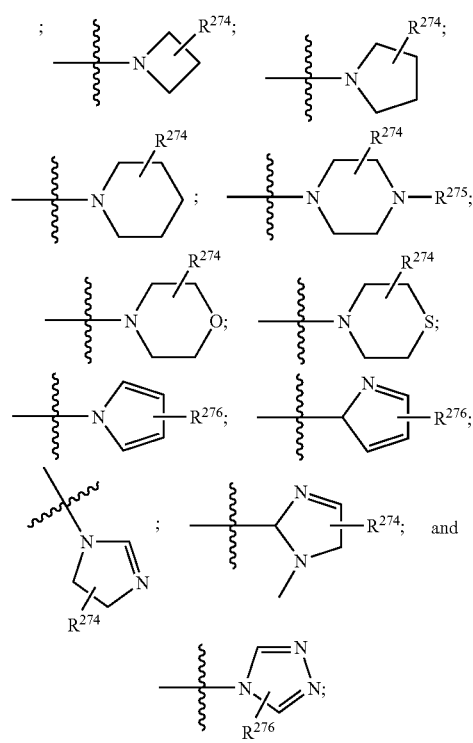

wherein
R$^{274}$ stands for 0 to 2 substituents, each independently selected from the group consisting of F, methyl, ethyl, CF$_3$ and —CH$_2$—CF$_3$; or two adjacent substituents $R^{274}$ together form an anellated aryl or heteroaryl ring; or two substituents $R^{274}$ together form a $C_{1-3}$ alkylene bridge so that the heterocyclyl group assumes a bicyclically bridged form;

$R^{275}$ represents H or a group selected from the group consisting of $C_{1-4}$ alkyl, $C_{3-6}$ cycloalkyl and a $C_{3-6}$ cycloalkyl group bound via a $C_{1-3}$ alkylene group; and $R^{276}$ stands for F, Cl, methyl or $CF_3$.

9. A compound as claimed in claim 8, wherein
$R^8$ stands for H, methyl or cyclopropyl;
u and v each stand for 1;
$\Pi^1$ and $\Pi^2$ both stand for CH or both stand for N;
α stands for 1;
each occurrence of $R^x$ and $R^y$ stands for H or methyl;
$R^{274}$ is absent; or two adjacent substituents $R^{274}$ together form a phenyl ring; and
$R^{275}$ stands for H or methyl.

10. A compound as claimed in claim 1, wherein said compound is in the form of a mixture of stereoisomers in any mixing ratio.

11. A compound as claimed in claim 10, wherein said mixture is a racemic mixture.

12. A compound as claimed in claim 1, wherein said compound is in the form of an isolated stereoisomer.

13. A compound as claimed in claim 1, wherein
B stands for O, and $R^{2a}$, $R^{2b}$, $R^{3a}$ and $R^{3b}$ each stand for H; or
B stands for $C(R^{6a})(R^{6b})$ or a single bond, and $R^{2a}$, $R^{2b}$, $R^{3a}$, $R^{3b}$, $R^{6a}$ and $R^{6b}$ each independently stand for H, F, $CF_3$, OH, $C_{1-6}$ alkyl or O—$C_{1-6}$alkyl.

14. A compound as claimed in claim 1, wherein $R^1$ stands for phenyl, naphthyl, indolyl, benzofuranyl, benzothiophenyl; benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl; or CH(phenyl)$_2$; each unsubstituted or monosubstituted or identically or differently polysubstituted with substituents independently selected from the group consisting of —O—$C_{1-3}$ alkyl, $C_{1-6}$ alkyl, F, Cl, Br, I, $CF_3$, $OCF_3$, OH, SH, phenyl, naphthyl, furyl, thiazolyl, thienyl and pyridinyl.

15. A compound as claimed in claim 1, wherein in formula (I) the group (Ac I)

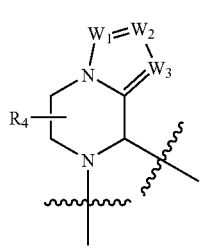

(Ac I)

is

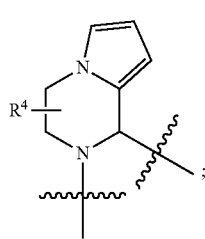

;

wherein
$R^4$ stands for 0 to 4 substituents selected from the group consisting of H, F and $C_{1-6}$ alkyl.

16. A compound as claimed in claim 1, wherein
a is 1, b is 1, B stands for O, and $R^{2a}$, $R^{2b}$, $R^{3a}$ and $R^{3b}$ each stand for H; or
a is 1 or 2; b is 0; B stands for a single bond, and $R^{2a}$ and $R^{2b}$ each stand for H.

17. A compound as claimed in claim 1, wherein
(a1) the substructure (IIc) can assume one of the following substructures (SP1) to (SP34):

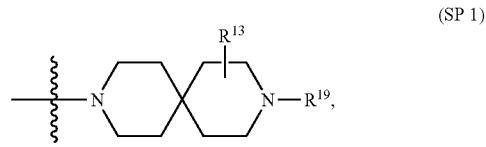
(SP 1)

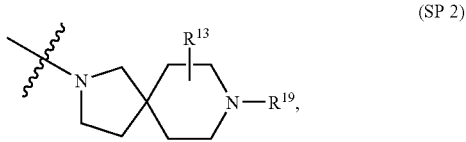
(SP 2)

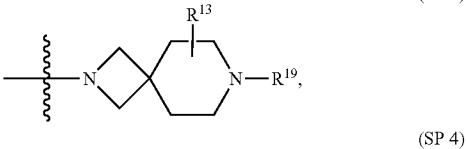
(SP 3)

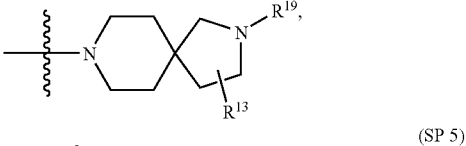
(SP 4)

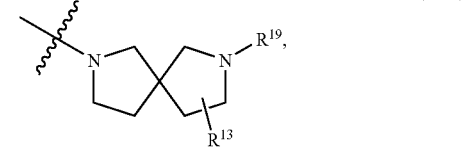
(SP 5)

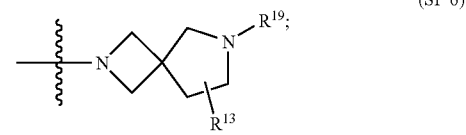
(SP 6)

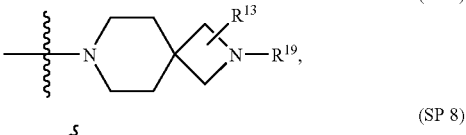
(SP 7)

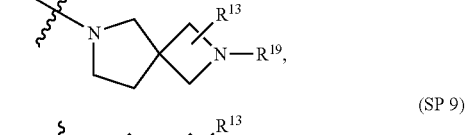
(SP 8)

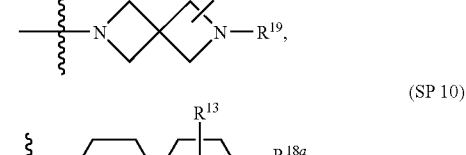
(SP 9)

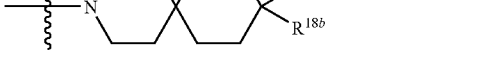
(SP 10)

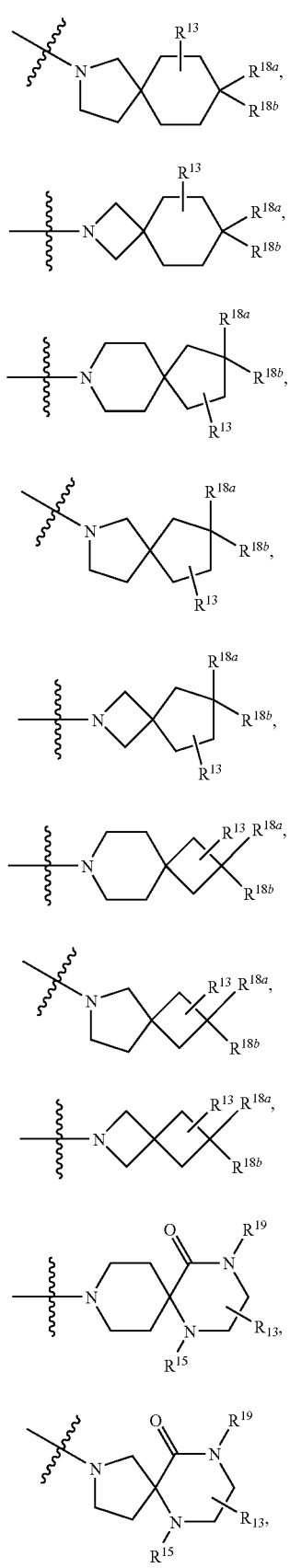
(SP 11)
(SP 12)
(SP 13)
(SP 14)
(SP 16)
(SP 17)
(SP 18)
(SP 19)
(SP 20)
(SP 21)
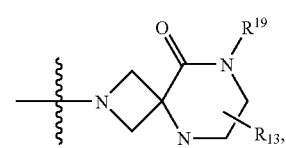 (SP 22)
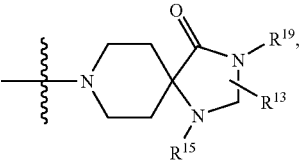 (SP 23)
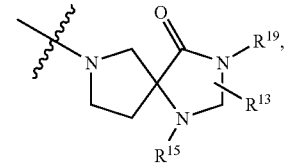 (SP 24)
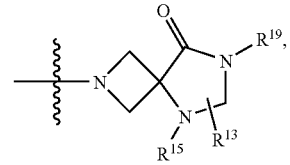 (SP 25)
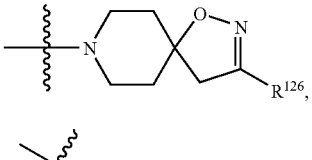 (SP 26)
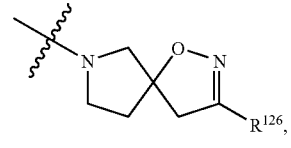 (SP 27)
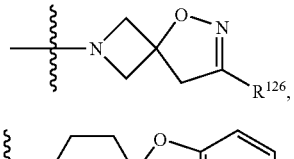 (SP 28)
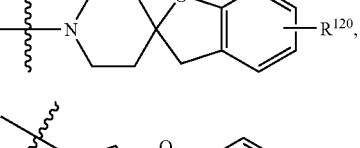 (SP 29)
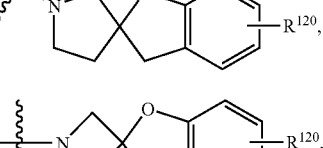 (SP 30)
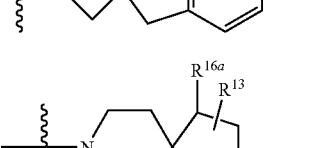 (SP 31)
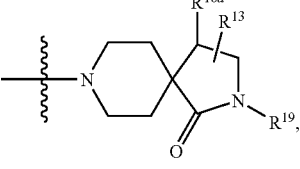 (SP 32)

-continued

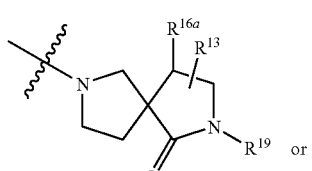
(SP 33)

or

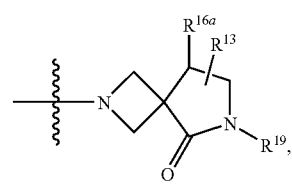
(SP 34)

wherein
$R^{13}$ stands for H or phenyl, each unsubstituted or mono- or polysubstituted with identical or different substituents; or
two substituents $R^{13}$ together form =O; or
two adjacent substituents $R^{13}$ form an anellated aryl or heteroaryl ring;
$R^{15}$ stands for H; $C_{3-8}$ cycloalkyl; phenyl, pyridyl, pyrimidinyl, imidazolyl, triazolyl, thiazolyl or thienyl, each unsubstituted or mono- or polysubstituted with identical or different substituents; or for phenyl, pyridyl, pyrimidinyl, imidazolyl, triazolyl, thiazolyl or thienyl bound via a $C_{1-6}$ alkylene group, each unsubstituted or mono- or polysubstituted with identical or different substituents;
$R^{16a}$ stands for H, $C_{1-6}$ alkyl, phenyl, pyridyl, pyrimidinyl, imidazolyl, triazolyl, thiazolyl or thienyl, each unsubstituted or mono- or polysubstituted with identical or different substituents;
$R^{18a}$ stands for H; $C_{1-8}$ alkyl; $C_{3-8}$ cycloalkyl, $N(C_{1-6}$ alkyl)$_2$; $NH(C_{1-6}$ alkyl); azetidinyl; pyrrolidinyl, piperidinyl, 4-($C_{1-6}$ alkyl)-piperazinyl; phenyl, pyridyl, pyrimidinyl, imidazolyl, triazolyl, thiazolyl or thienyl, each unsubstituted or mono- or polysubstituted with identical or different substituents; or for —N($C_{1-6}$ alkyl)$_2$; —NH($C_{1-6}$ alkyl); azetidinyl; pyrrolidinyl, piperidinyl, 4-($C_{1-6}$ alkyl)-piperazinyl; phenyl, pyridyl, pyrimidinyl, imidazolyl, triazolyl, thiazolyl or thienyl bound via an —(O)$_{0-1}$—$C_{1-6}$ alkylene group, each unsubstituted or mono- or polysubstituted with identical or different substituents;
$R^{18b}$ stands for H; OH; $C_{1-6}$ alkyl; phenyl, pyridyl, pyrimidinyl, imidazolyl, triazolyl, thiazolyl or thienyl, each unsubstituted or mono- or polysubstituted with identical or different substituents; or for phenyl, pyridyl, pyrimidinyl, imidazolyl, triazolyl, thiazolyl or thienyl bound via a $C_{1-6}$ alkylene group, each unsubstituted or mono- or polysubstituted with identical or different substituents;
$R^{19}$ stands for H; $C_{3-8}$ cycloalkyl; phenyl, pyridyl, pyrimidinyl, imidazolyl, triazolyl, thiazolyl or thienyl, each unsubstituted or mono- or polysubstituted with identical or different substituents; or for phenyl, pyridyl, pyrimidinyl, imidazolyl, triazolyl, thiazolyl or thienyl bound via a $C_{1-6}$ alkylene group or (C=O) group, each unsubstituted or mono- or polysubstituted with identical or different substituents;
$R^{120}$ stands for H; F; Cl; OH; OCH$_3$, $C_{1-6}$ alkyl; phenyl, each unsubstituted or mono- or polysubstituted with identical or different substituents;

$R^{126}$ stands for H; $C_{3-6}$ alkyl; $C_{3-6}$ cycloalkyl; phenyl, pyridyl, pyrimidinyl, imidazolyl, triazolyl, thiazolyl or thienyl; or for $C_{3-6}$ cycloalkyl, phenyl or pyridyl bound via a $C_{1-3}$ alkylene group, each unsubstituted or mono- or polysubstituted with identical or different substituents.

18. A compound as claimed in claim 1, wherein in formula (I) the substructure (B)

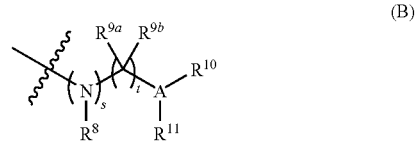
(B)

is selected from the group consisting of:

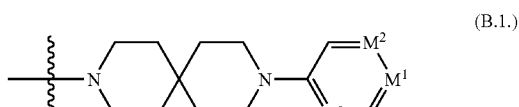
(B.1.)

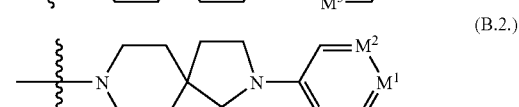
(B.2.)

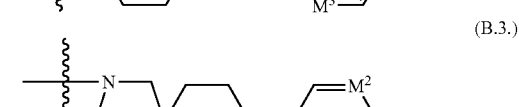
(B.3.)

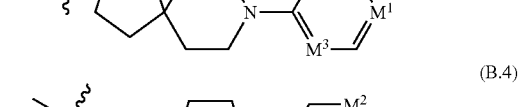
(B.4.)

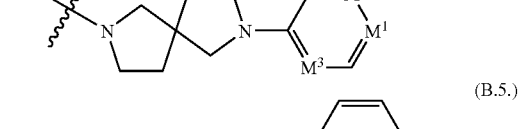
(B.5.)

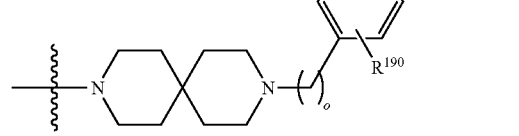
(B.6.)

(B.7.)

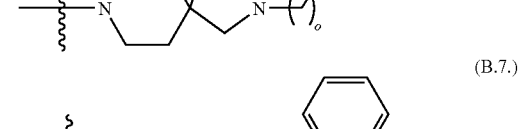
(B.8.)

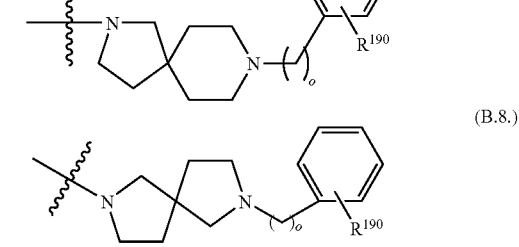

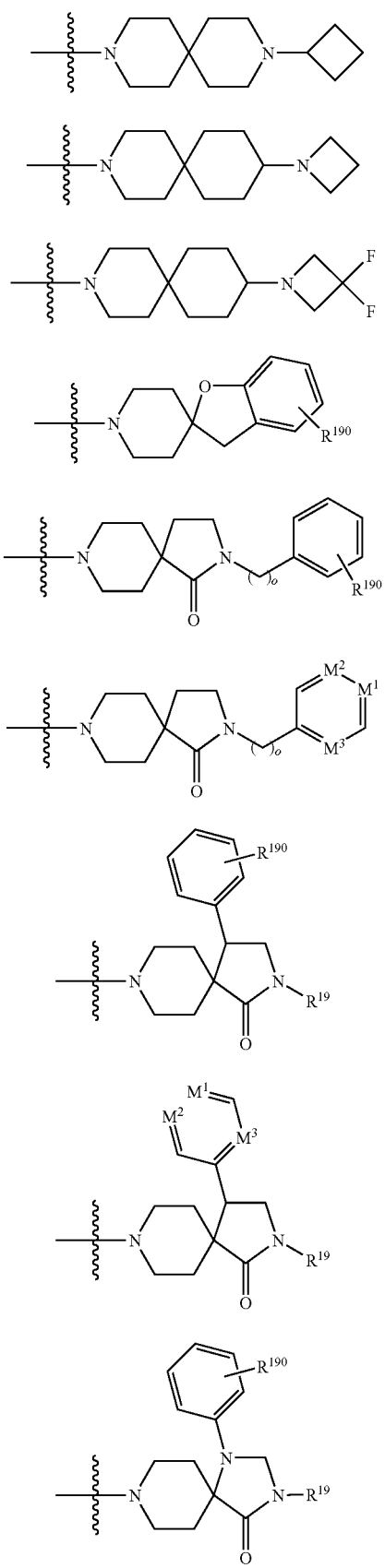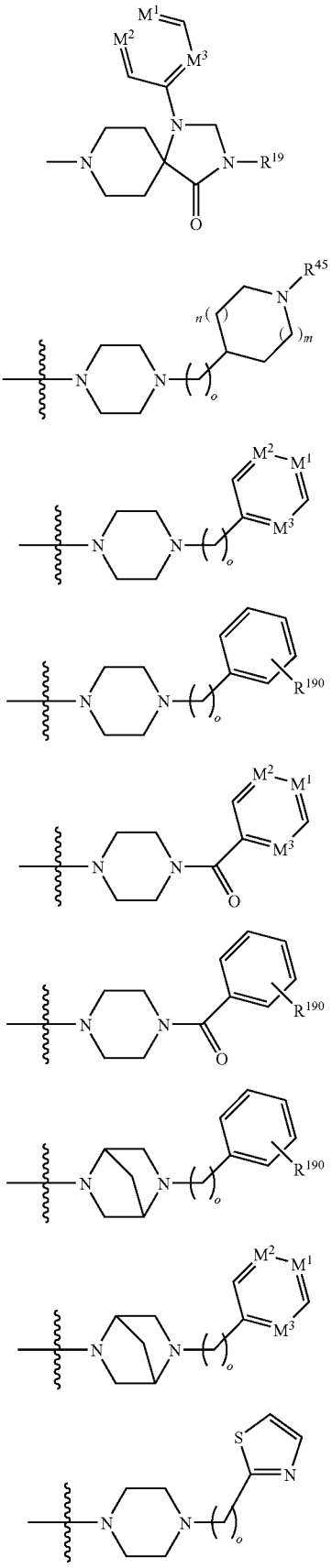

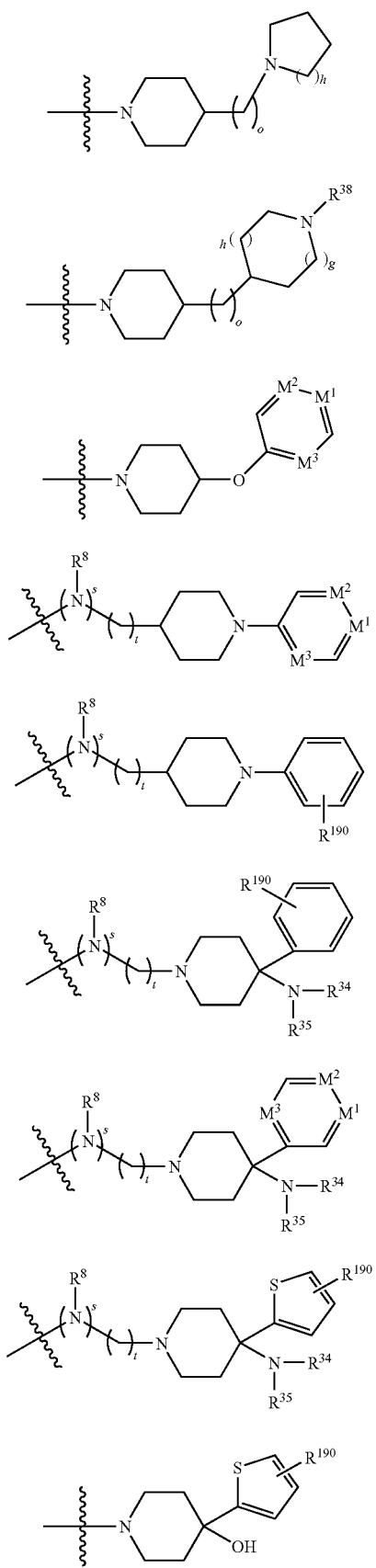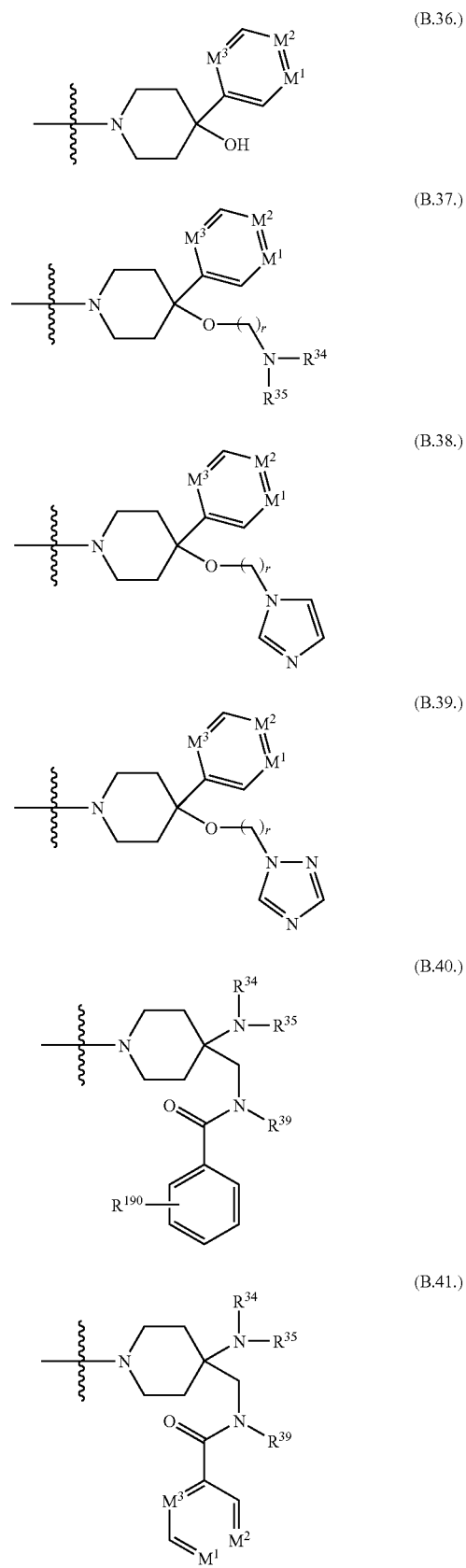

-continued

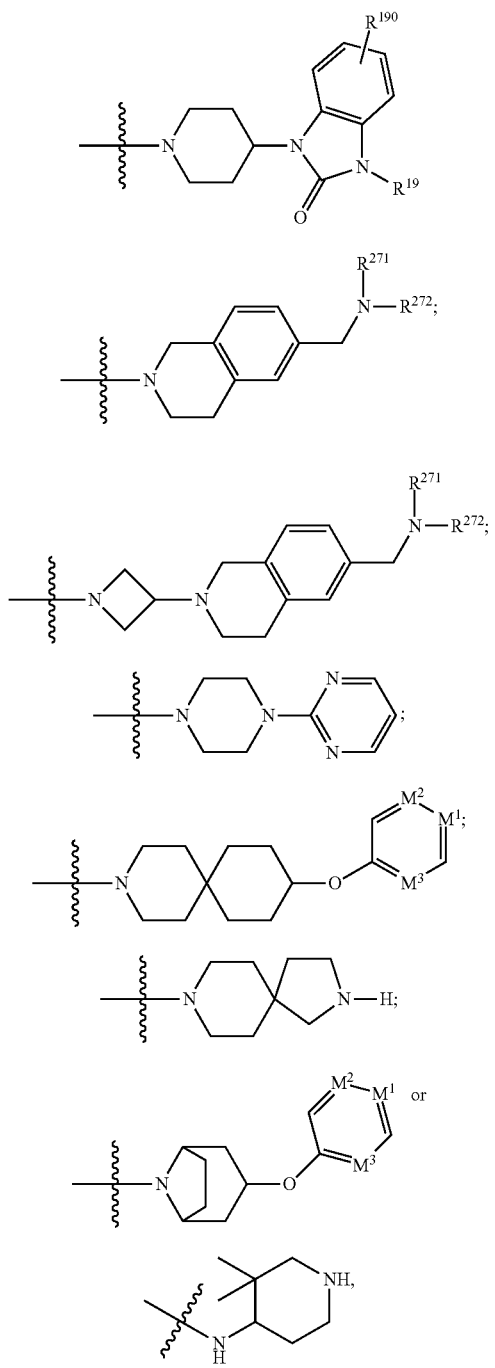

(B.42.)
(B.43.)
(B.44.)
(B.45.)
(B.46.)
(B.47.)
(B.48.)
(B.49.)

wherein
h is 0 or 1;
g is 0 or 1;
m is 0 or 1;
n is 0 or 1;
o is 0, 1, 2 or 3;
r is 1, 2 or 3;
s is 0 or 1;
t is 0, 1, 2 or 3, with the proviso that if s is 0, then t is 0;
$M^1$, $M^2$ and $M^3$ can each stand for N or CH, wherein one of $M^1$, $M^2$ and $M^3$ stands for N and the other two stand for CH;

$R^8$ stands for H; $C_{1-6}$ alkyl, or $C_{3-6}$ cycloalkyl, each unsubstituted or mono- or polysubstituted with identical or different substituents;

$R^{19}$ is selected from H; $C_{1-6}$ alkyl; or $C_{3-6}$ cycloalkyl; each unsubstituted or mono- or polysubstituted with identical or different substituents;

$R^{34}$ and $R^{35}$ are each independently methyl or ethyl or together with the N-atom linking them form an azetidinyl; pyrrolidinyl, piperidinyl, 4-($C_{1-6}$ alkyl)-piperazinyl group, each unsubstituted or mono- or polysubstituted with identical or different substituents;

$R^{38}$ stands for H, $C_{1-6}$ alkyl, $C_{3-6}$ cycloalkyl or pyridyl;

$R^{39}$ is selected from H; $C_{1-6}$ alkyl; or $C_{3-6}$ cycloalkyl, each unsubstituted or mono- or polysubstituted with identical or different substituents;

$R^{45}$ stands for H, $C_{1-6}$ alkyl, $C_{3-6}$ cycloalkyl or pyridyl;

$R^{190}$ represents 0 to 4 substituents each independently selected from the group consisting of F, Cl, O—$CF_3$, $CF_3$ and CN, $R^{271}$ stands for H; and $R^{272}$ stands for $C_{1-4}$ alkyl, $C_{3-6}$ cycloalkyl or a $C_{3-6}$ cycloalkyl group bound via a $C_{1-3}$ alkylene group; or $R^{271}$ and $R^{272}$ together form a 4- to 7-membered heterocyclyl group, which may be substituted by 0 to 2 substituents selected from the group consisting of F, Cl, O—$CF_3$, —$CF_3$, and CN; or two adjacent substituents may together form an anellated aryl or heteroary ring.

19. A compound as claimed in claim 1, selected from the group consisting of:

2-(2-(4-Methoxy-2,6-dimethylphenylsulfonyl)-1,2,3,4-tetrahydropyrrolo[1,2-a]pyrazin-1-yl)-1-(4-(1-methylpiperidin-4-yl)piperazin-1-yl)ethanone;

2-((2-(4-Methoxy-2,6-dimethylphenylsulfonyl)-1,2,3,4-tetrahydropyrrolo[1,2-a]pyrazin-1-yl)methoxy)-1-(4-(1-methylpiperidin-4-yl)piperazin-1-yl)ethanone;

1-(7-Cyclopropyl-2,7-diazaspiro[4.4]nonan-2-yl)-2-(2-(4-methoxy-2,6-dimethylphenylsulfonyl)-1,2,3,4-tetrahydropyrrolo[1,2-a]pyrazin-1-yl)ethanone;

2-((2-(4-Methoxy-2,6-dimethylphenylsulfonyl)-1,2,3,4-tetrahydropyrrolo[1,2-a]pyrazin-1-yl)methoxy)-1-(2-(pyridin-4-yl)-2,8-diazaspiro[4.5]decan-8-yl)ethanone;

1-(4-(Pyridin-4-yloxy)piperidin-1-yl)-2-((2-(2-(trifluoromethyl)phenylsulfonyl)-1,2,3,4-tetrahydropyrrolo[1,2-a]pyrazin-1-yl)methoxy)ethanone;

2-((2-(2-Chloro-6-methylphenylsulfonyl)-1,2,3,4-tetrahydropyrrolo[1,2-a]pyrazin-1-yl)methoxy)-1-(4-(pyridin-4-yloxy)piperidin-1-yl)ethanone;

2-((2-(4-Methoxy-2,6-dimethylphenylsulfonyl)-1,2,3,4-tetrahydropyrrolo[1,2-a]pyrazin-1-yl)methoxy)-N-methyl-N-(2-(1-(pyridin-4-yl)piperidin-4-yl)ethyl)acetamide;

2-(2-(6-Methoxynaphthalen-2-ylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide;

2-(2-(6-Methoxynaphthalen-2-ylsulfonyl)-1,2,3,4-tetrahydropyrrolo[1,2-a]pyrazin-1-yl)-N-(6-(piperidin-1-ylmethyl)-1,2,3,4-tetrahydronaphthalen-1-yl)acetamide;

2-((2-(4-Methoxy-2,6-dimethylphenylsulfonyl)-1,2,3,4-tetrahydropyrrolo[1,2-a]pyrazin-1-yl)methoxy)-1-(9-(pyridin-4-yl)-3,9-diazaspiro[5.5]undecan-3-yl)ethanone;

1-(9-(Pyridin-4-yl)-3,9-diazaspiro[5.5]undecan-3-yl)-2-((2-(2-(trifluoromethyl)phenylsulfonyl)-1,2,3,4-tetrahydropyrrolo[1,2-a]pyrazin-1-yl)methoxy)ethanone;

N-Methyl-N-(2-(1-(pyridin-4-yl)piperidin-4-yl)ethyl)-2-((2-(2-(trifluoromethyl)phenylsulfonyl)-1,2,3,4-tetrahydropyrrolo[1,2-a]pyrazin-1-yl)methoxy)acetamide;

2-((2-(4-Methoxy-2,6-dimethylphenylsulfonyl)-1,2,3,4-tetrahydropyrrolo[1,2-a]pyrazin-1-yl)methoxy)-1-(4-(pyridin-4-yloxy)piperidin-1-yl)ethanone;

2-((2-(2-Chloro-6-methylphenylsulfonyl)-1,2,3,4-tetrahydropyrrolo[1,2-a]pyrazin-1-yl)methoxy)-1-(2-(pyridin-4-yl)-2,8-diazaspiro[4.5]decan-8-yl)ethanone;

2-((2-(2-Chloro-6-methylphenylsulfonyl)-1,2,3,4-tetrahydropyrrolo[1,2-a]pyrazin-1-yl)methoxy)-1-(9-(pyridin-4-yl)-3,9-diazaspiro[5.5]undecan-3-yl)ethanone;

2-((2-(2-Chloro-6-methylphenylsulfonyl)-1,2,3,4-tetrahydropyrrolo[1,2-a]pyrazin-1-yl)methoxy)-N-methyl-N-(2-(1-(pyridin-4-yl)piperidin-4-yl)ethyl)acetamide;

N-(3,3-Dimethylpiperidin-4-yl)-2-(2-(4-methoxy-2,6-dimethylphenylsulfonyl)-1,2,3,4-tetrahydropyrrolo[1,2-a]pyrazin-1-yl)acetamide;

2-(2-(4-Methoxy-2,6-dimethylphenylsulfonyl)-1,2,3,4-tetrahydropyrrolo[1,2-a]pyrazin-1-yl)-1-(2-(pyridin-4-yl)-2,8-diazaspiro[4.5]decan-8-yl)ethanone;

2-(2-(2-Chloro-4-(trifluoromethyl)phenylsulfonyl)-1,2,3,4-tetrahydropyrrolo[1,2-a]pyrazin-1-yl)-1-(piperidin-1-yl)ethanone;

2-(2-(2-Chloro-4-(trifluoromethyl)phenylsulfonyl)-1,2,3,4-tetrahydropyrrolo[1,2-a]pyrazin-1-yl)-1-(3,4-dihydroisoquinolin-2(1H)-yl)ethanone;

1-(2-(Pyridin-4-yl)-2,8-diazaspiro[4.5]decan-8-yl)-2-((2-(2-(trifluoromethyl)phenylsulfonyl)-1,2,3,4-tetrahydropyrrolo[1,2-a]pyrazin-1-yl)methoxy)ethanone;

2-((2-(4-Methoxy-2,6-dimethylphenylsulfonyl)-1,2,3,4-tetrahydropyrrolo[1,2-a]pyrazin-1-yl)methoxy)-1-(2,8-diazaspiro[4.5]decan-8-yl)ethanone;

2-((2-(4-Methoxy-2,6-dimethylphenylsulfonyl)-1,2,3,4-tetrahydropyrrolo[1,2-a]pyrazin-1-yl)methoxy)-1-((1R,3S,5S)-3-(pyridin-4-yloxy)-8-azabicyclo[3.2.1]octan-8-yl)ethanone;

2-((2-(4-Methoxy-2,6-dimethylphenylsulfonyl)-1,2,3,4-tetrahydropyrrolo[1,2-a]pyrazin-1-yl)methoxy)-1-(4-(pyridin-3-yl)-4-(2-(pyrrolidin-1-yl)ethoxy)piperidin-1-yl)ethanone;

2-(2-(4-Chloro-2,5-dimethylphenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide;

2-(2-(3,4-Dichlorophenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide;

2-(2-(Phenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide;

2-(2-(2,3-Dichlorophenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide;

N-(6-(Piperidin-1-ylmethyl)-1,2,3,4-tetrahydronaphthalen-2-yl)-2-(2-tosyl-1,2,3,4-tetrahydropyrrolo[1,2-a]pyrazin-1-yl)acetamide;

N-(6-(Piperidin-1-ylmethyl)-1,2,3,4-tetrahydronaphthalen-2-yl)-2-(2-(3-(trifluoromethyl)phenylsulfonyl)-1,2,3,4-tetrahydropyrrolo[1,2-a]pyrazin-1-yl)acetamide;

N-(6-((tert-Butylamino)methyl)-1,2,3,4-tetrahydronaphthalen-2-yl)-2-(2-(6-methoxynaphthalen-2-ylsulfonyl)-1,2,3,4-tetrahydropyrrolo[1,2-a]pyrazin-1-yl)acetamide;

2-[[2-[(4-Methoxy-2,6-dimethyl-phenyl)sulfonyl]-1,2,3,4-tetrahydro-pyrrolo[1,2-a]pyrazin-1-yl]-methoxy]-N-[1-[5-(trifluoromethyl)-pyridin-2-yl]-piperidin-4-yl]-acetamide;

2-[[2-[(4-Methoxy-2,6-dimethyl-phenyl)sulfonyl]-1,2,3,4-tetrahydro-pyrrolo[1,2-a]pyrazin-1-yl]-methoxy]-N-[1-[5-(trifluoromethyl)-pyridin-2-yl]-pyrrolidin-3-yl]-acetamide;

2-[[2-[(4-Methoxy-2,6-dimethyl-phenyl)sulfonyl]-1,2,3,4-tetrahydro-pyrrolo[1,2-a]pyrazin-1-yl]-methoxy]-1-(4-pyridin-4-yl-piperidin-1-yl)-ethanone;

2-[[2-[(4-Methoxy-2,6-dimethyl-phenyl)sulfonyl]-1,2,3,4-tetrahydro-pyrrolo[1,2-a]pyrazin-1-yl]-methoxy]-1-[4-(pyridin-4-yl-methyl)-piperidin-1-yl]-ethanone;

2-[[2-[(4-Methoxy-2,6-dimethyl-phenyl)sulfonyl]-1,2,3,4-tetrahydro-pyrrolo[1,2-a]pyrazin-1-yl]-methoxy]-N-(1-pyridin-4-yl-piperidin-4-yl)-acetamide;

2-[[2-[(4-Methoxy-2,6-dimethyl-phenyl)sulfonyl]-1,2,3,4-tetrahydro-pyrrolo[1,2-a]pyrazin-1-yl]-methoxy]-1-[3-[(4-methyl-piperazin-1-yl)-methyl]-pyrrolidin-1-yl]-ethanone;

2-[[2-[(4-Methoxy-2,6-dimethyl-phenyl)sulfonyl]-1,2,3,4-tetrahydro-pyrrolo[1,2-a]pyrazin-1-yl]-methoxy]-1-(3-pyridin-4-yloxy-pyrrolidin-1-yl)-ethanone;

2-[[2-[(4-Methoxy-2,6-dimethyl-phenyl)sulfonyl]-1,2,3,4-tetrahydro-pyrrolo[1,2-a]pyrazin-1-yl]-methoxy]-N-methyl-N-(1-pyridin-4-yl-piperidin-4-yl)-acetamide;

2-[[2-[(4-Methoxy-2,6-dimethyl-phenyl)sulfonyl]-1,2,3,4-tetrahydro-pyrrolo[1,2-a]pyrazin-1-yl]-methoxy]-1-[4-(3-methyl-3,6-diazabicyclo[2.2.1]heptan-6-yl)-piperidin-1-yl]-ethanone;

N-[2-[4-(4,5-Dihydro-1H-imidazol-2-yl)-phenyl]-ethyl]-2-[2-[(6-methoxy-naphthalen-2-yl)sulfonyl]-1,2,3,4-tetrahydro-pyrrolo[1,2-a]pyrazin-1-yl]-acetamide;

N-[(1R)-6-[(tert-Butylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;

2-[2-[(6-Methoxy-naphthalen-2-yl)sulfonyl]-1,2,3,4-tetrahydro-pyrrolo[1,2-a]pyrazin-1-yl]-N-methyl-N-[6-(piperidin-1-yl-methyl)-1,2,3,4-tetrahydro-naphthalen-2-yl]-acetamide;

N-[(1R)-6-[(4-Fluoro-piperidin-1-yl)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;

2-[2-(p-Tolylsulfonyl)-1,2,3,4-tetrahydro-pyrrolo[1,2-a]pyrazin-1-yl]-N-[(1R)-6-[(2,2,2-trifluoro-ethylamino)-methyl]-1,2,3,4-tetrahydro-naphthalen-1-yl]-acetamide;

N-[(1R)-1-[4-[(tert-Butylamino)-methyl]-phenyl]-ethyl]-2-[2-(p-tolylsulfonyl)-1,2,3,4-tetrahydro-pyrrolo[1,2-a]pyrazin-1-yl]-acetamide;

2-(2-(3-chlorophenylsulfonyl)-1,2,3,4-tetrahydropyrrolo[1,2-a]pyrazin-1-yl)-N-(6-(piperidin-1-ylmethyl)-1,2,3,4-tetrahydronaphthalen-2-yl)acetamide;

2-(2-(6-methoxynaphthalen-2-ylsulfonyl)-1,2,3,4-tetrahydropyrrolo[1,2-a]pyrazin-1-yl)-N-(5-(piperidin-1-ylmethyl)-2,3-dihydro-1H-inden-2-yl)acetamide;

2-[2-[(3-Chloro-4-methyl-phenyl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-2-yl]-acetamide;

2-[2-[(3-Chloro-4-methyl-phenyl)sulfonyl]-1,2,3,4-tetrahydro-pyrrolo[1,2-a]pyrazin-1-yl]-N-[6-(piperidin-1-yl-methyl)-1,2,3,4-tetrahydro-naphthalen-2-yl]-acetamide;

- N-[6-[(Benzylamino)-methyl]-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide;
- 2-[2-[(3-Chloro-4-methyl-phenyl)sulfonyl]-1, 2,3,4-tetrahydro-pyrrolo[1,2-a]pyrazin-1-yl]-N-[6-(1, 2,3,4-tetrahydro-quinolin-1-yl-methyl)-1,2,3,4-tetrahydro-naphthalen-2-yl]-acetamide;
- N-[6-(Morpholin-4-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide;
- N-[6-(Morpholin-4-yl-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;
- 2-[2-[(3-Chloro-4-methyl-phenyl)sulfonyl]-1,2,3,4-tetrahydro-pyrrolo[1,2-a]pyrazin-1-yl]-N-[6-[(4-methyl-piperazin-1-yl)-methyl]-1, 2,3,4-tetrahydro-naphthalen-1-yl]-acetamide;
- 2-[2-[(3-Chloro-4-methyl-phenyl)sulfonyl]-1,2,3,4-tetrahydro-pyrrolo[1,2-a]pyrazin-1-yl]-N-[6-(piperidin-1-yl-methyl)-1,2,3,4-tetrahydro-naphthalen-1-yl]-acetamide;
- 2-[2-[(3-Chloro-4-methyl-phenyl)sulfonyl]-1, 2,3,4-tetrahydro-pyrrolo[1,2-a]pyrazin-1-yl]-N-[6-(morpholin-4-yl-methyl)-1,2,3,4-tetrahydro-naphthalen-1-yl]-acetamide;
- N-[6-(Dimethylaminomethyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide;
- N-[6-[(4-Methyl-piperazin-1-yl)-methyl]-1, 2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide;
- N-[6-[(tert-Butylamino)-methyl]-1, 2,3,4-tetrahydro-naphthalen-2-yl]-2-[2-[(3-chloro-4-methyl-phenyl)sulfonyl]-1, 2,3,4-tetrahydro-pyrrolo[1,2-a]pyrazin-1-yl]-acetamide;
- 2-[2-[(3-Chloro-4-methyl-phenyl)sulfonyl]-1, 2,3,4-tetrahydro-pyrrolo[1,2-a]pyrazin-1-yl]-N-[6-[(4-methyl-piperazin-1-yl)-methyl]-1, 2,3,4-tetrahydro-naphthalen-2-yl]-acetamide;
- N-[6-[(1-Methyl-propylamino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide;
- 2-[2-[(3-Chloro-4-methyl-phenyl)sulfonyl]-1,2,3,4-tetrahydro-pyrrolo[1,2-a]pyrazin-1-yl]-N-[6-[(1-methyl-propylamino)-methyl]-1, 2,3,4-tetrahydro-naphthalen-2-yl]-acetamide;
- N-[6-[(tert-Butylamino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide;
- N-[6-[(1-Methyl-propylamino)-methyl]-1, 2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide;
- 2-[2-[(3-Chloro-4-methyl-phenyl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-2-yl]-acetamide;
- N-[6-(Morpholin-4-yl-methyl)-1,2,3,4-tetrahydro-naphthalen-2-yl]-2-[2-[[3-(trifluoromethyl)phenyl]sulfonyl]-1, 2,3,4-tetrahydro-pyrrolo[1,2-a]pyrazin-1-yl]-acetamide;
- N-[6-[(4-Methyl-piperazin-1-yl)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide;
- N-[6-(1, 2,3,4-Tetrahydro-quinolin-1-yl-methyl)-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide;
- N-[6-[(tert-Butylamino)-methyl]-1, 2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide;
- N-[6-(8-Azabicyclo[3.2.1]octan-8-yl-methyl)-1,2,3,4-tetrahydro-naphthalen-2-yl]-2-[2-[(3-chloro-4-methyl-phenyl)sulfonyl]-1,2,3,4-tetrahydro-pyrrolo[1,2-a]pyrazin-1-yl]-acetamide;
- N-[6-[(tert-Butylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;
- N-[6-[(tert-Butyl-methyl-amino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide;
- N-[6-[(tert-Butyl-methyl-amino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;
- N-[6-[(tert-Butyl-methyl-amino)-methyl]-1,2,3,4-tetrahydro-naphthalen-2-yl]-2-[2-[(3-chloro-4-methyl-phenyl)sulfonyl]-1, 2,3,4-tetrahydro-pyrrolo[1,2a]pyrazin-1-yl]-acetamide;
- N-[6-[(tert-Butyl-methyl-amino)-methyl]-1,2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide;
- N-[6-(8-Azabicyclo[3.2.1]octan-8-yl-methyl)-1,2,3,4-tetrahydro-naphthalen-2-yl]-2-[2-(p-tolylsulfonyl)-1,2,3, 4-tetrahydro-pyrrolo[1,2-a]pyrazin-1-yl]-acetamide;
- N-[6-[(4-Methyl-piperazin-1-yl)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;
- 2-[2-(p-Tolylsulfonyl)-1,2,3,4-tetrahydro-pyrrolo[1,2-a]pyrazin-1-yl]-N-[6-(1, 2,3,4-tetrahydro-quinolin-1-yl-methyl)-1,2,3,4-tetrahydro-naphthalen-2-yl]-acetamide;
- N-[6-(Piperidin-1-yl-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;
- N-[6-[(4-Methyl-piperazin-1-yl)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide;
- N-[6-[(tert-Butylamino)-methyl]-1, 2,3,4-tetrahydro-naphthalen-1-yl]-2-[2-[[3-(trifluoromethyl)phenyl]sulfonyl]-1, 2,3,4-tetrahydro-pyrrolo[1,2-a]pyrazin-1-yl]-acetamide;
- N-[6-[(Benzylamino)-methyl]-1,2,3,4-tetrahydro-naphthalen-2-yl]-2-[2-[[3-(trifluoromethyl)phenyl]sulfonyl]-1, 2,3,4-tetrahydro-pyrrolo[1,2-a]pyrazin-1-yl]-acetamide;
- N-[6-(Pyrrolidin-1-yl-methyl)-1,2,3,4-tetrahydro-naphthalen-2-yl]-2-[2-[[3-(trifluoromethyl)phenyl]sulfonyl]-1, 2,3,4-tetrahydro-pyrrolo[1,2-a]pyrazin-1-yl]-acetamide;
- 2-[2-(p-Tolylsulfonyl)-1,2,3,4-tetrahydro-pyrrolo[1,2-a]pyrazin-1-yl]-N-[6-(pyrrolidin-1-yl-methyl)-1,2,3,4-tetrahydro-naphthalen-1-yl]-acetamide;

N-[6-(Pyrrolidin-1-yl-methyl)-1,2,3,4-tetrahydro-naphthalen-1-yl]-2-[2-[[3-(trifluoromethyl)phenyl]sulfonyl]-1, 2,3,4-tetrahydro-pyrrolo[1,2-a]pyrazin-1-yl]-acetamide;

N-[6-(Morpholin-4-yl-methyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide;

N-[6-(8-Azabicyclo[3.2.1]octan-8-yl-methyl)-1,2,3,4-tetrahydro-naphthalen-2-yl]-2-[2-[[3-(trifluoromethyl)phenyl]sulfonyl]-1, 2,3,4-tetrahydro-pyrrolo[1,2-a]pyrazin-1-yl]-acetamide;

N-[6-(Piperidin-1-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide;

N-[6-(1,2,3,4-Tetrahydro-quinolin-1-yl-methyl)-1,2,3,4-tetrahydro-naphthalen-1-yl]-2-[2-[[3-(trifluoromethyl)phenyl]sulfonyl]-1, 2,3,4-tetrahydro-pyrrolo[1,2-a]pyrazin-1-yl]-acetamide;

2-[2-[(3-Chloro-4-methyl-phenyl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-1-yl]-acetamide;

N-[6-(Dimethylaminomethyl)-1,2,3,4-tetrahydro-naphthalen-2-yl]-2-[2-[[3-(trifluoromethyl)phenyl]sulfonyl]-1, 2,3,4-tetrahydro-pyrrolo[1,2-a]pyrazin-1-yl]-acetamide;

N-[6-[(Benzylamino)-methyl]-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide;

2-[2-[(6-Methoxy-naphthalen-2-yl)sulfonyl]-1,2,3,4-tetrahydro-pyrrolo[1,2-a]pyrazin-1-yl]-N-[6-(pyrrolidin-1-yl-methyl)-1,2,3,4-tetrahydro-naphthalen-2-yl]-acetamide;

N-[6-(8-Azabicyclo[3.2.1]octan-8-yl-methyl)-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide;

N-[6-(Dimethylaminomethyl)-1,2,3,4-tetrahydro-naphthalen-2-yl]-2-[2-[(6-methoxy-naphthalen-2-yl)sulfonyl]-1, 2,3,4-tetrahydro-pyrrolo[1,2-a]pyrazin-1-yl]-acetamide;

N-[6-[(tert-Butyl-methyl-amino)-methyl]-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide;

2-[2-[(6-Methoxy-naphthalen-2-yl)sulfonyl]-1, 2,3,4-tetrahydro-pyrrolo[1,2-a]pyrazin-1-yl]-N-[6-(pyrrolidin-1-yl-methyl)-1,2,3,4-tetrahydro-naphthalen-1-yl]-acetamide;

2-[2-[(6-Methoxy-naphthalen-2-yl)sulfonyl]-1,2,3,4-tetrahydro-pyrrolo[1,2-a]pyrazin-1-yl]-N-[6-[(4-methyl-piperazin-1-yl)-methyl]-1, 2,3,4-tetrahydro-naphthalen-2-yl]-acetamide;

N-[6-[(Benzylamino)-methyl]-1, 2,3,4-tetrahydro-naphthalen-1-yl]-2-[2-[(6-methoxy-naphthalen-2-yl)sulfonyl]-1, 2,3,4-tetrahydro-pyrrolo[1,2-a]pyrazin-1-yl]-acetamide;

N-[6-[(Benzylamino)-methyl]-1,2,3,4-tetrahydro-naphthalen-2-yl]-2-[2-[(6-methoxy-naphthalen-2-yl)sulfonyl]-1, 2,3,4-tetrahydro-pyrrolo[1,2-a]pyrazin-1-yl]-acetamide;

2-[2-[(3-Chloro-4-methyl-phenyl)sulfonyl]-1, 2,3,4-tetrahydro-pyrrolo[1,2-a]pyrazin-1-yl]-N-[6-(dimethylaminomethyl)-1,2,3,4-tetrahydro-naphthalen-1-yl]-acetamide;

N-[6-(8-Azabicyclo[3.2.1]octan-8-yl-methyl)-1,2,3,4-tetrahydro-naphthalen-2-yl]-2-[2-[(6-methoxy-naphthalen-2-yl)sulfonyl]-1,2,3,4-tetrahydro-pyrrolo[1,2-a]pyrazin-1-yl]-acetamide;

N-[6-[(tert-Butyl-methyl-amino)-methyl]-1,2,3,4-tetrahydro-naphthalen-1-yl]-2-[2-[(6-methoxy-naphthalen-2-yl)sulfonyl]-1,2,3,4-tetrahydro-pyrrolo[1,2-a]pyrazin-1-yl]-acetamide;

2-[2-[(6-Methoxy-naphthalen-2-yl)sulfonyl]-1,2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-2-yl]-acetamide;

N-[6-(Dimethylaminomethyl)-1,2,3,4-tetrahydro-naphthalen-1-yl]-2-[2-[(6-methoxy-naphthalen-2-yl)sulfonyl]-1, 2,3,4-tetrahydro-pyrrolo[1,2-a]pyrazin-1-yl]-acetamide;

N-[6-(Dimethylaminomethyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;

N-[6-(8-Azabicyclo[3.2.1]octan-8-yl-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;

N-[6-(8-Azabicyclo[3.2.1]octan-8-yl-methyl)-1,2,3,4-tetrahydro-naphthalen-1-yl]-2-[2-[[3-(trifluoromethyl)phenyl]sulfonyl]-1,2,3,4-tetrahydro-pyrrolo[1,2a]pyrazin-1-yl]-acetamide;

N-[6-(8-Azabicyclo[3.2.1]octan-8-yl-methyl)-1,2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide;

N-[6-[(Benzylamino)-methyl]-1, 2,3,4-tetrahydro-naphthalen-1-yl]-2-[2-[(3-chloro-4-methyl-phenyl)sulfonyl]-1,2,3,4-tetrahydro-pyrrolo[1,2-a]pyrazin-1-yl]-acetamide;

N-[6-[(Benzylamino)-methyl]-1, 2,3,4-tetrahydro-naphthalen-1-yl]-2-[2-[[3-(trifluoromethyl)phenyl]sulfonyl]-1, 2,3,4-tetrahydro-pyrrolo[1,2-a]pyrazin-1-yl]-acetamide;

N-[6-[(tert-Butyl-methyl-amino)-methyl]-1,2,3,4-tetrahydro-naphthalen-2-yl]-2-[2-[[3-(trifluoromethyl)phenyl]sulfonyl]-1,2,3,4-tetrahydro-pyrrolo[1,2-a]pyrazin-1-yl]-acetamide;

N-[6-[(tert-Butylamino)-methyl]-1, 2,3,4-tetrahydro-naphthalen-1-yl]-2-[2-[(6-methoxy-naphthalen-2-yl)sulfonyl]-1, 2,3,4-tetrahydro-pyrrolo[1,2-a]pyrazin-1-yl]-acetamide;

2-[2-[(3-Chloro-4-methyl-phenyl)sulfonyl]-1, 2,3,4-tetrahydro-pyrrolo[1,2-a]pyrazin-1-yl]-N-[6-(dimethylaminomethyl)-1,2,3,4-tetrahydro-naphthalen-2-yl]-acetamide;

N-[6-[(tert-Butyl-methyl-amino)-methyl]-1, 2,3,4-tetrahydro-naphthalen-2-yl]-2-[2-[[3-(trifluoromethyl)phenyl]sulfonyl]-1, 2,3,4-tetrahydro-pyrrolo[1,2-a]pyrazin-1-yl]-acetamide;

2-[2-[(6-Methoxy-naphthalen-2-yl)sulfonyl]-1,2,3,4-tetrahydro-pyrrolo[1,2-a]pyrazin-1-yl]-N-[6-[(4-methyl-piperazin-1-yl)-methyl]-1,2,3,4-tetrahydro-naphthalen-1-yl]-acetamide;

2-[2-[(6-Methoxy-naphthalen-2-yl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-2-yl]-acetamide;

2-[2-[(3-Chloro-4-methyl-phenyl)sulfonyl]-1, 2,3,4-tetrahydro-pyrrolo[1,2-a]pyrazin-1-yl]-N-[6-(1,2,3,4-tetrahydro-quinolin-1-yl-methyl)-1,2,3,4-tetrahydro-naphthalen-1-yl]-acetamide;

2-[2-[(6-Methoxy-naphthalen-2-yl)sulfonyl]-1,2,3,4-tetrahydro-pyrrolo[1,2-a]pyrazin-1-yl]-N-[6-(morpholin-4-yl-methyl)-1,2,3,4-tetrahydro-naphthalen-1-yl]-acetamide;

2-[2-[(6-Methoxy-naphthalen-2-yl)sulfonyl]-1, 2,3,4-tetrahydro-pyrrolo[1,2-a]pyrazin-1-yl]-N-[6-[(1-methylpropylamino)-methyl]-1,2,3,4-tetrahydro-naphthalen-2-yl]-acetamide;

N-[6-[(tert-Butylamino)-methyl]-1, 2,3,4-tetrahydro-naphthalen-2-yl]-2-[2-(p-tolylsulfonyl)-1,2,3,4-tetrahydro-pyrrolo[1,2-a]pyrazin-1-yl]-acetamide;

2-[2-(p-Tolylsulfonyl)-1,2,3,4-tetrahydro-pyrrolo[1,2-a]pyrazin-1-yl]-N-[6-(pyrrolidin-1-yl-methyl)-1,2,3,4-tetrahydro-naphthalen-2-yl]-acetamide;

N-[6-(Dimethylaminomethyl)-1,2,3,4-tetrahydro-naphthalen-1-yl]-2-[2-[[3-(trifluoromethyl)phenyl]sulfonyl]-1, 2,3,4-tetrahydro-pyrrolo[1,2-a]pyrazin-1-yl]-acetamide;

2-[2-[(6-Methoxy-naphthalen-2-yl)sulfonyl]-1, 2,3,4-tetrahydro-pyrrolo[1,2-a]pyrazin-1-yl]-N-[6-[(1-methylpropylamino)-methyl]-1, 2,3,4-tetrahydro-naphthalen-1-yl]-acetamide;

N-[6-[(1-Methyl-propylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;

N-[6-[(Benzylamino)-methyl]-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;

2-[2-[(6-Methoxy-naphthalen-2-yl)sulfonyl]-1,2,3,4-tetrahydro-pyrrolo[1,2-a]pyrazin-1-yl]-N-[6-(piperidin-1-yl-methyl)-1,2,3,4-tetrahydro-naphthalen-1-yl]-acetamide;

2-[2-(p-Tolylsulfonyl)-1,2,3,4-tetrahydro-pyrrolo[1,2-a]pyrazin-1-yl]-N-[6-(1, 2,3,4-tetrahydro-quinolin-1-yl-methyl)-1,2,3,4-tetrahydro-naphthalen-1-yl]-acetamide;

2-[2-[(6-Methoxy-naphthalen-2-yl)sulfonyl]-1,2,3,4-tetrahydro-pyrrolo[1,2-a]pyrazin-1-yl]-N-[6-(1, 2,3,4-tetrahydro-quinolin-1-yl-methyl)-1,2,3,4-tetrahydro-naphthalen-1-yl]-acetamide;

N-[6-[(1-Methyl-propylamino)-methyl]-1, 2,3,4-tetrahydro-naphthalen-1-yl]-2-[2-[[3-(trifluoromethyl)phenyl]sulfonyl]-1,2,3,4-tetrahydro-pyrrolo[1,2-a]pyrazin-1-yl]-acetamide;

2-[2-[(3-Chloro-4-methyl-phenyl)sulfonyl]-1,2,3,4-tetrahydro-pyrrolo[1,2-a]pyrazin-1-yl]-N-[6-[(1-methylpropylamino)-methyl]-1,2,3,4-tetrahydro-naphthalen-1-yl]-acetamide;

N-[6-(Methylamino-methyl)-1,2,3,4-tetrahydro-naphthalen-1-yl]-2-[2-(p-tolylsulfonyl)-1,2,3,4-tetrahydro-pyrrolo[1,2-a]pyrazin-1-yl]-acetamide;

2-[2-[(6-Methoxy-naphthalen-2-yl)sulfonyl]-1,2,3,4-tetrahydro-pyrrolo[1,2-a]pyrazin-1-yl]-N-[6-(methylamino-methyl)-1,2,3,4-tetrahydro-naphthalen-1-yl]-acetamide;

N-[6-(Methylamino-methyl)-1,2,3,4-tetrahydro-naphthalen-1-yl]-2-[2-[[3-(trifluoromethyl)phenyl]sulfonyl]-1, 2,3,4-tetrahydro-pyrrolo[1,2-a]pyrazin-1-yl]-acetamide;

2-[2-[(3-Chloro-4-methyl-phenyl)sulfonyl]-1,2,3,4-tetrahydro-pyrrolo[1,2-a]pyrazin-1-yl]-N-[6-(methylamino-methyl)-1,2,3,4-tetrahydro-naphthalen-1-yl]-acetamide;

2-[2-[(6-Methoxy-naphthalen-2-yl)sulfonyl]-1, 2,3,4-tetrahydro-pyrrolo[1,2-a]pyrazin-1-yl]-N-[6-(methylamino-methyl)-1,2,3,4-tetrahydro-naphthalen-2-yl]-acetamide;

2-[2-[(3-Chloro-4-methyl-phenyl)sulfonyl]-1, 2,3,4-tetrahydro-pyrrolo[1,2-a]pyrazin-1-yl]-N-[6-(methylamino-methyl)-1,2,3,4-tetrahydro-naphthalen-2-yl]-acetamide;

N-[6-(Methylamino-methyl)-1,2,3,4-tetrahydro-naphthalen-2-yl]-2-[2-[[3-(trifluoromethyl)phenyl]sulfonyl]-1, 2,3,4-tetrahydro-pyrrolo[1,2-a]pyrazin-1-yl]-acetamide;

N-[6-(Methylamino-methyl)-1,2,3,4-tetrahydro-naphthalen-2-yl]-2-[2-(p-tolylsulfonyl)-1,2,3,4-tetrahydro-pyrrolo[1,2-a]pyrazin-1-yl]-acetamide;

1-(4-Hydroxy-4-pyridin-3-yl-piperidin-1-yl)-2-[2-[(4-methoxy-2,6-dimethyl-phenyl)sulfonyl]-1, 2,3,4-tetrahydro-pyrrolo[1,2-a]pyrazin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-N-(3-morpholin-4-yl-propyl)-acetamide;

N-[3-(2,6-Dimethyl-piperidin-1-yl)-propyl]-2-[2-[(4-methoxy-2,6-dimethyl-phenyl)sulfonyl]-1,2,3,4-tetrahydro-pyrrolo[1,2-a]pyrazin-1-yl]-acetamide;

1-[4-(2-Fluorophenyl)-piperazin-1-yl]-2-[2-[(4-methoxy-2,6-dimethyl-phenyl)sulfonyl]-1, 2,3,4-tetrahydro-pyrrolo[1,2-a]pyrazin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-1-(4-phenyl-piperazin-1-yl)-ethanone;

2-[2-[(4-Methoxy-2,6-dimethyl-phenyl)sulfonyl]-1,2,3,4-tetrahydro-pyrrolo[1,2-a]pyrazin-1-yl]-1-[4-(2-piperidin-1-yl-ethyl)-piperidin-1-yl]-ethanone;

1-[4-[2-(2,5-Dimethyl-1H-pyrrol-1-yl)-ethyl]-piperazin-1-yl]-2-[2-[(4-methoxy 2,6-dimethyl-phenyl)sulfonyl]-1,2,3,4-tetrahydro-pyrrolo[1,2-a]pyrazin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-1-(4-pyridin-2-yl-piperazin-1-yl)-ethanone;

2-[4-[2-[2-[(4-Methoxy-2,6-dimethyl-phenyl)sulfonyl]-1,2,3,4-tetrahydro-pyrrolo[1,2-a]pyrazin-1-yl]-acetyl]-[1,4]diazepan-1-yl]-pyridine-3-carbonitrile;

N-[(1-Benzyl-pyrrolidin-3-yl)-methyl]-2-[2-[(4-methoxy-2,6-dimethyl-phenyl)sulfonyl]-1,2,3,4-tetrahydro-pyrrolo[1,2-a]pyrazin-1-yl]-acetamide;

2-[2-[(4-Methoxy-2,6-dimethyl-phenyl)sulfonyl]-1, 2,3,4-tetrahydro-pyrrolo[1,2-a]pyrazin-1-yl]-1-[4-[5-(trifluoromethyl)-pyridin-2-yl]-piperazin-1-yl]-ethanone;

2-[2-[(2-Chloro-6-methyl-phenyl)sulfonyl]-1, 2,3,4-tetrahydro-pyrrolo[1,2-a]pyrazin-1-yl]-N-(2-pyrrolidin-1-yl-ethyl)-acetamide;

2-[2-[(2-Chloro-6-methyl-phenyl)sulfonyl]-1,2,3,4-tetrahydro-pyrrolo[1,2-a]pyrazin-1-yl]-N-(3-morpholin-4-yl-propyl)-acetamide;

2-[2-[(2-Chloro-6-methyl-phenyl)sulfonyl]-1,2,3,4-tetrahydro-pyrrolo[1,2-a]pyrazin-1-yl]-N-[3-(2,6-dimethyl-piperidin-1-yl)-propyl]-acetamide;

2-[2-[(2-Chloro-6-methyl-phenyl)sulfonyl]-1,2,3,4-tetrahydro-pyrrolo[1,2-a]pyrazin-1-yl]-N-[2-(4-methyl-piperazin-1-yl)-1-phenyl-ethyl]-acetamide;

N-(1-Benzyl-pyrrolidin-3-yl)-2-[2-[(2-chloro-6-methyl-phenyl)sulfonyl]-1, 2,3,4-tetrahydro-pyrrolo[1,2-a]pyrazin-1-yl]-acetamide;

2-[2-[(2-Chloro-6-methyl-phenyl)sulfonyl]-1, 2,3,4-tetrahydro-pyrrolo[1,2-a]pyrazin-1-yl]-1-[4-(2-fluorophenyl)-piperazin-1-yl]-ethanone;

2-[2-[(2-Chloro-6-methyl-phenyl)sulfonyl]-1,2,3,4-tetrahydro-pyrrolo[1,2-a]pyrazin-1-yl]-1-(4-morpholin-4-yl-piperidin-1-yl)-ethanone;
2-[2-[(2-Chloro-6-methyl-phenyl)sulfonyl]-1,2,3,4-tetrahydro-pyrrolo[1,2-a]pyrazin-1-yl]-1-(4-piperidin-1-yl-piperidin-1-yl)-ethanone;
2-[2-[(2-Chloro-6-methyl-phenyl)sulfonyl]-1, 2,3,4-tetrahydro-pyrrolo[1,2-a]pyrazin-1-yl]-1-[4-(4-methyl-piperazin-1-yl)-piperidin-1-yl]-ethanone;
2-[2-[(2-Chloro-6-methyl-phenyl)sulfonyl]-1,2,3,4-tetrahydro-pyrrolo[1,2-a]pyrazin-1-yl]-1-(4-pyrimidin-2-yl-piperazin-1-yl)-ethanone;
2-[2-[(2-Chloro-6-methyl-phenyl)sulfonyl]-1, 2,3,4-tetrahydro-pyrrolo[1,2-a]pyrazin-1-yl]-1-[4-(5-methyl-1H-benzoimidazol-2-yl)-piperidin-1-yl]-ethanone;
2-[4-[2-[2-[(2-Chloro-6-methyl-phenyl)sulfonyl]-1,2,3,4-tetrahydro-pyrrolo[1,2-a]pyrazin-1-yl]-acetyl]-[1,4]diazepan-1-yl]-pyridine-3-carbonitrile;
2-[2-[(2-Chloro-6-methyl-phenyl)sulfonyl]-1, 2,3,4-tetrahydro-pyrrolo[1,2-a]pyrazin-1-yl]-1-[4-(2-piperidin-1-yl-ethyl)-piperidin-1-yl]-ethanone;
N-[(1-Benzyl-pyrrolidin-3-yl)-methyl]-2-[2-[(2-chloro-6-methyl-phenyl)sulfonyl]-1,2,3,4-tetrahydro-pyrrolo[1,2-a]pyrazin-1-yl]-acetamide;
2-[2-(Benzenesulfonyl)-1,2,3,4-tetrahydro-pyrrolo[1,2-a]pyrazin-1-yl]-1-(4-hydroxy-4-pyridin-3-yl-piperidin-1-yl)-ethanone;
2-[2-(Benzenesulfonyl)-1,2,3,4-tetrahydro-pyrrolo[1,2-a]pyrazin-1-yl]-N-(2-pyrrolidin-1-yl-ethyl)-acetamide;
2-[2-(Benzenesulfonyl)-1,2,3,4-tetrahydro-pyrrolo[1,2-a]pyrazin-1-yl]-N-[3-(2,6-dimethyl-piperidin-1-yl)-propyl]-acetamide;
2-[2-(Benzenesulfonyl)-1,2,3,4-tetrahydro-pyrrolo[1,2-a]pyrazin-1-yl]-N-[2-(4-methyl-piperazin-1-yl)-1-phenyl-ethyl]-acetamide;
2-[2-(Benzenesulfonyl)-1,2,3,4-tetrahydro-pyrrolo[1,2-a]pyrazin-1-yl]-N-(1-benzyl-pyrrolidin-3-yl)-acetamide;
2-[2-(Benzenesulfonyl)-1,2,3,4-tetrahydro-pyrrolo[1,2-a]pyrazin-1-yl]-1-[4-(2-fluorophenyl)-piperazin-1-yl]-ethanone;
2-[2-(Benzenesulfonyl)-1,2,3,4-tetrahydro-pyrrolo[1,2-a]pyrazin-1-yl]-1-(4-ethyl-piperazin-1-yl)-ethanone;
2-[2-(Benzenesulfonyl)-1,2,3,4-tetrahydro-pyrrolo[1,2-a]pyrazin-1-yl]-1-(4-phenyl-piperazin-1-yl)-ethanone;
2-[2-(Benzenesulfonyl)-1,2,3,4-tetrahydro-pyrrolo[1,2-a]pyrazin-1-yl]-1-(4-pyrrolidin-1-yl-piperidin-1-yl)-ethanone;
2-[2-(Benzenesulfonyl)-1,2,3,4-tetrahydro-pyrrolo[1,2-a]pyrazin-1-yl]-1-(4-morpholin-4-yl-piperidin-1-yl)-ethanone;
2-[2-(Benzenesulfonyl)-1,2,3,4-tetrahydro-pyrrolo[1,2-a]pyrazin-1-yl]-1-[4-(4-methyl-piperazin-1-yl)-piperidin-1-yl]-ethanone;
2-[2-(Benzenesulfonyl)-1,2,3,4-tetrahydro-pyrrolo[1,2-a]pyrazin-1-yl]-1-[4-[2-(2,5-dimethyl-1H-pyrrol-1-yl)-ethyl]-piperazin-1-yl]-ethanone;
2-[2-(Benzenesulfonyl)-1,2,3,4-tetrahydro-pyrrolo[1,2-a]pyrazin-1-yl]-1-(4-pyrimidin-2-yl-piperazin-1-yl)-ethanone;
2-[2-(Benzenesulfonyl)-1,2,3,4-tetrahydro-pyrrolo[1,2-a]pyrazin-1-yl]-1-[4-(5-methyl-1H-benzoimidazol-2-yl)-piperidin-1-yl]-ethanone;
2-[4-[2-[2-(Benzenesulfonyl)-1,2,3,4-tetrahydro-pyrrolo[1,2-a]pyrazin-1-yl]-acetyl]-[1,4]diazepan-1-yl]-pyridine-3-carbonitrile;
2-[2-(Benzenesulfonyl)-1,2,3,4-tetrahydro-pyrrolo[1,2-a]pyrazin-1-yl]-N-[(1-benzyl-pyrrolidin-3-yl)-methyl]-acetamide;
2-[2-(Benzenesulfonyl)-1,2,3,4-tetrahydro-pyrrolo[1,2-a]pyrazin-1-yl]-1-[4-[5-(trifluoromethyl)-pyridin-2-yl]-piperazin-1-yl]-ethanone;
N-[3-(2,6-Dimethyl-piperidin-1-yl)-propyl]-2-[2-[[3-(trifluoromethyl)phenyl]sulfonyl]-1,2,3,4-tetrahydro-pyrrolo[1,2-a]pyrazin-1-yl]-acetamide;
N-[2-(4-Methyl-piperazin-1-yl)-1-phenyl-ethyl]-2-[2-[[3-(trifluoromethyl)phenyl]sulfonyl]-1, 2,3,4-tetrahydro-pyrrolo[1,2-a]pyrazin-1-yl]-acetamide;
1-[4-(2-Fluorophenyl)-piperazin-1-yl]-2-[2-[[3-(trifluoromethyl)phenyl]sulfonyl]-1, 2,3,4-tetrahydro-pyrrolo[1,2-a]pyrazin-1-yl]-ethanone;
1-(4-Ethyl-piperazin-1-yl)-2-[2-[[3-(trifluoromethyl)phenyl]sulfonyl]-1,2,3,4-tetrahydro-pyrrolo[1,2-a]pyrazin-1-yl]-ethanone;
1-(4-Piperidin-1-yl-piperidin-1-yl)-2-[2-[[3-(trifluoromethyl)phenyl]sulfonyl]-1,2,3,4-tetrahydro-pyrrolo[1,2-a]pyrazin-1-yl]-ethanone;
1-[4-(5-Methyl-1H-benzoimidazol-2-yl)-piperidin-1-yl]-2-[2-[[3-(trifluoromethyl)phenyl]sulfonyl]-1,2,3,4-tetrahydro-pyrrolo[1,2-a]pyrazin-1-yl]-ethanone;
1-(4-Pyridin-2-yl-piperazin-1-yl)-2-[2-[[3-(trifluoromethyl)phenyl]sulfonyl]-1,2,3,4-tetrahydro-pyrrolo[1,2-a]pyrazin-1-yl]-ethanone;
2-[4-[2-[2-[[3-(Trifluoromethyl)phenyl]sulfonyl]-1, 2,3,4-tetrahydro-pyrrolo[1,2-a]pyrazin-1-yl]-acetyl]-[1,4]diazepan-1-yl]-pyridine-3-carbonitrile;
N-[(1-Benzyl-pyrrolidin-3-yl)-methyl]-2-[2-[[3-(trifluoromethyl)phenyl]sulfonyl]-1,2,3,4-tetrahydro-pyrrolo[1,2-a]pyrazin-1-yl]-acetamide;
2-[2-[(4-Chloro-2,5-dimethyl-phenyl)sulfonyl]-1,2,3,4-tetrahydro-pyrrolo[1,2-a]pyrazin-1-yl]-N-[3-(2,6-dimethyl-piperidin-1-yl)-propyl]-acetamide;
2-[2-[(4-Chloro-2,5-dimethyl-phenyl)sulfonyl]-1,2,3,4-tetrahydro-pyrrolo[1,2-a]pyrazin-1-yl]-N-[2-(4-methyl-piperazin-1-yl)-1-phenyl-ethyl]-acetamide;
2-[2-[(4-Chloro-2,5-dimethyl-phenyl)sulfonyl]-1,2,3,4-tetrahydro-pyrrolo[1,2-a]pyrazin-1-yl]-1-[4-(2-fluorophenyl)-piperazin-1-yl]-ethanone;
2-[2-[(4-Chloro-2,5-dimethyl-phenyl)sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone;
2-[4-[2-[2-[(4-Chloro-2,5-dimethyl-phenyl)sulfonyl]-1,2,3,4-tetrahydro-pyrrolo[1,2-a]pyrazin-1-yl]-acetyl]-[1,4]diazepan-1-yl]-pyridine-3-carbonitrile;
N-[(1-Benzyl-pyrrolidin-3-yl)-methyl]-2-[2-[(4-chloro-2,5-dimethyl-phenyl)sulfonyl]-1,2,3,4-tetrahydro-pyrrolo[1,2-a]pyrazin-1-yl]-acetamide;
2-[2-[[2-Chloro-4-(trifluoromethyl)-phenyl]sulfonyl]-1,2,3,4-tetrahydro-pyrrolo[1,2-a]pyrazin-1-yl]-N-[3-(2,6-dimethyl-piperidin-1-yl)-propyl]-acetamide;
2-[2-[[2-Chloro-4-(trifluoromethyl)-phenyl]sulfonyl]-1,2,3,4-tetrahydro-pyrrolo[1,2-a]pyrazin-1-yl]-N-[2-(4-methyl-piperazin-1-yl)-1-phenyl-ethyl]-acetamide;
2-[2-[[2-Chloro-4-(trifluoromethyl)-phenyl]sulfonyl]-1,2,3,4-tetrahydro-pyrrolo[1,2-a]pyrazin-1-yl]-1-[4-(2-fluorophenyl)-piperazin-1-yl]-ethanone;
2-[2-[[2-Chloro-4-(trifluoromethyl)-phenyl]sulfonyl]-1,2,3,4-tetrahydro-pyrrolo[1,2-a]pyrazin-1-yl]-1-[4-(5-methyl-1H-benzoimidazol-2-yl)-piperidin-1-yl]-ethanone;
2-[2-[[2-Chloro-4-(trifluoromethyl)-phenyl]sulfonyl]-1,2,3,4-tetrahydro-pyrrolo[1,2-a]pyrazin-1-yl]-1-(4-pyridin-2-yl-piperazin-1-yl)-ethanone;

2-[4-[2-[2-[[2-Chloro-4-(trifluoromethyl)-phenyl]sulfonyl]-1,2,3,4-tetrahydro-pyrrolo[1,2-a]pyrazin-1-yl]-acetyl]-[1,4]diazepan-1-yl]-pyridine-3-carbonitrile;

N-[(1-Benzyl-pyrrolidin-3-yl)-methyl]-2-[2-[[2-chloro-4-(trifluoromethyl)-phenyl]sulfonyl]-1,2,3,4-tetrahydro-pyrrolo[1,2-a]pyrazin-1-yl]-acetamide;

2-[2-[(4-Methoxy-2,6-dimethyl-phenyl)sulfonyl]-1,2,3,4-tetrahydro-pyrrolo[1,2-a]pyrazin-1-yl]-1-[2-(pyridin-2-yl-methyl)-pyrrolidin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-N-(3-piperidin-1-yl-propyl)-acetamide;

1-[4-(5-Chloro-2-methyl-phenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone;

1-[4-(4-Chlorophenyl)-4-hydroxy-piperidin-1-yl]-2-[2-[(4-methoxy-2,6-dimethyl-phenyl)sulfonyl]-1,2,3,4-tetrahydro-pyrrolo[1,2-a]pyrazin-1-yl]-ethanone;

1-(4-Benzyl-4-hydroxy-piperidin-1-yl)-2-[2-[(4-methoxy-2,6-dimethyl-phenyl)sulfonyl]-1,2,3,4-tetrahydro-pyrrolo[1,2-a]pyrazin-1-yl]-ethanone;

1-[4-Hydroxy-4-[3-(trifluoromethyl)phenyl]-piperidin-1-yl]-2-[2-[(4-methoxy-2,6-dimethyl-phenyl)sulfonyl]-1,2,3,4-tetrahydro-pyrrolo[1,2-a]pyrazin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-N-methyl-N-(2-piperidin-1-yl-ethyl)-acetamide;

2-[2-[(4-Methoxy-2,6-dimethyl-phenyl)sulfonyl]-1,2,3,4-tetrahydro-pyrrolo[1,2-a]pyrazin-1-yl]-1-[2-(piperidin-1-yl-methyl)-pyrrolidin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-1-[4-(3-methoxyphenyl)-piperazin-1-yl]-ethanone;

1-[4-(4-Fluorophenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone;

1-(4-Isopropyl-piperazin-1-yl)-2-[2-[(4-methoxy-2,6-dimethyl-phenyl)sulfonyl]-1,2,3,4-tetrahydro-pyrrolo[1,2-a]pyrazin-1-yl]-ethanone;

2-[2-[(2-Chloro-6-methyl-phenyl)sulfonyl]-1,2,3,4-tetrahydro-pyrrolo[1,2-a]pyrazin-1-yl]-1-[2-(pyridin-2-yl-methyl)-pyrrolidin-1-yl]-ethanone;

2-[2-[(2-Chloro-6-methyl-phenyl)sulfonyl]-1,2,3,4-tetrahydro-pyrrolo[1,2-a]pyrazin-1-yl]-N-(3-piperidin-1-yl-propyl)-acetamide;

2-[2-[(2-Chloro-6-methyl-phenyl)sulfonyl]-1,2,3,4-tetrahydro-pyrrolo[1,2-a]pyrazin-1-yl]-1-(4-hydroxy-4-phenyl-piperidin-1-yl)-ethanone;

2-[2-[(2-Chloro-6-methyl-phenyl)sulfonyl]-1,2,3,4-tetrahydro-pyrrolo[1,2-a]pyrazin-1-yl]-1-[4-hydroxy-4-[3-(trifluoromethyl)phenyl]-piperidin-1-yl]-ethanone;

2-[2-[(2-Chloro-6-methyl-phenyl)sulfonyl]-1,2,3,4-tetrahydro-pyrrolo[1,2-a]pyrazin-1-yl]-N-methyl-N-[2-(4-methyl-piperazin-1-yl)-1-phenyl-ethyl]-acetamide;

2-[2-[(2-Chloro-6-methyl-phenyl)sulfonyl]-1,2,3,4-tetrahydro-pyrrolo[1,2-a]pyrazin-1-yl]-N-methyl-N-(2-piperidin-1-yl-ethyl)-acetamide;

2-[2-[(2-Chloro-6-methyl-phenyl)sulfonyl]-1,2,3,4-tetrahydro-pyrrolo[1,2-a]pyrazin-1-yl]-1-[4-(3-methoxyphenyl)-piperazin-1-yl]-ethanone;

2-[2-[(2-Chloro-6-methyl-phenyl)sulfonyl]-1,2,3,4-tetrahydro-pyrrolo[1,2-a]pyrazin-1-yl]-1-[4-(4-fluorophenyl)-piperazin-1-yl]-ethanone;

2-[2-[(2-Chloro-6-methyl-phenyl)sulfonyl]-1,2,3,4-tetrahydro-pyrrolo[1,2-a]pyrazin-n-1-yl]-1-(4-isopropyl-piperazin-1-yl)-ethanone;

2-[2-(Benzenesulfonyl)-1,2,3,4-tetrahydro-pyrrolo[1,2-a]pyrazin-1-yl]-1-[4-(5-chloro-2-methyl-phenyl)-piperazin-1-yl]-ethanone;

2-[2-(Benzenesulfonyl)-1,2,3,4-tetrahydro-pyrrolo[1,2-a]pyrazin-1-yl]-1-[4-(4-chlorophenyl)-4-hydroxy-piperidin-1-yl]-ethanone;

2-[2-(Benzenesulfonyl)-1,2,3,4-tetrahydro-pyrrolo[1,2-a]pyrazin-1-yl]-1-(4-hydroxy-4-phenyl-piperidin-1-yl)-ethanone;

2-[2-(Benzenesulfonyl)-1,2,3,4-tetrahydro-pyrrolo[1,2-a]pyrazin-1-yl]-1-[4-(4-methoxyphenyl)-piperazin-1-yl]-ethanone;

2-[2-[(4-Chloro-2,5-dimethyl-phenyl)sulfonyl]-1,2,3,4-tetrahydro-pyrrolo[1,2-a]pyrazin-1-yl]-N-methyl-N-[2-(4-methyl-piperazin-1-yl)-1-phenyl-ethyl]-acetamide;

2-[2-(Benzenesulfonyl)-1,2,3,4-tetrahydro-pyrrolo[1,2-a]pyrazin-1-yl]-1-[4-(3,4-dichlorophenyl)-piperazin-1-yl]-ethanone;

2-[2-(Benzenesulfonyl)-1,2,3,4-tetrahydro-pyrrolo[1,2-a]pyrazin-1-yl]-1-[4-(p-tolyl-methyl)-piperazin-1-yl]-ethanone;

2-[2-(Benzenesulfonyl)-1,2,3,4-tetrahydro-pyrrolo[1,2-a]pyrazin-1-yl]-1-[4-[(4-methoxyphenyl)-methyl]-piperazin-1-yl]-ethanone;

2-[2-(Benzenesulfonyl)-1,2,3,4-tetrahydro-pyrrolo[1,2-a]pyrazin-1-yl]-1-[4-[(2-fluorophenyl)-methyl]-piperazin-1-yl]-ethanone;

2-[2-(Benzenesulfonyl)-1,2,3,4-tetrahydro-pyrrolo[1,2-a]pyrazin-1-yl]-N-[(1-benzyl-piperidin-3-yl)-methyl]-acetamide;

2-[2-[[3-(Trifluoromethyl)phenyl]sulfonyl]-1,2,3,4-tetrahydro-pyrrolo[1,2-a]pyrazin-1-yl]-1-[4-[(2,4,6-trimethyl-phenyl)-methyl]-piperazin-1-yl]-ethanone;

2-[2-[[2-Chloro-4-(trifluoromethyl)-phenyl]sulfonyl]-1,2,3,4-tetrahydro-pyrrolo[1,2-a]pyrazin-1-yl]-1-[4-(4-methoxyphenyl)-piperazin-1-yl]-ethanone;

1-[4(3,4-Dichlorophenyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-1-[4-[(2,4,6-trimethyl-phenyl)-methyl]-piperazin-1-yl]-ethanone;

1-[4-[(4-Chlorophenyl)-methyl]-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-1-[4-(p-tolyl-methyl)-piperazin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-1-[4-[(4-methoxyphenyl)-methyl]-piperazin-1-yl]-ethanone;

1-[4-[(2-Fluorophenyl)-methyl]-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-1-[2-(pyridin-2-yl-methyl)-piperidin-1-yl]-ethanone;

2-[2-[(4-Methoxy-2,6-dimethyl-phenyl)sulfonyl]-1,2,3,4-tetrahydro-pyrrolo[1,2-a]pyrazin-1-yl]-1-[2-(pyridin-4-yl-methyl)-piperidin-1-yl]-ethanone;

1-[4-(1,3-Benzodioxol-5-yl-methyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone;

3-[4-[2-[2-[(4-Methoxy-2,6-dimethyl-phenyl)sulfonyl]-1,2,3,4-tetrahydro-pyrrolo[1,2-a]pyrazin-1-yl]-acetyl]-piperazin-1-yl]-propionitrile;

N-[(1-Benzyl-piperidin-3-yl)-methyl]-2-[2-[(4-methoxy-2,6-dimethyl-phenyl)sulfonyl]-1,2,3,4-tetrahydro-pyrrolo[1,2-a]pyrazin-1-yl]-acetamide;

2-[2-[(2-Chloro-6-methyl-phenyl)sulfonyl]-1,2,3,4-tetrahydro-pyrrolo[1,2-a]pyrazin-1-yl]-1-[4-[(4-chlorophenyl)-methyl]-piperazin-1-yl]-ethanone;

2-[2-[(2-Chloro-6-methyl-phenyl)sulfonyl]-1,2,3,4-tetrahydro-pyrrolo[1,2-a]pyrazin-1-yl]-1-[2-(pyridin-2-yl-methyl)-piperidin-1-yl]-ethanone;

2-[2-[(2-Chloro-6-methyl-phenyl)sulfonyl]-1,2,3,4-tetrahydro-pyrrolo[1,2-a]pyrazin-1-yl]-1-[2-(pyridin-4-yl-methyl)-piperidin-1-yl]-ethanone;

1-[4-(1,3-Benzodioxol-5-yl-methyl)-piperazin-1-yl]-2-[2-[(2-chloro-6-methyl-phenyl)sulfonyl]-1,2,3,4-tetrahydro-pyrrolo[1,2-a]pyrazin-1-yl]-ethanone;

3-[4-[2-[2-[(2-Chloro-6-methyl-phenyl)sulfonyl]-1, 2,3,4-tetrahydro-pyrrolo[1,2-a]pyrazin-1-yl]-acetyl]-piperazin-1-yl]-propionitrile;

N-[(1-Benzyl-piperidin-3-yl)-methyl]-2-[2-[[2-chloro-4-(trifluoromethyl)-phenyl]sulfonyl]-1,2,3,4-tetrahydropyrrolo[1,2-a]pyrazin-1-yl]-acetamide;

1-[2-(4-Dimethylaminophenyl)-azepan-1-yl]-2-[2-[(4-methoxy-2,6-dimethyl-phenyl)sulfonyl]-1, 2,3,4-tetrahydro-pyrrolo[1,2-a]pyrazin-1-yl]-ethanone;

2-[2-[(4-Methoxy-2,6-dimethyl-phenyl)sulfonyl]-1, 2,3,4-tetrahydro-pyrrolo[1,2-a]pyrazin-1-yl]-N-methyl-N-(2-morpholin-4-yl-1-phenyl-ethyl)-acetamide;

1-(4-Benzyl-piperidin-1-yl)-2-[2-[(4-methoxy-2,6-dimethyl-phenyl)sulfonyl]-1,2,3,4-tetrahydro-pyrrolo[1,2-a]pyrazin-1-yl]-ethanone;

1-[4-(2-Hydroxy-ethyl)-piperazin-1-yl]-2-[2-[(4-methoxy-2,6-dimethyl-phenyl)sulfonyl]-1,2,3,4-tetrahydro-pyrrolo[1,2-a]pyrazin-1-yl]-ethanone;

2-[2-[(2-Chloro-6-methyl-phenyl)sulfonyl]-1, 2,3,4-tetrahydro-pyrrolo[1,2-a]pyrazin-1-yl]-N-methyl-N-(2-morpholin-4-yl-1-phenyl-ethyl)-acetamide;

2-[2-[(2-Chloro-6-methyl-phenyl)sulfonyl]-1,2,3,4-tetrahydro-pyrrolo[1,2-a]pyrazin-1-yl]-1-[(2S)-2-(pyrrolidin-1-yl-methyl)-pyrrolidin-1-yl]-ethanone;

2-[4-[2-[2-[(2-Chloro-6-methyl-phenyl)sulfonyl]-1,2,3,4-tetrahydro-pyrrolo[1,2-a]pyrazin-1-yl]-acetyl]-piperazin-1-yl]-pyridine-3-carbonitrile;

2-[2-[(2-Chloro-6-methyl-phenyl)sulfonyl]-1,2,3,4-tetrahydro-pyrrolo[1,2-a]pyrazin-1-yl]-1-[4-[3-chloro-5-(trifluoromethyl)-pyridin-2-yl]-piperazin-1-yl]-ethanone;

2-[2-[(2-Chloro-6-methyl-phenyl)sulfonyl]-1,2,3,4-tetrahydro-pyrrolo[1,2-a]pyrazin-1-yl]-1-[4-(2-hydroxyethyl)-piperazin-1-yl]-ethanone;

2-[2-(Benzenesulfonyl)-1,2,3,4-tetrahydro-pyrrolo[1,2-a]pyrazin-1-yl]-1-[(2S)-2-(pyrrolidin-1-yl-methyl)-pyrrolidin-1-yl]-ethanone;

2-[2-(Benzenesulfonyl)-1,2,3,4-tetrahydro-pyrrolo[1,2-a]pyrazin-1-yl]-1-[4-[3-chloro-5-(trifluoromethyl)-pyridin-2-yl]-piperazin-1-yl]-ethanone;

2-[2-(Benzenesulfonyl)-1,2,3,4-tetrahydro-pyrrolo[1,2-a]pyrazin-1-yl]-1-[4-[(3,4-dichlorophenyl)-methyl]-piperazin-1-yl]-ethanone;

2-[2-(Benzenesulfonyl)-1,2,3,4-tetrahydro-pyrrolo[1,2-a]pyrazin-1-yl]-1-(4-methyl-2-phenyl-piperazin-1-yl)-ethanone;

2-[2-(Benzenesulfonyl)-1,2,3,4-tetrahydro-pyrrolo[1,2-a]pyrazin-1-yl]-1-(4-phenyl-piperidin-1-yl)-ethanone;

2-[4-[2-[2-[[3-(Trifluoromethyl)phenyl]sulfonyl]-1,2,3,4-tetrahydro-pyrrolo[1,2-a]pyrazin-1-yl]-acetyl]-piperazin-1-yl]-pyridine-3-carbonitrile;

2-[2-[[2-Chloro-4-(trifluoromethyl)-phenyl]sulfonyl]-1, 2,3,4-tetrahydro-pyrrolo[1,2-a]pyrazin-1-yl]-1-[2-(4-dimethylaminophenyl)-pyrrolidin-1-yl]-ethanone;

or a physiologically compatible salt thereof.

20. A pharmaceutical composition comprising a compound as claimed in claim 1 and at least one pharmaceutically acceptable carrier or auxiliary substance.

* * * * *